US012729235B2

(12) United States Patent
Bergeron et al.

(10) Patent No.: US 12,729,235 B2
(45) Date of Patent: Sep. 8, 2026

(54) CANINIZED ANTI-TGFβ ANTIBODIES

(71) Applicant: Zoetis Services LLC, Parsippany, NJ (US)

(72) Inventors: Lisa Marie Bergeron, Boulder, CO (US); Gary F. Bammert, Kalamazoo, MI (US); Henry Luis Campos, Kalamazoo, MI (US); Sandra Ann Marie Lightle, Kalamazoo, MI (US); Catherine J. Strietzel, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 304 days.

(21) Appl. No.: 17/341,212

(22) Filed: Jun. 7, 2021

(65) Prior Publication Data

US 2022/0119513 A1 Apr. 21, 2022

Related U.S. Application Data

(60) Provisional application No. 63/036,092, filed on Jun. 8, 2020.

(51) Int. Cl.

| | |
|---|---|
| ***A61K 39/395*** | (2006.01) |
| ***A61P 13/12*** | (2006.01) |
| ***C07K 16/22*** | (2006.01) |
| *A61K 39/00* | (2006.01) |

(52) U.S. Cl.

CPC .............. *C07K 16/22* (2013.01); *A61P 13/12* (2018.01); *A61K 2039/505* (2013.01); *C07K 2317/24* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 5,350,576 | A | 9/1994 | Payne et al. |
| 5,500,362 | A | 3/1996 | Robinson et al. |
| 5,624,821 | A | 4/1997 | Winter et al. |
| 5,648,260 | A | 7/1997 | Winter et al. |
| 5,821,337 | A | 10/1998 | Carter et al. |
| 6,194,167 | B1 | 2/2001 | Browse et al. |
| 6,492,497 | B1 | 12/2002 | Thompson et al. |
| 6,774,107 | B1 | 8/2004 | Strittmatter et al. |
| 6,790,639 | B2 | 9/2004 | Brown et al. |
| 7,261,890 | B2 | 8/2007 | Krah, III et al. |
| 7,723,486 | B2 | 5/2010 | Ledbetter et al. |
| 9,505,829 | B2 | 11/2016 | Lacy et al. |
| 9,617,334 | B2 | 4/2017 | Bergeron et al. |
| 10,106,607 | B2 | 10/2018 | Morsey et al. |
| 10,421,807 | B2 | 9/2019 | Gonzales et al. |
| 10,982,002 | B2 | 4/2021 | Steiniger et al. |
| 12,168,683 | B2 | 12/2024 | Kumar et al. |
| 2003/0031671 | A1 | 2/2003 | Welt et al. |
| 2018/0244763 | A1 | 8/2018 | Shapiro et al. |

FOREIGN PATENT DOCUMENTS

| | | | |
|---|---|---|---|
| EP | 0388151 | A1 | 9/1990 |
| WO | 2005092925 | A2 | 10/2005 |
| WO | WO 2013/134365 | A1 | 9/2013 |
| WO | WO 2014/164709 | A2 | 10/2014 |
| WO | WO 2016/141245 | A1 | 9/2016 |
| WO | WO 2018/208670 | A1 | 11/2018 |
| WO | 2018237157 | A1 | 12/2018 |
| WO | 2019108900 | A1 | 6/2019 |
| WO | WO 2020/095113 | A1 | 5/2020 |
| WO | 2021252455 | A1 | 12/2021 |
| WO | 2023049917 | A1 | 3/2023 |

OTHER PUBLICATIONS

Simpson et al. (The Laryngoscope 118: 543-551, 2008).*

Silva, R. F. et al., 2012, "Comparison of the effect of calcium gluconate and batroxobin on the release of transforming growth factor beta 1 in canine platelet concentrates", BMC Veterinary Research, Biomed Central, vol. 8, pp. 121-127.

Uniprot Database, Oct. 10, 2018, "TGFBR2—TGF-beta receptor type-2—Felis catus (Cat)—TGFBR2 Gene & protein", Accession No. M3W233.

Jin, G. et al., 2007, "TGFB1 and TGFBR2 functional polymorphisms and risk of esophageal squamous cell carcinoma: a case-control analysis in a Chinese population", Journal of Cancer Research and Clinical Oncology, vol. 134, pp. 345-351.

Maeda, M. et al., 2017, "Effects of Gelatin Hydrogel Containing Anti-Transforming Growth Factor-β Antibody in a Canine Filtration Surgery Model", International Journal of Molecular Sciences, vol. 18, p. 985.

Simpson, C. B. et al., 2008, "Anti-transforming growth factor beta as a treatment for laryngotracheal stenosis in a canine model", The Laryngoscope, Wiley-Blackwell, vol. 118, No. 3, Mar. 1.

Davis, R. J., et al., 2020, "Inflammatory pathways in the pathogenesis of iatrogenic laryngotracheal stenosis: what do we know?", Translational Cancer Research, vol. 9, pp. 2108-2116.

Buhren, J. et al., 2009, "Optical Effects of Anti-TGFβ Treatment after Photorefractive Keratectomy in a Cat Model", Investigative Ophthalmology & Visual Science, vol. 50, pp. 634-643.

Dasch, J. R. et al., 1989, "Monoclonal Antibodies Recognizing Transforming Growth Factor-β, Bioactivity Neutralization and Transforming Growth Factor β2 Affinity Purification", The Journal of Immunology, vol. 142, pp. 1536-1541.

Komai, T. et al., 2018, "Transforming Growth Factor-β and Interleukin-10 Synergistically Regulate Humoral Immunity via Modulating Metabolic Signals", Frontiers in Immunology, vo. 9, article 1364.

(Continued)

*Primary Examiner* — Christine J Saoud

(74) *Attorney, Agent, or Firm* — Kelly M. Sullivan

(57) ABSTRACT

The present disclosure encompasses anti-TGFβ antibodies, antigen binding proteins and polynucleotides encoding the same. The disclosure further provides use of the novel antibodies, antigen binding proteins and/or nucleotide of the invention for the treatment of TGFβ-related disorders, particularly in for the management of fibrosis related disorders in canines and felines.

8 Claims, 22 Drawing Sheets

Specification includes a Sequence Listing.

(56) References Cited

OTHER PUBLICATIONS

Tabe, Y. et al, 2013, "TGF-β-Neutralizing Antibody 1D11 Enhances Cytarabine-Induced Apoptosis in AML Cells in the Bone Marrow Microenvironment", PLoS One, vol. 8, e62785.
Bedinger, D. et al., 2016, "Development and characterization of human monoclonal antibodies that neutralize multiple TGFβ Isoforms", MABS, vol. 8, pp. 389-404.
Rice, L. M. et al., 2015, "Fresolimumab treatment decreases biomarkers and improves clinical symptoms in systemic sclerosis patients", The Journal of Clinical Investigation, vo. 125, pp. 2795-2807.
Liang, X. et al., 2016, "Anti-TGF-β Antibody, 1D11, Ameliorates Glomerular Fibrosis in Mouse Models after the Onset of Proteinuria", PLoS One, pp. 1-17.
Lord, D. M. et al., 2018, "Structure-based engineering to restore high affinity binding of an isoform-selective anti-TGFβ1 antibody", MABS, vol. 10, pp. 444-452.
Denton, C. P. et al, 2007, "Recombinant Human Anti-Transforming Growth Factor β1 Antibody Therapy in Systemic Sclerosis; A multicenter, randomized, placebo-controlled phase I/II trial of CAT-192", Arthritis & Rheumatism, vol. 56, pp. 323-333.
Voelker, J. et al., 2017, "Anti-TGF-β1 Antibody Therapy in Patients with diabetic Nephropathy", Journal of American Society of Nephrology, vol. 28, pp. 953-962.
Kanasaki, K. et al., 2013, "Diabetic nephropathy: the role of inflammation in fibroblast activation and kidney fibrosis", Frontiers in Endocrinology, vol. 4, article 7.
Zoetis, "Advances in Veterinary Medicine: Therapeutic Monoclonal Antibodies for Companion Animals" Internet: URL:https://www.zoetisus.com/conditions/dogs/itchycle/downloads/resorces/publications/zoetisn marfnl.pdf [retrieved Sep. 13, 2021].
Lawson, J. S. et al., 2018, "The cat as a naturally occurring model of renal interstitial fibrosis: Characterisation of primary feline proximal tubular epithelial cells and comparative pro-fibrotic effects of TGF-β1", PLoS One, vol. 13, e0202577.
Gu, Y. et al., 2020, "Diverse Role of TGF-β in Kidney Disease," Frontiers in Cell and Developmental Biology, vol. 8, article 123.
Perez, J. M. et al., 2018, "Critical Approach to the Alternative Treatment of Chronic Kidney Disease in Dogs and Cats", Slovenian Veterinary Research, vol. 55, pp. 59-71.
Kabat et al.,1991, Sequences of Proteins of Immunological Interest, 5th Ed. Public Health Service, National Institutes of Health, Bethesda, MD, "Kapa Light Constant Chains", pp. 647-652.
Kabat et al., 1991, Sequences of Proteins of Immunological Interest, 5th Ed. Public Health Service, National Institutes of Health, Bethesda, MD, "Lambda Light Chains", pp. 653-660.
Kabat et al., 1991, Sequences of Proteins of Immunological Interest, 5th Ed. Public Health Service, National Institutes of Health, Bethesda, MD, "Heavy Chains CH1 Region", pp. 660-669.
Chothia, C, et al., 1987, "Canonical Structures for the Hypervariable Regions of Immunoglobulins", Journal of Molecular Biology, vol. 196, pp. 901-917.
Daẽron, M., 1997, "Fc Receptor Biology", Annual Review of Immunology, vol. 15, pp. 203-234.
Armour, K. L. et al., 1999, "Recombinant human IgG molecules lacking Fcγ receptor I binding and monocyte triggering activities", European Journal of Immunology, vol. 29, pp. 2613-2624.
Clynes, R. A. et al., 2000, "Inhibitory FC receptors modulate in vivo cytoxicity against tumor targets", Nature Medicine, vol. 6, pp. 443-446.
Schifferli, J. A. et al., 1986, "The Role of Complement and its Receptor in the Elimination of Immune Complexes", The New England Journal of Medicine, vol. 315, pp. 488-495.
Garred, P. et al., 1989, "The IgG Subclass Pattern of Complement Activation Depends on Epitope density and Antibody and Complement Concentration", Scandinavian Journal of Immunology, vol. 30, pp. 379-382.
Moore, G. L. et al., 2010, "Engineered Fc variant antibodies with enhanced ability to recruit complement and mediate effector functions", mABs, vol. 2, pp. 181-189.
Ghetie, V. et al., 1996, "Abnormally short serum half-lives of IgG in B2 microglobulin-deficient mice", European Journal of Immunology, vol. 26, pp. 690-696.
Israel, E. J. et al., 1996, "Increased clearance of IgG in mice that lack $β_2$-microglobulin: possible protective role of FcRn", Immunology, vol. 89, pp. 573-578.
Praetor, A. et al., 2002, "Membrane-anchored Human FcRn can Oligomerize in the Absence of IgG", Journal of Molecular Biology, vol. 321, pp. 277-284.
Jefferis, R., 2007, Antibody therapeutics: isotype and glycoform selection, Expert Opinion on Biological Therapy, vol. 7, pp. 1401-1413.
Mazza, G. et al., 1993, "The separation and identification by monoclonal antibodies of dog IgG fractions", Journal of Immunological Methods, vol. 161, pp. 193-203.
Bergeron, L. M. et al., 2014, "Comparative functional characterization of canine IgG subclasses", Veterinary Immunology and Immunopathology, vol. 157, pp. 31-41.
Strietzel, C. J. et al., 2014, "In Vitro functional characterization of feline IgGs," Veterinary Immunology and Immunopathology, vol. 158, pp. 214-223.
Kanai, T. H. et al., 2000, "Identification of two allelic IgG1 CH coding regions (Cy1) of cat", Veterinary Immunology and Immunopathology, vol. 73, pp. 53-62.
Ravetch, J. V. et al., 1991, "Fc receptors", Annual Review Immunology, vol. 9, pp. 457-492.
Capel, P. J. A. et al., 1994, "Heterogeneity of Human IgG Fc Receptors", Immunomethods, vol. 4, pp. 25-34.
De Haas et al., 1995, "Fc gamma receptors of phagocytes", Journal of Laboratory and Clinical Medicine, vol. 126, pp. 330-341.
Guyer, R. L. et al., 1976, "Immunoglobulin Binding by Mouse Intestinal Epithelial Cell Receptors", Journal of Immunology, vol. 117, pp. 587-593.
Kim, J. et al., 1994, Localization of the site of the murine IgG1 molecule that is involved in binding to the murine intestinal Fc receptor, Journal of Immunology, vol. 24, pp. 2429-2434.
Clynes, R. et al., 1998, "Fc receptors are required in passive and active immunity to melanoma", PNAS (USA), vol. 95, pp. 652-656.
Gazzano-Santoro, H. et al., 1997, "A non-radioactive complement-dependent cytotoxicity assay for anti-CD20 monoclonal antibody," Journal of Immunological Methods, vol. 202, p. 163-171.
Kohler, G. et al., 1975, "Continuous cultures of fused cells secreting antibody of predefined specificity", Nature, vol. 256, pp. 495-497.
Clackson, T. et al., 1991, "Making antibody fragments using phage display libraries", Nature, vol. 352, pp. 624-628.
Marks, J. D. et al., 1991, "By-passing Immunization: Human Antibodies from V-gene Libraries Displayed on Phage", Journal of Molecular Biology, vol. 222, pp. 581-597.
Taylor, L. D. et al., 1992, "A transgenic mouse that expresses a diversity of human sequence heavy and light chain immunoglobulins", Nucleic Acids Research, vol. 20, pp. 6287-6295.
Sivalingam, G. N. et al., 2012, "An analysis of B-cell epitope discontinuity", Molecular Immunology, vol. 51, pp. 304-309.
McCumber, L. J. et al., 1979, "The Complete Amino-Acid Sequence of a Canine MU Chain", Molecular Immunology, vol. 16, pp. 565-570.
Tang, L. et al., 2001, "Cloning and characterization of cDNAs encoding four different canine immunoglobulin y chains", Veterinary Immunology and Immunopathology, vol. 80, pp. 259-270.
Potter, K. N. et al., 1993, "Antibody Production in the Baculovirus Expression System", International Reviews of Immunology, vol. 10, pp. 103-112.
Houdebine, L., 2002, Antibody manufacture in transgenic animals and comparisons with other systems, Current Opinion in Biotechnology, vol. 13, pp. 625-629.
Schillberg, S. et al., 2003 "Molecular farming of recombinant antibodies in plants", Cellular and Molecular Life Sciences, vol. 60, pp. 433-445.
Lathe, R., 1985, "Synthetic oligonucleotide probes deduced from amino acid sequence data: theoretical and practical considerations", Journal of Molecular Biology, vol. 183, pp. 1-12.

(56) References Cited

OTHER PUBLICATIONS

PCT International Search Report and Written Opinion, International Application No. PCT/US2021/036347, International Filing Date Jun. 8, 2021, Date of Mailing Nov. 23, 2021, Bumb, P.—authorized officer.
Akhurst R.J., et al., "Targeting the TGFBeta Signalling Pathway in Disease", Nature Reviews Drug Discovery, 2012, vol. 11, No. 10, pp. 790-811.
Bedouelle H., et al., "Diversity and Junction Residues as Hotspots of Binding Energy in a Antibody Neutralizing the dengue Virus," FEBS Journal, Jan. 2006, vol. 273, pp. 34-46.
Brown M., et al., "Tolerance of Single, but Not Multiple, Amino Acid Replacements in Antibody VH CDR 2: A Means of Minimizing B Cell Wastage From Somatic Hypermutation?," Journal of Immunology, May 1996, vol. 156, No. 9, pp. 3285-3291, 8 Pages, Abstract.
Chen C., et al., "Enhancement and Destruction of Antibody Function by Somatic Mutation: Unequal Occurrence Is Controlled by V Gene Combinatorial Associations", The EMBO Journal, vol. 14, No. 12, Jun. 15, 1995, pp. 2784-2794.
Colman P. M., et al., "Effects of Amino Acid Sequence Changes on Antibody-antigen Interactions", Research in Immunology, vol. 145, No. 1, Jan. 1994, pp. 33-36.
"Integrated Into UniProtKB/Swiss-Prot", Accession No. P04202, Entry Version 216, Apr. 20, 2020, 9 Pages, Retrieved from https://rest.uniprot.org/unisave/P04202?format=txt&versions=216, Search Date May 9, 2025.
"Integrated Into UniProtKB/Swiss-Prot" Accession No. P17125, Entry Version 165, Feb. 26, 2020, 5 Pages, Retrieved from https://rest.uniprot.org/unisave/P17125?format=txt&versions=165, Search Date May 9, 2025.
"Integrated Into UniProtKB/Swiss-Prot", Accession No. P27090, Entry Version 175, Apr. 22, 2020, 7 Pages, Retrieved from https://rest.uniprot.org/unisave/P27090?format=txt&versions=175, Search Date May 9, 2025.
"Integrated into UniProtKB/TrEMBL", Accession No. F1PKH0, Apr. 22, 2020, Entry Version 60, 4 Pages, Retrieved from https://rest.uniprot.org/unisave/F1PKH0?format=txt&versions=60, Last Accessed on May 9, 2025.
"Integrated Into UniProtKB/TrEMBL", Accession No. Q2PPL2, Entry Version 61, Feb. 26, 2020, 2 Pages, Retrieved from https://rest.uniprot.org/unisave/Q2PPL2?format=txt&versions=61, Last Searched on May 9, 2025.
International Preliminary Report on Patentability for International Application No. PCT/US2022/077053, dated Apr. 11, 2024, 8 Pages.
International Search Report and Written Opinion for International Application No. PCT/US2022/077053, dated Feb. 7, 2023, 11 Pages.
Janeway C.A., et al., "The Recognition of Antigen," Immuno Biology, The Immune System in Health and Disease, Immunology, 3rd edition, Garland Publications, Inc., 1997, pp. 3:1-3:11 (14 Pages).
Johnston S.A., et al., "Mitochondrial Transformation in Yeast by Bombardment with Microprojectiles", Science, 1988, vol. 240, pp. 1538-1541.
Krafft E., et al., "Transforming Growth Factor Beta 1 Activation, Storage, and Signaling Pathways in Idiopathic Pulmonary Fibrosis in Dogs", Journal of Veterinary Internal Medicine, 2014, vol. 28, No. 6, pp. 1666-1675, 11 Pages.
Liang W-C., et al., "Dramatic Activation of an Antibody by a Single Amino Acid Change in Framework", Scientific Reports, 2021, vol. 11, No. 22365, 9 Pages, See Abstract.
Macarenhas J., et al., "Anti-Transforming Growth Factor-(beta) Therapy in Patients with Myelofibrosis," Leukemia & Lymphoma, Feb. 2014, vol. 55, No. 2, pp. 450-452 (4 Pages).
NCI: "Anti-TGF-beta Monoclonal Antibody GC1008," National Cancer Institute, 2024, 1 Page, [Retrieved on Dec. 13, 2024].
Pascal B.D., et al., "HDX Workbench: Software for the Analysis of H/D Exchange MS Data", Journal of the American Society for Mass Spectrometry, 2012, vol. 23, No. 9, pp. 1512-1521.
Rudikoff S., et al., "Single Amino Acid Substitution Altering Antigen-binding Specificity," Proceedings of the National Academy of Sciences of the United States of America, Mar. 1982, vol. 79, pp. 1979-1983(5 Pages).
Schenderov K., et al., "Immune Dysregulation as a driver of Idiopathic Pulmonary Fibrosis," Journal of Clinical Investigation, Jan. 19, 2021, vol. 131, No. 2, Article No. e143226, 9 Pages.
Shah P.V., et al., "A Review of Pirfenidone as an Anti-Fibrotic in Idiopathic Pulmonary Fibrosis and Its Probable Role in Other Diseases," Cureus, Jan. 4, 2021, vol. 13, No. 1, Article No. e12482, 8 Pages, doi: 10.7759/cureus.12482. PMID: 33564498; PMCID: PMC7861090.
Trachtman H., et al., "A Phase 1, Single-Dose Study of Fresolimumab, an Anti-TGF-(beta) Antibody, in Treatment-Resistant Primary Focal Segmental Glomerulosclerosis," Kidney International, Mar. 2, 2021, vol. 79, pp. 1236-1243.
Vajdos F.F., et al., "Comprehensive Functional Maps of the Antigen-Binding Site of an Anti-ErbB2 Antibody Obtained with Shotgun Scanning Mutagenesis," Journal of Molecular Biology, 2002, vol. 320, No. 2, pp. 415-428.
Wasserman R.L., et al., "Primary Structure of the Variable Regions of Two Canine Immunoglobulin Heavy Chains", Biochemistry, 1977, vol. 6, pp. 3160-3168.
Wasserman R.L., et al., "The Amino Acid Sequence of the Light Chain Variable Region of a Canine Myeloma Immunoglobulin: Evidence That the VK Subgroups Predated Mammalian Speciation", Immunochemistry, 1978, vol. 15, pp. 303-305.
Yarilin A.A., "Fundamentals Immunology: Textbook. Moscow", Medicine, 1999, 608 Pages, 5 Pages, See p. 171, Second Paragraph, pp. 171-173.

* cited by examiner

| ANTI-TGFb ANTIBODIES EPITOPE MAPPING RESULT SUMMARY BY HDX | | | | | | | | | | | |
|---|---|---|---|---|---|---|---|---|---|---|---|
| HUMAN/CANINE/FELINE TGFb1 SEQUENCE | | | | | | | | | | | |
| ALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS | | | | | | | | | | | (SEQ ID NO. 223) |
| | EPITOPE (PRIMARY -SOLID BLACK, SECONDARY -STRIPES) RESIDUE # | | | | | | | | RESIDUES SHOWING DEUTERIUM UPTAKE | | |
| mAb ID | 25-43 | 44-56 | 57-59 | 60-64 | 65-81 | 82-91 | 91-104 | | PRIMARY (BLACK) | SECONDARY (STRIPES) | |
| SL501 (CANINE) | | | | | | | | | 92-101 | 60-64 | |
| SL501 (HUMAN) | | | | | | | | | 91-104 | 25-43, 57-90 | |
| HcLb (MOUSE) | | | | | | | | | 82-104 | 57-64 | |
| HcLb (CANINE) | | | | | | | | | 57-66, 90-103 | 25-43, 67-89 | |
| 04H09 (MOUSE) | | | | | | | | | 82-91 | 60-64 | |

FIG. 1

| TREATMENT | SERUM CREATININE < 5.0 n | % | ≥ 5.0 mg/dL n | % | ALL n | % |
|---|---|---|---|---|---|---|
| T01 | 10 | 62.5 | 6 | 37.5 | 16 | 100.0 |
| T02 | 26 | 78.8 | 7 | 21.2 | 33 | 100.0 |

| TREATMENT | SERUM PHOSPHORUS ≤ 4.5 mg/dL n | % | SERUM PHOSPHORUS > 4.5 mg/dL n | % | ALL n | % |
|---|---|---|---|---|---|---|
| T01 | 2 | 12.5 | 14 | 87.5 | 16 | 100.0 |
| T02 | 7 | 21.2 | 26 | 78.8 | 33 | 100.0 |

| TREATMENT | WITHDRAWAL DUE TO CKD | | | | | | ALL | |
|---|---|---|---|---|---|---|---|---|
| | NON-CKD WITHDRAWAL | | CKD WITHDRAWAL | | ONGOING | | | |
| | n | % | n | % | n | % | n | % |
| T01 | 5 | 31.3 | 7 | 43.8 | 4 | 25.0 | 16 | 100.0 |
| T02 | 2 | 6.1 | 3 | 9.1 | 28 | 84.8 | 33 | 100.0 |

| TREATMENT | EXITED THE STUDY? YES n | % | NO n | % | ALL n | % |
|---|---|---|---|---|---|---|
| T01 | 12 | 75.0 | 4 | 25.0 | 16 | 100.0 |
| T02 | 5 | 15.2 | 28 | 84.8 | 33 | 100.0 |

| TREATMENT | CREATININE DOUBLING? NO n | NO % | YES n | YES % | ALL n | ALL % |
|---|---|---|---|---|---|---|
| T01 | 10 | 62.5 | 6 | 37.5 | 16 | 100.0 |
| T02 | 32 | 97.0 | 1 | 3.0 | 33 | 100.0 |

| TREATMENT | WITHDRAWAL DUE TO CKD | | | | | | ALL | |
|---|---|---|---|---|---|---|---|---|
| | NON-CKD WITHDRAWAL | | CKD WITHDRAWAL | | ONGOING | | | |
| | n | % | n | % | n | % | n | % |
| T01 | 5 | 31.3 | 7 | 43.8 | 4 | 25.0 | 16 | 100.0 |
| T02 | 2 | 6.1 | 3 | 9.1 | 28 | 84.8 | 33 | 100.0 |

| TREATMENT | EXITED THE STUDY? | | | | ALL | |
|---|---|---|---|---|---|---|
| | YES | | NO | | | |
| | n | % | n | % | n | % |
| T01 | 12 | 75.0 | 4 | 25.0 | 16 | 100.0 |
| T02 | 5 | 15.2 | 28 | 84.8 | 33 | 100.0 |

CANINIZED ANTI-TGFβ ANTIBODIES

CROSS REFERENCE TO RELATED APPLICATIONS

This application claims the benefit under 35 USC 119(e) to U.S. Provisional Application No. 63/036,092 filed on Jun. 8, 2020, which is hereby incorporated by reference in its entirety.

FIELD OF THE DISCLOSURE

The present application relates to monoclonal antibodies, methods of their production, and therapeutic uses of those antibodies. In certain embodiments, the monoclonal antibodies are directed toward Transforming Growth Factor-Beta (TGFβ, TGFB or TGFbeta). In other embodiments, the antibodies are chimeric or speciated antibodies. In other embodiments method of treatments comprising the antibodies of the invention are disclosed.

BACKGROUND OF THE INVENTION

Transforming Growth Factor-Beta (TGFB, TGFβ or TGF beta, as used interchangeably herein) is a cytokine that controls many key cellular functions including proliferation, differentiation, survival, migration and epithelial mesenchymal transition. It is a member of a superfamily of 38 cytokines that include TGFβ, bone morphogenetic proteins (BMP), growth differentiation factors, inhibins, and activins. TGFβ proteins regulate diverse biologic processes such as extracellular matrix formation, wound healing, embryonic development, bone development, hematopoiesis, immune and inflammatory responses and malignant transformation. Deregulation of TGFβ leads to pathological conditions that include birth defects, cancer, chronic inflammation, autoimmune and fibrotic diseases.

TGFβ has three known isoforms, TGFβ1,2, and 3. All three isoforms are initially translated as a pro-peptide. The isoforms are synthesized as large precursor proteins (pro-TGFβ) forming dimeric complexes in the endoplasmic reticulum and are subsequently cleaved near the carboxy-terminus to yield mature 112-amino acid polypeptides which share 60-80% conservation across the three TGFβ isoforms. The mature TGFβ dimer remains associated with the cleaved latency peptide portion of the precursor as an inactive latent complex. Newly synthesized TGFβ bound to the latency-associated peptide (LAP) forming a small latent complex (SLC) is biologically inactive and cannot bind to its receptor, TGFβRII. Through the formation of disulfide bonds this complex loosely binds to a latent TGFβ binding protein (LTBP) to form a large latent complex (LLC). TGFβ is then secreted in a latent state and is stored in the extracellular matrix (ECM). Activation of TGFβ involves release from the latent complex following exposure to a number of different factors, including integrins, proteases, metalloproteinases, reactive oxygen species (ROS), plasmin, and acid, that allow binding to its cell surface receptors for initiation of TGFβ signaling.

TGFβ1,2 and 3 are pleiotropic in their function and are expressed in different patterns across cell and tissue types. They have similar in vitro activities, but individual knockouts in specific cell types suggest non-identical roles in vivo despite their shared ability to bind to the same receptor (Akhurst et al., Nat Rev Drug Discov (2012) 11 (10): 790-811). Upon TGFβ binding to TGF3RII, the constitutive kinase activity of the receptor phosphorylates and activates TGF3RI which in turn phosphorylates SMAD2/3 allowing for association with SMAD4. This complex localizes to the nucleus and serve as a transcription factor for TGFβ responsive genes. In addition to this canonical signaling cascade, a non-canonical pathway transmits signals through other factors including p38, MAPK, PI3K, AKT, JUN, JNK and NK-KB. The end result is a crosstalk of all of these signalling pathways that integrate the state and environment of the cell.

Many severe diseases are linked to malfunctions of the TGFβ induced signaling pathway. The present invention is directed towards the potential treatment of both canine and feline Chronic Kidney Disease (CKD). CKD involves a loss of functional kidney tissue due to a prolonged, progressive process. Dramatic changes in kidney structure may be seen, although structural and functional changes in the kidney are only loosely correlated. Disease is usually present for many months or years before it becomes clinically apparent and it is invariably irreversible. Although congenital disease results in a transient increase in prevalence in animals >3 years old, the prevalence increases with advancing age from 5-6 years onward. In geriatric populations CKD affects as many as 10% of dogs and 40-80% of cats. In the field of veterinary medicine there is a distinct and unmet need to treat CKD in both dogs and cats which is suggested to be a condition influenced by an overproduction of TGFβ proteins.

SUMMARY OF THE INVENTION

The present invention provides novel anti-Transforming Growth Factor Beta (TGFB, TGFbeta or TGFβ as defined and used interchangeably herein) antigen binding proteins (antibody, antibody fragment, antagonist antibody, as defined and used interchangeably herein) that binds to TGF31. In all embodiments the present invention provides an antibody that binds to TGFβ1. In some embodiments the present invention provides an antigen binding protein that additionally binds to TGFβ3. In some embodiments the present invention provides an antigen binding protein that binds to TGFβ1, TGF32 and TGF33. The antigen binding protein of the invention blocks the biological activity of TGFβ1,2 and/or 3 from preventing the binding of TGFβ1, 2 and/or 3 to its receptor and prevents activation of the pathways associated with binding. Additionally, the present invention provides that the antagonist action of the antibody of the invention prevents and/or treats a TGFβ related disorder, as defined herein. The invention further provides nucleotides that encode the antigen binding protein of the invention as well as the production of vectors and host cells. The invention further provides methods of making and using said antibody/antigen binding protein as well as methods of treatment of treating TGFβ disorders in canines, felines and humans by administering the antibody of the invention.

In one aspect the present invention provides an antibody/antigen binding protein (as used interchangeably herein) that binds to TGFβ1. In one or more embodiments the antigen binding protein also specifically binds to TGFβ33. In one or more embodiments the antigen binding protein also specifically binds to TGFβ2 and TGF33. In one or more embodiments the antigen binding protein of the present invention binds to canine TGFβ1. In one or more embodiments the antigen binding protein of the present invention binds to feline TGFβ1. In one or more embodiments the antigen binding protein of the present invention is administered as a pharmaceutical composition further comprising an excipient in order to treat a TGFβ related disorder. In one or more embodiments the TGFβ related disorder comprises kidney fibrosis/chronic kidney disease.

In one or more embodiments the present invention provides an antigen binding protein that specifically binds to canine or feline Transforming Growth Factor Beta-1 (TGFβ1). In one embodiment the antigen binding protein of the invention specifically binds to canine TGFβ1 which comprises the amino acid sequence comprising SEQ ID NO. 220. In one embodiment the antigen binding protein of the invention specifically binds to canine TGF31 which comprises the amino acid sequence comprising SEQ ID NO. 222. In one embodiment, the antigen binding protein is capable of binding to epitope regions on TGF31 which comprise amino acids 91-104 of SEQ ID NO.223. In one embodiment the antigen binding protein is further capable of binding to amino acids 60-64 of SEQ ID NO: 223.

In one embodiment, the present invention provides an antigen binding protein that specifically binds to canine or feline TGFβ1 and not to TGFβ2 or TGFβ3 t comprising a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising: SEQ ID NO: 224 [Threonine (T)-Glycine (G)-Glutamic Acid (E)-Tyrosine (Y)-Serine (S)-Glycine (G)-Tyrosine (Y)-Aspartic Acid (D)-Threonine (T)-(X1)-(X2)-(X3)-(X4)-(X5)] wherein: X1 comprises Lysine (K) or Arginine (R); X2 comprises Threonine (T) or Alanine (A); X3 comprises Glutamine (Q), Asparagine (N), Aspartic Acid (D), Glutamic Acid (E) or Lysine (K) and X4 comprises Serine (S), Glutamic Acid (E), Glutamine (Q) or Aspartic Acid (D); and a light chain variable region (VL) comprising a Complimentary Determining Region 1 (CDR1) comprising an amino acid sequence having at least about 95% sequence identity to the amino acid sequence comprising SEQ ID NO. 44; a Complimentary Determining Region 2 (CDR2) comprising an amino acid sequence having at least about 95% sequence identity to the amino acid sequence comprising SEQ ID NO. 45; a Complimentary Determining Region 3 (CDR3) comprising an amino acid sequence having at least about 95% sequence identity to the amino acid sequence comprising SEQ ID NO: 46; and any variants thereof having one or more conservative amino acid substitutions. In one or more embodiments, the antigen binding protein of the invention comprises variants that are not conservative amino acid substitutions.

In one or one embodiments, the present invention provides an antigen binding protein that specifically binds to canine or feline TGFβ1 and not to TGFβ2 or TGFβ3 comprising a heavy chain variable region comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; a Complimentary Determining Region 3 (CDR3) comprising an amino acid sequence having at least about 95% sequence identity to the amino acid sequence selected from the group consisting of: SEQ ID NO:43; SEQ ID NO:141; SEQ ID NO: 142; SEQ ID NO: 149; SEQ ID NO:150; SEQ ID NO:153; SEQ ID NO:154; SEQ ID NO:155; SEQ ID NO:156; SEQ ID NO:162; SEQ ID NO:166; SEQ ID NO:167; SEQ ID NO:169; SEQ ID NO:170; SEQ ID NO: 171; SEQ ID NO:172; and SEQ ID NO:178; and a light chain variable region (VL) comprising: a Complimentary Determining Region 1 (CDR1) comprising an amino acid sequence having at least about 95% sequence identity to the amino acid sequence comprising SEQ ID NO. 44; a Complimentary Determining Region 2 (CDR2) comprising an amino acid sequence having at least about 95% sequence identity to the amino acid sequence comprising SEQ ID NO. 45; a Complimentary Determining Region 3 (CDR3) comprising an amino acid sequence having at least about 95% sequence identity to the amino acid sequence comprising SEQ ID NO: 46; and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO:43 any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 141 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 142 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO:149 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 150 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 153 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 154 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO:155 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 156 and any variants thereof having one or more conservative amino acid substitutions In one or more embodiments, the antigen binding protein of the invention comprises variants that are not conservative amino acid substitutions.

In one or more embodiments the antigen binding protein of the invention that specifically binds to canine or feline TGF01 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 162 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 166 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 167 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO:169 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 170 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 171 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence comprising SEQ ID NO: 172 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a heavy chain variable region (VH) comprising a Complimentary Determining Region 1 (CDR1) comprising an amino acid sequence having at least about 95% sequence identity to the amino acid sequence comprising SEQ ID NO. 41; a Complimentary Determining Region 2 (CDR2) comprising an amino acid sequence having at least about 95% sequence identity to the amino acid sequence comprising SEQ ID NO. 42; and a Complimentary Determining Region 3 (CDR3) comprising an amino acid sequence having at least about 95% sequence identity to the amino acid sequence, comprising SEQ ID NO:178 and any variants thereof having one or more conservative amino acid substitutions. In one or more embodiments, the antigen binding protein of the invention comprises variants that are not conservative amino acid substitutions.

In one or more embodiments the antigen binding protein of the invention that specifically binds to canine or feline TGFβ1 and not to TGFβ2 or TGFβ3 comprises a caninized, felinized, humanized or chimeric binding protein. In one or more embodiments the antigen binding protein is a caninized antigen binding protein. In one or more embodiments the antigen binding protein is a felinized antigen binding protein. In one or more embodiments the antigen binding protein is a humanized antigen binding protein. In one or more embodiments the antigen binding protein is a chimeric antigen binding protein.

In one embodiment the invention provides an antigen binding protein that specifically binds to canine or feline TGFβ1 and not to TGFβ2 or TGFβ3 comprising a heavy chain variable region (VH) having at least 95% sequence identity to the amino acid sequences selected from the group consisting of: SEQ ID NO:38; SEQ ID NO:47; SEQ ID NO:48; SEQ ID NO:55; SEQ ID NO:57; SEQ ID NO:231; SEQ ID NO:232; SEQ ID NO:239; SEQ ID NO:240; SEQ ID NO:243; SEQ ID NO:244; SEQ ID NO:245; SEQ ID NO:246; SEQ ID NO:252; SEQ ID NO:256; SEQ ID NO:257; SEQ ID NO:259; SEQ ID NO:260; SEQ ID NO:261; SEQ ID NO:262; and SEQ ID NO:268; and a light chain variable region (VL) having at least 95% sequence identity to the amino acid sequences selected from the group consisting of: SEQ ID NO: 49; SEQ ID NO:51; and SEQ ID NO: 53; and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO: 38 and a light chain variable region (VL) having at least about 95% sequence identity to the amino acid sequence comprising SEQ ID NO:49 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:38 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:38 and a light chain variable region (VL) having at least about 95% sequence identity to the amino acid sequence comprising SEQ ID NO:53 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:47 and a light chain variable region (VL) having at least about 95% sequence identity to the amino acid sequence comprising SEQ ID NO:53 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:56 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:231 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:232 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:239 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions. In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:240 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:243 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO: 244 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO: 245 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:246 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGF02 or TGFβ3 comprising a heavy chain variable region (VH) having at least about 95% sequence identity to the amino acid sequence comprising SEQ ID NO:252 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:256 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:257 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:259 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:260 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:261 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:262 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a heavy chain variable region (VH) having at least about 95% sequence identity to the amino acid sequence comprising SEQ ID NO:268 and a light chain variable region (VL) having at least about 95% sequence identity to the amino acid sequence comprising SEQ ID NO:51 and any variants thereof having one or more conservative amino acid substitutions. In one or more embodiments, the antigen binding protein of the invention comprises variants that are not conservative amino acid substitutions.

In one or more embodiments the invention provides the caninized antigen binding protein of the invention that specifically binds to canine or feline TGFβ1 and not to TGFβ2 or TGFβ3 which further comprises the canine heavy chain constant region comprising amino acid sequences having at least about 95% sequence identity to the amino acid sequence comprising SEQ ID NO:127 and any variants thereof having one or more conservative amino acid substitutions. In one or more embodiments, the antigen binding protein of the invention comprises variants that are not conservative amino acid substitutions.

In one or more embodiments the invention provides an caninized antigen binding protein of the invention that specifically binds to canine or feline TGFβ1 and not to TGFβ2 or TGFβ3 further comprises the canine light chain constant region comprising amino acid sequences having at least about 95% sequence identity to the amino acid sequence comprising SEQ ID NO:129. In one embodiment the antigen binding protein of the invention comprises a heavy chain variable region (VH) having at least about 95% sequence identity to the amino acid sequence comprising SEQ ID NO:55 and a light chain variable region (VL) having at least about 95% sequence identity to the amino acid sequence comprising SEQ ID NO:49; a constant region of the heavy chain (SEQ ID NO:127) and the constant region of the light chain (SEQ ID NO:129); and any variant thereof having one or more conservative amino acid substitutions. In one or more embodiments, the antigen binding protein of the invention comprises variants that are not conservative amino acid substitutions.

In one embodiment, the present invention provides an antigen binding protein that specifically binds to canine or feline TGFβ1 and not to TGFβ2 or TGFβ3 comprising a felinized antigen binding protein. In one embodiment the antigen binding protein comprises a heavy chain variable region (VH) having at least about 95% sequence identity to the amino acid sequences selected from SEQ ID NO:38 or SEQ ID NO: 59; and a light chain variable region (VL) having at least about 95% sequence identity to the amino acid sequences selected from SEQ ID NO:40 or SEQ ID NO:61; and any variants thereof having one or more conservative amino acid substitutions. In one or more embodiments, the antigen binding protein of the invention comprises variants that are not conservative amino acid substitutions.

In one embodiment the invention provides an antigen binding protein that specifically binds to canine or feline TGFβ1 and not to TGFβ2 or TGFβ3 comprising a heavy chain variable region (VH) having at least about 95% sequence identity to the amino acid sequences SEQ ID NO:59; and a light chain variable region (VL) having at least about 95% sequence identity to the amino acid comprising SEQ ID NO:61; and any variants thereof having one or more conservative amino acid substitutions. In one or more embodiments, the antigen binding protein of the invention comprises variants that are not conservative amino acid substitutions.

In one or more embodiments the invention provides an antigen binding protein that specifically binds to canine or feline TGFβ1 and not to TGFβ2 or TGFβ3 further comprising the feline heavy chain constant region comprising amino acid sequences having at least about 95% sequence identity to the amino acid sequence comprising SEQ ID NO:131; and any variants thereof having one or more conservative amino acid substitutions. In one or more embodiments, the antigen binding protein of the invention comprises variants that are not conservative amino acid substitutions.

In one or more embodiments the invention provides an antigen binding protein that specifically binds to canine or feline TGFβ1 and not to TGFβ2 or TGFβ3 further comprising the feline light chain constant region comprising amino acid sequences having at least about 95% sequence identity to the amino acid sequence comprising SEQ ID NO:133; and any variants thereof having one or more conservative amino acid substitutions. In one or more embodiments, the antigen binding protein of the invention comprises variants that are not conservative amino acid substitutions.

In one embodiment the present invention provides an antigen binding protein that specifically binds to canine or feline TGFβ1 and not to TGFβ2 or TGFβ3 that comprises a humanized antigen binding protein. In one embodiment the present invention provides an antigen binding protein that comprises a chimeric antigen binding protein and any variants thereof having one or more conservative amino acid substitutions. In one or more embodiments, the antigen binding protein of the invention comprises variants that are not conservative amino acid substitutions.

In one embodiment the present invention provides an antigen binding protein that specifically binds to canine or feline TGFβ1 and not to TGFβ2 or TGFβ3 that comprises a chimeric antigen binding protein. In one embodiment the chimeric antigen binding protein comprises a heavy chain variable region (VH) having at least about 95% sequence identity to the amino acid sequences selected from the group consisting of SEQ ID NO:38 and a light chain variable region (VL) having at least about 95% sequence identity to the amino acid comprising SEQ ID NO:40; and SEQ ID NO:61 and any variants thereof having one or more conservative amino acid substitutions. In one or more embodiments, the antigen binding protein of the invention comprises variants that are not conservative amino acid substitutions.

In one or more embodiments the present invention provides an antigen binding protein that specifically binds to canine or feline TGFβ1 and not to TGFβ2 or TGFβ3 wherein said protein is selected from the group consisting of: a monoclonal antigen binding protein; a single chain antigen binding protein, a tetrameric antigen binding protein, a tetravalent antigen binding protein, a multispecific antigen binding protein, a domain-specific antigen binding protein, a domain-deleted antigen binding protein, a fusion protein, an ScFc fusion protein, an Fab fragment, an Fab' fragment, an $F(ab')_2$ fragment, an Fv fragment, an ScFv fragment, an Fd fragment, a single domain antigen binding protein, a dAb fragment, a small modular immunopharmaceutical (SMIP) a nanobody, and IgNAR molecule. In one embodiment the antigen binding protein is a monoclonal antigen binding protein.

In one or more embodiments the antigen binding protein of the invention that specifically binds to canine or feline TGFβ1 and not to TGFβ2 or TGFβ3 is for use in treating a canine for a TGFβ related disorder. In one or more embodiments the antigen binding protein of the invention is for use in treating a feline for a TGFβ related disorder. In one or more embodiments the antigen binding protein of the invention is for use in treating a human for a TGFβ related disorder.

In one or more embodiment the present invention provides an antigen binding protein that specifically binds to canine or feline TGFβ1 and not to TGFβ2 or TGFβ3 wherein said binding protein is used to reduce or eliminate a TGFβ related disorder. In one embodiment the TGFβ-related disorder is selected from the group consisting of fibrosis disorder, connective tissue disorder, bone disorders and cell proliferation disorders. In one embodiment the TGFβ-related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a pharmaceutical composition that specifically binds to canine or feline TGFβ1 and not to TGFβ2 or TGFβ3 that comprises a therapeutically effective amount of the antigen binding protein of the invention and a pharmaceutically acceptable carrier.

In one or more embodiment the antigen binding protein of the invention that specifically binds to canine or feline TGFβ1 and not to TGFβ2 or TGFβ3 provides a method of treating a subject for a TGFβ related disorder by administering to said subject a therapeutic amount of the pharmaceutical composition of the invention. In one or more embodiments, the present invention provides a method of treating a canine for a TGFβ-related disorder. In one embodiment the present invention provides a method for treating a feline for a TGFβ-related disorder. In one embodiment the present invention provides a method for treating a human for a TGFβ-related disorder. In one embodiment the method provides administering a therapeutically effective amount of the pharmaceutical composition comprising the antigen binding protein of the invention. In one or more embodiments the present invention provides that the TGFβ-related disorder is selected from the group consisting of: fibrosis disorder, connective tissue disorder, bone disorders and cell proliferation disorders. In one embodiment the TGF3 related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a method of inhibiting TGFβ activity in a subject by administering the pharmaceutical composition which comprises the antigen binding protein of the invention that specifically binds to canine or feline TGFβ1 and not to TGFβ2 or TGFβ3. In one embodiment the subject comprises canines, felines or humans. In one embodiment the subject comprises canines. In one embodiment the subject comprises felines. In one embodiment the subject comprises humans.

In one or more embodiments the present invention provides an isolated nucleic acid sequence having at least about 95% sequence identity to the nucleic acid sequence encoding the antigen binding protein of the invention that specifically binds to canine or feline TGFβ1 and not to TGFβ2 or TGFβ3 and any variants thereof having one or more nucleic acid substitutions resulting in conservative amino acid substitutions. In one or more embodiments the present invention provides an isolated nucleic acid sequence encoding the antigen binding protein of the invention wherein said sequence comprises a nucleotide sequence encoding the VH having 95% sequence identity to SEQ ID NO:54 and a nucleotide sequence encoding the VL having 95% sequence identity to SEQ ID NO:293 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1 and not to TGFβ2 or TGFβ3 wherein said nucleic acid sequences comprises a nucleotide sequence encoding the VH having 95% sequence identity to SEQ ID NO:54; a nucleotide sequence encoding the VL having 95% sequence identity to SEQ ID NO:293; a nucleotide sequence encoding the canine heavy chain constant region having 95% sequence identity to SEQ ID NO:128; and a nucleotide sequence encoding the canine light chain constant region having 95% sequence identity to SEQ ID NO:130 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:58 and a nucleotide sequence encoding the VL having 95% sequence identity to SEQ ID NO:60 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:58 and a nucleotide sequence encoding the VL having 95% sequence identity to SEQ ID NO:39 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:37 and a nucleotide sequence encoding the VL having 95% sequence identity to SEQ ID NO:60 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:58; a nucleotide sequence encoding the VL having 95% sequence identity to SEQ ID NO. 60; a nucleotide sequence encoding the feline heavy chain constant region having 95% sequence identity to SEQ ID NO:132; and a nucleotide sequence encoding the feline light chain constant region having 95% sequence identity to SEQ ID NO:134 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:58; a nucleotide sequence encoding the VL having 95% sequence identity to SEQ ID NO. 39; a nucleotide sequence encoding the feline heavy chain constant region having 95% sequence identity to SEQ ID NO:132; and a nucleotide sequence encoding the feline light chain constant region having 95% sequence identity to SEQ ID NO:134 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and not to TGFβ2 or TGFβ3 wherein said sequence comprises a nucleotide sequence encoding the VH having 95% sequence identity to SEQ ID NO:37; a nucleotide sequence encoding the VL having 95% sequence identity to SEQ ID NO:60; a nucleotide sequence encoding the feline heavy chain constant region having 95% sequence identity to SEQ ID NO:132; and a nucleotide sequence encoding the feline light chain constant region having 95% sequence identity to SEQ ID NO:134 and any variants thereof having one or more nucleic acid substitutions resulting in conservative amino acid substitutions.

In one or more embodiments the present invention provides a vector comprising the nucleic acid sequence that encodes for the antigen binding protein of the invention that specifically binds to canine or feline TGFβ1 and not to TGFβ2 or TGFβ3.

In one embodiment the invention provides a host cell that comprises the nucleic acid sequence that encodes the antigen binding protein of the present invention that specifically binds to canine or feline TGFβ1 and not to TGFβ2 or TGFβ3. In one embodiment the invention provides a host cell that comprises the vector comprising the nucleic acid that encodes the antigen binding protein of the present invention. In one embodiment the invention provides a host cell that produces the antigen binding protein of the invention.

In one or more embodiments the present invention provides a method of producing the antigen binding protein of the invention that specifically binds to canine or feline TGFβ1 and not to TGFβ2 or TGFβ3 comprising culturing the host cell of the invention under conditions that result in production of the antigen binding protein and isolating the antigen binding protein from the host cell or culture medium of the host cell.

In one or more embodiments the present invention provides an antigen binding protein that specifically binds to canine or feline Transforming Growth Factor Beta-1 (TGFβ1) and Transforming Growth Factor-3 (TGFβ3). In one embodiment the antigen binding protein of the invention is capable of binding to epitope regions on TGFβ1 which comprises amino acids 82-91 of SEQ ID NO.223. In one embodiment the antigen binding protein of the invention is further capable of binding to amino acids 60-64 of SEQ ID NO:223.

In one or more embodiments the present invention provides the antigen binding protein of the invention that specifically binds to canine or feline TGFβ1 and TGFβ3 but not to TGFβ2 comprising a heavy chain variable region (VH) comprising a Complimentary Determining Region 1 (CDR1) comprising an amino acid sequence comprising at least about 95% sequence identity to the amino acid sequence comprising SEQ ID NO:5; a Complimentary Determining Region 2 (CDR2) comprising an amino acid sequence comprising at least about 95% sequence identity to the amino acid sequence comprising SEQ ID NO:6; a Complimentary Determining Region 3 (CDR3) comprising an amino acid sequence comprising at least about 95% sequence identity to the amino acid sequence comprising SEQ ID NO: 7; and a light chain variable region (VL) comprising: a Complimentary Determining Region 1 (CDR1) comprising an amino acid sequence comprising at least about 95% sequence identity to the amino acid sequence comprising SEQ ID NO. 8; a Complimentary Determining Region 2 (CDR2) comprising an amino acid sequence comprising at least about 95% sequence identity to the amino acid sequence comprising SEQ ID NO:9; a Complimentary Determining Region 3 (CDR3) comprising an amino acid sequence comprising at least about 95% sequence identity to the amino acid sequence comprising SEQ ID NO:10; and any variants thereof having one or more conservative amino acid substitutions. In one or more embodiments the variants of the antigen binding protein of the invention do not comprise conservative amino acid substitutions.

In one or more embodiments the present invention provides the antigen binding protein of the invention that specifically binds to canine or feline TGFβ1 and TGFβ3 but not to TGFβ2 comprising a heavy chain variable region (VH) comprising: a Complimentary Determining Region 1 (CDR1) comprising amino acid sequence SEQ ID NO. 5; a Complimentary Determining Region 2 (CDR2) comprising amino acid SEQ ID NO:6; a Complimentary Determining Region 3 (CDR3) comprising amino acid sequence SEQ ID NO: 7; and a light chain variable region (VL) comprising: a Complimentary Determining Region 1 (CDR1) comprising amino acid SEQ ID NO: 8; a Complimentary Determining Region 2 (CDR2) comprising amino acid sequence SEQ ID NO: 9; a Complimentary Determining Region 3 (CDR3) comprising amino acid sequence SEQ ID NO: 10; and any variants thereof having one or more conservative amino acid substitutions. In one or more embodiments the variants of the antigen binding protein of the invention are not conservative amino acid substitutions.

In one or more embodiments the present invention provides an antigen binding protein that specifically binds to canine or feline TGFβ1 and TGFβ3 but not to TGFβ2 wherein the antigen binding protein comprises a caninized, felinized, humanized, murine or chimeric antigen binding protein. In one embodiment the antigen binding protein comprises a caninized antigen binding protein. In one embodiment the antigen binding protein comprises a heavy chain variable region (VH) having at least 95% sequence identity to the amino acid sequences selected from the group consisting of: SEQ ID NO:12; SEQ ID NO:14; SEQ ID NO:16; and a light chain variable region (VL) having at least 95% sequence identity to the amino acid sequences selected from the group consisting of: SEQ ID NO:18; SEQ ID NO:20; SEQ ID NO:22; SEQ ID NO:24; and any variants thereof having one or more conservative amino acid substitutions. In one or more embodiments, the antigen binding protein of the invention comprises variants that are not conservative amino acid substitutions.

In one or more embodiments the present invention provides an antigen binding protein that specifically binds to canine or feline TGFβ1 and TGFβ3 but not to TGFβ2 wherein the antigen binding protein comprises a caninized, felinized, humanized, murine or chimeric antigen binding protein. In one embodiment the antigen binding protein comprises a caninized antigen binding protein. In one embodiment the antigen binding protein comprises a heavy chain variable region (VH) comprising the amino acid sequences selected from the group consisting of: SEQ ID NO:12; SEQ ID NO:14; SEQ ID NO:16; and a light chain variable region (VL) comprising the amino acid sequences selected from the group consisting of: SEQ ID NO:18; SEQ ID NO:20; SEQ ID NO:22; SEQ ID NO:24; and any variants thereof having one or more conservative amino acid. In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGF02 comprising a heavy chain variable region (VH) having at least 95% sequence identity to the amino acid sequence comprising SEQ ID NO:12 and a light chain variable region (VL) having at least 95% sequence identity to the amino acid sequence comprising SEQ ID NO:24 and any variants thereof having one or more conservative amino acid substitutions In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a heavy chain variable region (VH) having at least 95% sequence identity to the amino acid sequence comprising SEQ ID NO:14 and a light chain variable region (VL) having at least 95% sequence identity to the amino acid sequence comprising SEQ ID NO:24 and any variants thereof having one or more conservative amino acid substitutions. In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a heavy chain variable region (VH) having at least 95% sequence identity to the amino acid sequence comprising SEQ ID NO:13 and a light chain variable region (VL) having at least 95% sequence identity to the amino acid sequence comprising SEQ ID NO:23 and any variants thereof having one or more conservative amino acid substitutions. In one or more embodiments the variants of the antigen binding protein of the invention are not conservative amino acid substitutions.

In one or more embodiments the invention further provides an antigen binding protein that specifically binds to canine or feline TGFβ1 and TGFβ3 but not to TGFβ2 comprising the canine heavy chain constant region comprising amino acid sequences having at least about 95% sequence identity to the amino acid sequence comprising SEQ ID NO: 127. In one or more embodiments the canine heavy chain constant region comprises conservative amino acid substitutions. In one or more embodiments the amino acid substitutions are not conservative.

In one or more embodiments the invention provides an antigen binding protein that specifically binds to canine or feline TGFβ1 and TGFβ3 but not to TGFβ2 comprising the canine heavy chain constant region comprising amino acid sequences SEQ ID NO:127. In one or more embodiments the canine heavy chain constant region comprises conservative amino acid substitutions. In one or more embodiments the amino acid substitutions are not conservative.

In one or more embodiments the invention provides an antigen binding protein that specifically binds to canine or feline TGFβ1 and TGFβ3 but not to TGFβ2 comprising the canine light chain constant region comprising amino acid sequences having at least about 95% sequence identity to the amino acid sequence comprising SEQ ID NO:129. In one or more embodiments the invention provides an antigen binding protein comprising the canine light chain constant region comprising amino acid sequence SEQ ID NO:129. In one or more embodiments the canine light chain constant region comprises conservative amino acid substitutions. In one or more embodiments the amino acid substitutions are not conservative.

In one embodiment the present invention provides an antigen binding protein that specifically binds to canine or feline TGFβ1 and TGFβ3 but not to TGFβ2 comprising a heavy chain variable region (VH) having at least 95% sequence identity to the amino acid sequence comprising SEQ ID NO:12 and a light chain variable region (VL) having at least 95% sequence identity to the amino acid sequence comprising SEQ ID NO:24; a canine heavy chain constant region comprising amino acid sequences having at least about 95% sequence identity to the amino acid sequence comprising SEQ ID NO:127 and the canine light chain constant region comprising amino acid sequences having at least about 95% sequence identity to the amino acid sequence comprising SEQ ID NO:129 and any variants thereof having one or more conservative amino acid substitutions In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a heavy chain variable region (VH) comprising the amino acid sequence SEQ ID NO:12 and a light chain variable region (VL) comprising the amino acid sequence SEQ ID NO: 24; a canine heavy chain constant region comprising the amino acid sequence comprising SEQ ID NO: 127 and the canine light chain constant region comprising the amino acid sequence comprising SEQ ID NO: 129 and any variants thereof having one or more conservative amino acid substitutions In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a felinized antigen binding protein. In one embodiment the antigen binding protein comprises a heavy chain variable region (VH) having at least 95% sequence identity to the amino acid sequences selected from SEQ ID NO: 26; SEQ ID NO: 28; and SEQ ID NO: 30 and a light chain variable region (VL) having at least 95% sequence identity to the amino acid sequences selected from SEQ ID NO: 32 or SEQ ID NO: 34; and SEQ ID NO:36 and any variants thereof having one or more conservative amino acid substitutions In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprises a heavy chain variable region (VH) having at least 95% sequence identity to the amino acid sequence comprising SEQ ID NO:26 and a light chain variable region (VL) having at least 95% sequence identity to the amino acid sequence comprising SEQ ID NO:32 and any variants thereof having one or more conservative amino acid substitutions In one or more embodiments the variants of the antigen binding protein of the invention are not conservative amino acid substitutions.

In one or more embodiments the invention provides an antigen binding protein that specifically binds to canine or feline TGFβ1 and TGFβ3 but not to TGFβ2 further comprising a feline heavy chain constant region comprising amino acid sequences having at least about 95% sequence identity to the amino acid sequence comprising SEQ ID NO:131. and any variants thereof having one or more conservative amino acid substitutions. In one or more embodiments the variants of the antigen binding protein of the invention are not conservative amino acid substitutions.

In one or more embodiments the invention provides an antigen binding protein that specifically binds to canine or feline TGFβ1 and TGFβ3 but not to TGFβ2 comprising a feline light chain constant region comprising amino acid sequences having at least about 95% sequence identity to the amino acid sequence comprising SEQ ID NO:133. and any variants thereof having one or more conservative amino acid substitutions. In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a heavy chain variable region (VH) having at least 95% sequence identity to the amino acid sequence comprising SEQ ID NO:26 and a light chain variable region (VL) having at least 95% sequence identity to the amino acid sequence comprising SEQ ID NO:32; the feline heavy chain constant region comprising amino acid sequences having at least about 95% sequence identity to the amino acid sequence comprising SEQ ID NO: 131; and the feline light chain constant region comprising amino acid sequences having at least about 95% sequence identity to the amino acid sequence comprising SEQ ID NO:133 and any variants thereof having one or more conservative amino acid substitutions. In one or more embodiments the variants of the antigen binding protein of the invention are not conservative amino acid substitutions.

In one embodiment the present invention provides an antigen binding protein that specifically binds to canine or feline TGFβ1 and TGFβ3 but not to TGFβ2 comprising a humanized antigen binding protein. In one embodiment the present invention provides an antigen binding protein comprising a chimeric antigen binding protein.

In one or more embodiments the antigen binding protein of the invention that specifically binds to canine or feline TGFβ1 and TGFβ3 but not to TGFβ2 is for use in treating a canine for a TGFβ related disorder. In one or more embodiments the antigen binding protein of the invention is for use in treating a feline for a TGFβ related disorder. In one or more embodiments the antigen binding protein of the invention is for use in treating a human for a TGFβ related disorder.

In one or more embodiments the present invention provides an antigen binding protein that specifically binds to canine or feline TGFβ1 and TGFβ3 but not to TGFβ2 wherein said protein is selected from the group consisting of: a monoclonal antigen binding protein; a single chain antigen binding protein, a tetrameric antigen binding protein, a tetravalent antigen binding protein, a multispecific antigen binding protein, a domain-specific antigen binding protein, a domain-deleted antigen binding protein, a fusion protein, an ScFc fusion protein, an Fab fragment, an Fab' fragment, an $F(ab')_2$ fragment, an Fv fragment, an ScFv fragment, an Fd fragment, a single domain antigen binding protein, a dAb fragment, a small modular immunopharmaceutical (SMIP) a nanobody, and IgNAR molecule. In one embodiment the antigen binding protein is a monoclonal antigen binding protein.

In one or more embodiment the present invention provides an antigen binding protein for use in treating a TGFβ related disorder that specifically binds to canine or feline TGFβ1 and TGFβ3 but not to TGFβ2 and wherein said binding protein reduces or eliminates TGFβ related disorder. In one embodiment the TGFβ-related disorder is selected from the group consisting of fibrosis disorder, connective tissue disorder, bone disorders and cell proliferation disorders. In one embodiment the TGFβ-related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a pharmaceutical composition that comprises a therapeutically effective amount of the antigen binding protein of the invention that specifically binds to canine or feline TGFβ1 and TGFβ3 but not to TGFβ2 and a pharmaceutically acceptable carrier.

In one or more embodiment the antigen binding protein of the invention that specifically binds to canine or feline TGFβ1 and TGFβ3 but not to TGFβ2 provides a method of treating a subject for a TGFβ related disorder by administering to said subject a therapeutic amount of the pharmaceutical composition of the invention. In one or more embodiments, the present invention provides a method of treating a canine for a TGFβ-related disorder. In one embodiment the present invention provides a method for treating a feline for a TGFβ-related disorder. In one embodiment the present invention provides a method for treating a human for a TGFβ-related disorder. In one embodiment the method provides administering a therapeutically effective amount of the pharmaceutical composition comprising the antigen binding protein of the invention. In one or more embodiments the present invention provides that the TGFβ-related disorder is selected from the group consisting of: fibrosis disorder, connective tissue disorder, bone disorders and cell proliferation disorders. In one embodiment the TGFβ related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a method of inhibiting TGFβ activity in a subject by administering the pharmaceutical composition comprising the antigen binding protein of the invention that specifically binds to canine or feline TGFβ1 and TGFβ3 but not to TGFβ2. In one embodiment the subject comprises canines, felines or humans. In one embodiment the subject comprises canines. In one embodiment the subject comprises felines. In one embodiment the subject comprises humans.

In one or more embodiments the present invention provides an isolated nucleic acid sequence having at least about 95% sequence identity to the nucleic acid sequence encoding the antigen binding protein of the invention that specifically binds to canine or feline TGFβ1 and TGFβ3 but not to TGFβ2 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1 and TGFβ3 but not to TGFβ2 wherein said sequence comprises a nucleotide sequence encoding the VH having 95% sequence identity to SEQ ID NO. 11 and a nucleotide sequence encoding the VL having 95% sequence identity to SEQ ID NO. 23 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1 and TGFβ3 but not to TGFβ2 wherein said nucleic acid sequences comprises a nucleotide sequence encoding the VH having 95% sequence identity to SEQ ID NO. 11; a nucleotide sequence encoding the VL having 95% sequence identity to SEQ ID NO. 23; a nucleotide sequence encoding the canine heavy chain constant region having 95% sequence identity to SEQ ID NO. 128; and a nucleotide sequence encoding the canine light chain constant region having 95% sequence identity to SEQ ID NO. 130 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and TGFβ3 but not to TGFβ2 wherein said sequence comprises a nucleotide sequence encoding the VH having 95% sequence identity to SEQ ID NO. 13 and a nucleotide sequence encoding the VL having 95% sequence identity to SEQ ID NO. 23 and any variants thereof having one or more nucleic acid substitutions resulting in conservative amino acid substitutions.

In one or more embodiments, the present invention provides an isolated nucleic acid sequence encoding the antigen binding protein of the invention that specifically binds to canine or feline TGFβ1 and TGFβ3 but not to TGFβ2 wherein said sequence comprises a nucleotide sequence encoding the VH having 95% sequence identity to SEQ ID NO. 15 and a nucleotide sequence encoding the VL having 95% sequence identity to SEQ ID NO. 23 and any variants thereof having one or more nucleic acid substitutions resulting in conservative amino acid substitutions. In one or more embodiments, the present invention further provides an isolated nucleic acid sequence encoding the canine heavy chain constant region having 95% sequence identity to SEQ ID NO. 128; and a nucleotide sequence encoding the canine light chain constant region having 95% sequence identity to SEQ ID NO. 130 and any variants thereof having one or more nucleic acid substitutions resulting in conservative amino acid substitutions.

In one or more embodiments the present invention provides isolated nucleic acid sequence encoding the antigen binding protein of the invention that specifically binds to canine or feline TGFβ1 and TGFβ3 but not to TGFβ2 wherein said sequence comprises a nucleotide sequence encoding the VH having 95% sequence identity to SEQ ID NO. 25 and a nucleotide sequence encoding the VL having 95% sequence identity to SEQ ID NO. 32 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1 and TGFβ3 but not to TGFβ2 wherein said nucleic acid sequence further comprises a nucleotide sequence encoding a nucleotide sequence encoding the feline heavy chain constant region having 95% sequence identity to SEQ ID NO. 132; and a nucleotide sequence encoding the feline light chain constant region having 95% sequence identity to SEQ ID NO. 134 and any variants thereof having one or more nucleic acid substitutions resulting in conservative amino acid substitutions.

In one or more embodiments the present invention provides a vector comprising the nucleic acid sequence that encodes for the antigen binding protein of the invention that specifically binds to canine or feline TGFβ1 and TGFβ3 but not to TGFβ2.

In one embodiment the invention provides a host cell that comprises the nucleic acid sequence that encodes the antigen binding protein of the present invention that specifically binds to canine or feline TGFβ1 and TGFβ3 but not to TGF02. In one embodiment the invention provides a host cell that comprises the vector comprising the nucleic acid that encodes the antigen binding protein of the present invention. In one embodiment the invention provides a host cell that produces the antigen binding protein of the invention.

In one or more embodiments the present invention provides a method of producing the antigen binding protein of the invention that specifically binds to canine or feline TGFβ1 and TGFβ3 but not to TGFβ2 comprising culturing the host cell of the invention under conditions that result in production of the antigen binding protein and isolating the antigen binding protein from the host cell or culture medium of the host cell.

In one or more embodiments the present invention provides an antigen binding protein that specifically binds to canine or feline Transforming Growth Factor Beta-1 (TGFβ1), Transforming Growth Factor 2 (TGFβ2) and Transforming Growth Factor 3 (TGFβ3). In one embodiment the antigen binding protein is capable of binding to epitope regions on TGF01 which comprise amino acids 57-66 and amino acids 90-103 of SEQ ID NO.223. In one embodiment the antigen binding protein is further capable of binding to amino acids 25-43 of SEQ ID NO: 223. In one embodiment the antigen binding protein is further capable of binding to amino acids 67-89 of SEQ ID NO: 223.

In one or more embodiments the present invention provides the antigen binding protein that specifically binds to canine or feline TGFβ1, TGFβ32 and TGFβ3 that comprises a heavy chain variable region (VH) comprising a Complimentary Determining Region 1 (CDR1) comprising an amino acid sequence having at least about 95% sequence identity to the amino acid sequence comprising SEQ ID NO. 270 [Glycine(G)-Tyrosine(Y)-(X1)-Phenylalanine(F)-(X2)-(X3)-Tyrosine(Y)] wherein (X1) comprises Threonine (T) or Isoleucine (I); (X2) comprises Isoleucine (1) or Methionine (M); and (X3) comprises Threonine (T) or Lysine (K); and a Complimentary Determining Region 2 (CDR2) comprising an amino acid sequence having at least about 95% sequence identity to the amino acid sequence comprising SEQ ID NO. 271 [Phenylalanine(F)-Proline(P)-(X4)-(X5)-Glycine(G)-(X6)] wherein (X4) comprises Alanine(A) or Glycine(G); (X5) comprises Serine(S) or Tryptophan(W); and (X6) comprises Serine(S), Methionine (M) or Valine (V); and a Complimentary Determining Region 3 (CDR3) comprising an amino acid sequence having at least about 95% sequence identity to the amino acid sequence comprising SEQ ID NO: 272 [Glycine(G)-(X7)-Glycine(G)-Asparagine(N)-Tyrosine(Y)-Alanine(A)-Leucine(L)-Aspartic Acid (D)-Alanine(A)-Methionine(M)-Aspartic Acid(D)-Tyrosine (Y) wherein (X7) comprises Aspartic Acid(D) or Tyrosine (Y); and a light chain variable region (VL) comprising: a Complimentary Determining Region 1 (CDR1) comprising an amino acid sequence having at least about 95% sequence identity to the amino acid sequence comprising SEQ ID NO. 69; a Complimentary Determining Region 2 (CDR2) comprising an amino acid sequence having at least about 95% sequence identity to the amino acid sequence comprising SEQ ID NO. 70; a Complimentary Determining Region 3 (CDR3) comprising an amino acid sequence having at least about 95% sequence identity to the amino acid sequence comprising SEQ ID NO: 273 [Glutamine(Q)-Glutamine(Q)-Asparagine(N)-(X8)-Glutamic Acid (E)-Aspartic Acid (D)-Proline(P)-Leucine (L)-(X9)) wherein (X8) comprises Asparagine(N) or Aspartic Acid(D); and (X9) comprises Threonine (T) or Serine(S); and any variants thereof having one or more conservative amino acid substitutions. In some embodiments the variants are not conservative amino acid substitutions.

In one or more embodiments the present invention provides the antigen binding protein that specifically binds to canine or feline TGFβ1, TGFβ2 and TGFβ3 that comprises a heavy chain variable region (VH) comprising a Complimentary Determining Region 1 (CDR1) comprising an amino acid sequence having at least about 95% sequence identity to the amino acid sequence selected from the group consisting of: SEQ ID NO:66; SEQ ID NO: 274; SEQ ID NO:275; SEQ ID NO:276; and SEQ ID NO:277; a Complimentary Determining Region 2 (CDR2) comprising an amino acid sequence having at least about 95% sequence identity to the amino acid sequence comprising SEQ ID NO: 67; SEQ ID NO:278; SEQ ID NO:279; and SEQ ID NO:280; a Complimentary Determining Region 3 (CDR3) comprising an amino acid sequence having at least about 95% sequence identity to the amino acid sequence selected from the group consisting of: SEQ ID NO:68 or SEQ ID NO:281; and a light chain variable region (VL) comprising a Complimentary Determining Region 1 (CDR1) comprising an amino acid sequence having at least about 95% sequence identity to the amino acid sequence comprising SEQ ID NO. 69; a Complimentary Determining Region 2 (CDR2) comprising an amino acid sequence having at least about 95% sequence identity to the amino acid sequence comprising SEQ ID NO. 70; a Complimentary Determining Region 3 (CDR3) comprising an amino acid sequence having at least about 95% sequence identity to the amino acid sequence selected from the group consisting of: SEQ ID NO:71; SEQ ID NO:282 and SEQ ID NO:283; and any variants thereof having one or more conservative amino acid substitutions. In one or more embodiments the variants are not conservative amino acid substitutions.

In one embodiment the present invention provides the antigen binding protein that specifically binds to canine or feline TGFβ1, TGFβ2 and TGFβ3 that comprises a heavy chain variable region (VH) comprising a Complimentary Determining Region 1 (CDR1) comprising an amino acid sequence having at least about 95% sequence identity to the amino acid sequence SEQ ID NO:66; a Complimentary Determining Region 2 (CDR2) comprising an amino acid sequence having at least about 95% sequence identity to the amino acid sequence comprising SEQ ID NO: 67; a Complimentary Determining Region 3 (CDR3) comprising an amino acid sequence having at least about 95% sequence identity to the amino acid sequence comprising: SEQ ID NO:68; and a light chain variable region (VL) comprising a Complimentary Determining Region 1 (CDR1) comprising an amino acid sequence having at least about 95% sequence identity to the amino acid sequence comprising SEQ ID NO. 69; a Complimentary Determining Region 2 (CDR2) comprising an amino acid sequence having at least about 95% sequence identity to the amino acid sequence comprising SEQ ID NO. 70; a Complimentary Determining Region 3 (CDR3) comprising an amino acid sequence having at least about 95% sequence identity to the amino acid sequence SEQ ID NO:71 and any variants thereof having one or more conservative amino acid substitutions. In one or more embodiments the variants are not conservative amino acid substitutions.

In one or more embodiments the present invention provides the antigen binding protein that specifically binds to canine or feline TGFβ1, TGFβ2 and TGFβ3 comprising a caninized, felinized, humanized or chimeric antigen binding protein. In one embodiment the antigen binding protein comprises a caninized antigen binding protein.

In one embodiment the present invention provides the antigen binding protein that specifically binds to canine or feline TGFβ1, TGFβ2 and TGFβ3 comprising a heavy chain variable region (VH) having at least 95% sequence identity to the amino acid sequences selected from the group consisting of: SEQ ID NO:73; SEQ ID NO:75: SEQ ID NO:77; SEQ ID NO:181; SEQ ID NO:183; SEQ ID NO:185; SEQ ID NO: SEQ ID NO:187; SEQ ID NO:189; SEQ ID NO:191; SEQ ID NO:193; SEQ ID NO:195; SEQ ID NO:197; SEQ ID NO:199; SEQ ID NO:201; SEQ ID NO:203; SEQ ID NO:205; SEQ ID NO:207; SEQ ID NO:209; SEQ ID NO:211; SEQ ID NO:213; and SEQ ID NO: 215; and a light chain variable region (VL) having at least 95% sequence identity to the amino acid sequences selected from the group consisting of: SEQ ID NO:79; SEQ ID NO:81; SEQ ID NO:83; SEQ ID NO:85; SEQ ID NO:87; SEQ ID NO:89; SEQ ID NO:91; SEQ ID NO:93; SEQ ID NO:216; and SEQ ID NO: 218; and any variants thereof having one or more conservative amino acid substitutions. In one or more embodiments the variants are not conservative amino substitutions.

In one embodiment the present invention provides an antigen binding protein comprising a heavy chain variable region (VH) paired with a light chain variable region (VL) both having at least 95% sequence identity to the amino acids comprising:

a. a heavy chain variable region (VH) comprising SEQ ID NO:181 and a light chain variable region (VL) comprising SEQ ID NO:85;
b. a heavy chain variable region (VH) comprising SEQ ID NO:181 and a light chain variable region (VL) comprising SEQ ID NO:216;
c. a heavy chain variable region (VH) comprising SEQ ID NO:183 and a light chain variable region (VL) comprising SEQ ID NO:85;
d. a heavy chain variable region (VH) comprising SEQ ID NO:185 and a light chain variable region (VL) comprising SEQ ID NO:85;
e. a heavy chain variable region (VH) comprising SEQ ID NO:187 and a light chain variable region (VL) comprising SEQ ID NO:85;
f. a heavy chain variable region (VH) comprising SEQ ID NO:187 and a light chain variable region (VL) comprising SEQ ID NO:218;

g. a heavy chain variable region (VH) comprising SEQ ID NO:185 and a light chain variable region (VL) comprising SEQ ID NO:218;
h. a heavy chain variable region (VH) comprising SEQ ID NO:189 and a light chain variable region (VL) comprising SEQ ID NO:218;
i. a heavy chain variable region (VH) comprising SEQ ID NO:191 and a light chain variable region (VL) comprising SEQ ID NO:218;
j. a heavy chain variable region (VH) comprising SEQ ID NO:193 and a light chain variable region (VL) comprising SEQ ID NO:218;
k. a heavy chain variable region (VH) comprising SEQ ID NO:195 and a light chain variable region (VL) comprising SEQ ID NO:218;
l. a heavy chain variable region (VH) comprising SEQ ID NO:197 and a light chain variable region (VL) comprising SEQ ID NO:218;
m. a heavy chain variable region (VH) comprising SEQ ID NO:199 and a light chain variable region (VL) comprising SEQ ID NO: 218;
n. a heavy chain variable region (VH) comprising SEQ ID NO:199 and a light chain variable region (VL) comprising SEQ ID NO:85;
o. a heavy chain variable region (VH) comprising SEQ ID NO:193 and a light chain variable region (VL) comprising SEQ ID NO:85;
p. a heavy chain variable region (VH) comprising SEQ ID NO:195 and a light chain variable region (VL) comprising SEQ ID NO:85;
q. a heavy chain variable region (VH) comprising SEQ ID NO:191 and a light chain variable region (VL) comprising SEQ ID NO:85;
r. a heavy chain variable region (VH) comprising SEQ ID NO:197 and a light chain variable region (VL) comprising SEQ ID NO:85;
s. a heavy chain variable region (VH) comprising SEQ ID NO:189 and a light chain variable region (VL) comprising SEQ ID NO:85;
t. a heavy chain variable region (VH) comprising SEQ ID NO: 201 and a light chain variable region (VL) comprising SEQ ID NO: 218
u. a heavy chain variable region (VH) comprising SEQ ID NO:203 and a light chain variable region (VL) comprising SEQ ID NO:218;
v. a heavy chain variable region (VH) comprising SEQ ID NO:205 and a light chain variable region (VL) comprising SEQ ID NO:218
w. a heavy chain variable region (VH) comprising SEQ ID NO:201 and a light chain variable region (VL) comprising SEQ ID NO:85;
x. a heavy chain variable region (VH) comprising SEQ ID NO:205 and a light chain variable region (VL) comprising SEQ ID NO:85
y. a heavy chain variable region (VH) comprising SEQ ID NO: 215 and a light chain variable region (VL) comprising SEQ ID NO:218; and any variants thereof having one or more conservative amino acid substitutions. In one or more embodiments the variants are not conservative amino acid substitutions.

In one or more embodiments the invention provides an antigen binding protein that specifically binds to canine or feline TGFβ1, TGFβ2 and TGFβ3 comprising the canine heavy chain constant region comprising amino acid sequences having at least about 95% sequence identity to the amino acid sequence comprising SEQ ID NO: 127. In one or more embodiments the invention provides an antigen binding protein comprising the canine heavy chain constant region comprising amino acid sequence SEQ ID NO: 127. In one or more embodiments the canine heavy chain constant region comprises conservative amino acid substitutions. In one or more embodiment the variants are not conservative amino acid substitutions.

In one or more embodiments the invention provides an antigen binding protein comprising the canine light chain constant region comprising amino acid sequences having at least about 95% sequence identity to the amino acid sequence comprising SEQ ID NO: 129. In one or more embodiments the invention provides an antigen binding protein comprising the canine light chain constant region comprising amino acid sequences SEQ ID NO: 129. In one or more embodiments the canine light chain constant region comprises conservative amino acid substitutions. In one or more embodiments the variants are not conservative amino acid substitutions.

In one embodiment the present invention provides an antigen binding protein that specifically binds to canine or feline TGFβ1, TGFβ2 and TGFβ33 comprising a felinized antigen binding protein. In one embodiment the antigen binding protein comprises a heavy chain variable region (VH) having at least 95% sequence identity to the amino acid sequences selected from SEQ ID NO: 120 or SEQ ID NO: 122; and a light chain variable region (VL) having at least 95% sequence identity to the amino acid sequence comprising SEQ ID NO: 99 and any variants thereof having one or more conservative amino acid substitutions. In one or more embodiments the variants are not conservative amino acid substitutions.

In one embodiment the present invention provides an antigen binding protein that specifically binds to canine or feline TGFβ1, TGFβ2 and TGFβ3 comprising a heavy chain variable region (VH) having at least 95% sequence identity to the amino acid sequence comprising SEQ ID NO: 73 and a light chain variable region (VL) having at least 95% sequence identity to the amino acid sequence comprising SEQ ID NO: 85 and any variants thereof having one or more conservative amino acid substitutions In one or more embodiments the antigen binding protein of the invention that specifically binds to canine or feline TGFβ1, TGFβ2 and TGFβ3 wherein said antigen binding protein further comprising a constant region of the heavy chain having at least 95% sequence identity to the amino acid sequence comprising SEQ ID NO.127 and the constant region of the light chain having at least 95% sequence identity to the amino acid sequence SEQ ID NO. 129; and any variant thereof having one or more conservative amino acid substitutions. In one or more embodiments the variants are not conservative amino acid substitutions.

In one or more embodiments the invention provides an antigen binding protein that specifically binds to canine or feline TGFβ1, TGFβ2 and TGFβ3 comprising the feline heavy chain constant region comprising amino acid sequences having at least about 95% sequence identity to the amino acid sequence comprising SEQ ID NO: 131. In one or more embodiments the invention provides an antigen binding protein that specifically binds to canine or feline TGFβ1, TGFβ2 and TGFβ3 comprising the feline light chain constant region comprising amino acid sequences having at least about 95% sequence identity to the amino acid sequence comprising SEQ ID NO: 133.

In one embodiment the present invention provides an antigen binding protein that specifically binds to canine or feline TGFβ1, TGFβ2 and TGFβ3 comprising a humanized antigen binding protein. In one embodiment the present invention provides an antigen binding protein comprising a chimeric antigen binding protein.

In one or more embodiments the present invention provides an antigen binding protein that specifically binds to canine or feline TGFβ1, TGFβ2 and TGFβ3 wherein said protein is selected from the group consisting of: a monoclonal antigen binding protein; a single chain antigen binding protein, a tetrameric antigen binding protein, a tetravalent antigen binding protein, a multispecific antigen binding protein, a domain-specific antigen binding protein, a domain-deleted antigen binding protein, a fusion protein, an ScFc fusion protein, an Fab fragment, an Fab' fragment, an F(ab')2 fragment, an Fv fragment, an ScFv fragment, an Fd fragment, a single domain antigen binding protein, a dAb fragment, a small modular immunopharmaceutical (SMIP) a nanobody, and IgNAR molecule. In one embodiment the antigen binding protein is a monoclonal antigen binding protein.

In one or more embodiment the present invention provides an antigen binding protein that specifically binds to canine or feline TGFβ1, TGFβ2 and TGFβ3 wherein said binding protein is for use in reducing or eliminating a TGFβ related disorder. In one embodiment the TGFβ-related disorder is selected from the group consisting of fibrosis disorder, connective tissue disorder, bone disorders and cell proliferation disorders. In one embodiment the TGFβ-related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a pharmaceutical composition that comprises a therapeutically effective amount of the antigen binding protein of the invention that specifically binds to canine or feline TGFβ1, TGFβ2 and TGFβ3 and a pharmaceutically acceptable carrier.

In one or more embodiment the antigen binding protein of the invention that specifically binds to canine or feline that specifically binds to canine or feline TGFβ1, TGFβ2 and TGFβ3 provides a method of treating a subject for a TGFβ related disorder by administering to said subject a therapeutic amount of the pharmaceutical composition of the invention. In one or more embodiments, the present invention provides a method of treating a canine for a TGFβ-related disorder. In one embodiment the present invention provides a method for treating a feline for a TGFβ-related disorder. In one embodiment the present invention provides a method for treating a human for a TGFβ-related disorder. In one embodiment the method provides administering a therapeutically effective amount of the pharmaceutical composition comprising the antigen binding protein of the invention. In one or more embodiments the present invention provides that the TGFβ-related disorder is selected from the group consisting of: fibrosis disorder, connective tissue disorder, bone disorders and cell proliferation disorders. In one embodiment the TGFβ related disorder comprises a fibrosis disorder. In one embodiment the fibrosis disorder is selected from the group consisting of kidney fibrosis/chronic kidney disease; pulmonary fibrosis; cirrhosis of the liver; glial scarring; and systemic sclerosis/scleroderma. In one embodiment the TGFβ disorder is kidney fibrosis/chronic kidney disease.

In one or more embodiments the present invention provides a method of inhibiting TGFβ activity in a subject by administering the pharmaceutical composition comprising the antigen binding protein of the invention that specifically binds to canine or feline TGFβ1, TGFβ2 and TGFβ3. In one embodiment the subject comprises canines, felines or humans. In one embodiment the subject comprises canines. In one embodiment the subject comprises felines. In one embodiment the subject comprises humans.

In one or more embodiments the present invention provides an isolated nucleic acid sequence having at least about 95% sequence identity to the nucleic acid sequence encoding the antigen binding protein of the invention that specifically binds to canine or feline TGFβ1, TGFβ2 and TGFβ3 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1, TGFβ2 and TGFβ3 wherein said sequence comprises a nucleotide sequence encoding the VH having 95% sequence identity to SEQ ID NO. 72 and a nucleotide sequence encoding the VL having 95% sequence identity to SEQ ID NO. 84 and any variants thereof having one or more nucleic acid substitutions resulting in conservative amino acid substitutions.

In one or more embodiments the present invention provides an isolated nucleic acid sequence encoding the antigen binding protein of the invention that specifically binds to canine or feline TGFβ1, TGFβ2 and TGFβ3 wherein said nucleic acid sequences comprises a nucleotide sequence encoding the VH having 95% sequence identity to SEQ ID NO. 72; a nucleotide sequence encoding the VL having 95% sequence identity to SEQ ID NO. 84; a nucleotide sequence encoding the canine heavy chain constant region having 95% sequence identity to SEQ ID NO. 128; and a nucleotide sequence encoding the canine light chain constant region having 95% sequence identity to SEQ ID NO. 130 and any variants thereof having one or more nucleic acid substitutions resulting in conservative amino acid substitutions.

In one or more embodiments the present invention provides a vector comprising the nucleic acid sequence that encodes for the antigen binding protein of the invention that specifically binds to canine or feline TGFβ1, TGFβ2 and TGFβ3.

In one embodiment the invention provides a host cell that comprises the nucleic acid sequence that encodes the antigen binding protein of the present that specifically binds to canine or feline TGFβ1, TGFβ2 and TGFβ3. In one embodiment the invention provides a host cell that comprises the vector comprising the nucleic acid that encodes the antigen binding protein of the present invention. In one embodiment the invention provides a host cell that produces the antigen binding protein of the invention.

In one or more embodiments the present invention provides a method of producing the antigen binding protein of the invention that specifically binds to canine or feline TGFβ1, TGFβ2 and TGFβ3 comprising culturing the host cell of the invention under conditions that result in production of the antigen binding protein and isolating the antigen binding protein from the host cell or culture medium of the host cell.

BRIEF DESCRIPTION OF THE DRAWINGS

FIG. 1 presents epitope mapping data for the anti-TGFβ antibodies of the present invention binding to TGFβ1.

BRIEF DESCRIPTION OF THE SEQUENCES

Figure 2:
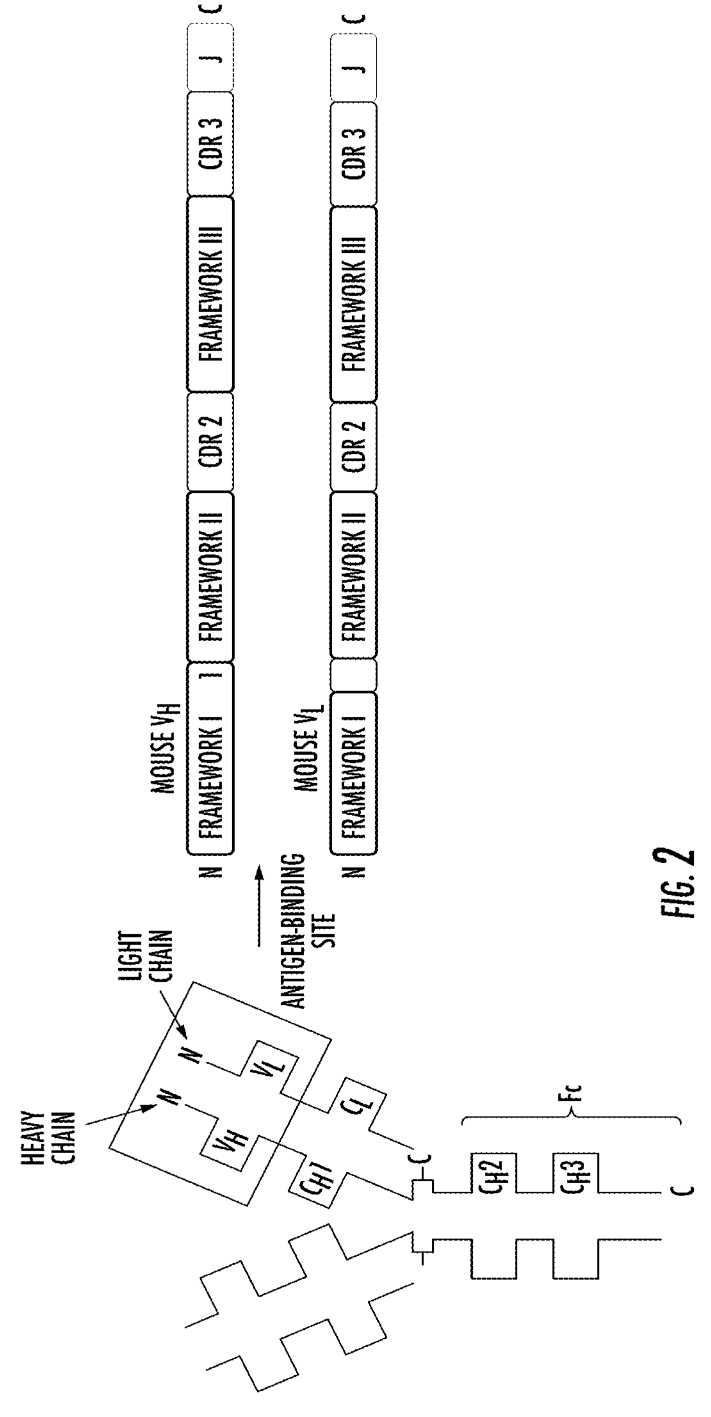
FIG. 2 represents the general structure of a native mouse immunoglobulin G (IgG) highlighting the antigen binding site.

SEQ ID NO: 1 comprises the nucleotide sequence of the DNA encoding the variable region of the heavy chain (VH) of the mouse 04H09 monoclonal antibody.

SEQ ID NO: 2 comprises the amino acid sequence of the variable region of the heavy chain (VH) of the mouse 04H09 monoclonal antibody.

SEQ ID NO: 3 comprises the nucleotide sequence of the DNA encoding the variable region of the light chain (VL) of the mouse 04H09 monoclonal antibody.

SEQ ID NO: 4 comprises the amino acid sequence of the variable region of the light chain (VL) of the mouse 04H09 monoclonal antibody.

SEQ ID NO: 5 comprises the amino acid sequence of the first CDR in the heavy chain of the 04H09 monoclonal antibody, referred to herein as 04H09 CDR-H1.

SEQ ID NO: 6 comprises the amino acid sequence of the second CDR in the heavy chain of the 04H09 monoclonal antibody, referred to herein as 04H09 CDR-H2.

SEQ ID NO: 7 comprises the amino acid sequence of the third CDR in the heavy chain of the 04H09 monoclonal antibody, referred to herein as 04H09 CDR-H3.

SEQ ID NO: 8 comprises the amino acid sequence of the first CDR in the light chain of the 04H09 monoclonal antibody, referred to herein as 04H09 CDR-K1.

SEQ ID NO: 9 comprises the amino acid sequence of the second CDR in the light chain of the 04H09 monoclonal antibody, referred to herein as 04H09 CDR-K2.

SEQ ID NO: 10 comprises the amino acid sequence of the third CDR in the light chain of the 04H09 monoclonal antibody, referred to herein as 04H09 CDR-K3.

SEQ ID NO: 11 comprises the nucleotide sequence of the DNA encoding the variable region of the heavy chain (VH) of caninized 04H09 antibody, referred to herein as Can04H09-VH1.

SEQ ID NO: 12 comprises the amino acid sequence of the variable region of the heavy chain (VH) of caninized 04H09 antibody, referred to herein as Can04H09-VH1.

SEQ ID NO: 13 comprises the nucleotide sequence of the DNA encoding the variable region of the heavy chain (VH) of caninized 04H09 antibody, referred to herein as Can04H09-VH2.

SEQ ID NO: 14 comprises the amino acid sequence of the variable region of the heavy chain (VH) of caninized 04H09 antibody, referred to herein as Can04H09-VH2.

SEQ ID NO: 15 comprises the nucleotide sequence of the DNA encoding the variable region of the heavy chain (VH) of caninized 04H09 antibody, referred to herein as Can04H09-VH3.

SEQ ID NO: 16 comprises the amino acid sequence of the variable region of the heavy chain (VH) of caninized 04H09 antibody, referred to herein as Can04H09-VH3.

SEQ ID NO: 17 comprises the nucleotide sequence of the DNA encoding the variable region of the light chain (VL) of caninized 04H09 antibody, referred to herein as Can04H09-VL1.

SEQ ID NO: 18 comprises the amino acid sequence of the variable region of the light chain (VL) of caninized 04H09 antibody, referred to herein as Can04H09-VL1.

SEQ ID NO: 19 comprises the nucleotide sequence of the DNA encoding the variable region of the light chain (VL) of caninized 04H09 antibody, referred to herein as Can04H09-VL2.

SEQ ID NO: 20 comprises the amino acid sequence of the variable region of the light chain (VL) of caninized 04H09 antibody, referred to herein as Can04H09-VL2.

SEQ ID NO: 21 comprises the nucleotide sequence of the DNA encoding the variable region of the light chain (VL) of caninized 04H09 antibody, referred to herein as Can04H09-VL3.

SEQ ID NO: 22 comprises the amino acid sequence of the variable region of the light chain (VL) of caninized 04H09 antibody, referred to herein as Can04H09-VL3.

SEQ ID NO: 23 comprises the nucleotide sequence of the DNA encoding the variable region of the light chain (VL) of caninized 04H09 antibody, referred to herein as Can04H09-VL4.

SEQ ID NO: 24 comprises the amino acid sequence of the variable region of the light chain (VL) of caninized 04H09 antibody, referred to herein as Can04H09-VL4.

SEQ ID NO: 25 comprises the nucleotide sequence of the DNA encoding the variable region of the heavy chain (VH) of felinized 04H09 antibody, referred to herein as Fel04H09-H636.

SEQ ID NO: 26 comprises the amino acid sequence of the variable region of the heavy chain (VH) of felinized 04H09 antibody, referred to herein as Fel4H09-H636.

SEQ ID NO: 27 comprises the nucleotide sequence of the DNA encoding the variable region of the heavy chain (VH) of felinized 04H09 antibody, referred to herein as Fel04H09-H1-2.

SEQ ID NO: 28 comprises the amino acid sequence of the variable region of the heavy chain (VH) of felinized 04H09 antibody, referred to herein as Fel4H09-H1-2.

SEQ ID NO: 29 comprises the nucleotide sequence of the DNA encoding the variable region of the heavy chain (VH) of felinized 04H09 antibody, referred to herein as Fel04H09-H618.

SEQ ID NO: 30 comprises the amino acid sequence of the variable region of the heavy chain (VH) of felinized 04H09 antibody, referred to herein as Fel4H09-H618.

SEQ ID NO: 31 comprises the nucleotide sequence of the DNA encoding the variable region of the light chain (VL) of felinized 04H09 antibody, referred to herein as Fel04H09-K4-1.

SEQ ID NO: 32 comprises the amino acid sequence of the variable region of the light chain (VL) of felinized 04H09 antibody, referred to herein as Fel4H09-K4-1.

SEQ ID NO: 33 comprises the nucleotide sequence of the DNA encoding the variable region of the light chain (VL) of felinized 04H09 antibody, referred to herein as Fel04H09-K36.

SEQ ID NO: 34 comprises the amino acid sequence of the variable region of the light chain (VL) of felinized 04H09 antibody, referred to herein as Fel04H09-K36.

SEQ ID NO: 35 comprises the nucleotide sequence of the DNA encoding the variable region of the light chain (VL) of felinized 04H09 antibody, referred to herein as Fel4H09-K1-1.

SEQ ID NO: 36 comprises the amino acid sequence of the variable region of the light chain (VL) of felinized 04H09 antibody, referred to herein as Fel04H09-K1-1.

SEQ ID NO: 37 comprises the nucleotide sequence of the DNA encoding the variable region of the heavy chain (VH) of the mouse SL501 monoclonal antibody.

SEQ ID NO: 38 comprises the amino acid sequence of the variable region of the heavy chain (VH) of the mouse SL501 monoclonal antibody.

SEQ ID NO: 39 comprises the nucleotide sequence of the DNA encoding the variable region of the light chain (VL) of the mouse SL501 monoclonal antibody.

SEQ ID NO: 40 comprises the amino acid sequence of the variable region of the light chain (VL) of the mouse SL501 monoclonal antibody.

SEQ ID NO: 41 comprises the amino acid sequence of the first CDR in the heavy chain of the SL501 monoclonal antibody, referred to herein as SL501 CDR-H1.

SEQ ID NO: 42 comprises the amino acid sequence of the second CDR in the heavy chain of the SL501 monoclonal antibody, referred to herein as SL501 CDR-H2.

SEQ ID NO: 43 comprises the amino acid sequence of the third CDR in the heavy chain of the SL501 monoclonal antibody, referred to herein as SL501 CDR-H3.

SEQ ID NO: 44 comprises the amino acid sequence of the first CDR in the light chain of the SL501 monoclonal antibody, referred to herein as SL501 CDR-K1.

SEQ ID NO: 45 comprises the amino acid sequence of the second CDR in the light chain of the SL501 monoclonal antibody, referred to herein as SL501 CDR-K2.

SEQ ID NO: 46 comprises the amino acid sequence of the third CDR in the light chain of the SL501 monoclonal antibody, referred to herein as SL501 CDR-K3.

SEQ ID NO: 47 comprises the amino acid sequence of the variable region of the heavy chain (VH) of caninized SL501 antibody, referred to herein as Can SL501-VH1.

SEQ ID NO: 48 comprises the amino acid sequence of the variable region of the heavy chain (VH) of caninized SL501 antibody, referred to herein as Can SL501-VH2.

SEQ ID NO: 49 comprises the amino acid sequence of the variable region of the light chain (VL) of caninized SL501 antibody, referred to herein as Can SL501-VL1.

SEQ ID NO: 50 comprises the nucleotide sequence of the DNA encoding the variable region of the light chain (VL) of caninized SL501 antibody, referred to herein as Can SL501-VL2.

SEQ ID NO: 51 comprises the amino acid sequence of the variable region of the light chain (VL) of caninized SL501 antibody, referred to herein as Can SL501-VL2.

SEQ ID NO: 52 comprises the nucleotide sequence of the DNA encoding the variable region of the light chain (VL) of partially-caninized SL501 antibody, referred to herein as Can SL501-VL-Hybrid.

SEQ ID NO: 53 comprises the amino acid sequence of the variable region of the light chain (VL) of partially-caninized SL501 antibody, referred to herein as Can SL501-VL-Hybrid.

SEQ ID NO: 54 comprises the nucleotide sequence of the DNA encoding the variable region of the heavy chain (VH) of caninized SL501 antibody, referred to herein as Can SL501-VH3.

SEQ ID NO: 55 comprises the amino acid sequence of the variable region of the heavy chain (VH) of caninized SL501 antibody, referred to herein as Can SL501-VH3.

SEQ ID NO: 56 comprises the nucleotide sequence of the DNA encoding the variable region of the heavy chain (VH) of can SL501-VH3 antibody that has nucleotide substitutions that result in amino acid substitutions at positions 44 and 46 within the framework 2 region of can SL501-VH3, which is referred to herein as can SL501-VH3-FW2.

SEQ ID NO: 57 comprises the amino acid sequence of the variable region of the heavy chain (VH) of can SL501-VH3 antibody that has amino acid substitutions at positions 44 and 46 within the framework 2 region of can SL501-VH3, which is referred to herein as can SL501-VH3-FW2.

SEQ ID NO: 58 comprises the nucleotide sequence of the DNA encoding the variable region of the heavy chain (VH) of felinized SL501 antibody, referred to herein as Fel SL501-VH3-9.

SEQ ID NO: 59 comprises the amino acid sequence of the variable region of the heavy chain (VH) of felinized SL501 antibody, referred to herein as Fel SL501-VH3-9.

SEQ ID NO: 60 comprises the nucleotide sequence of the DNA encoding the variable region of the light chain (VL) of felinized SL501 antibody, referred to herein as Fel SL501-VL1-1.

SEQ ID NO: 61 comprises the amino acid sequence of the variable region of the light chain (VL) of felinized SL501 antibody, referred to herein as Fel SL501-VL1-1.

SEQ ID NO: 62 comprises the nucleotide sequence of the DNA encoding the variable region of the heavy chain (VH) of the mHcLb monoclonal antibody.

SEQ ID NO: 63 comprises the amino acid sequence of the variable region of the heavy chain (VH) of the mHcLb monoclonal antibody.

SEQ ID NO: 64 comprises the nucleotide sequence of the DNA encoding the variable region of the light chain (VL) of the mHcLb monoclonal antibody.

SEQ ID NO: 65 comprises the amino acid sequence of the variable region of the light chain (VL) of the mHcLb monoclonal antibody.

SEQ ID NO: 66 comprises the amino acid sequence of the first CDR in the heavy chain of the mHcLb monoclonal antibody, referred to herein as mHcLb CDR-H1.

SEQ ID NO: 67 comprises the amino acid sequence of the second CDR in the heavy chain of the mHcLb monoclonal antibody, referred to herein as mHcLb CDR-H2.

SEQ ID NO: 68 comprises the amino acid sequence of the third CDR in the heavy chain of the mHcLb monoclonal antibody, referred to herein as mHcLb CDR-H3.

SEQ ID NO: 69 comprises the amino acid sequence of the first CDR in the light chain of the mHcLb monoclonal antibody, referred to herein as mHcLb CDR-K1.

SEQ ID NO: 70 comprises the amino acid sequence of the second CDR in the light chain of the mHcLb monoclonal antibody, referred to herein as mHcLb CDR-K2.

SEQ ID NO: 71 comprises the amino acid sequence of the third CDR in the light chain of the mHcLb monoclonal antibody, referred to herein as mHcLb CDR-K3.

SEQ ID NO: 72 comprises the nucleotide sequence of the DNA encoding the variable region of the heavy chain (VH) of caninized HcLb antibody, referred to herein as CanHcLb-VH1.

SEQ ID NO: 73 comprises the amino acid sequence of the variable region of the heavy chain (VH) of caninized HcLb antibody, referred to herein as CanHcLb-VH1.

SEQ ID NO: 74 comprises the nucleotide sequence of the DNA encoding the variable region of the heavy chain (VH) of caninized HcLb antibody, referred to herein as CanHcLb-VH2.

SEQ ID NO: 75 comprises the amino acid sequence of the variable region of the heavy chain (VH) of caninized HcLb antibody, referred to herein as CanHcLb-VH2.

SEQ ID NO: 76 comprises the nucleotide sequence of the DNA encoding the variable region of the heavy chain (VH) of caninized HcLb antibody, referred to herein as CanHcLb-VH3.

SEQ ID NO: 77 comprises the amino acid sequence of the variable region of the heavy chain (VH) of caninized HcLb antibody, referred to herein as CanHcLb-VH3.

SEQ ID NO: 78 comprises the nucleotide sequence of the DNA encoding the variable region of the light chain (VL) of caninized HcLb antibody, referred to herein as CanHcLb-VL1.

SEQ ID NO: 79 comprises the amino acid sequence of the variable region of the light chain (VL) of caninized HcLb antibody, referred to herein as CanHcLb-VL1.

SEQ ID NO: 80 comprises the nucleotide sequence of the DNA encoding the variable region of the light chain (VL) of caninized HcLb antibody, referred to herein as CanHcLb-VL2.

SEQ ID NO: 81 comprises the amino acid sequence of the variable region of the light chain (VL) of caninized HcLb antibody, referred to herein as CanHcLb-VL2.

SEQ ID NO: 82 comprises the nucleotide sequence of the DNA encoding the variable region of the light chain (VL) of caninized HcLb antibody, referred to herein as CanHcLb-VL3.

SEQ ID NO: 83 comprises the amino acid sequence of the variable region of the light chain (VL) of caninized HcLb antibody, referred to herein as CanHcLb-VL3.

SEQ ID NO: 84 comprises the nucleotide sequence of the DNA encoding the variable region of the light chain (VL) of caninized HcLb antibody, referred to herein as CanHcLb-VL4.

SEQ ID NO: 85 comprises the amino acid sequence of the variable region of the light chain (VL) of caninized HcLb antibody, referred to herein as CanHcLb-VL4.

SEQ ID NO: 86 comprises the nucleotide sequence of the DNA encoding the variable region of the light chain (VL) of caninized HcLb antibody, referred to herein as CanHcLb-VL5.

SEQ ID NO: 87 comprises the amino acid sequence of the variable region of the light chain (VL) of caninized HcLb antibody, referred to herein as CanHcLb-VL5.

SEQ ID NO: 88 comprises the nucleotide sequence of the DNA encoding the variable region of the light chain (VL) of canHcLb-VL4 antibody that has nucleotide substitutions that result in an amino acid substitution at position 71 within the framework 2 region of canHcLb-VL4, which is referred to herein as canHcLb-VL4-S71P.

SEQ ID NO: 89 comprises the amino acid sequence of the variable region of the light chain (VH) of canHcLb-VL4 antibody that has an amino acid substitution at position 71 within the framework 2 region of canHcLb-VL4, which is referred to herein as canHcLb-VL4-S71P.

SEQ ID NO: 90 comprises the nucleotide sequence of the DNA encoding the variable region of the light chain (VL) of canHcLb-VL4 antibody that has nucleotide substitutions that result in an amino acid substitution at position 73 within the framework 2 region of canHcLb-VL4, which is referred to herein as canHcLb-VL4-Q73K.

SEQ ID NO: 91 comprises the amino acid sequence of the variable region of the light chain (VH) of canHcLb-VL4 antibody that has an amino acid substitution at position 73 within the framework 2 region of canHcLb-VL4, which is referred to herein as canHcLb-VL4-Q73K.

SEQ ID NO: 92 comprises the nucleotide sequence of the DNA encoding the variable region of the light chain (VL) of canHcLb-VL4 antibody that has nucleotide substitutions that result in amino acid substitutions at positions 71 and 73 within the framework 2 region of canHcLb-VL4, which is referred to herein as canHcLb-VL4-S71P.

SEQ ID NO: 93 comprises the amino acid sequence of the variable region of the light chain (VH) of canHcLb-VL4 antibody that has amino acid substitutions at positions 71 and 73 within the framework 2 region of canHcLb-VL4, which is referred to herein as canHcLb-VL4-S71P-Q73K.

SEQ ID NO: 94 comprises the nucleotide sequence of the DNA encoding the variable region of the heavy chain (VH) of felinized HcLb antibody, referred to herein as FelHcLb-H636.

SEQ ID NO: 95 comprises the amino acid sequence of the variable region of the heavy chain (VH) of felinized HcLb antibody, referred to herein as FelHcLb-H636.

SEQ ID NO: 96 comprises the nucleotide sequence of the DNA encoding the variable region of the heavy chain (VH) of felinized HcLb antibody, referred to herein as FelHcLb-H1-1.

SEQ ID NO: 97 comprises the amino acid sequence of the variable region of the heavy chain (VH) of felinized HcLb antibody, referred to herein as FelHcLb-H1-1.

SEQ ID NO: 98 comprises the nucleotide sequence of the DNA encoding the variable region of the light chain (VL) of felinized HcLb antibody, referred to herein as FeiHcLb-K1-1.

SEQ ID NO: 99 comprises the amino acid sequence of the variable region of the light chain (VL) of felinized HcLb antibody, referred to herein as FelHcLb-K1-1.

SEQ ID NO: 100 comprises the nucleotide sequence of the DNA encoding the variable region of the light chain (VL) of felinized HcLb antibody, referred to herein as FelHcLb-K36.

SEQ ID NO: 101 comprises the amino acid sequence of the variable region of the light chain (VL) of felinized HcLb antibody, referred to herein as FelHcLb-K36.

SEQ ID NO: 102 comprises the nucleotide sequence of the DNA encoding the variable region of the light chain (VL) of felinized HcLb antibody, referred to herein as FelHcLb-K4-1.

SEQ ID NO: 103 comprises the amino acid sequence of the variable region of the light chain (VL) of felinized HcLb antibody, referred to herein as FelHcLb-K2D-2.

SEQ ID NO: 104 comprises the nucleotide sequence of the DNA encoding the variable region of the light chain (VL) of felinized HcLb antibody, referred to herein as FelHcLb-K1-1.

SEQ ID NO: 105 comprises the amino acid sequence of the variable region of the light chain (VL) of felinized HcLb antibody, referred to herein as FelHcLb-K2D-2.

SEQ ID NO: 106 comprises the nucleotide sequence of the DNA encoding the variable region of the heavy chain (VH) of felinized HcLb antibody, referred to herein as FelHcLb-H618s.

SEQ ID NO: 107 comprises the amino acid sequence of the variable region of the heavy chain (VH) of felinized HcLb antibody, referred to herein as FelHcLb-H618s.

SEQ ID NO: 108 comprises the nucleotide sequence of the DNA encoding the variable region of the heavy chain (VH) of felinized HcLb antibody with modified CDR-H2 region, referred to herein as FelHcLb-H636x.

SEQ ID NO: 109 comprises the amino acid sequence of the variable region of the heavy chain (VH) of felinized HcLb antibody with modified CDR-H2 region, referred to herein as FelHcLb-H636x.

SEQ ID NO: 110 comprises the nucleotide sequence of the DNA encoding the variable region of the heavy chain (VH) of felinized HcLb antibody with modified CDR-H2 region, referred to herein as FelHcLb-H1-1x.

SEQ ID NO: 111 comprises the amino acid sequence of the variable region of the heavy chain (VH) of felinized HcLb antibody with modified CDR-H2 region, referred to herein as FelHcLb-H1-1x.

SEQ ID NO: 112 comprises the nucleotide sequence of the DNA encoding the variable region of the heavy chain (VH) of felinized HcLb antibody with modified CDR-H2 region, referred to herein as FelHcLb-H618x.

SEQ ID NO: 113 comprises the amino acid sequence of the variable region of the heavy chain (VH) of felinized HcLb antibody with modified CDR-H2 region, referred to herein as FelHcLb-H618x.

SEQ ID NO: 114 comprises the nucleotide sequence of the DNA encoding the variable region of the heavy chain (VH) of felinized HcLb antibody with modified CDR-H2 region, referred to herein as FelHcLb-H634x.

SEQ ID NO: 115 comprises the amino acid sequence of the variable region of the heavy chain (VH) of felinized HcLb antibody with modified CDR-H2 region, referred to herein as FelHcLb-H634x.

SEQ ID NO: 116 comprises the amino acid sequence of the modified version of the second CDR in the heavy chain of the mHcLb monoclonal antibody, referred to herein as mHcLb CDR-H2x.

SEQ ID NO: 117 comprises the amino acid sequence of the modified version of the first CDR in the heavy chain of the mHcLb monoclonal antibody, referred to herein as mHcLb CDR-H1-WMN.

SEQ ID NO: 118 comprises the amino acid sequence of the modified version of the first CDR in the heavy chain of the mHcLb monoclonal antibody, referred to herein as mHcLb CDR-H1-MN.

SEQ ID NO: 119 comprises the nucleotide sequence of the DNA encoding the variable region of the heavy chain (VH) of felinized HcLb antibody with modified CDR-H1 region, referred to herein as FelHcLb-H1-1WMN.

SEQ ID NO: 120 comprises the amino acid sequence of the variable region of the heavy chain (VH) of felinized HcLb antibody with modified CDR-H1 region, referred to herein as FelHcLb-H1-1WMN.

SEQ ID NO: 121 comprises the nucleotide sequence of the DNA encoding the variable region of the heavy chain (VH) of felinized HcLb antibody with modified CDR-H1 and CDR-H2 regions, referred to herein as FelHcLb-H1-1×WMN.

SEQ ID NO: 122 comprises the amino acid sequence of the variable region of the heavy chain (VH) of felinized HcLb antibody with modified CDR-H1 and CDR-H2 regions, referred to herein as FelHcLb-H1-1×WMN.

SEQ ID NO: 123 comprises the nucleotide sequence of the DNA encoding the variable region of the heavy chain (VH) of felinized HcLb antibody with modified CDR-H1 region, referred to herein as FelHcLb-H1-1WM.

SEQ ID NO: 124 comprises the amino acid sequence of the variable region of the heavy chain (VH) of felinized HcLb antibody with modified CDR-H1 region, referred to herein as FelHcLb-H1-1WM.

SEQ ID NO: 125 comprises the nucleotide sequence of the DNA encoding the variable region of the heavy chain (VH) of felinized HcLb antibody with modified CDR-H1 and CDR-H2 regions, referred to herein as FelHcLb-H1-1×WM.

SEQ ID NO: 126 comprises the amino acid sequence of the variable region of the heavy chain (VH) of felinized HcLb antibody with modified CDR-H1 and CDR-H2 regions, referred to herein as FelHcLb-H1-1×WM.

SEQ ID NO: 127 comprises the amino acid sequence of the canine heavy chain constant region of caninized antibodies of the present invention.

SEQ ID NO: 128 comprises the nucleotide sequence of the DNA encoding the canine heavy chain constant region of the caninized antibodies of the present invention.

SEQ ID NO: 129 comprises the amino acid sequence of the canine light (kappa) chain constant region of caninized antibodies of the present invention.

SEQ ID NO: 130 comprises the nucleotide sequence coding for the canine light chain constant region of the caninized antibodies of the present invention.

SEQ ID NO: 131 comprises the amino acid sequence of the feline heavy chain constant region of the felinized antibodies of the present invention.

SEQ ID NO: 132 comprises the nucleotide sequence that codes for the feline heavy chain constant region of the felinized antibodies of the present invention.

SEQ ID NO: 133 comprises the amino acid sequence of the feline light chain constant region of the felinized antibodies of the present invention.

SEQ ID NO. 134 comprises the nucleotide sequence that codes for the feline light chain constant region of the felinized antibodies of the present invention.

SEQ ID NO: 135 comprises the single substituted (D108E) amino acid sequence in CDR H3 in the heavy chain variable region (VH) of Can SL501-VH3.

SEQ ID NO: 136 comprises the single substituted (D108P) amino acid sequence in CDR H3 in the heavy chain variable region (VH) of Can SL501-VH3.

SEQ ID NO: 137 comprises the single substituted (D108Q) amino acid sequence in CDR H3 in the heavy chain variable region (VH) of Can SL501-VH3.

SEQ ID NO: 138 comprises the single substituted (D108N) amino acid sequence in CDR H3 in the heavy chain variable region (VH) of Can SL501-VH3.

SEQ ID NO: 139 comprises the single substituted (D108S) amino acid sequence in CDR H3 in the heavy chain variable region (VH) of Can SL501-VH3.

SEQ ID NO: 140 comprises the single substituted (D108T) amino acid sequence in CDR H3 in the heavy chain variable region (VH) of Can SL501-VH3.

SEQ ID NO: 141 comprises the single substituted (D108K) amino acid sequence in CDR H3 in the heavy chain variable region (VH) of Can SL501-VH3.

SEQ ID NO: 142 comprises the single substituted (D108R) amino acid sequence in CDR H3 in the heavy chain variable region (VH) of Can SL501-VH3.

SEQ ID NO: 143 comprises the single substituted (D108H) amino acid sequence in CDR H3 in the heavy chain variable region (VH) of Can SL501-VH3.

SEQ ID NO: 144 comprises the single substituted (P109S) amino acid sequence in CDR H3 in the heavy chain variable region (VH) of Can SL501-VH3.

SEQ ID NO: 145 comprises the single substituted (P109H) amino acid sequence in CDR H3 in the heavy chain variable region (VH) of Can SL501-VH3.

SEQ ID NO: 146 comprises the single substituted (P109Y) amino acid sequence in CDR H3 in the heavy chain variable region (VH) of Can SL501-VH3.

SEQ ID NO: 147 comprises the single substituted (P109W) amino acid sequence in CDR H3 in the heavy chain variable region (VH) of Can SL501-VH3.

SEQ ID NO: 148 comprises the single substituted (P109F) amino acid sequence in CDR H3 in the heavy chain variable region (VH) of Can SL501-VH3.

SEQ ID NO: 149 comprises the single substituted (P109T) amino acid sequence in CDR H3 in the heavy chain variable region (VH) of Can SL501-VH3.

SEQ ID NO: 150 comprises the single substituted (P109A) amino acid sequence in CDR H3 in the heavy chain variable region (VH) of Can SL501-VH3.

SEQ ID NO: 151 comprises the single substituted (P109G) amino acid sequence in CDR H3 in the heavy chain variable region (VH) of Can SL501-VH3.

SEQ ID NO: 152 comprises the single substituted (Q110S) amino acid sequence in CDR H3 in the heavy chain variable region (VH) of Can SL501-VH3.

SEQ ID NO: 153 comprises the single substituted (Q11 ON) amino acid sequence in CDR H3 in the heavy chain variable region (VH) of Can SL501-VH3.

SEQ ID NO: 154 comprises the single substituted (Q110D) amino acid sequence in CDR H3 in the heavy chain variable region (VH) of Can SL501-VH3.

SEQ ID NO: 155 comprises the single substituted (Q110E) amino acid sequence in CDR H3 in the heavy chain variable region (VH) of Can SL501-VH3.

SEQ ID NO: 156 comprises the single substituted (Q110K) amino acid sequence in CDR H3 in the heavy chain variable region (VH) of Can SL501-VH3.

SEQ ID NO: 157 comprises the single substituted (Q110R) amino acid sequence in CDR H3 in the heavy chain variable region (VH) of Can SL501-VH3.

SEQ ID NO: 158 comprises the single substituted (Q110H) amino acid sequence in CDR H3 in the heavy chain variable region (VH) of Can SL501-VH3.

SEQ ID NO: 159 comprises the single substituted (Q110T) amino acid sequence in CDR H3 in the heavy chain variable region (VH) of Can SL501-VH3.

SEQ ID NO: 160 comprises the single substituted (Q110V) amino acid sequence in CDR H3 in the heavy chain variable region (VH) of Can SL501-VH3.

SEQ ID NO: 161 comprises the single substituted (Y111P) amino acid sequence in CDR H3 in the heavy chain variable region (VH) of Can SL501-VH3.

SEQ ID NO: 162 comprises the single substituted (Y111F) amino acid sequence in CDR H3 in the heavy chain variable region (VH) of Can SL501-VH3.

SEQ ID NO: 163 comprises the single substituted (Y111W) amino acid sequence in CDR H3 in the heavy chain variable region (VH) of Can SL501-VH3.

SEQ ID NO: 164 comprises the single substituted (Y111H) amino acid sequence in CDR H3 in the heavy chain variable region (VH) of Can SL501-VH3.

SEQ ID NO: 165 comprises the single substituted (Y111M) amino acid sequence in CDR H3 in the heavy chain variable region (VH) of Can SL501-VH3.

SEQ ID NO: 166 comprises the single substituted (Y1111) amino acid sequence in CDR H3 in the heavy chain variable region (VH) of Can SL501-VH3.

SEQ ID NO: 167 comprises the single substituted (Y111L) amino acid sequence in CDR H3 in the heavy chain variable region (VH) of Can SL501-VH3.

SEQ ID NO: 168 comprises the single substituted (Y111V) amino acid sequence in CDR H3 in the heavy chain variable region (VH) of Can SL501-VH3.

SEQ ID NO: 169 comprises the single substituted (Y111T) amino acid sequence in CDR H3 in the heavy chain variable region (VH) of Can SL501-VH3.

SEQ ID NO: 170 comprises the single substituted (Y111E) amino acid sequence in CDR H3 in the heavy chain variable region (VH) of Can SL501-VH3.

SEQ ID NO: 171 comprises the single substituted (S112E) amino acid sequence in CDR H3 in the heavy chain variable region (VH) of Can SL501-VH3.

SEQ ID NO: 172 comprises the single substituted (S112Q) amino acid sequence in CDR H3 in the heavy chain variable region (VH) of Can SL501-VH3.

SEQ ID NO: 173 comprises the single substituted (S112N) amino acid sequence in CDR H3 in the heavy chain variable region (VH) of Can SL501-VH3.

SEQ ID NO: 174 comprises the single substituted (S112T) amino acid sequence in CDR H3 in the heavy chain variable region (VH) of Can SL501-VH3.

SEQ ID NO: 175 comprises the single substituted (S112A) amino acid sequence in CDR H3 in the heavy chain variable region (VH) of Can SL501-VH3.

SEQ ID NO: 176 comprises the single substituted (S112G) amino acid sequence in CDR H3 in the heavy chain variable region (VH) of Can SL501-VH3.

SEQ ID NO: 177 comprises the single substituted (S112P) amino acid sequence in CDR H3 in the heavy chain variable region (VH) of Can SL501-VH3.

SEQ ID NO: 178 comprises the single substituted (S112D) amino acid sequence in CDR H3 in the heavy chain variable region (VH) of Can SL501-VH3.

SEQ ID NO: 179 comprises the single substituted (S112L) amino acid sequence in CDR H3 in the heavy chain variable region (VH) of Can SL501-VH3.

SEQ ID NO: 180 comprises the nucleotide sequence of the DNA encoding the variable region of the heavy chain (VH) of affinity matured caninized Hclb H1K4 antibody referred to herein as HcLb/mat/P/H3/100/DY.

SEQ ID NO: 181 comprises the amino acid sequence of the variable region of the heavy chain (VH) of affinity matured caninized Hclb H1K4 antibody referred to herein as HcLb/mat/P/H3/100/DY.

SEQ ID NO: 182 comprises the nucleotide sequence of the DNA encoding the variable region of the heavy chain (VH) of affinity matured caninized Hclb H1K4 antibody referred to herein as HcLb/mat/P/H2/55/SW.

SEQ ID NO: 183 comprises the amino acid sequence of the variable region of the heavy chain (VH) of affinity matured caninized Hclb H1K4 antibody referred to herein as HcLb/mat/P/H2/55/SW.

SEQ ID NO: 184 comprises the nucleotide sequence of the DNA encoding the variable region of the heavy chain (VH) of affinity matured caninized Hclb H1K4 antibody referred to herein as canHcLb/54AG/100DY.

SEQ ID NO: 185 comprises the amino acid sequence of the variable region of the heavy chain (VH) of affinity matured caninized Hclb H1K4 antibody referred to herein as canHcLb/54AG/100DY.

SEQ ID NO: 186 comprises the nucleotide sequence of the DNA encoding the variable region of the heavy chain (VH) of affinity matured caninized Hclb H1K4 antibody referred to herein as canHcLb/55SW/100DY.

SEQ ID NO: 187 comprises the amino acid sequence of the variable region of the heavy chain (VH) of affinity matured caninized Hclb H1K4 antibody referred to herein as canHcLb/55SW/100DY.

SEQ ID NO: 188 comprises the nucleotide sequence of the DNA encoding the variable region of the heavy chain (VH) of affinity matured caninized Hclb H1K4 antibody referred to herein as canHcLb/55SW/100DY/28/TI.

SEQ ID NO: 189 comprises the amino acid sequence of the variable region of the heavy chain (VH) of affinity matured caninized Hclb H1K4 antibody referred to herein as canHcLb/55SW/100DY/28/TI.

SEQ ID NO: 190 comprises the nucleotide sequence of the DNA encoding the variable region of the heavy chain (VH) of affinity matured caninized Hclb H1K4 antibody referred to herein as canHcLb/55SW/100DY/30/IM.

SEQ ID NO: 191 comprises the amino acid sequence of the variable region of the heavy chain (VH) of affinity matured caninized Hclb H1K4 antibody referred to herein as canHcLb/55SW/100DY/30/IM.

SEQ ID NO: 192 comprises the nucleotide sequence of the DNA encoding the variable region of the heavy chain (VH) of affinity matured caninized Hclb H1K4 antibody referred to herein as CanHcLb/55SW/100DY/57/SM.

SEQ ID NO: 193 comprises the amino acid sequence of the variable region of the heavy chain (VH) of affinity matured caninized Hclb H1K4 antibody referred to herein as CanHcLb/55SW/100DY/57/SM.

SEQ ID NO: 194 comprises the nucleotide sequence of the DNA encoding the variable region of the heavy chain (VH) of affinity matured caninized Hclb H1K4 antibody referred to herein as canHcLb/55SW/100DY/57/SV.

SEQ ID NO: 195 comprises the amino acid sequence of the variable region of the heavy chain (VH) of affinity matured caninized Hclb H1K4 antibody referred to herein as canHcLb/55SW/100DY/57/SV.

SEQ ID NO: 196 comprises the nucleotide sequence of the DNA encoding the variable region of the heavy chain (VH) of affinity matured caninized Hclb H1K4 antibody referred to herein as canHcLb/55SW/100DY/31/TK.

SEQ ID NO: 197 comprises the amino acid sequence of the variable region of the heavy chain (VH) of affinity matured caninized Hclb H1K4 antibody referred to herein as canHcLb/55SW/100DY/31/TK.

SEQ ID NO: 198 comprises the nucleotide sequence of the DNA encoding the variable region of the heavy chain (VH) of affinity matured caninized Hclb H1K4 antibody referred to herein as canHcLb/55SW/100DY/301M/31TK.

SEQ ID NO: 199 comprises the amino acid sequence of the variable region of the heavy chain (VH) of affinity matured caninized Hclb H1K4 antibody referred to herein as canHcLb/55SW/100DY/301M/31TK.

SEQ ID NO: 200 comprises the nucleotide sequence of the DNA encoding the variable region of the heavy chain (VH) of affinity matured caninized Hclb H1K4 antibody referred to herein as canHcLb/55SW/100DY/301M/31TK/28TI.

SEQ ID NO: 201 comprises the amino acid sequence of the variable region of the heavy chain (VH) of affinity matured caninized Hclb H1K4 antibody referred to herein as canHcLb/55SW/100DY/30IM/31TK/28TI.

SEQ ID NO: 202 comprises the nucleotide sequence of the DNA encoding the variable region of the heavy chain (VH) of affinity matured caninized Hclb H1K4 antibody referred to herein as canHcLb/55SW/100DY/301M/31TK/57SM.

SEQ ID NO: 203 comprises the amino acid sequence of the variable region of the heavy chain (VH) of affinity matured caninized Hclb H1K4 antibody referred to herein as canHcLb/55SW/100DY/301M/31TK/57SM.

SEQ ID NO: 204 comprises the nucleotide sequence of the DNA encoding the variable region of the heavy chain (VH) of affinity matured caninized Hclb H1K4 antibody referred to herein as canHcLb/55SW/100DY/301M/31TK/28TI/57SM.

SEQ ID NO: 205 comprises the amino acid sequence of the variable region of the heavy chain (VH) of affinity matured caninized Hclb-H1K4 antibody referred to herein as canHcLb/55SW/100DY/301M/31TK/28TI/57SM.

SEQ ID NO: 206 comprises the nucleotide sequence of the DNA encoding the variable region of the heavy chain (VH) of affinity matured caninized Hclb H1K4 antibody referred to herein as canHcLb/55SW/100DY/57SM/301M.

SEQ ID NO: 207 comprises the amino acid sequence of the variable region of the heavy chain (VH) of affinity matured caninized Hclb H1K4 antibody referred to herein as canHcLb/55SW/100DY/57SM/301M.

SEQ ID NO: 208 comprises the nucleotide sequence of the DNA encoding the variable region of the heavy chain (VH) of affinity matured caninized Hclb H1K4 antibody referred to herein as canHcLb/55SW/100DY/57SV/301M.

SEQ ID NO: 209 comprises the amino acid sequence of the variable region of the heavy chain (VH) of affinity matured caninized Hclb H1K4 antibody referred to herein as canHcLb/55SW/100DY/57SV/301M.

SEQ ID NO: 210 comprises the nucleotide sequence of the DNA encoding the variable region of the heavy chain (VH) of affinity matured caninized Hclb H1K4 antibody referred to herein as canHcLb/55SW/100DY/57SM/301M/31TF.

SEQ ID NO: 211 comprises the amino acid sequence of the variable region of the heavy chain (VH) of affinity matured caninized Hclb H1K4 antibody referred to herein as canHcLb/55SW/100DY/57SM/301M/31TF.

SEQ ID NO: 212 comprises the nucleotide sequence of the DNA encoding the variable region of the heavy chain (VH) of affinity matured caninized Hclb H1K4 antibody referred to herein as canHcLb/55SW/100DY/57SM/30IM/31TF/28TK.

SEQ ID NO: 213 comprises the amino acid sequence of the variable region of the heavy chain (VH) of affinity matured caninized Hclb H1K4 antibody referred to herein as canHcLb/55SW/100DY/57SM/301M/31TF/28TK.

SEQ ID NO: 214 comprises the nucleotide sequence of the DNA encoding the variable region of the heavy chain (VH) of affinity matured caninized Hclb H1K4 antibody referred to herein as canHcLb/55SW/100DY/57SM/301W/31TF/28TK.

SEQ ID NO: 215 comprises the amino acid sequence of the variable region of the heavy chain (VH) of affinity matured caninized Hclb H1K4 antibody referred to herein as canHcLb/55SW/100DY/57SM/301W/31TF/28TK.

SEQ ID NO: 216 comprises the nucleotide sequence of the DNA encoding the variable region of the light chain (VL) of affinity matured caninized Hclb H1K4 antibody referred to herein as HcLb/mat/K3/237/ND.

SEQ ID NO: 217 comprises the amino acid sequence of the variable region of the light chain (VL) of affinity matured caninized Hclb H1K4 antibody referred to herein as HcLb/mat/K3/237/ND.

SEQ ID NO: 218 comprises the nucleotide sequence of the DNA encoding the variable region of the light chain (VL) of affinity matured caninized Hclb H1K4 antibody referred to herein as canHcLb/237ND/242TS.

SEQ ID NO: 219 comprises the amino acid sequence of the variable region of the light chain (VL) of affinity matured caninized Hclb H1K4 antibody referred to herein as canHcLb/237ND/242TS.

SEQ ID NO: 220 comprises the amino acid sequence of canine TGFβ1.

SEQ ID NO: 221 comprises the amino acid sequence of human TGFβ1.

SEQ ID NO: 222 comprises the amino acid sequence of feline TGFβ1.

SEQ ID NO: 223 comprises the amino acid sequence of TGFβ1 fragment containing epitope for anti-TGF antibodies of the invention and as illustrated on FIG. 1.

SEQ ID NO: 224 comprises the amino acid sequence of VH CDR3 of the SL501 antigen binding protein wherein (X1) can be (K or R), wherein (X2) can be (T or A), wherein (X3) can be (Q, N, D, E or K) and wherein X4 can be (S, E, Q or D).

SEQ ID NO: 225 comprises the amino acid sequence of the variable region of the heavy chain (VH) of caninized SL501 antibody comprising the D108E point mutation.

SEQ ID NO: 226 comprises the amino acid sequence of the variable region of the heavy chain (VH) of caninized SL501 antibody comprising the D108P point mutation.

SEQ ID NO: 227 comprises the amino acid sequence of the variable region of the heavy chain (VH) of caninized SL501 antibody comprising the D108Q point mutation.

SEQ ID NO: 228 comprises the amino acid sequence of the variable region of the heavy chain (VH) of caninized SL501 antibody comprising the D108N point mutation.

SEQ ID NO: 229 comprises the amino acid sequence of the variable region of the heavy chain (VH) of caninized SL501 antibody comprising the D108S point mutation.

SEQ ID NO: 230 comprises the amino acid sequence of the variable region of the heavy chain (VH) of caninized SL501 antibody comprising the D108T point mutation.

SEQ ID NO: 231 comprises the amino acid sequence of the variable region of the heavy chain (VH) of caninized SL501 antibody comprising the D108K point mutation.

SEQ ID NO: 232 comprises the amino acid sequence of the variable region of the heavy chain (VH) of caninized SL501 antibody comprising the D108R point mutation.

SEQ ID NO: 233 comprises the amino acid sequence of the variable region of the heavy chain (VH) of caninized SL501 antibody comprising the D108H point mutation.

SEQ ID NO: 234 comprises the amino acid sequence of the variable region of the heavy chain (VH) of caninized SL501 antibody comprising the P109S point mutation.

SEQ ID NO: 235 comprises the amino acid sequence of the variable region of the heavy chain (VH) of caninized SL501 antibody comprising the P109H point mutation.

SEQ ID NO: 236 comprises the amino acid sequence of the variable region of the heavy chain (VH) of caninized SL501 antibody comprising the P109Y point mutation.

SEQ ID NO: 237 comprises the amino acid sequence of the variable region of the heavy chain (VH) of caninized SL501 antibody comprising the P109W point mutation.

SEQ ID NO: 238 comprises the amino acid sequence of the variable region of the heavy chain (VH) of caninized SL501 antibody comprising the P109F point mutation.

SEQ ID NO: 239 comprises the amino acid sequence of the variable region of the heavy chain (VH) of caninized SL501 antibody comprising the P109T point mutation.

SEQ ID NO: 240 comprises the amino acid sequence of the variable region of the heavy chain (VH) of caninized SL501 antibody comprising the P109A point mutation.

SEQ ID NO: 241 comprises the amino acid sequence of the variable region of the heavy chain (VH) of caninized SL501 antibody comprising the P109G point mutation.

SEQ ID NO: 242 comprises the amino acid sequence of the variable region of the heavy chain (VH) of caninized SL501 antibody comprising the Q110S point mutation.

SEQ ID NO: 243 comprises the amino acid sequence of the variable region of the heavy chain (VH) of caninized SL501 antibody comprising the Q110N point mutation.

SEQ ID NO: 244 comprises the amino acid sequence of the variable region of the heavy chain (VH) of caninized SL501 antibody comprising the Q110D point mutation.

SEQ ID NO: 245 comprises the amino acid sequence of the variable region of the heavy chain (VH) of caninized SL501 antibody comprising the Q110E point mutation.

SEQ ID NO: 246 comprises the amino acid sequence of the variable region of the heavy chain (VH) of caninized SL501 antibody comprising the Q110K point mutation.

SEQ ID NO: 247 comprises the amino acid sequence of the variable region of the heavy chain (VH) of caninized SL501 antibody comprising the Q11 OR point mutation.

SEQ ID NO: 248 comprises the amino acid sequence of the variable region of the heavy chain (VH) of caninized SL501 antibody comprising the Q110H point mutation.

SEQ ID NO: 249 comprises the amino acid sequence of the variable region of the heavy chain (VH) of caninized SL501 antibody comprising the Q110T point mutation.

SEQ ID NO: 250 comprises the amino acid sequence of the variable region of the heavy chain (VH) of caninized SL501 antibody comprising the Q110V point mutation.

SEQ ID NO: 251 comprises the amino acid sequence of the variable region of the heavy chain (VH) of caninized SL501 antibody comprising the Y111P point mutation.

SEQ ID NO: 252 comprises the amino acid sequence of the variable region of the heavy chain (VH) of caninized SL501 antibody comprising the Y111F point mutation.

SEQ ID NO: 253 comprises the amino acid sequence of the variable region of the heavy chain (VH) of caninized SL501 antibody comprising the Y111W point mutation.

SEQ ID NO: 254 comprises the amino acid sequence of the variable region of the heavy chain (VH) of caninized SL501 antibody comprising the Y111H point mutation.

SEQ ID NO: 255 comprises the amino acid sequence of the variable region of the heavy chain (VH) of caninized SL501 antibody comprising the Y111M point mutation.

SEQ ID NO: 256 comprises the amino acid sequence of the variable region of the heavy chain (VH) of caninized SL501 antibody comprising the Y1111 point mutation.

SEQ ID NO: 257 comprises the amino acid sequence of the variable region of the heavy chain (VH) of caninized SL501 antibody comprising the Y111L point mutation.

SEQ ID NO: 258 comprises the amino acid sequence of the variable region of the heavy chain (VH) of caninized SL501 antibody comprising the Y111V point mutation.

SEQ ID NO: 259 comprises the amino acid sequence of the variable region of the heavy chain (VH) of caninized SL501 antibody comprising the Y111T point mutation.

SEQ ID NO: 260 comprises the amino acid sequence of the variable region of the heavy chain (VH) of caninized SL501 antibody comprising the Y111E point mutation.

SEQ ID NO: 261 comprises the amino acid sequence of the variable region of the heavy chain (VH) of caninized SL501 antibody comprising the S112E point mutation.

SEQ ID NO: 262 comprises the amino acid sequence of the variable region of the heavy chain (VH) of caninized SL501 antibody comprising the S112Q point mutation.

SEQ ID NO: 263 comprises the amino acid sequence of the variable region of the heavy chain (VH) of caninized SL501 antibody comprising the S112N point mutation.

SEQ ID NO: 264 comprises the amino acid sequence of the variable region of the heavy chain (VH) of caninized SL501 antibody comprising the S112T point mutation.

SEQ ID NO: 265 comprises the amino acid sequence of the variable region of the heavy chain (VH) of caninized SL501 antibody comprising the S112A point mutation.

SEQ ID NO: 266 comprises the amino acid sequence of the variable region of the heavy chain (VH) of caninized SL501 antibody comprising the S112G point mutation.

SEQ ID NO: 267 comprises the amino acid sequence of the variable region of the heavy chain (VH) of caninized SL501 antibody comprising the S112P point mutation.

SEQ ID NO: 268 comprises the amino acid sequence of the variable region of the heavy chain (VH) of caninized SL501 antibody comprising the S112D point mutation.

SEQ ID NO: 269 comprises the amino acid sequence of the variable region of the heavy chain (VH) of caninized SL501 antibody comprising the S112L point mutation.

SEQ ID NO: 270 comprises the amino acid sequence of the variable region of the heavy chain (VH) CDR1 of the HcLB comprising the amino acid sequence of: G-Y-(X1)-F-(X2)-(X3)-Y wherein (X1) comprises T or I, (X2) comprises I or M and (X3) comprises T or K.

SEQ ID NO: 271 comprises the amino acid sequence of the variable region of the heavy chain (VH) CDR2 of the HcLB comprising the amino acid sequence of: F-P-(X4)-(X5)-G-(X6) wherein (X4) comprises A or G, (X5) comprises S or W and (X6) comprises S, M or V.

SEQ ID NO: 272 comprises the amino acid sequence of the variable region of the heavy chain (VH) CDR3 of the HcLB comprising the amino acid sequence of: G-(X7)-G-N-Y-A-L-D-A-M-D-Y wherein (X7) comprises D or Y.

SEQ ID NO: 273 comprises the amino acid sequence of the variable region of the light chain (VL) CDR3 of HcLB comprising the amino acid sequence of: Q-Q-

N-(X8)-E-D-P-L-(X9) wherein (X8) comprises N or D and (X9) comprises T or S.

SEQ ID NO: 274 comprises the amino acid sequence of CDR1 of the variable region of the heavy chain (VH) the HcLB antibody comprising the T281 point mutation.

SEQ ID NO: 275 comprises the amino acid sequence of CDR1 of the variable region of the heavy chain (VH) of the HcLB antibody comprising the 130M point mutation.

SEQ ID NO: 276 comprises the amino acid sequence of CDR1 of the variable region of the heavy chain (VH) of the HcLB antibody comprising the T31K point mutation.

SEQ ID NO: 277 comprises the amino acid sequence of CDR1 of the variable region of the heavy chain (VH) of the HcLB antibody comprising the 130M and T31K point mutation.

SEQ ID NO: 278 comprises the amino acid sequence of CDR1 of the variable region of the heavy chain (VH) of the HcLB antibody comprising the T281, 130M and T31K point mutations.

SEQ ID NO: 279 comprises the amino acid sequence of CDR2 of the variable region of the heavy chain (VH) of the HcLB antibody comprising the A54G point mutation.

SEQ ID NO: 280 comprises the amino acid sequence of CDR2 of the variable region of the heavy chain (VH) of the HcLB antibody comprising the S55W point mutation.

SEQ ID NO: 281 comprises the amino acid sequence of CDR2 of the variable region of the heavy chain (VH) of the HcLB antibody comprising the S57M point mutation.

SEQ ID NO: 282 comprises the amino acid sequence of CDR2 of the variable region of the heavy chain (VH) of the HcLB antibody comprising the S55W and S57M point mutations.

SEQ ID NO: 283 comprises the amino acid sequence of CDR3 of the variable region of the heavy chain (VH) of the HcLB antibody comprising the D100Y point mutation.

SEQ ID NO: 284 comprises the amino acid sequence of CDR3 of the variable region of the light chain (VL) of the HcLB antibody comprising the N237D point mutation.

SEQ ID NO: 285 comprises the amino acid sequence of CDR3 of the variable region of the light chain (VH) of the HcLB antibody comprising the T242S point mutation.

SEQ ID NO: 286 comprises the amino acid sequence of CDR3 of the variable region of the light chain (VL) of the HcLB antibody comprising the N237D and T242S point mutations.

SEQ ID NO: 287 comprises the nucleic acid sequence of the HC-65e canine heavy chain constant region.

SEQ ID NO: 288 comprises the amino acid sequence of the HC-65e canine heavy chain constant region.

SEQ ID NO: 289 comprises the nucleotide sequence of the feline heavy chain constant region.

SEQ ID NO: 290 comprises the amino acid sequence of the feline heavy chain constant region.

SEQ ID NO. 291 comprises the nucleic acid sequence of the HC-65 canine heavy chain constant region.

SEQ ID NO.292 comprises the amino acid sequence of the HC-65 canine heavy chain constant region.

SEQ ID NO.293 comprises the nucleotide sequence that encodes the amino acid sequence of the variable region of the light chain (VL) of caninized SL501 antibody, referred to herein as Can SL501-VL1.

DETAILED DESCRIPTION OF THE INVENTION

The invention disclosed herein provides anti-TGF3 antigen binding proteins/antibodies/antibody fragments (terms used interchangeably) that bind TGFβ1 and/or TGF02 and/or TGFβ proteins with high affinity and specificity. The invention further provides antigen binding proteins and polypeptides that also bind to any one of the TGFβ proteins or polypeptides described herein that are variants of said antigen binding proteins as well as methods of making and using said proteins. In some embodiments, the invention also provides polynucleotides encoding said antigen binding proteins and/or polypeptides. The invention disclosed herein also provides methods for preventing and/or treating a TGFβ related disorder selected from the group of fibrosis disorder, connective tissue disorder, bone disorders and cell proliferation disorders by administration of a therapeutically effective amount of the anti-TGF3 antigen binding proteins and the respective variants of the invention described herein.

General Techniques and Definitions

It should be understood that this invention is not limited to the particular methodology, protocols, and reagents etc., described herein and as such may vary. The terminology used herein is only for the purpose of describing particular embodiments and is not intended to limit the scope of the present invention which is defined solely by the claims. Unless otherwise defined, scientific and technical terms used in connection with the invention as described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art and are not limited to a single description. It is well known in the art that different techniques may be substituted for what is described.

All patents and other publications identified are expressly incorporated herein by reference for the purpose of describing and disclosing, for example, the methodologies described in such publications that might be used in connection with the present invention. These publications are provided solely for their disclosure prior to the filing date of the present application Standard techniques are used for recombinant DNA, oligonucleotide and polynucleotide synthesis, tissue culture, transfection and transformation of cells, among many other commonly used techniques well known to one of skill in the art. General techniques well known to those of skill in the art are performed per manufacturer's specifications or as commonly accomplished in the art or as described herein. The foregoing techniques and procedures are generally performed according to conventional methods well known in the art and as described, but not limited to, the various general and more specific references that are cited and discussed throughout the present specification: see for example; Sambrook et al. MOLECULAR CLONING: LAB.

MANUAL (3rd ed., Cold Spring Harbor Lab. Press, Cold Spring Harbor, N.Y., 2001) and Ausubel et al. Current Protocols in Molecular Biology (New York: Greene Publishing Association J Wiley Interscience), Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. 1. Freshney, ed. 1987); *Introduction to Cell and Tissue Culture* (1. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (E. Coligan et al., eds., 1991); Short Protocols in Molecular Biology (Wiley and Sons, 1999); *Immunobiology* (C. A. Janeway and P. Travers, 1997); Antibodies (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (Y. T. DeVita et al., eds., J.B. Lippincott Company, 1993) as well as different and current protocols used by those of skill in the art. Before describing the present invention in detail, several terms used in the context of the present invention will be defined. In addition to these terms, others are defined elsewhere in the specification as necessary. As employed above and throughout the disclosure, the following terms and abbreviations, unless otherwise indicated, shall be understood to have the following meanings. Unless otherwise expressly defined herein, terms of art used in this specification will have their art-recognized meanings.

As used in the specification and claims, the singular form "a", "an" and "the" includes plural references unless the context clearly dictates otherwise. For example, reference to "an antibody" includes a plurality of such antibodies.

It is noted that in this disclosure, terms such as "comprises", "comprised", "comprising", "contains", "containing", "consisting", "consisted", "consisting essentially of", "includes", "included" and the like are defined according to standard United States and international patent law practice The term "about" is used herein to indicate that a value includes the standard deviation of error for the device or method being employed to determine the value. The term "at least about" is used herein to indicate the lower limit of a range. For example, when the term "having at least about 95% sequence identity", it should be clear to those of skill in the art that this includes 95% sequence identity through 100% sequence identity. The use of the term "or" in the claims is used to mean "and/or" unless explicitly indicated to refer to alternatives only or the alternatives are mutually exclusive, although the disclosure supports a definition that refers to only alternatives and to "and/or."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, ex. hydroxyproline, γ-carboxyglutamate, and O-phosphoserine. Amino acid analogs refer to compounds that have but are not limited to the same basic chemical structure as a naturally occurring amino acid, i.e., an a carbon that is bound to a hydrogen, a carboxyl group, an amino group, and an R group, ex. homoserine, norleucine, methionine sulfoxide, methionine methyl sulfonium. Such analogs have modified R groups (ex. norleucine) or modified peptide backbones but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Macromolecular structures such as polypeptide structures may be described in terms of various levels of organization. "Primary structure" refers to the amino acid sequence of a particular peptide. "Secondary structure" refers to locally ordered, three dimensional structures within a polypeptide. These structures are commonly known as domains, for example enzymatic domains, extracellular domains, transmembrane domains, pore domains, or cytoplasmic tail domains. Domains are portions of a polypeptide that form a compact unit of the polypeptide. Exemplary domains include domains with enzymatic activity. A domain may be made up of sections of lesser organization such as stretches of β-sheet and α-helices. "Tertiary structure" refers to the complete three-dimensional structure of a polypeptide monomer. "Quaternary structure" refers to the three-dimensional structure formed by the noncovalent association of independent tertiary units.

The term 'conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5350576. In a preferred embodiment, a conservative amino acid substitution will be anyone that occurs within one of the following six groups:

Small aliphatic, substantially non-polar residues: Ala, Gly, Pro, Ser, and Thr;

Large aliphatic, non-polar residues: lie, Leu, and Val; Met;

Polar, negatively charged residues and their amides: Asp and Glu;

Amides of polar, negatively charged residues: Asn and Gin; His;

Polar, positively charged residues: Arg and Lys; His; and

Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gin; His); Asp (Glu); Gin (Asn); Glu (Asp); Gly (Pro); His (Asn; Gin); Ile (Leu; Val); Leu (Ile; Val); Lys (Arg; Gin; Glu); Met (Leu; Ile); Phe (Met; Leu; Tyr); Ser (Thr); Thr (Ser); Trp (Tyr); Tyr (Trp; Phe); and Val (Ile; Leu).

The terms "polypeptide", "oligopeptide", "peptide" and "protein" are used interchangeably herein to refer to polymers of amino acids of any length. The polymer may be linear or branched, it may possibly comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also, included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

As used herein, an "antibody", "antigen binding protein" and the like refers to a polypeptide comprising a region coded by an immunoglobulin gene or antibody fragments thereof that specifically binds and recognizes an antigen. An exemplary immunoglobulin (antibody) structural unit may comprise a tetramer, with each tetramer composed of two identical pairs of polypeptide chains, each pair having one "light" (about 25-kD) and one "heavy" chain (about 50-70 kD). The N-terminus of each chain defines a variable region of about 100 to 110 or more amino acids primarily responsible for antigen recognition. The terms variable light chain and variable heavy chain refer to these light and heavy chains. Antibodies exist, for example, as intact immunoglobulins or as several well-characterized fragments produced by digestion with various peptidases. While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies or those identified using other methods known in the art The light chains of intact antibodies, as used herein, from any vertebrate species can be assigned to one of two clearly distinct types, called kappa (κ) and lambda (A), based on the amino acid sequences of their constant domains. All light chains contain one variable domain (VL) and one constant domain (CL) Several different types of heavy chains, as described herein, exist that define the class or isotype of an antibody. All heavy chains contain a series of immunoglobulin domains, usually with three constant domains ($C_{H1}$, $C_{H2}$ and $C_{H3}$) and one variable domain (VH) that is important for binding antigen.

The term "variable" region comprises framework and CDRs (otherwise known as "hypervariable regions") and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called "Complementarity Determining Regions (CDRs)" or "hypervariable regions" both in the light chain and the heavy chain variable domains. The more highly conserved portions of variable domains are called the framework region (FR). The variable domains of native heavy and light chains each comprise multiple FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat, et al., *Sequences of Proteins of Immunological Interest,* 5th Ed. Public Health Service, National Institutes of Health, Bethesda, Md. (1991), pages 647-669 and Chothia and Lesk *J. Mol. Biol.* 196:901-917 (1987)). The constant domains are not involved directly in binding an antibody to an antigen, but exhibit various effector functions, as described herein.

Properties of the four human IgG subclasses have been well established; each having distinct characteristics and engages the immune system quite differently. Human IgG subclasses are differentiated by their binding affinities for immune effector proteins including the neonatal Fc receptor (FcRn), Fc gamma receptors (FcγR), and the complement protein C1q. These receptor proteins play roles in serum half-life, antibody-dependent cell-mediated cytotoxicity (ADCC), and complement-dependent cytotoxicity (CDC), respectively. Affinity to these receptors has often been used to characterize the functional properties of antibodies (Bruggemann et al., 1987). A higher affinity to FcγR1 and FcγRIII indicate that the antibody has ADCC activity, whereas binding to the inhibitory receptor, FcγRIIb, contributes to less ADCC activity (Daeron, 1997; Armour et al., 1999; Clynes et al., 2000). Similarly, binding to C1q, the first protein in the complement cascade, indicates complement activity helping to activate phagocytes and destroy pathogens (Schifferli et al., 1986; Garred et al., 1989; Moore et al., 2010). FcRn binding is associated with antibody recycling and is correlative of in vivo half-life (Ghetie et al., 1996; Israel et al., 1996; *Praetor* and Hunziker, 2002; Jefferis, 2007). The unique functions of IgG subclasses assist in the design of antibody therapeutics.

In 1967, Johnson and Vaughan reported the existence of six canine immunoglobulins (Johnson and Vaughan, 1967; Johnson et al., 1967). Subsequent work narrowed the focus to IgGs for which Mazza et al. (1993) isolated four fractions from canine serum rich in IgG and separated each by gel filtration, protein A/G binding and electrophoretic mobilities. These fractions were used to obtain antibody reagents specific to canine IgGs (Mazza et al., 1994). While this work initiated a body of research investigating canine IgGs in various disease states, the functionalities of canine immunoglobulins and how they interact with immune effector proteins remained unclear. In 2001, Tang et al. (2001) provided canine IgG sequences necessary to begin to answer these questions. Like human IgGs, canine IgGs consist of four subclasses. By order of accession number [AF354264, AF354265, AF354266, and AF354267], Bergeron et al (Veterinary Immunology and Immunopathology 157 (2014) 31-41) referred to these canine IgG subclasses as A, B, C, and D, respectively. The alphabetical nomenclature associated with the canine IgG sequences is based on prevalence in the body. Bergeron et al provided functional analysis of each subclass.

Until 2014 very little was known about feline IgGs when Strietzel et al. (Veterinary Immunology and Immunopathology 158 (2014) 214-223) disclosed the functional properties associated with the two known sequences that had been previously isolated from a feline splenic cDNA library. These two IgG sequences, IgG1a and IgG1b had been isolated but not characterized (Kanai, T. H., et al., 2000 Vet Immunol, Immunopathol. 73 (1), 53-62). Strietzel et al reported a third feline IgG sequence, termed IgG2 and described the three feline IgG interactions with the identified feline FcγRI, FcγRIII, FcRn and C1q. Feline kappa and lambda light chains regions were additionally isolated.

A "functional Fc region" possesses at least one effector function of a native sequence Fc region. Exemplary "effector functions" include C1q binding; complement dependent cytotoxicity (CDC); Fc receptor binding; neonatal receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A non-limiting example of a sequence for a native Fc region sequence comprises an amino acid sequence that has between about 80-99% sequence identity to SEQ ID NO.292. In one embodiment the antibody of the invention comprises a native Fc region comprising SEQ ID No. 292. The native Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith. A "variant Fc region" or a "mutated" or "mutant" Fc region comprises an amino acid sequence which differs from that of a native sequence Fc region by virtue of at least one amino acid modification and may or may not retain at least one effector function of the native sequence Fc region as compared to the native Fc region sequence. Preferably, the variant Fc region has at least one amino acid substitution compared to a native sequence Fc region or to the Fc region of a parent polypeptide, ex. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith. A variant or mutated Fc region may also essentially eliminate the function of the Fc region of the antibody. A variant or mutated Fc region may also add or enhance the function of the Fc region of an antibody. For example, Fc region mutations may eliminate effector function of an antibody. In another example a mutated Fc region may enhance effector function of an antibody. In yet another example, a mutated Fc region may alter the half-life or affect the binding of other factors in a cell that may determine properties of the antibody. In one embodiment the antibody of the invention comprises a mutated Fc region. In one embodiment the antibody of the invention comprises a variant or mutated Fc region comprising an amino acid sequence comprising between about 80-99% sequence identity to SEQ ID NO.288. In one embodiment the antibody of the invention comprises a variant or mutated Fc region comprising the amino acid sequence comprising SEQ ID NO.288.

As used herein, "Fc receptor" and "FcR" describe a receptor that binds to the Fc region of an antibody. The preferred FcR is a native sequence FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.,* 9:457-92; Capel et al., 1994, *Immunomethods,* 4:25-34; and de Haas et al., 1995, *J. Lab. Clin. Med.,* 126:330-41. "FcR" also includes the neonatal receptor, FcRn, which is responsible for the transfer of maternal IgGs to the fetus (Guyer et al., 1976, *J. Immunol.,* 117:587; and Kim et al., 1994, *J. Immunol.,* 24:249).

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, for example, in an animal model such as that disclosed in Clynes et al., 1998, *PNAS* (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods,* 202:163 (1996), may be performed.

For preparation of antibodies, ex. recombinant, monoclonal, or polyclonal antibodies, many techniques known in the art may be used. The genes encoding the heavy and light chains of an antibody of interest can be cloned from a cell and used to produce a recombinant monoclonal antibody. Gene libraries encoding heavy and light chains of monoclonal antibodies may also be used. Random combinations of the heavy and light chain gene products generate a large pool of antibodies with different antigenic specificity. Techniques to produce single chain antibodies or recombinant antibodies are found in the art and may be adapted to produce antibodies to polypeptides according to the invention. Phage display technology may also be used to identify antibodies and heteromeric fragments that specifically bind to selected antigens. Antibodies may also be made bispecific, i.e., able to recognize two different antigens, or heteroconjugates, ex. two covalently joined antibodies, or immunotoxins.

"Native antibodies" and "native immunoglobulins" are usually heterotetrameric glycoproteins of about 150,000 Daltons, composed of two identical light (1) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. FIG. 2 is an example of the general structure of a native mouse immunoglobulin G (IgG) highlighting the antigen binding site.

As used herein, the term "antigen binding protein", "antibody", "antagonist antibody", "antigen binding fragment" and the like, which may be used interchangeably herein, refers to a polypeptide, or fragment thereof, comprising an antigen binding site. Thus, an isolated antibody or fragment may be a polyclonal antibody, a monoclonal antibody, a synthetic antibody, a recombinant antibody, a chimeric antibody, a heterochimeric antibody, a caninized antibody, a felinized antibody, a humanized antibody, a fully canine antibody, a fully feline antibody, or a fully human antibody.

In some embodiments, the term "antigen binding protein" "antibody" "antagonist antibody" and the like preferably refers to monoclonal antibodies and fragments thereof, and immunologic binding equivalents thereof that can bind to a TGFβ protein and fragments thereof. Exemplary antibody fragments include Fab, Fab', $F(ab')_2$, Fv, scFv, Fd, dAb, diabodies, their antigen-recognizing fragments, small modular immunopharmaceuticals (SMIPs) nanobodies, IgNAR molecules and the equivalents that are recognized by one of skill in the art to be an antigen binding protein or antibody fragment and any of above mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example but not limited to, via traditional hybridoma techniques (Kohler et al., Nature 256:495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991)) or other techniques employed and well known by those of skill in the art.

A "monoclonal antibody" as defined herein is a single pure homogeneous type of antibody. All monoclonal antibodies produced are identical and have the same antigen specificity. Monoclonal antibodies are a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (Fab, Fab', $F(ab')_2$, Fv, scFv, Fd, dAb, diabodies, their antigen-recognizing fragments, small modular immunopharmaceuticals (SMIPs) nanobodies, IgNAR molecules and the like), mutants thereof, fusion proteins comprising an antibody portion, and any other modified configuration of the immunoglobulin molecule that comprises an antigen recognition site of the required specificity and the ability to bind to an antigen. It is not intended to be limited to the source of the antibody or the manner in which it is made (ex. by hybridoma, phage selection, recombinant expression, transgenic animals, etc.).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, noncovalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

Figure 3:
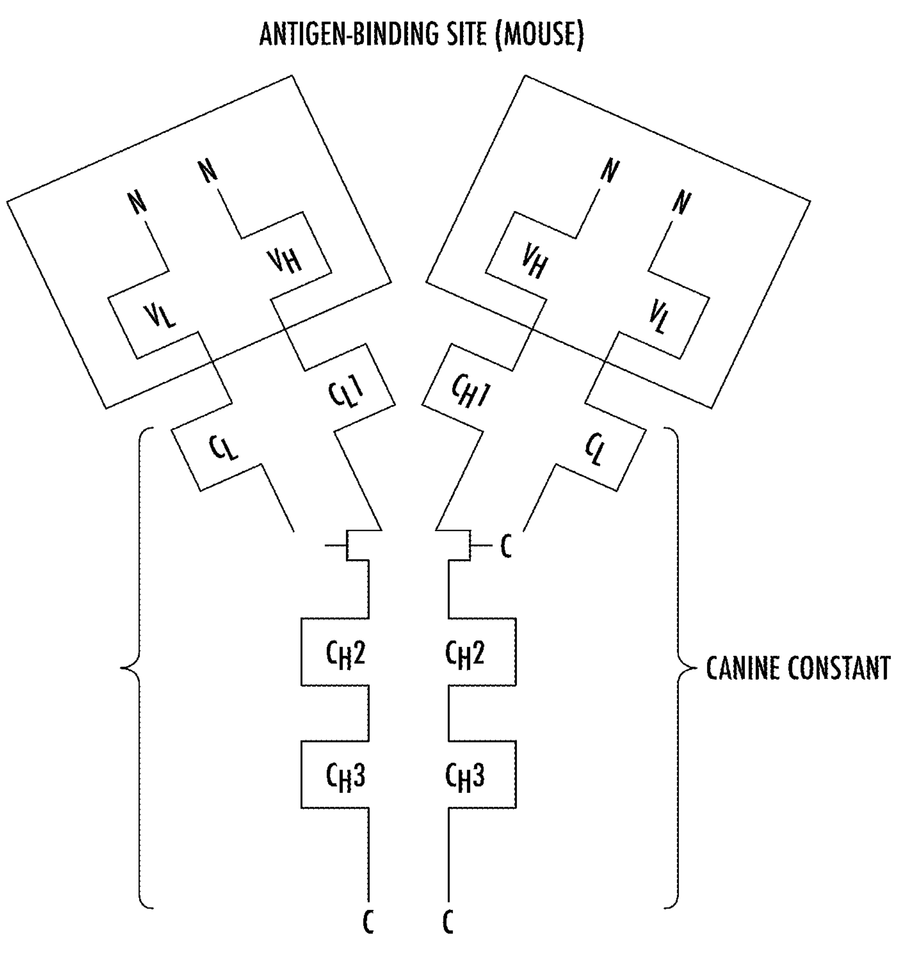
FIG. 3 is a schematic representation of the general structure of one embodiment of a mouse: canine IgG.

The monoclonal antibodies described herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody (or any other species antibody including human and feline) may be joined to canine constant segments, for example the amino acid sequence of the HC-65e canine heavy chain constant region represented herein by SEQ ID NO.288. Additionally, a chimeric feline antibody is produced in the same fashion except that the amino acid sequence comprising SEQ ID NO. 290, the feline heavy chain constant region, is joined to the variable segments of another species antibody (mouse, canine, human etc.). FIG. 3 is a schematic representation of the general structure of one embodiment of a mouse: canine IgG. In this embodiment the antigen binding site is derived from mouse while the Fc portion is canine. This illustration does not limit the claimed invention solely to a mouse/canine chimera but can also be applied to combinations of any species antibodies: canine, feline, murine and human to list a few, as described herein.

Figure 4:
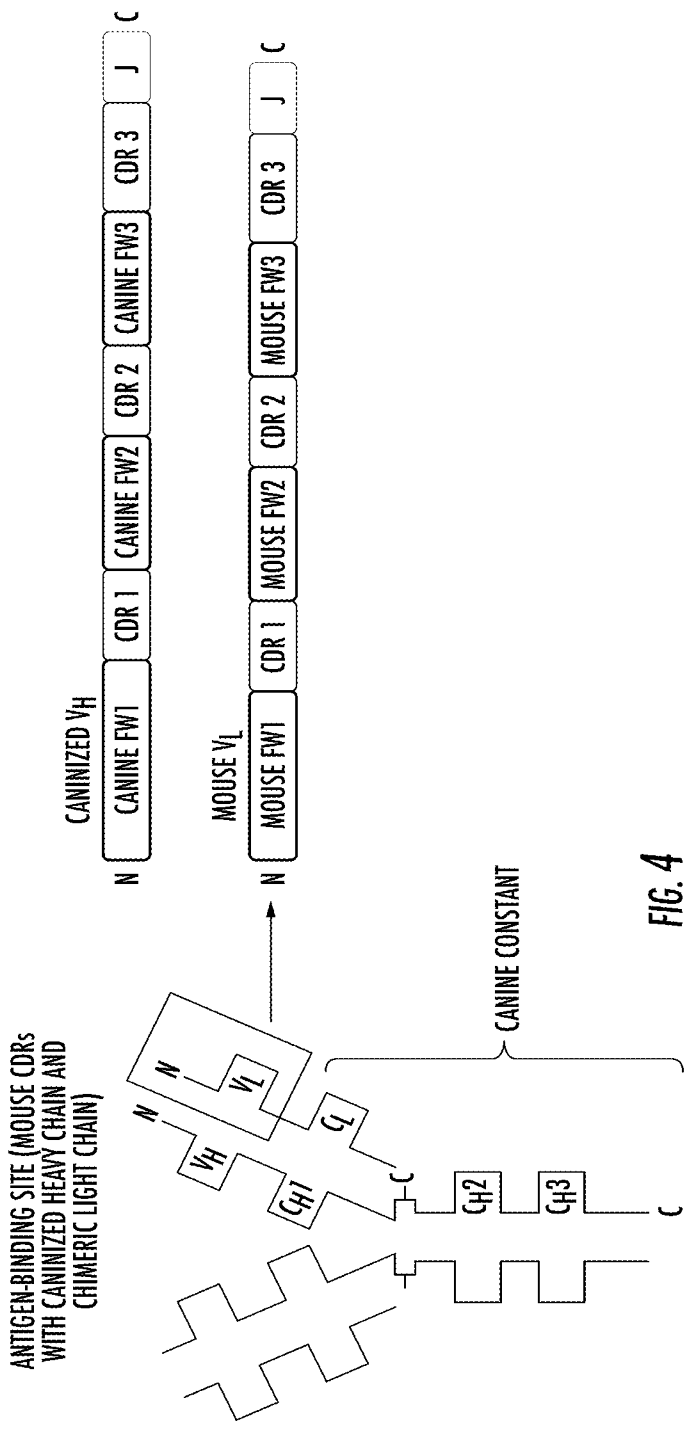
FIG. 4 represents a heterochimeric molecule.

The term "heterochimeric" as defined herein, refers to an antibody in which one of the antibody chains (heavy or light) is speciated (i.e. caninized or felinized) while the other is chimeric. FIG. 4 depicts one embodiment of a heterochimeric molecule. In this embodiment, a caninized variable heavy chain (where all of the CDRs are mouse and all FRs are canine) is paired with a chimeric variable light chain (where all of the CDRs are mouse and all FRs are mouse. In this embodiment, both the variable heavy and variable light chains are fused to a canine constant region. As with the chimeric antibodies, there are no limitations on the combinations of species and portions of antibodies.

The term "canine antibody", "feline antibody", "human antibody" and the like, as used herein, refers to an antibody (antigen binding protein) that is generated against a target and antibodies isolated from lymphocytes from within the target species. These antibodies, as described herein, have been recombinantly modified in vitro to include specific constant regions of the target species. Additionally, the antibodies as described herein were identified, isolated, modified to alter the antibody constant region followed by an expression and isolation from in vitro cell culture systems known and used routinely by those of skill in the art.

The phrase "recombinant canine antibody", "recombinant feline antibody", "recombinant human antibody" and the like all include speciated antibodies that are prepared, expressed, created or isolated by recombinant means, such as antibodies expressed using a recombinant expression vector transfected into a host cell, antibodies isolated from a recombinant, combinatorial canine (or feline, human, etc.) antibody library, antibodies isolated from an animal (ex. a mouse) that is transgenic for canine immunoglobulin genes (see ex. Taylor, L. D., et al. (1992) Nucl. Acids Res. 20:6287-6295) or antibodies prepared, expressed, created or isolated by any other means that involves recombining canine (or feline, human etc.) immunoglobulin gene sequences to other DNA sequences.

Figure 5:
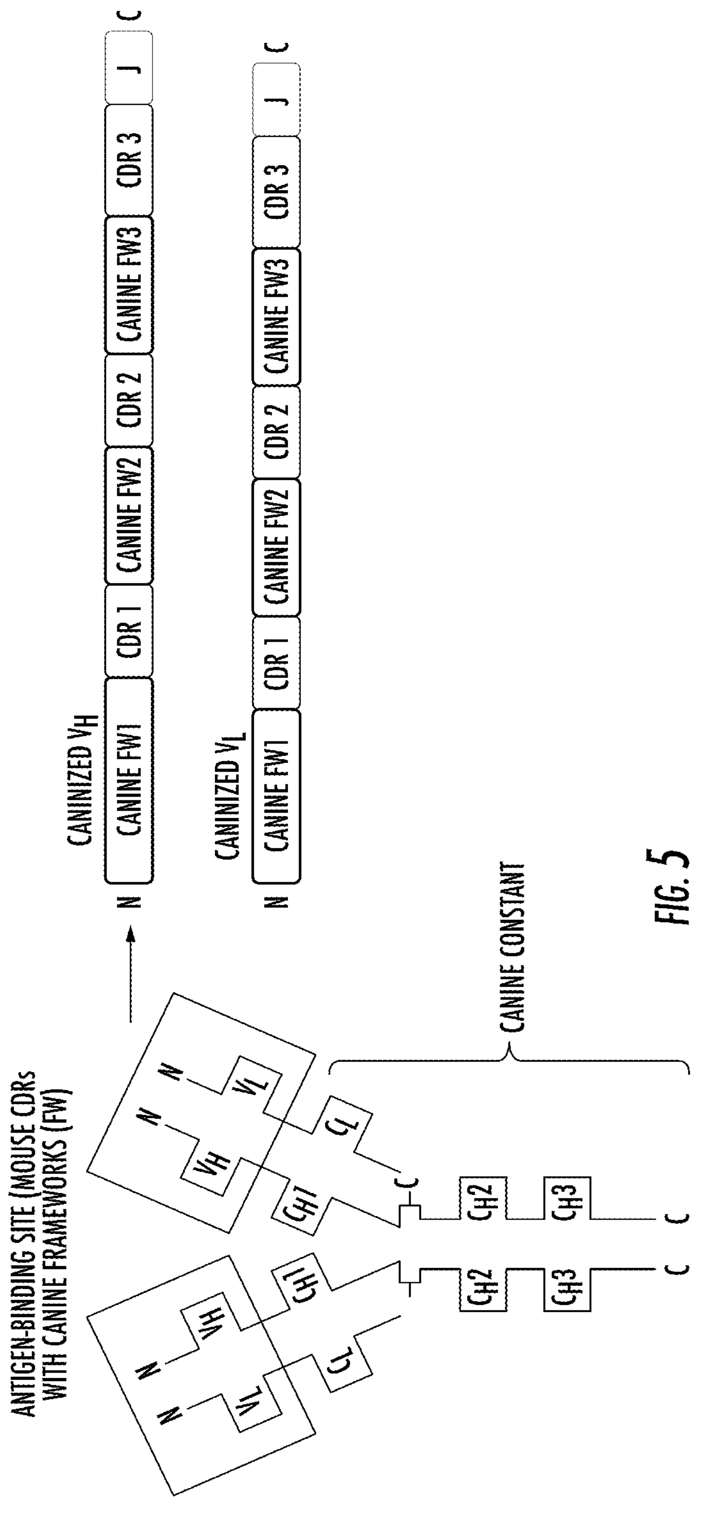
FIG. 5 represents speciation or caninization of a mouse IgG.
Figure 6:
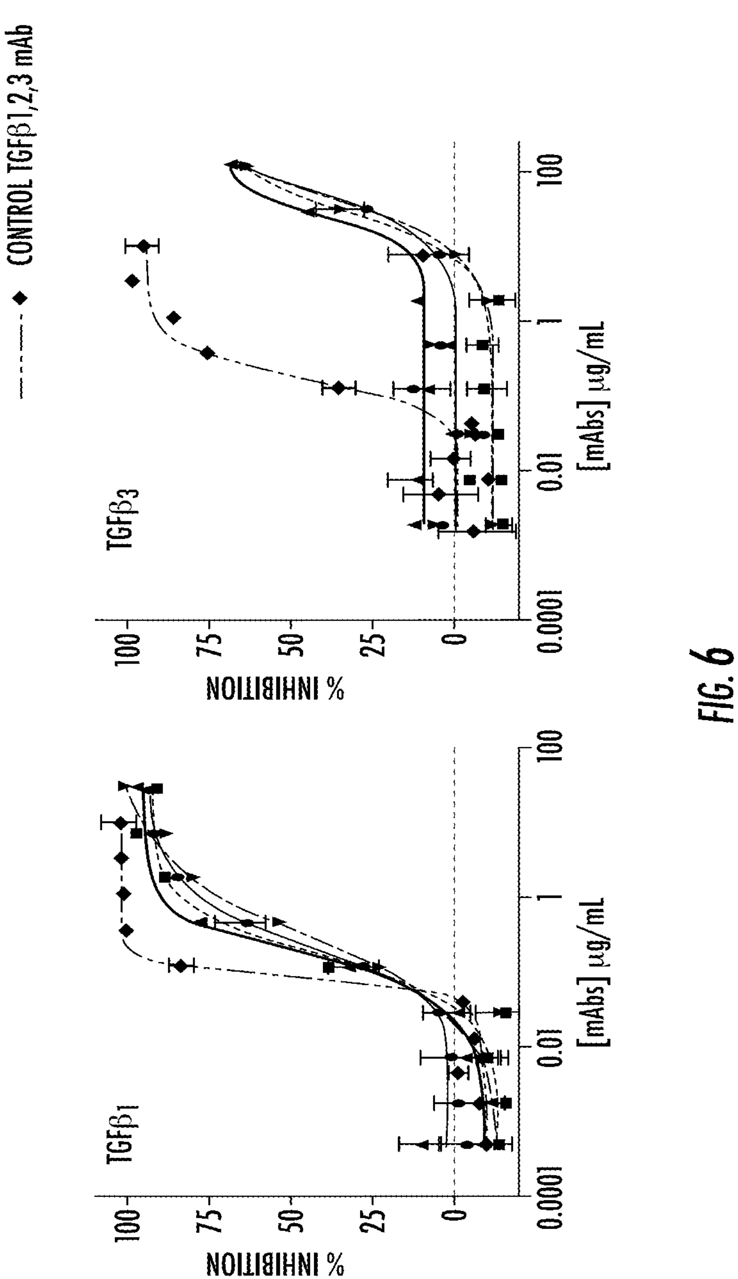
FIG. 6 is a graphical representation of the ZTS-426 SMAD3 inhibition curves for TGFβ1 and TGFβ3.

For the sake of simplicity, the following describes "caninized" antibodies, however the same can be applied to felinized, humanized or any other "speciated" antigen binding protein. As an example, "caninization" is defined as a method for transferring non-canine antigen-binding regions from a donor antibody to a less immunogenic canine antibody acceptor to generate treatments useful as therapeutics in dogs. Caninized antibodies are canine antibody sequences in which hypervariable region residues of the recipient are replaced by hypervariable region residues from a non-canine species (donor antibody) such as such as mouse, rat, rabbit, cat, dogs, goat, chicken, bovine, horse, llama, camel, dromedaries, sharks, non-human primates, human, humanized, recombinant sequence, or an engineered sequence having the desired properties, specificity, affinity, and capacity. Furthermore, caninized antibodies may include residues that are not found in the recipient antibody or in the donor antibody. These modifications are made to further refine antibody performance. The modifications to the hypervariable regions and/or the framework regions, as described herein, are determined for each separately engineered speciated (caninized) antibody based on experimentation known to those in the art yet cannot be predicted prior to said experimentation. The caninized antibody optionally may comprise a complete, or at least a portion of an immunoglobulin constant region (Fc), typically that of a canine immunoglobulin. FIG. 5 is an illustration of one embodiment showing speciation or caninization of a mouse IgG. In this embodiment, mouse CDRs are grafted onto canine frameworks. In some cases, mouse frameworks or residues therein that are outside of the hypervariable region are maintained. All descriptions of caninization of an antigen binding protein and that of a caninized antigen binding protein can be applicable, in concept, to any "speciated" antibody, whether it is caninization, felinization, humanization etc.

The "parent" antibody, as described herein, is one that is encoded by an amino acid sequence used for the preparation of the variant. Preferably, with caninized or canine antibodies the parent antibody has a canine framework region and, if present, has canine antibody constant region(s). For example, the parent antibody may be a caninized or canine antibody. The same is true for felinized, humanized, equinized, bovinized antibodies.

The term "backmutation" refers to a process in which some or all of the somatically mutated amino acids of a canine antibody are replaced with the corresponding germline residues from a homologous germline antibody sequence. The heavy and light chain sequences of the canine antibody of the invention are aligned separately with the germline sequences to identify the sequences with the highest homology. Differences in the canine antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the canine antibody should not be included in the final canine antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and co-linear to the sequence of the canine antibody of the invention. Back mutation of selected target framework residues to the corresponding donor residues might be required to restore and or improved affinity.

An "antigen" is a molecule, or a portion of a molecule, capable of being bound by an antibody. In general, epitopes consist of chemically active surface groupings of molecules, for example, amino acids or sugar side chains, and have specific three-dimensional structural characteristics as well as specific charge characteristics. Epitopes are the antigenic determinant on a protein that is recognized by the immune system. The components of the immune system recognizing epitopes are antibodies, T-cells, and B-cells. T-cell epitopes are displayed on the surface of antigen-presenting cells (APCs) and are typically 8-11 (MHC class I) or 15 plus (MHC class II) amino acids in length. Recognition of the displayed MHC-peptide complex by T-cells is critical to their activation. These mechanisms allow for the appropriate recognition of "self"-versus "non-self" proteins such as bacteria and viruses. Independent amino acid residues that are not necessarily contiguous contribute to interactions with the APC binding cleft and subsequent recognition by the T-Cell receptor (Janeway, Travers, Walport, Immunobiology: The Immune System in Health and Disease. 5$^{th}$ edition New York: Garland Science; 2001). Epitopes that are recognized by soluble antibodies and cell surface associated B-cell receptors vary greatly in length and degree of continuity (Sivalingam and Shepherd, Immunol. 2012; 51(3-4): 304-309). Again, even linear epitopes or epitopes found in a continuous stretch of protein sequence will often have discontiguous amino acids that represent the key points of contact with the antibody paratopes or B-cell receptor. Epitopes recognized by antibodies and B-cells can be conformational with amino acids comprising a common area of contact on the protein in three-dimensional space and are dependent on tertiary and quaternary structural features of the protein. These residues are often found in spatially distinct areas of the primary amino acid sequence.

As used herein, the term "TGF beta", "TGF β" and "TGFB", as used interchangeably herein, refers to Transforming Growth Factor Beta protein 1 (TGFβ1), Transforming Growth Factor Beta protein 2 (TGFβ2) and Transforming Growth Factor Beta protein 3 (TGFβ3). TGFβ proteins are part of a superfamily of related growth factors that exert pleiotropic effects on wound healing by regulating cell proliferation and migration, cellular differentiation, apoptosis, ECM (extra cellular matrix) production and immune modulation. As used herein, the inhibition of TGFβ proteins through use of the antigen binding protein of the invention are used to treat TGFβ related disorders such as fibrosis disorders, bone disorders and cell proliferation disorders.

As used herein, an "anti-TGFβ antigen binding protein" can be interchangeably termed "anti-TGFβ antibody" and "anti-TGFβ antagonist antibody", "anti-TGFβ antigen binding fragment", "anti-TGFβ antigen binding portion" and the like describing any functional molecule that inhibits binding of TGFβ1 and/or TGFβ2 and/or TGFβ3 proteins from binding to its specific receptor thus inhibiting the biological function of the respective TGF3 signaling pathways associated thereof. In some embodiments, the present invention provides that the anti-TGFβ antigen binding protein binds to the TGFβ1 protein. In some embodiments the antigen binding protein of the invention has stronger binding to and functional inhibition against TGFβ1 but may still have weaker binding and functional inhibition against TGFβ2 and/or TGFβ3. In some embodiments, the present invention provides that the anti-TGFβ antigen binding protein binds to the TGFβ2 protein. In some embodiments, the present invention provides that the anti-TGF3 antigen binding protein bind to the TGFβ3 protein. In some embodiments, the anti-TGFβ antigen binding protein binds to the TGFβ1, 2 and 3 proteins. In some embodiments the anti-TGFβ antigen binding protein binds to TGFβ 1 and TGFβ2. In some embodiments, the TGFβ antigen binding protein of the invention binds to TGFβ1 and 3 proteins. The anti-TGFβ antigen binding proteins of the invention encompass binding proteins and antibodies that block, antagonize, suppress or reduce (including significantly reduce) TGFβ biological activity, including downstream pathways mediated by TGFβ1 and/or TGFβ2 and/or TGFβ3 signaling, or any combination thereof, and/or inhibit TGFβ proteins from binding the TGFβ2 receptor, such as receptor binding and/or elicitation of a cellular response to TGFβ1 and/or TGFβ2 and/or TGFβ3 proteins. For purpose of the present invention, it will be explicitly understood that the term "anti-TGFβ antigen binding protein" or "anti-TGFβ-antagonist antibody" or "TGFβ B antibody" encompass all the previously identified terms, titles, and functional states and characteristics whereby the biological activity of TGFβ itself including, but not limited to, its ability to mediate any aspect of the development or treatment of a TGFβ related disorder such as fibrosis disorder, bone disorders and/or cell proliferation disorders or the consequences of the biological activity, are substantially nullified, decreased, or neutralized to any meaningful degree. Examples of anti-TGFβ antigen binding proteins are provided herein.

A "variant" anti-TGFβ antibody, refers herein to a molecule which differs in amino acid sequence from a "parent" anti-TGFβ antibody amino acid sequence by virtue of addition, deletion, and/or substitution of one or more amino acid residue(s) in the parent antibody sequence and retains at least one desired activity of the parent anti-TGFβ-antibody. Desired activities can include the ability to bind the antigen specifically, the ability to reduce, inhibit or neutralize TGFβ activity in an animal, and the ability to inhibit TGFβ-mediated SMAD signaling in a cell-based assay. In one embodiment, the variant comprises one or more amino acid substitution(s) in one or more hypervariable and/or framework region(s) of the parent antibody. For example, the variant may comprise at least one, or from about one to about ten or from about two to about five, substitutions in one or more hypervariable and/or framework regions of the parent antibody. Ordinarily, the variant will have an amino acid sequence having at least 50% amino acid sequence identity with the parent antibody heavy or light chain variable domain sequences or at least between about 65%, 75%, 80%, 85%, 90%, 91%, 92%, 93%, 94% 95%, 96%, 97%, 98% or 99% sequence identity with the parent antibody. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind an TGFβ variant may have a stronger binding affinity, enhanced ability to reduce, inhibit or neutralize TGFβ activity in an animal, and/or enhanced ability to inhibit TGFβ-mediated SMAD signaling in a cell-based assay.

"TGFβ receptor" refers to a polypeptide that is bound by or activated by a TGFβ protein. TGFβ receptors are single-pass serine/threonine kinase receptors that belong to TGFβ receptor family. They exist in several different isoforms that can be homo- or heterodimeric. Three TGFβ receptors specific for TGFβ proteins can be distinguished by their structural and functional properties. TGFβR1 (ALK5) and TGFβ R2 have similar ligand-binding affinities. Both TGFβ R1 and TGFβ R2 have a high affinity for TGFβ1 and low affinity for TGFβ2. TGFβR3 (β-glycan) has a high affinity for both homodimeric TGFβ1 and TGFβ2 and in addition the heterodimer TGFβ1,2. The TGFβ receptors also bind TGFβ3. Mechanistically TGFβ proteins initially bind to TGFβR2 receptor, which recruits and phosphorylates TGFβR1. TGFβR1 then phosphorylates receptor-regulated SMADs (R-SMADs) which can then bind the co-SMAD SMAD4. R-SMAD/co-SMAD complexes accumulate in the nucleus where they act as transcription factors and participate in the regulation of target gene expression The term "neutralize" as used herein with respect to an activity of a monoclonal antibody of the invention means the ability to substantially antagonize, prohibit, prevent, restrain, slow, disrupt, eliminate, stop, reduce or reverse progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher. An antigen binding protein is said to "neutralize" its antigen if antibody binding to the antigen results in partial or complete inhibition or reduction of a biological function of the antigen. Neutralization of a TGFβ protein's biological activity is assessed by measuring the partial or complete inhibition or reduction of one or more in vitro or in vivo indicators of TGFβ activity such as, differences in TGFβ receptor binding and signaling pathways. The ability to neutralize TGFβ activity is assessed, as described herein, by measuring the inhibition of Smad2 phosphorylation, as described in the in vitro assays described herein. The neutralization of TGFβ in vivo may result in inhibition of cell phenotype switching, cell proliferation, and cell survival due to TGFβ in conditions of disease.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins, additionally also meaning that the antibody of the invention will also bind the target antigen at the epitope in vivo). An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance comprising said antigen than it does with alternative cells or substances. An antibody "specifically binds" or "preferentially binds" to a target if it binds with greater affinity, avidity, more readily, and/or with greater duration than it binds to other substances. For example, an antigen binding protein that specifically or preferentially binds to a TGF3 epitope is a protein that binds this epitope with greater affinity, avidity, more readily, and/or with greater duration than it binds to other epitopes or non-TGFB epitopes.

The term "specifically" in the context of antibody binding, refers to high avidity and/or high affinity binding of an antibody to a specific antigen, i.e., a polypeptide, or epitope. Antibody specifically binding an antigen is stronger than binding of the same antibody to other antigens. Antibodies which bind specifically to a polypeptide may be capable of binding other polypeptides at a weak, yet detectable level (for example, 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_D$ of $10^{-7}$ M or less, $10^{-8}$ M or less $10^{-9}$ M or less, $10^{-10}$ M or less, $10^{-11}$ M or less, $10^{-12}$ M or less, or $10^{-13}$ M or less etc.

As used herein, the term "affinity" refers to the strength of the binding of a single antigen-combining site with an antigenic determinant. Affinity depends on the closeness of stereochemical fit between antibody or antigen binding protein combining sites and antigen determinants, on the size of the area of contact between them, on the distribution of charged and hydrophobic groups, etc. Antibody affinity can be measured by equilibrium analysis or by the Surface Plasmon Resonance "SPR" method (for example BIACORE™) The SPR method relies on the phenomenon of surface plasmon resonance (SPR), which occurs when surface plasmon waves are excited at a metal/liquid interface. Light is directed at, and reflected from, the side of the surface not in contact with sample, and SPR causes a reduction in the reflected light intensity at a specific combination of angle and wavelength. Bimolecular binding events cause changes in the refractive index at the surface layer, which are detected as changes in the SPR signal.

The term "$K_D$", as used herein, is intended to refer to the dissociation constant of an antibody-antigen interaction. The dissociation constant, $K_D$, and the association constant, $K_a$, are quantitative measures of affinity. At equilibrium, free antigen (Ag) and free antibody (Ab) are in equilibrium with antigen-antibody complex (Ag-Ab), and the rate constants, $k_a$ and $k_d$, quantitate the rates of the individual reactions. At equilibrium, ka [Ab][Ag]=kd [Ag-Ab]. The dissociation constant, $K_d$, is given by: $K_D$=kd/ka=[Ag][Ab]/[Ag-Ab]. $K_D$ has units of concentration, most typically M, mM, μM, nM, pM, etc. When comparing antibody affinities expressed as $K_D$, having greater affinity for TGFB is indicated by a lower value. The association constant, $K_a$, is given by: Ka=ka/kd=[Ag-Ab]/[Ag][Ab]. $K_a$ has units of inverse concentration, most typically $M^{-1}$, $mM^{-1}$, $\mu M^{-1}$, $nM^{-1}$, $pM^{-1}$, etc. As used herein, the term "avidity" refers to the strength of the antigen-antibody bond after formation of reversible complexes. Anti-TGFB antibodies may be characterized in terms of the $K_D$ for their binding to a TGFB protein, as binding "with a dissociation constant ($K_D$) in the range of from about (lower $K_D$ value) to about (upper $K_D$ value)."

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns; a DNA molecule (ex. cDNA), an RNA molecule (ex. mRNA), recombinant nucleic acids, plasmids, and other vectors, primers and probes. Both 5' to 3' (sense) and 3' to 5' (antisense) polynucleotides are included. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (for example, methyl phosphonates, phosphotriesters, phosphoamidates, cabamates, etc.) and with charged linkages (ex. phosphorothioates, phosphorodithioates, etc.), those containing pendant moieties, such as, for example, proteins (ex. nucleases, toxins, antibodies, signal peptides, poly-L-lysine, etc.), those with intercalators (ex. acridine, psoralen, etc.), those containing chelators (ex., metals, radioactive metals, boron, oxidative metals, etc.), those containing alkylators, those with modified linkages (ex. alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Vectors, as described herein, have expression control sequences meaning that a nucleic acid sequence that directs transcription of a nucleic acid. An expression control sequence can be a promoter, such as a constitutive or an inducible promoter, or an enhancer. The expression control sequence is 'operably linked' to the nucleic acid sequence to be transcribed. A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Just as a polypeptide may contain conservative amino acid substitution(s), a polynucleotide thereof may contain conservative codon substitution(s). A codon substitution is considered conservative if, when expressed, it produces a conservative amino acid substitution, as described above. Degenerate codon substitution, which results in no amino acid substitution, may also be useful in polynucleotides of the present invention. Thus, for example, a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

A "variant" nucleic acid refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The term "isolated" means that the material (for example, antigen binding protein as described herein or nucleic acid) is separated and/or recovered from a component of its natural environment. Contaminant components of its natural environment are materials that would interfere with diagnostic or therapeutic uses for the material, and may include enzymes, hormones, and other proteinaceous or non-proteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification steps used herein.

The terms "cell", "cell line", and "cell culture" may be used interchangeably. These terms also include their progeny, which are all subsequent generations. It is understood that all progeny may not be identical due to deliberate or inadvertent mutations. In the context of expressing a heterologous nucleic acid sequence, "host cell" refers to a prokaryotic or eukaryotic cell (for example, bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

The word "label" when used herein refers to a detectable compound or composition that is conjugated directly or indirectly to the antibody or nucleic acid. The label may itself be detectable by itself (for example, radioisotope labels or fluorescent labels) or, in the case of an enzymatic label, may catalyze chemical alteration of a substrate compound or composition that is detectable.

A "subject" or "patient" refers to an animal in need of treatment that can be affected by molecules of the invention. Animals that can be treated in accordance with the invention include vertebrates, specifically mammals such as canine, feline, or human being particularly preferred examples.

A "composition" is intended to mean a combination of active agent, whether chemical composition, biological composition or biotherapeutic (particularly antigen binding proteins as described herein) and another compound or composition which can be inert (for example, a label), or active, such as an adjuvant.

As defined herein, "pharmaceutically acceptable carriers" suitable for use in the invention are well known to those of skill in the art. Such carriers include but are not limited to, water, saline, buffered saline, phosphate buffer, alcohol/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, citrates, ascorbic acid, gluconic acid, histidine-Hel, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (ex. EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, for example, texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

A "therapeutically effective amount" (or "effective amount") refers to an amount of an active ingredient, for example, an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated TGFB related condition(s) sufficient to effect beneficial or desired results including clinical results such as alleviation or reduction in pain sensation. An effective amount can be administered in one or more administrations. For purposes of this invention, an effective amount of composition is an amount sufficient to prevent, treat, reduce or eliminate a TGFβ related disorder, which is defined herein as a fibrosis disorder, a bone disorder or a cell proliferation disorder. The therapeutically effective amount will vary depending upon the particular subject and condition being treated, the weight and age of the subject, the severity of the condition, the particular composition chosen, the dosing regimen to be followed, timing of administration, the manner of administration and the like, all of which can readily be determined by one of ordinary skill in the art.

As used herein, the term "therapeutic" encompasses the full spectrum of treatments for a disease, condition or disorder. A "therapeutic" agent of the invention may act in a manner that is prophylactic or preventive, including those that incorporate procedures designed to target subjects that can be identified as being at risk; or in a manner that is ameliorative or curative in nature; or may act to slow the rate or extent of the progression of at least one symptom of a disease or disorder being treated.

In a further aspect, the invention features veterinary compositions in which antibodies of the present invention are provided for therapeutic or prophylactic uses. The invention features a method for treating a canine, feline, or human subject having a particular antigen, for example, one associated with a disease or condition. The method includes administering a therapeutically effective amount of an antibody specific for one or more TGFβ proteins with the antibody of the invention as described herein.

The antigen binding protein of the invention can be incorporated into pharmaceutical compositions suitable for administration to a subject. The compounds of the invention may be administered alone or in combination with a pharmaceutically acceptable carrier, diluent, and/or excipients, in single or multiple doses. The compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate.

A composition comprising the antigen binding protein of the invention may be administered to a subject exhibiting-pathologies or disorders as described herein using standard administration techniques including intravenous, intraperitoneal, subcutaneous, pulmonary, transdermal, intramuscular, intranasal, buccal, sublingual, or suppository administration. The route of administration of an antibody of the invention may be parenteral. Infusions typically are given by intravenous route. Preferably, antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Further, the subject of the method of the invention is also referred to as the patient and is described herein as a canine, feline, or human.

A TGFβ related disorder, as used herein, is a disorder in which the regulation or overall levels of one or more TGFβ proteins leads to a connective tissue disorder, a fibrosis/fibrotic disorder, a bone disorder or a cell proliferation disorder. TGFβ regulates diverse cellular functions including proliferation, apoptosis, differentiation and inflammation and as such a dysregulation of these proteins can lead to several of the named disorders.

As used herein a connective tissue disorder refers to a group of disorders involving the protein-rich tissue that supports organs and other parts of the body. Examples of connective tissue are fat, bone, and cartilage. These disorders often involve the joints, muscles, and skin, but they can also involve other organs and organ systems, including the eyes, heart, lungs, kidneys, gastrointestinal tract, and blood vessels.

Fibrosis related disorders, as described herein, relates to a pathologic process which includes scar formation and over production of extracellular matrix by the connective tissue as a response to tissue damage. The molecular process is not different from normal formation of connective tissue and extracellular matrix in the normal organs. Physiologically, fibrosis acts to deposit connective tissue, which can interfere with or completely inhibit the normal architecture and function of the underlying organ or tissue. Fibrosis can be used to describe the pathological state of excess deposition of fibrous tissue, as well as the process of connective tissue deposition in healing. Defined by the pathological accumulation of extracellular matrix (ECM) proteins, fibrosis results in scarring and thickening of the affected tissue, it is in essence an exaggerated wound healing response which interferes with normal organ function. Fibrosis formation includes interaction between many cell types and cytokines, and when the balance becomes profibrotic, there is fibrosis formation. Fibrosis is similar to the process of scarring, in that both involve stimulated fibroblasts laying down connective tissue, including collagen and glycosaminoglycans. The process is initiated when immune cells such as macrophages release soluble factors that stimulate fibroblasts. The most well characterized pro-fibrotic mediator is TGFβ which is released by macrophages as well as any damaged tissue between surfaces called interstitium. Fibrotic conditions, as defined herein, are selected from the group consisting of: pulmonary fibrosis which includes both cystic and idiopathic pulmonary fibrosis; cirrhosis of the liver; glial scarring in the brain, arthrofibrosis in the knee, shoulder and other joints, retroperitoneal fibrosis, systemic sclerosis (scleroderma), and in particular kidney fibrosis leading to chronic kidney disease (CKD). Fibrosis is a progressive degenerative disorder of the blood vessels, skin, lungs, kidneys, heart and GI tract and until the present is considered an irreversible process and has classically been treated by anti-inflammatory and immunosuppressive agents, which many times causes harm.

Chronic Kidney Disease (CKD), as described herein, involves a loss of functional kidney tissue due to a prolonged, progressive fibrotic process. Dramatic changes in kidney structure may be seen, although structural and functional changes in the kidney are only loosely correlated. Disease is usually present for many months or years before it becomes clinically apparent, and it is invariably irreversible. Many causes of CKD are associated with progressive interstitial fibrosis. The severity of interstitial fibrosis is positively correlated to the magnitude of decline in GFR and negatively correlated with the prognosis. The glomerular, tubulointerstitial, and vascular lesions found in animals with generalized CKD are often similar, regardless of the initiating cause. TGFβ has been described as the most important pro-fibrotic mediator responsible for myofibroblast activation. It drives a convergent pathway that integrates the effects of many other fibrogenic factors. TGFβ1 is the most abundant isoform and is synthesized by all cell types of the kidney. TGFβ, as well as functioning as a profibrotic cytokine as discussed, is also an abundant bone matrix protein that influences the formation, function and cell-cell interactions of osteoblasts and osteoclasts to control bone remodeling and maintain adequate bone mass and it has been shown that TGFβ inhibition is a potential mechanism for decreasing bone demineralization during SRHP due to CKD.

"Treatment" "treating", and the like refers to both therapeutic treatment and prophylactic or preventative measures. Animals in need of treatment include those already with the disorder as well as those in which the disorder is to be prevented from starting or progressing. Treatment may also be described as delaying the onset or delaying the severity of the onset of symptoms or condition. The term "treatment" or "treating" of a disease or disorder includes preventing or protecting against the disease- or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

Before the present methods are described, it is to be understood that this invention is not limited to particular methods, and experimental conditions described, as such methods and conditions may vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

The invention disclosed herein concerns antigen binding proteins (used interchangeably with the terms "antibodies", "antagonist antibodies" "antibody fragments" and the like, as described herein), that specifically bind to one or more of the TGFβ proteins and in particular antibodies, whether it be canine, feline, murine, human or any other species, caninized, felinized, humanized or any other speciated antibodies produced by recombinant methods, hybridoma technologies or phage display technology or fully speciated monoclonal antibodies that specifically binds to TGFβ31 and TGFβ2 or TGFβ3 thus preventing TGFβ from binding to the TGFβRII receptors, thus serving as an antagonist in that the signaling pathway is prevented from being activated by one of the TGFβ proteins. In one embodiment the present invention provides an antibody that binds only to TGFβ1 with or without TGF02 or TGFβ3. In one embodiment the present invention provides an antibody that binds to TGFβ1 and TGFβ3. In one embodiment the present invention provides an antibody that binds to TGFβ1 and TGFβ2 and TGFβ3.

While the properties of antibodies make them very attractive therapeutic agents, there are a number of limitations. The vast majority of monoclonal antibodies (mAbs) are of rodent origin, as previously noted. When such antibodies are administered in a different species, patients/subjects can mount their own antibody response to such xenogenic antibodies. Such response may result in the eventual neutralization and elimination of the antibody. As described above mice are used extensively in the production of monoclonal antibodies, although production of antibodies is not limited to mice. Species such as canines can be immunized with an antigen and antibodies recovered and characterized One problem in the using of antibodies produced by a particular species, for example if originally generated in a mouse, is that a non-murine subject being treated with said antibodies react to the mouse antibodies as if they were a foreign substance thus creating a new set of antibodies to the mouse antibodies. Mouse antibodies are "seen" by the non-murine, for example, the canine (or any other non-murine species), immune system will "see" a xenogenic antibody as foreign and may then mount an immune response against the molecule. Those skilled in the field will recognize the need to be able to treat a subject with an antigen specific antibody but have that antibody species specific for use. Part of the reaction generated from cross species antibody administration, for example a mouse monoclonal antibody being administered to a canine, can range from a mild form, like a rash, to a more extreme and life-threatening response, such as renal failure. This immune response can also decrease the effectiveness of the treatment or create a future reaction if the subject is given a subsequent treatment containing mouse antibodies. Accordingly, as set forth in the present invention set forth to overcome this disadvantage by "caninization" or "felinizing" of the antibody of the invention. In particular this process focuses on the framework regions of the immunoglobulin variable domain but could also include the complementarity determinant regions (CDR's) of the variable domain. The enabling steps and reduction to practice for this process are described in this disclosure and the process of affinity maturation around the sequences of the CDRs is well known in the field.

The process of modifying a monoclonal antibody (antigen binding protein, antagonist antibody etc as described herein and terms used interchangeably) from an animal to render it less immunogenic for therapeutic administration to a different species has been aggressively pursued and has been described in a number of publications (e.g. Antibody Engineering: A practical Guide. Carl A. K. Borrebaeck ed. W.H. Freeman and Company, 1992). However, this process has not been routinely applied for the development of therapeutic or diagnostics for non-humans until recently. In fact, very little has been published with regard to canine, feline, or other species-specific variable domains at all. Wasserman and Capra, *Biochem.* 6, 3160 (1977), determined the amino acid sequence of the variable regions of both a canine heavy chain. Wasserman and Capra, Immunochem. 15, 303 (1978), determined the amino acid sequence of the K light chain from a canine IgA. McCumber and Capra, *Mol. Immunol.* 16, 565 (1979), disclose the complete amino-acid sequence of a canine mu chain. Tang et al., *Vet. Immunology Immunopathology* 80, 259 (2001), discloses a single canine IgG-A y chain cDNA and four canine IgG-A y chain protein sequences. Bergeron et al. describes the functional properties of the four canine heavy chains. To this point the paucity of information available on canine antibodies has prevented their development as therapeutics for the treatment canine disease.

These noted limitations have prompted the development of engineering technologies known as "speciation" that is well known to those in the art in terms of "humanization" of therapeutic antibodies. The "caninization", "felinization", "humanization" of antibodies are a few examples of the technique of "speciation", These molecules are generated as antibodies or fragments which contain minimal sequence derived from non-target immunoglobulin. As an example, caninized antibodies ("target species antibody") in which residues from a complementarity determining region (CDR) of the recipient/target are replaced by residues from a CDR of a non-target species (i.e. "donor antibody" or "originating species antibody") such as mouse, having the desired properties such as specificity, affinity, and potency. This strategy is based on identifying the most appropriate target (germline antibody sequence for CDR grafting). Following extensive analysis of all available germline sequences for both the variable heavy and light chain, germline candidates are selected based on their homology to the mouse/donor mAbs, and the CDRs from the mouse/donor progenitor mAbs were used to replace native canine CDRs. The objective is always to retain high affinity and eventual in vivo efficacy if being used as a therapeutic. Using canine antibody frameworks will generally minimize the potential of immunogenicity in vivo when administered to a dog. In some instances, however, framework region (FR) residues of the canine immunoglobulin are replaced by corresponding non-canine residues when reduced affinity or function is observed. Back mutation of selected target framework residues to the corresponding donor residues might be required to restore and or improved affinity, as noted. Structure-based methods may also be employed for caninization and affinity maturation. as described in U.S. Pat. No. 7,261,890. The above description uses canine as the target species and mouse as the donor species. Speciated antibodies are not limited to these targets and donors. Felines, and the like can be used as target species.

Another challenge for developing therapeutic antibodies targeting proteins is that epitopes on the homologous protein in a different species are frequently different, and the potential for cross-reactivity with other proteins is also different. As a consequence, antibodies have to be made, tested and developed for the specific target in the particular species to be treated. Antibody binding between homologous targets in different species is unpredictable and requires testing and evaluation of efficacy.

Antibodies target an antigen through its binding of a specific epitope on an antigen by the interaction with the variable region of the antibody molecule. Furthermore, antibodies have the ability to mediate, inhibit (as in the case of the antagonistic anti-TGFB antigen binding protein of the present invention) and/or initiate a variety of biological activities. There are a wide range of functions for therapeutic antibodies, for example, antibodies can modulate receptor-ligand interactions as agonists or antagonists. Antibody binding can initiate intracellular signaling to stimulate cell growth, cytokine production, or apoptosis. Antibodies can deliver agents bound to the Fc region to specific sites. Antibodies also elicit antibody-mediated cytotoxicity (ADCC), complement-mediated cytotoxicity (CDC), and phagocytosis through the binding of the Fc region of the antibody to respective molecules in the cell which elicit ADCC, CDC etc. There are also antibodies that have been altered where the ADCC, CDC, C1q binding and phagocytosis functions have been eliminated. In one embodiment, the present invention provides an antigen binding protein comprising alterations in the Fc region of the antibody that alters effector function of said antibody. The present invention further provides cells and cell lines expressing antibodies of the invention. Representative host cells include bacterial, yeast, mammalian and human cells, such as CHO cells, HEK-293 cells, HeLa cells, CV-1 cells, and COS cells. Methods for generating a stable cell line following transformation of a heterologous construct into a host cell are well known in the art. Representative non-mammalian host cells include insect cells (Potter et al. (1993) Int. Rev. Immunol. 10(2-3):103-112). Antibodies may also be produced in transgenic animals (Houdebine (2002) Curr. Opin. Biotechnol. 13(6):625-629) and transgenic plants (Schillberg et al. (2003) Cell Mol. Life Sci. 60(3):433-45).

As discussed above, monoclonal, chimeric, species specific and speciated antibodies, which have been modified by, ex., deleting, adding, or substituting other portions of the antibody, ex. the constant region, are also within the scope of the invention. For example, an antibody can be modified as follows: (i) by deleting the constant region; (ii) by replacing the constant region with another constant region, ex., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others. In one embodiment of the present invention the antibody of the invention comprises an altered Fc region that alters effector function of the antibody. In some embodiments of the present invention the Fc region of the antigen binding protein of the invention has been replaced, modified or removed.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see ex., EP388151 A1, U.S. Pat. Nos. 5,624,821 and 5,648,260, the contents of all of which are hereby incorporated by reference).

For example, it is possible to alter the affinity of an Fc region of an antibody for an FcR (ex. Fc.gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see ex., U.S. Pat. No. 5,624,821). The antibody or binding fragment thereof may be conjugated with a cytotoxin, a therapeutic agent, or a radioactive metal ion. In one embodiment, the protein that is conjugated is an antibody or fragment thereof. A cytotoxin or cytotoxic agent includes any agent that is detrimental to cells. Non-limiting examples include, calicheamicin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs, or homologs thereof. Therapeutic agents include, but are not limited to, antimetabolites (ex., methotrexate, 6-mercaptopurine, 6-thioguanine, cytarabine, and 5-fluorouracil decarbazine), alkylating agents (ex., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP), cisplatin), anthracyclines (ex., daunorubicin and doxorubicin), antibiotics (ex., dactinomycin, bleomycin, mithramycin, and anthramycin), and anti-mitotic agents (ex., vincristine and vinblastine). Techniques for conjugating such moieties to proteins are well known in the art.

Compositions, Derived Compositions, and Methods of Making the Compositions

This invention encompasses compositions, including pharmaceutical compositions, comprising antigen binding proteins ("antibodies", "antibody fragments", "antagonist antibodies" and the like as used interchangeably herein), polypeptides and polynucleotides comprising sequences encoding antigen binding proteins or polypeptides of the invention.

As used herein, compositions comprise one or more antibodies, antigen binding proteins or polypeptides (which may or may not be an antibody) that bind to one or more of the TGFB proteins, and/or one or more polynucleotides comprising sequences encoding one or more antibodies or polypeptides that bind to one or more of the TGFB proteins. These compositions may further comprise suitable excipients, such as pharmaceutically/veterinary acceptable excipients including buffers, which are well known in the art. The invention also encompasses isolated antibody, polypeptide and polynucleotide embodiments. The invention also encompasses substantially pure antibody, polypeptide and polynucleotide embodiments.

In one or more embodiment, the present invention provides for novel antigen binding proteins that specifically bind to one or more of the TGF3 proteins. In one or more embodiments, the antigen binding protein is defined as an antibody or antibody fragment. In one or more embodiments, the antigen binding protein is fully canine, fully feline, feline, fully human, caninized, felinized or humanized. In one or more embodiments, the antigen binding protein of the present invention binds to one or more of the canine, feline or human TGFβ proteins. In one embodiment, the antigen binding protein is a monoclonal antibody. In one embodiment, a monoclonal antibody of the invention binds to one or more of the TGFβ and prevents its binding to, and activation of, its receptors, thus preventing the signaling cascade as described herein.

In one or more embodiments, the present invention provides an isolated and recombinant antigen binding protein that binds to one or more of the TGFβ proteins, wherein the variable heavy chain comprises amino acid sequence having at least about 85%, 86%, 87%, 88%, 89%, 90%, 91%, 92%, 93%, 94%, 95%, 96%, 97%, 98% or 99% sequence identity to the amino acid sequence of the antigen binding protein of the invention as described herein and wherein the variable light chain comprises amino acid sequence having at least about 85%, 86%, 87%, 88%, 89%, 90%, 91%, 92%, 93%, 94%, 95%, 96%, 97%, 98% or 99% sequence identity to the amino acid sequence comprising the antigen binding protein of the invention as described herein and any variants thereof having one or more conservative amino acid substitutions in at least one of CDR1, CDR2 or CDR3 within any of the variable light or variable heavy chains of said antigen binding protein.

The present invention provides for recombinant antigen binding proteins, in some embodiments described herein, monoclonal antibodies, and antibody fragments and their uses in clinical administrations and scientific procedures, including diagnostic procedures. With the use of methods of molecular biology and recombinant technology, it is possible to produce an antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, how they are constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3-dimensional structure. This structure is often given as H2L2 and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

The present invention further provides a vector including at least one of the nucleic acids described above. Because of the degeneracy of the genetic code, more than one codon can be used to encode a particular amino acid. Using the genetic code, one or more different nucleotide sequences can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an anti-TGFB antibody or portion. Such "codon usage rules" are disclosed by Lathe, et al., 183 *J. Molec. Biol.* 1-12 (1985). Using the "codon usage rules" of Lathe, a single nucleotide sequence, or a set of nucleotide sequences that contains a theoretical "most probable" nucleotide sequence capable of encoding anti-TGFB sequences can be identified. It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-TGFB antibodies or peptides.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (251,1311), carbon (4C), sulfur (35S), indium, tritium ($H^3$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (ex., by lengthening the time to clearance from the blood stream. Such techniques include, for example, adding PEG moieties (also termed pegilation), and are well-known in the art. See U.S. Patent. Appl. Pub. No. 20030031671.

Recombinant Expression of Antibodies

In some embodiments, the nucleic acids encoding the antigen binding protein of the invention are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing. Traditionally, monoclonal antibodies have been produced as native molecules in murine hybridoma lines. In addition to that technology, the present invention provides for recombinant DNA expression of monoclonal antibodies. This allows the production of said antibodies, as well as a spectrum of antibody derivatives and fusion proteins in a host species of choice.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in-which the regulatory DNA sequences and the DNA sequence sought to be expressed are connected in such a way as to permit gene expression as anti-TGFβ antigen binding proteins or antibody fragments in recoverable amounts. The precise nature of the regulatory regions needed for gene expression may vary from organism to organism, as is well known in the analogous art.

The present invention accordingly encompasses the expression of an anti-TGF3 antigen binding protein or, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used without limitation.

The expression vector carrying a chimeric, speciated antigen binding protein construct or anti-TGFB antigen binding protein of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et at, 240 *Science* 1538 (1988) or other techniques known to one of skill in the art without limitation For long-term, high-yield production of recombinant antibodies, stable expression may be used. For example, cell lines, which stably express the antibody molecule may be engineered. Rather than using expression vectors which contain origins of replication, host cells can be transformed with immunoglobulin expression cassettes and a selectable marker. Following the introduction of the foreign DNA, engineered cells may be allowed to grow in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once the antibody of the invention has been produced, it may be purified by any method known in the art for purification of an immunoglobulin molecule, for example but without limitation, by chromatography (ex. ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical and Veterinary Applications

The anti-TGF3 antigen binding protein or antibody fragments of the invention as described herein can be used for example in the treatment of TGFβ related disorders in canines and felines. More specifically, the invention further provides for a pharmaceutical composition comprising a pharmaceutically acceptable carrier or diluent and, as active ingredient, an antibody or antibody fragment per the invention. The antibody can be a chimeric, heterochimeric, caninized, felinized, humanized or speciated antigen binding protein to accommodate a different species. Intact immunoglobulins or their binding fragments, are also envisioned. The antibody and pharmaceutical compositions thereof of this invention are useful for parenteral administration, ex., subcutaneously, intramuscularly or intravenously.

In some desired embodiments, the antibodies of the invention are administered by parenteral injection. For parenteral administration, anti-TGFβ antibodies or fragments can be formulated as a solution, suspension, emulsion or lyophilized powder in association with a pharmaceutically acceptable parenteral vehicle. For example, the vehicle may be a solution of the antibody or a cocktail thereof dissolved in an acceptable carrier, such as, but not limited to, an aqueous carrier such vehicles are water, saline, Ringer's solution, dextrose solution, trehalose or sucrose solution, or serum albumin, glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (ex., sodium chloride, mannitol) and chemical stability (ex., buffers and preservatives). The formulation is sterilized by commonly used techniques. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate. The antibody compositions of the present invention may provide a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art among other references well known to those of skill in the art. In therapeutic application, compositions are administered to a subject already suffering from a disease or condition, in an amount sufficient to cure or at least partially arrest or alleviate the disease or conditions and its complications. An amount adequate to accomplish this is defined as a "therapeutically effective dose" or a "therapeutically effective amount".

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of TGFβ-related pathologies in dogs and cats can be provided in the dosage range as needed. Example antibodies for canine or feline therapeutic use are high affinity antibodies, and fragments, regions and derivatives thereof having potent in vivo anti-TGFB activity, according to the present invention. Single or multiple administrations of the compositions can be carried out with dose levels and pattern being selected by the treating veterinarian. In any event, the pharmaceutical formulations should provide a quantity of the antibody(ies) of this invention sufficient to effectively treat the subject.

Diagnostic Applications

The present invention also provides the above anti-TGFB antibodies for use in diagnostic methods for detecting TGFβ in species, particularly canines, felines or humans known to be or suspected of having an TGFβ related disorder. Anti-TGFB antibodies of the present invention are useful for immunoassays which detect or quantitate one or more TGFB, or anti-TGFB antibodies, in a sample. An immunoassay for TGFβ typically comprises incubating a clinical or biological sample in the presence of a detectably labeled high affinity (or high avidity) anti-TGFB antibody of the present invention capable of selectively binding to TGFβ and detecting the labeled peptide or antibody which is bound in a sample. Various clinical assay procedures are well known in the art. Such samples include tissue biopsy, blood, serum, and fecal samples, or liquids collected from animal subjects and subjected to ELISA analysis as known to those of skill in the art.

"Solid phase support" or "carrier" refers to any support capable of binding peptide, antigen, or antibody. Well-known supports, or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to one or more TGFβ proteins or an anti-TGFβ antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation. Well known method steps can determine binding activity of a given lot of an anti-TGFB peptide and/or antibody or antigen binding protein. Those skilled in the art can determine operative and optimal assay conditions by routine experimentation.

Detectably labeling an TGFβ-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example but not limited to, spectrophotometric, fluorometric or by visual means. Enzymes which can be used to detectably label the TGFβ-specific antibodies of the present invention include, but are not limited to, malate dehydrogenase, staphylococcal nuclease, delta5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. By radioactively labeling the TGFβ-specific antibodies, it is possible to detect TGFB through the use of a radioimmunoassay (RIA). The radioactive isotope can be detected by such means as the use of a gamma counter or a scintillation counter or by autoradiography. Isotopes which are particularly useful for the purpose of the present invention include: $^{3}H$, $^{125}I$, $^{131}I$, $^{35}S$ and $^{14}C$.

It is also possible to label the TGFβ-specific antibodies with a fluorescent compound. When the fluorescent labeled antibody is exposed to light of the proper wavelength, its presence can then be detected due to fluorescence. Among the most commonly used fluorescent labeling compounds are fluorescein isothiocyanate, ~rhodamine, phycoerythrin, phycocyanin, allophycocyanin, o-phthaldehyde and fluorescamine among those known to those of skill in the art. The TGFβ-specific antibodies or antigen binding proteins can also be delectably labeled using fluorescence-emitting metals such a $^{125}Eu$, or others of the lanthanide series. These metals can be attached to the TGFβ specific antibody using such metal chelating groups as diethylenetriaminepentaacetic acid (DTPA) or ethylenediamine-tetraacetic acid (EDTA).

The TGFβ-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the TGFβ-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the TGFβ-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the TGFβ which is detected by the above assays can be present in a biological sample. Any sample containing TGFβ may be used. For example, the sample is a biological fluid such as, for example, blood, serum, lymph, urine, feces, inflammatory exudate, cerebrospinal fluid, amniotic fluid, a tissue extract or homogenate, and the like as well as any biopsy related material. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of TGFB but also the distribution of TGFβ in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid phase antibody, antigen, and labeled antibody.

The antibodies may be used to quantitatively or qualitatively detect one or more TGFβ proteins in a sample or to detect presence of cells that express one or more of the TGFβ proteins. This can be accomplished by immunofluorescence techniques employing a fluorescently labeled antibody (see below) coupled with fluorescence microscopy, flow cytometric, or f1uorometric detection. For diagnostic purposes, the antibodies may either be labeled or unlabeled. Unlabeled antibodies can be used in combination with other labeled antibodies (second antibodies) that are reactive with the antibody, such as antibodies specific for canine immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art. Importantly, the antibodies of the present invention may be helpful in diagnosing a TGFB related disorder in canines, felines, humans and the like. More specifically, the antibody/antigen binding protein of the present invention may identify the overexpression of TGFβ in companion animals. Thus, the antibody of the present invention may provide an important immunohistochemistry tool. The antibodies of the present invention may be used on antibody arrays, highly suitable for measuring gene expression profiles and other diagnostic tools well known to those of skill in the art.

Kits

Also included within the scope of the present invention are kits for practicing the subject methods. The kits at least include one or more of the antibodies of the present invention, a nucleic acid encoding the same, or a cell containing the same. An antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, ex., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about, 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use Before the present methods are described, it is to be understood that this invention is not limited to particular methods, and experimental conditions described, as such methods and conditions may vary yet are well known to those of skill in the art. It is also to be understood that the terminology used herein is for the purpose of describing particular embodiments only and is not intended to be limiting. The invention will now be described further by the non-limiting examples below.

EXAMPLES

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

Example 1

Anti-TGFβ 1,3 Antibody

Identification of a Mouse Monoclonal Antibody Recognizing Canine TGFβ 1

AJ, CF-1, and BalbC mice were immunized according to a standard RIMMS protocol with a combination of amphibian and trout TGFβ1 formulated with freunds complete then incomplete adjuvant. Following vaccination, serum antibody titers from immunized animals were determined using an enzyme linked immunosorbent assay (ELISA). Individual ELISAs were run to determine the antibody titer to the individual immunogens and to probe for the cross-reactive antibody response to canine TGFβ1 Canine TGFβ1, SEQ ID NO.220 (50 ng/well) or a mixture of amphibian and trout TGFβ1 (100 ng/well) were immobilized to polystyrene microplates and used as a capture antigen. Serum from immunized animals was diluted in phosphate buffered saline with 0.05% tween-20 (PBST). The presence of anti-TGFβ1 antibodies was detected with goat anti-mouse secondary antibody labeled with horseradish peroxidase (HRP) (KPL, Inc., Gaithersburg, MD). Following addition of a chromogenic substrate (SureBlue Reserve TMB 1-Component Microwell Peroxidase Substrate, KPL, Inc., Gaithersburg, MD) and a ten-minute incubation at room temperature (RT) the reaction was stopped with the addition of 100 μL of 0.1 N HCl. The absorbance of each well was determined at an optical density (OD) of 450 nm. Under these circumstances all groups of animals showed a robust response to their respective immunogen however failed to generate an immune response directed against the canine form of TGFβ1. The highest response was exemplified by the CF-1 group whose titers were 1:31250 for all three animals (data not shown).

In an effort to overcome possible self-tolerance due to the conserved nature of TGFβ3 across species, canine TGFβ1 (SEQ ID NO.220) was conjugated to a carrier protein which is an inactive mutant (non-toxic) form of diphtheria toxin (CRM197) using standard cross-linking chemistry to create an immunogen referred to herein as TGFβ1-CRM. Two additional immunizations with TGFβ1-CRM were carried out using mice from the AJ and CF-1 groups two weeks apart. These efforts again did not result in any of the mice mounting an immune response to the canine TGFβ1 protein as assessed by ELISA, as described above.

A final strategy giving two additional doses, two weeks apart, of alum-adjuvanted TGFβ1-CRM by intra-peritoneal (IP) injection was undertaken. These efforts yielded a single mouse having a sufficient titer to perform a fusion. A pool of donor splenocytes from this mouse were used for fusion and the results of the primary screen to detect anti-TGFβ1 antibodies resulted in eight wells being chosen for expansion and secondary screening. Secondary screening confirmed that five fusions retained the ability to produce anti-TGFβ1 antibodies. Exhausted supernatants from 15 ml cultures were purified using protein A/G resin to obtain enriched population of IgGs for further evaluation.

DNA sequences Encoding Mouse Antibody 04H09

Ribonucleic acid (RNA) was isolated from 04H09 hybridoma cells using the RNeasy-mini kit (Qiagen, Inc., Germantown, MD) and the manufacturer's protocol. Briefly, one million frozen cells were harvested by centrifugation and RNA was purified from cell lysates using the RNeasy spin column. RNA was eluted from each column and used immediately for quantitation and cDNA preparation. The RNA was analyzed for yield and purity by measuring its absorbance at 260 nm and 280 nm using a GeneQuant pro spectrophotometer (GE Healthcare, Uppsala, Sweden). Following isolation, the remaining RNA was stored at −80° C. for further use.

Oligonucleotide primers designed for amplification of the mouse immunoglobulin (Ig) variable domains were used according to the manufacturer's instructions (EMD Chemicals, Inc., Gibbstown, NJ). cDNA was prepared from total hybridoma RNA by reverse transcription (RT) using the thermoscript RT kit (Invitrogen Corp., Carlsbad, CA) according to the manufacturer's instructions. Briefly, 200-400 ng of RNA was added to an individual reaction tube containing a 3' Ig constant region primer, which hybridizes to the Ig gene at a position proximal to the variable Ig region, and thus will transcribe first strand cDNA representing the variable region of the mouse antibody. An individual RT reaction was performed using a 3' constant heavy chain primer and 3' constant kappa light chain primer.

These cDNAs from the 04H09 hybridoma were used as a template in polymerase chain reactions (PCR) to amplify the variable IgG heavy and kappa light chain cDNA for the purpose of sequence determination. Multiple reactions were performed for each PCR using a degenerate 5' primer or primer pools designed to anneal to the signal sequence-coding regions of the mouse Ig variable domain. Separate PCR reactions were performed with a degenerate primer or primer pools for amplification of murine variable heavy and variable light chain regions. PCR was performed with 1 ul of the cDNA reaction using the Expand High Fidelity DNA polymerase kit (Roche Diagnostics Corp., Indianapolis, IN) according to the manufacturer's protocol. Thermocycling parameters for the PCR were as follows; 94° C. for 2 min., 35 cycles (94° C. 15 sec., 55° C. 30 sec., 72° C. 1 min.), 72° C. 7 min. Fragments amplified from the PCR were separated by gel electrophoresis on a 1% agarose gel and purified using Qiagen gel extraction kit (Qiagen, Inc., Germantown, MD). Forward primers for the heavy and light chain variable region incorporate EcoRI or SalI cleavage sites, and reverse primers incorporate HindIII cleavage sites to facilitate cloning into the pUC19 plasmid. Purified PCR fragments and pUC19 plasmid were digested with the above restriction endonucleases (New England Biolabs (NEB), Inc., Ipswich, MA) at 37° C. for 1-2 hrs. Following digestion, PCR fragments were purified using a Qiaquick PCR cleanup kit (Qiagen, Inc., Germantown, MD). Digested plasmid was separated by gel electrophoresis on a 1% agarose gel and purified using Qiagen gel extraction kit. Purified PCR fragments representing variable IgG heavy and kappa light chain DNA were ligated into pUC19 plasmid using T4 DNA ligase and ligation buffer (NEB, Inc., Ipswich, MA) at 4° C. overnight. 3 ul of each ligation reaction was used to transform *E. coli* TOP10 cells (Invitrogen Corp., Carlsbad, CA).

Plasmids were isolated from positive clones representing the variable regions of each hybridoma using a Qiagen mini prep kit (Qiagen 27106) according to the manufacturer's protocol. M13 forward and reverse primers were used to amplify DNA sequence for each cloned insert using the BigDye sequencing reaction (Applied Biosystems by Life Technologies Corp., Carlsbad, CA) according to manufacturer's protocol. Sequencing reactions were purified using a 96 well purification kit (Zymo Research, Irvine, CA) according to the manufacturer's protocol. Samples were loaded onto an ABI-3730 capillary sequencer and resulting sequence traces were analyzed using Sequencher (Gene-Codes v. 4.2) for presence of complete open reading frames. The murine anti-TGFβ variable sequences determined for antibody 04H09 are as follows:

SEQ ID NO: 1: 04H09 VH nucleotide sequence;
SEQ ID NO: 2: 04H09 VH amino acid sequence;
SEQ ID NO: 3: 04H09 VL nucleotide sequence;
SEQ ID NO: 4: 04H09 VL amino acid sequence.

Further, the six CDRs for the 04H09 monoclonal antibody are as follows:

TABLE 1

| SEQ ID NO: | Description | Amino Acid Sequence |
|---|---|---|
| 5 | 04H09 heavy chain CDR #1 (CDR-H1) | SSWMN |
| 6 | 04H09 heavy chain CDR #2 (CDR-H2) | QIYPGDGDTNYNGKFKG |
| 7 | 04H09 heavy chain CDR #3 (CDR-H3) | ARHYDGSTDY |
| 8 | 04H09 light chain CDR #1 (CDR-K1) | RASENIYSNLA |
| 9 | 04H09 light chain CDR #2 (CDR-K2) | AATNLAD |
| 10 | 04H09 light chain CDR #3 (CDR-K3) | QHFWGTPYT |

Construction of Recombinant Mouse: Canine Chimeric 04H09

Antibody variable domains are responsible for antigen binding, and therefore grafting of the full variable domain of the 04H09 antibody onto a different constant region, for example a constant region from a different species, should have little or no impact on the antibody's ability to bind the canine TGFβ1 immunogen. As such, expression vectors were designed to produce recombinant chimeric or fully canine antibodies in mammalian expression systems. Chimeric antibodies described herein consist of the variable sequence (both CDR and framework) from the host species antibody grafted onto the respective heavy and light constant regions of an IgG molecule from a different species. For example, the variable region could be from a mouse host species, e.g., SEQ ID NOS: 2 and 4 of 04H09, and the heavy chain constant region from a canine species (SEQ ID NO.127), which would be referred to herein as a mouse: canine chimera. To produce the desired chimeric antibodies, synthetic DNA sequences were constructed for the variable heavy (VH) and variable light (VL) sequences of selected antibodies which contain unique restriction endonuclease sites, Kozak consensus sequence and, an N-terminal secretion leader to facilitate expression and secretion of the recombinant antibody from a mammalian cell line.

For the mouse: canine 04H09 chimera, referred to herein as chi04H09, each mouse variable region (SEQ ID NOS: 1 and 3) was cloned into a mammalian expression plasmid containing either the canine IgG heavy (SEQ ID NO: 127) or light chain (SEQ ID NO: 129) constant regions The plasmids encoding each heavy and light chain, under the control of the CMV promoter, were co-transfected into HEK 293 cells using standard methods. Following six days of expression, chimeric mAbs were purified from 50 ml of transiently transfected HEK293FS cell supernatants using MabSelect Sure protein A resin (GE Healthcare, Uppsala, Sweden) according to standard methods for protein purification. Eluted fractions were neutralized, concentrated to −0.5-1.0 mL using a 10,000 nominal MW cutoff Amicon Ultra centrifugal device (Millipore Sigma, Burlington, MA), dialyzed overnight at 4° C. in 20 mM sodium Acetate pH 5.0, 85 g/L sucrose, +/−0.05 g/L EDTA, and stored at 4° C. for further use.

Affinity and cell-based potency of 04H09 and chi04H09 were assessed using surface plasmon resonance (SPR) To characterize the affinity with which candidate monoclonal antibodies (mAbs) bind TGFβ, surface plasmon resonance (SPR) was evaluated using a Biacore T200 system (Biocore Life Sciences (GE Healthcare), Uppsala, Sweden). To avoid affinity differences associated with differential surface preparation that can occur when immobilizing antibodies to surfaces, TGF01, TGFβ2, and TGFβ3 (R&D Systems) were directly conjugated to the individual surface. Immobilization was obtained by amine coupling 5 μg/mL using N-hydroxysuccinimide (NHS)/1-Ethyl-3-(3-dimethylaminopropyl) carbodiimide (EDC) chemistry. Chips were quenched with ethanolamine and the affinity with which all candidate mAbs bound to the immobilized TGFβ was evaluated. All curves were fit to a 1:1 model. Affinities $<10^{-1}$ are below the lower limit of quantitation of detection for the instrument. This resulted in the identification of a single mouse antibody, referred to as 04H09, having a range of affinity to TGFβ1>TGFβ3>TGFβ2 (see KD data in Table 3 below). Mouse anti-TGFβ 04H09 was furthered subcloned to generate a hybridoma producing homogeneous antibody and for sequencing of the variable heavy and light chains.

To assay for potency a primary bell-based assay measuring inhibition of TGFβ1-induced SMAD3 phosphorylation in canine mitral valve interstitial cells (CMVICs). For this assay, TGFβ1, 2, or 3 was added to the cells with or without antibody and SMAD3 signaling was determined via AlphaLISA detection kit. The affinity of both the mouse (04H09) and chimeric (chi04H09) forms of the anti-TGFβ antibody to TGFβ1, 2, and 3 surfaces and potency of each antibody are shown in Table. 3 (below) (KD data and CMVIC data, respectively).

These observations indicate that conversion to the chimeric form results in some loss in affinity to all three isoforms: However, they also show a gain in potency through blockade of TGFβ1 and 3 mediated pSmad signaling in CMVIC cells (compare CMVIC data for 04H09 and chi04H09 in Table 3). These results are likely due to the higher level of homogeneity and purity for the recombinant mouse: canine chimera compared to the purified material from the mouse hybridoma subclone. Blockade of TGF01 and 3 was encouraging and resulted in further work at pursuing a caninized form of this antibody.

Caninization of Antibody 04H09

The generation of anti-drug antibodies (ADAs) can been associated with loss of efficacy for any biotherapeutic protein, including monoclonal antibodies. Speciation of monoclonal antibodies can reduce the propensity for mAbs to be immunogenic, although examples of immunogenic fully human mAbs and non-immunogenic chimeric mAbs can be found. To help mitigate risks associated with ADA formation for the 04H09 monoclonal antibody provided herein, a caninization strategy was employed. This caninization strategy is based on identifying the most appropriate canine germline antibody sequence for CDR grafting.

Following extensive analysis of available canine germline sequences for both the variable heavy and light chains, germline candidates were selected based on their homology to the framework regions of the mouse 04H09 antibody variable regions, and the CDRs from the mouse progenitor 04H09 antibody (SEQ ID NOS: 5-10) were used to replace native canine CDRs. The objective was to retain high affinity and cell-based activity using canine antibody frameworks to minimize the potential of immunogenicity in vivo.

Synthetic nucleotide constructs representing the caninized variable heavy and light chains for the 04H09 antibody were made. Caninization efforts with mouse antibody 04H09 focused on three canine VH frameworks and four canine VL frameworks, as follows:

TABLE 2

| Alias | Heavy or light chain | SEQ ID NO for Nucleic acid | SEQ ID NO for Amino Acid |
|---|---|---|---|
| can04H09-VH1 | Heavy | 11 | 12 |
| can04H09-VH2 | Heavy | 13 | 14 |

TABLE 2-continued

| Alias | Heavy or light chain | SEQ ID NO for Nucleic acid | SEQ ID NO for Amino Acid |
|---|---|---|---|
| can04H09-VH3 | Heavy | 15 | 16 |
| can04H09-VL1 | Light | 17 | 18 |
| can04H09-VL2 | Light | 19 | 20 |
| can04H09-VL3 | Light | 21 | 22 |
| can04H09-VL4 | Light | 23 | 24 |

Following subcloning of each variable chain into plasmids containing the respective canine heavy (SEQ ID NO: 127) or light (kappa) constant region (SEQ ID NO: 129) plasmids were co-transfected for antibody expression in HEK 293 cells in all twelve possible combinations (can04H09 VH1NL1, can04H09 VH1NL2, can04H09 VH1NL3, can04H09 VH1NL4, can04H09 VH2NL1, can04H09 VH2NL2, can04H09 VH2NL3, can04H09 VH2NL4, can04H09 VH3NL1, can04H09 VH3NL2, can04H09 VH3NL3, and can04H09 VH3NL4). All combinations were capable of producing antibody transiently except for any heavy chains paired with can04H09-VL2

Following expression, the caninized mAbs were characterized for their affinity to bind canine TGFβ1, 2, and 3 in addition to evaluating their potency in cell-based assays, as described above (Please refer to data in Table 3 below). In general, all combinations of canine frameworks with grafted 04H09 CDRs resulted in comparable affinities to canine TGFβ 2 and 3. The most dramatic loss in affinity was observed to TGFβ1 with antibodies can04H09 VH1NL1, can04H09 VH2/VL1, and can04H09 VH3NL1. As observed with the conversion of mouse 04H09 to chi04H09, caninization had a variable effect on the potency of each antibody with respect to cellular pSmad signaling in response to each TGFβ isoform. Similar to mouse 04H09 and chi04H09, none of the framework combinations resulted in activity against TGFβ2 mediated cellular signaling. With the exception of the canine VL2 framework, a representative pairing from each heavy and light canine framework produced an antibody capable of inhibiting signaling induced by TGFβ1 and 3. Together these data indicate that the CDRs from mouse antibody 04H09 form a robust combination with candidate canine frameworks and speciation can be accomplished without any modifications to canine germline sequences to retain the binding and potency phenotype.

TABLE 3

| Alias | KD [M] TGFβ1 | KD [M] TGFβ2 | KD [M] TGFβ3 | CMVIC pSmad-3, IC50 [nM] TGFβ1 | CMVIC pSmad-3, IC50 [nM] TGFβ2 | CMVIC pSmad-3, IC50 [nM] TGFβ3 |
|---|---|---|---|---|---|---|
| 04H09 (mouse) | 4.43E−11 | 7.13E−09 | 1.26E−09 | 4.66 | inactive | inactive |
| chi04H09 (mouse-dog) | 4.01E−09 | 2.77E−08 | 4.64E−09 | 3.50 | inactive | 66.50 |
| Can04H09 VH1/VL1 | 2.84E−07 | No binding | No binding | ND | ND | ND |
| Can04H09 VH1/VL2 | Not successfully expressed | | | | | |
| Can04H09 VH1/VL3 | 2.43E−09 | 3.20E−08 | 6.52E−09 | 0.66 | inactive | 467.00 |
| Can04H09 VH1/VL4 | 2.18E−09 | 2.97E−08 | 4.78E−09 | 0.88 | inactive | 136.5 |
| Can04H09 VH2/VL1 | 2.19E−06 | No binding | No binding | ND | ND | ND |
| Can04H09 VH2/VL2 | Not successfully expressed | | | | | |
| Can04H09 VH2/VL3 | Not successfully expressed | | | | | |
| Can04H09 VH2/VL4 | 1.42E−09 | 3.29E−08 | 6.03E−09 | 0.84 | inactive | 69.53 |
| Can04H09 VH3/VL1 | 3.98E−06 | No binding | No binding | ND | ND | ND |
| Can04H09 VH3/VL2 | 4.57E−08 | No binding | No binding | ND | ND | ND |
| Can04H09 VH3/VL3 | 2.79E−09 | 4.88E−08 | 9.08E−09 | 1.18 | inactive | 72.80 |
| Can04H09 VH3/VL4 | 1.38E−09 | 3.21E−08 | 6.06E−09 | 0.74 | inactive | 52.80 |

Epitope Mappin of Caninized ZTS-426

Figure 7:
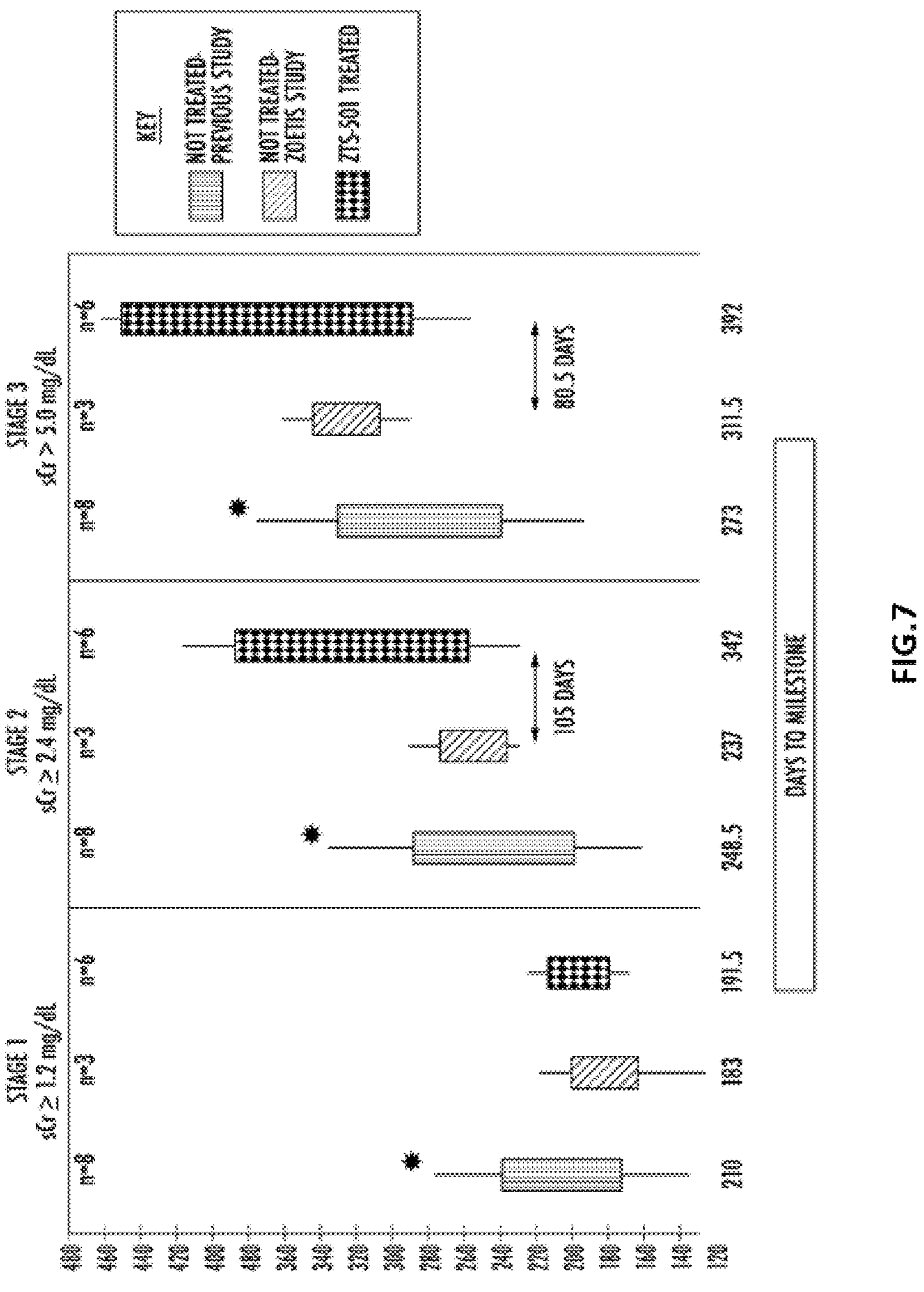
FIG. 7 represents a model of the secondary structure of the mature TGFβ1 dimer with bound Fab fragments of ZTS-426.

Co-crystallization of ZTS-426 Fab (VH SEQ ID NO. 12 and VL SEQ ID NO. 24) and TGFβ1, and subsequent antigen bound mAb Fab fragment structure, was solved to a final resolution of 2.2 Å. FIG. 7 is a representation of the secondary ZTS-426:TGFβ1 dimer crystal structure. The complex structure provides structural insights into the key recognition elements governing the interaction of ZTS-426 Fab with residues of the mature TGFβ1.

Mammalian systems consists of at least three TGFβ isoforms (TGFβ1, TGFβ2, TGFβ3) therefore the subtype specificity was additionally probed. Based on the interaction analysis of ZTS-426 Fab with mature TGFβ1, approximately sixteen unique antigen residues that are proximal to the Fab were identified.

The overall architecture was determined from the crystal structure asymmetric unit that comprises two ZTS-426 Fab molecules bound diagonally opposite with respect to the reference TGFβ1 homodimer (FIG. 7) and displayed a near 2-fold rotational symmetry from the overall complex centroid. The mature TGFβ1homodimer is held together by a series of covalent disulfide bonds formed by the cysteine sidechain thio functionality within and between the TGFβ1 monomer. Most notably, each of the Fab fragment exclusively interacts with only one of the TGFβ1 monomer. The x-ray B-factors suggest that the TGFβ1 and Fab interface residues to be adequately resolved for elucidating the key interactions contributing to the binding affinity.

The complex x-ray structure was prepared using the protein preparation module within MAESTRO modeling application suite from Schrödinger to have a full description of the complex devoid of any missing atoms/residues and energy minimized to relieve any undue sterics. This final structure is used for all subsequent analysis along with the Kabat numbering scheme for the Fab residues. One of the antigen-antibody binding hypotheses suggests that the lipophilic antibody CDR residues prefer to bury the hydrophobic surface on the antigen surface. Accordingly, surface properties probe identified a discontinuous yet proximal patch covering ~388.5 Å$^2$ hydrophobic surface area comprising F8, Q19, Y21, H34, E35, H40, V89, R94, P96, V98 residues. This region serves as the docking site for the ZTS-426 residues L_12, L_Y30, L_Y49, L_A50, L_F91, L_W92, H_W33, H_Y52, H_H95, and H_Y96 from the Fab light (L) and heavy (H) chains spanning a hydrophobic surface area of ~343.1 Å$^2$. Overall, the ZTS-426:(TGFβ$_1$)$_2$: ZTS-426 complex shields ~3514 Å$^2$ van der Waals surface area and ~1939 Å$^2$ is contributed by the hydrophobic surface component. Qualitatively, the light chain CDR-1 and -2 contribute minimally with CDR-3 residues displaying significant contributions.

TABLE 4

Hypervariable region residues of ZTS-426 Fab at the interface of the mature TGFβ1 dimer residues. Kabat numbering used for CDR definitions

| TGFβ$_1$ | ZTS-426 | CDR_ Heavy | CDR_ Light | ZTS-426 | TGFβ$_1$ |
|---|---|---|---|---|---|
| D23 | S | 31 | 24 | R | |
| | S | 32 | 25 | A | |
| R25, K37 | W | 33 | 26 | S | |
| | M | 34 | 27 | E | |
| | N | 35 | 28 | N | |
| | | | 29 | I | |
| E35, K37 | Q | 50 | 30 | Y | P87, Q100 |
| | I | 51 | 31 | S | |
| R25 | Y | 52 | 32 | N | P36 |
| | P | 52A | 33 | L | |
| | G | 53 | 34 | A | |
| R25, K31 | D | 54 | | | |
| | G | 55 | | | |
| R25 | D | 56 | 49[a] | Y | Y21, P36, G38, H40 |
| | T | 57 | 50 | A | |
| H34, K37 | N | 58 | 51 | A | |
| | Y | 59 | 52 | T | |
| | N | 60 | 53 | N | Q19, H40 |
| | G | 61 | 54 | L | |
| | K | 62 | 55 | A | |
| | F | 63 | 56 | D | |
| | K | 64 | | | |
| | G | 65 | | | |
| | A | 93 | | | |
| | R | 94 | | | |
| K37 | H | 95 | 89 | Q | |
| Y21, H40 | Y | 96 | 90 | H | |
| Y21 | D | 97 | 91 | F | E35, P36 |
| Y21, H40 | G | 98 | 92 | W | P87,188, V89, V98 |
| | S | 99 | 93 | G | H34, E35, V89 |
| | T | 100 | 94 | T | H34, E35 |
| | D | 101 | 95 | P | |
| | Y | 102 | 96 | Y | E35, K37 |
| | | | 97 | T | |

Table 4 lists some of the proximal residues and specific interactions accounting for the binding strength between the mature TGFβ1 and the ZTS-426 Fab interface. Specifically, an ionic bond between the R25 sidechain and the heavy chain D54 and D56 carboxylate functionality anchors the antigen-Fab complex. This is further supported by the additional ionic bond between the sidechains of the antigen K31 and D54 from the Fab heavy chain residues. A network of explicit H-bond interactions between the sidechain of Q19 . . . L_N53, E35 . . . L_Y96, K37 . . . H_Q50, and H40 . . . H_Y96 pairs further contribute to the binding strength.

Superposing the structures of TGFβ2 and TGFβ3 complexes onto the current x-ray structure, revealed that ten of the antigen residues were entirely conserved in the TGFβ sub-family members. However, four of the unique residues are of homologous polarity (human sequences compared), and two residues (Q19P and P87T) are identified as polarity switches that may affect the binding and subsequent potency. Any impact to the binding of ZTS-426 to the other TGFβ sub-family members can be attributed to the differences in these residues.

Additional structural superposition of the ZTS-426 Fab bound TGFB1 complex with the literature reported GC1008 scFv bound TGF01 complex reveal that the current antibody does not occupy the same binding region as that of GC1008. Moreover, the structural superposition is indicative of a non-competitive binding between the GC1008 and ZTS-426 antibodies. However, superposition of the current complex with the TGFβ1 bound TGFβRI/TGFβRII extracellular domain receptor ternary complex is suggestive of a competitive binding.

Field Study Investigating the Effects of ZTS-426 on the Clinical Progression of Advanced CKD in Client Owned Dogs A proof of concept (PoC) field study was conducted to investigate whether the beneficial effects noted in the Alport dogs treated with ZTS-501 (study described in following Example) were translated into canine veterinary patients with naturally occurring CKD. The PoC study described herein evaluated the safety and mechanism of action of ZTS-426 on the clinical progression of advanced stage CKD in client-owned dogs with naturally occurring CKD.

The study was conducted as a randomized, double-blinded, multi-centered clinical study in the United States. Dogs diagnosed with progressive CKD (IRIS stages 2, 3, and 4) were enrolled from eleven general veterinary practices. IRIS staging is based initially on fasting blood creatinine or fasting blood SDMA concentration, or both, assessed on at least two occasions in a hydrated, stable patient. See Table 5 describing IRIS staging for canines.

TABLE 5

| IRIS Stage | Blood creatinine (umol/l, mg/dl) | SDMA (ug/dl) | |
|---|---|---|---|
| 1 | <125 umol/l<br><1.4 mg/dl | <18 | Normal blood creatinine or normal or mild increase blood SDMA. Some other renal abnormality present (such as, abnormal renal palpation or renal imagingf indings, proteinuria of renal origin, abnormal renal biopsy results, increasing blood creatinine or SDMA concentrations in samples collected serially). Persistently elevated blood SDMA concentration (>14 μg/dl) may be used to diagnose early CKD |
| 2 | 125-250 umol/l<br>1.4-2.8 mg/dl | 18-35 | Normal or mildly increased creatinine, mild renal azotemia. Mildly increased SDMA. Clinical signs usually mild or absent |
| 3 | 251-440 umol/l<br>2.9-5.0 mg/dl | 36-54 | Moderate renal azotemia. Many extrarenal signs may be present, but their extent and severity may vary. If signs are absent, the case could be considered as early Stage 3, while presence of many or marked systemic signs might justify classification as late Stage 3. |
| 4 | >440 umol/l<br>>5 mg/dl | >54 | Increasing risk of systemic clinical signs and uremic crises |

Canines are then sub-staged based on systolic blood pressure in mm Hg:

| | |
|---|---|
| Normotensive: <140 | Prehypertensive: 140-159 |
| Hypertensive 160-179 | Severely Hypertensive: >180 |

UPC ratio based on proteinuria:
- Nonproteinuric <0.2
- Borderline proteinuria 0.2-0.5
- Proteinuria >0.5

At enrolment dogs were required to show inadequately concentrated urine (urine specific gravity (USG)<1.030) and at least one of the following, a serum Creatinine (sCr)>2.0 mg/dL (IRIS stage 3 and 4), or >1.4 mg/dL sCr (IRIS stage 2) in addition to having clinical signs attributed to CKD, or renal proteinuria (urine protein/creatinine ratio (UP/C)>0.5).

IRIS stage 2 and 3 dogs were randomized in a 3:1 ratio to receive IVP or control product (CP) (saline) as shown in Table 6.

TABLE 6

ZTS-426 PoC study design

| Treatment Group | Test Substance | Dose and Route | Days of Treatment† | Days of Study Visit | Target Number of Evaluable Cases* |
|---|---|---|---|---|---|
| T01 | CP | 0 mg/kg SC | Day 0 and every 28 days thereafter | 28, 0, 14, 28, and every 28 days thereafter | 10 |
| T02 | IVP | 1 mg/kg SC | | | 30 |

*Cases from IRIS stage 2 and 3 only

Dogs with IRIS stage 4 CKD were not randomized but were assigned to receive IVP and followed the same schedule as dogs enrolled in T02. All animals (including placebo) received Standard of Care (SoC) treatment as recommended by the IRIS guidelines and the examining Veterinarian. A total of 65 dogs were enrolled in the study, with 19 in T01 (5 IRIS stage 2 and 14 IRIS stage 3) and 46 in T02 (13 IRIS stage 2, 27 IRIS stage 3, and 4 IRIS stage 4).

Comprehensive physical examinations (including body condition scoring, muscle condition scoring, and blood pressure measurements) were conducted and blood and urine samples were collected at every visit. Quality of Life (QoL) assessments associated with CKD were also collected. This was done via a QoL questionnaire which considered parameters such as food consumption, vomiting, activity, and energy levels, which was completed by owners at each visit. Additionally, owners completed at each visit, a visual analog score (VAS) assessment, to record the total impact of CKD on their dog's overall QoL. Owners were instructed to consider the last 7 days prior to their scheduled study visit when completing these forms.

Collected blood and urine samples were analyzed for established biomarkers consistent with IRIS staging of CKD. Laboratory results of the established biomarkers reported and evaluated during the study. A determination of uremic crisis events was made based on IRIS guidelines.

Figure 10:
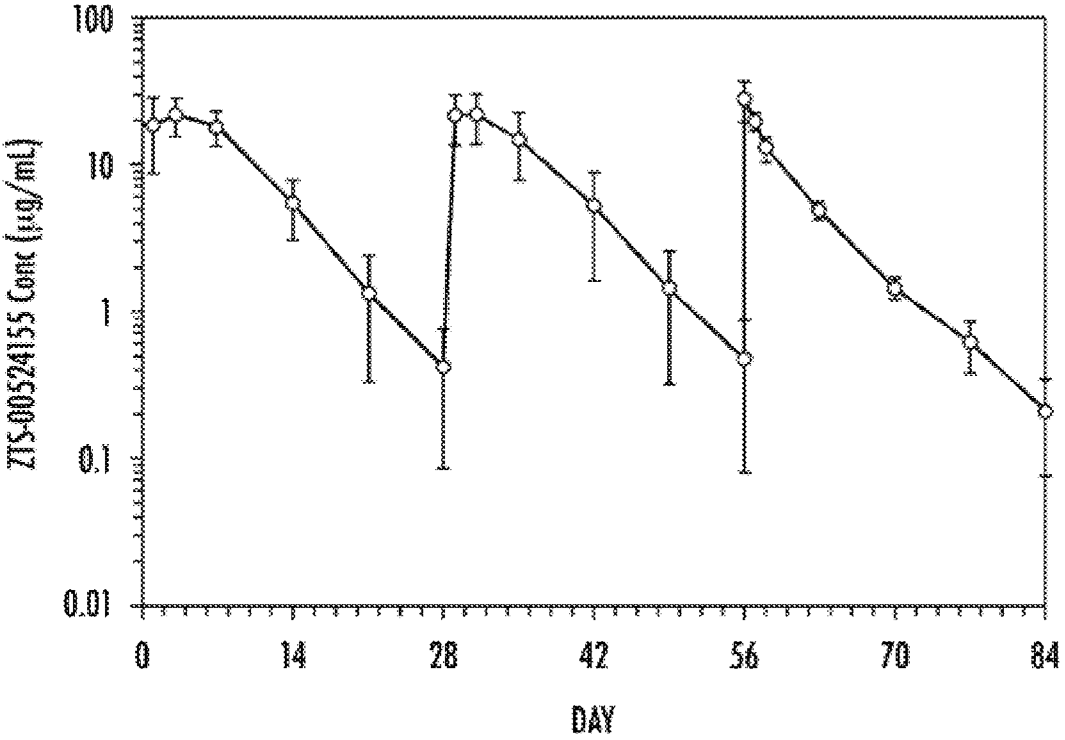
FIG. 10 represents Phase 2 scenario planning for the study relating to treatment of CKD.
Figure 11A:
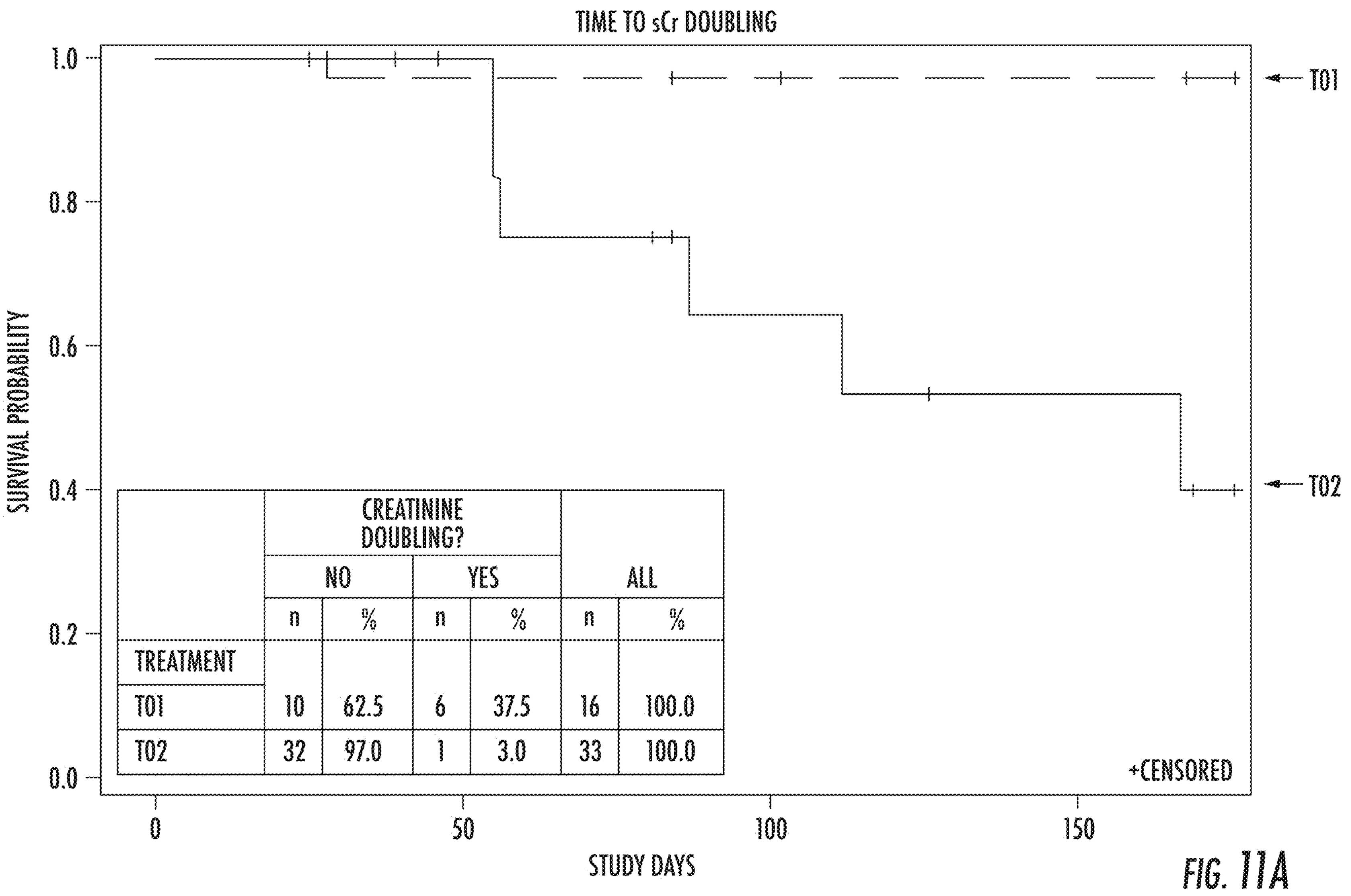
FIG. 11A is a graphical representation of the survival curves as it relates to time to sCr doubling after treatment with ZTS-426.
Figure 11B:
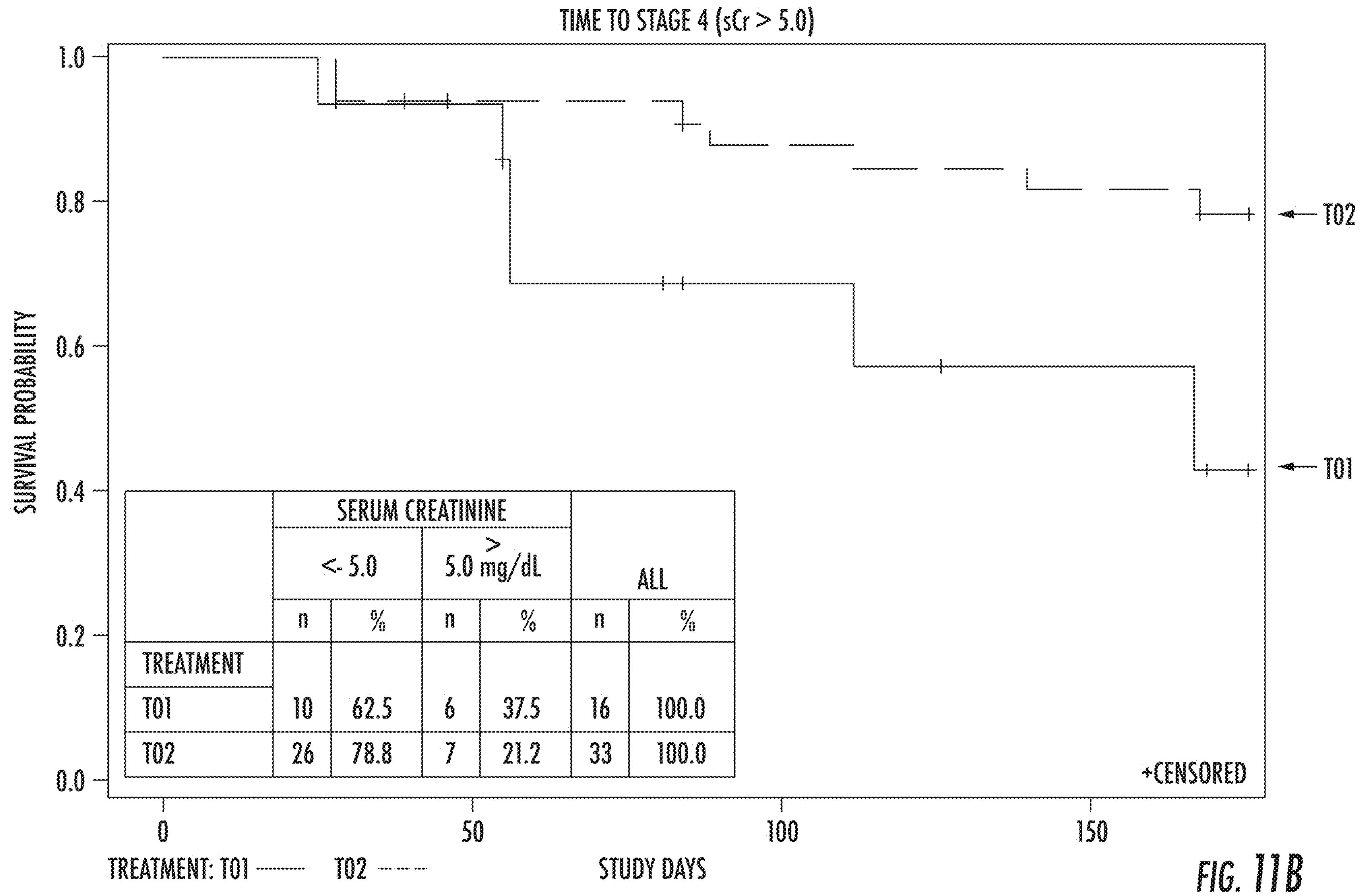
FIG. 11B is a graphical representation of the survival curves/time to Stage 4 (sCr>5.0) after treatment with ZTS-426.
Figure 11C:
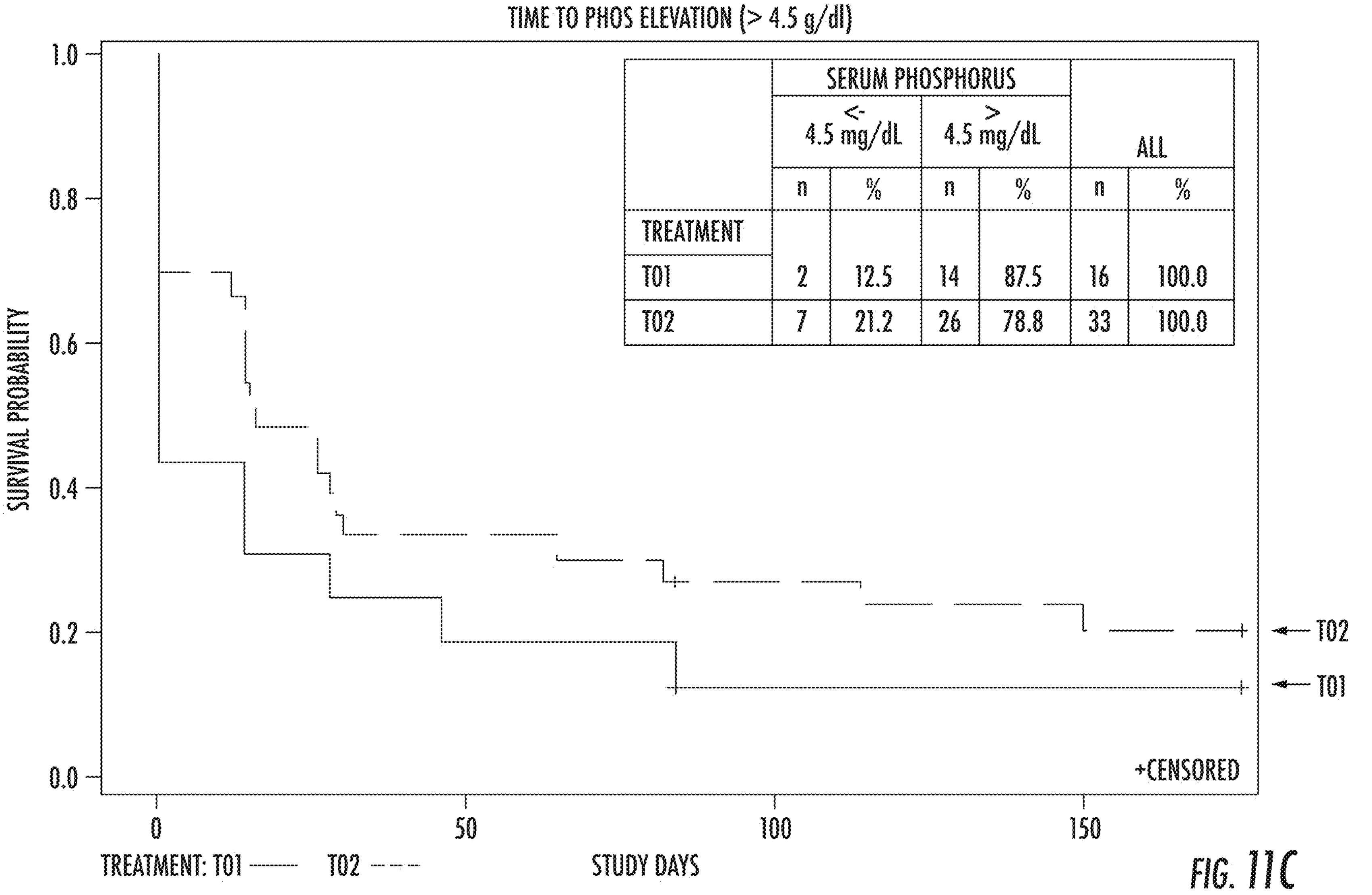
FIG. 11C is a graphical representation of the survival curves/time to Phos Elevation (>4.5 g/dl) after treatment with ZTS-426.
Figure 11D:
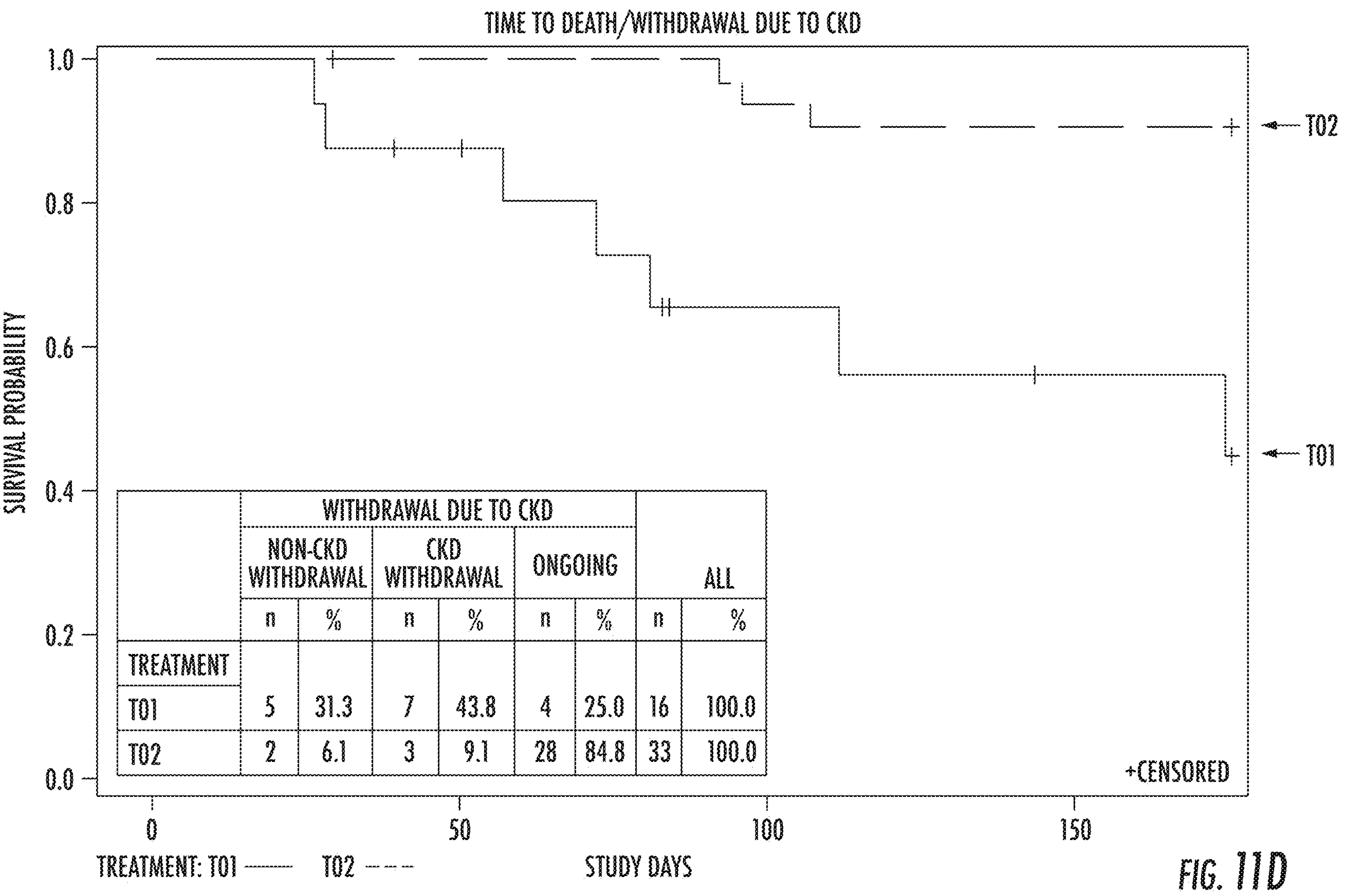
FIG. 11D is a graphical representation of the survival curves/time to death/withdrawal due to CKD after treatment with ZTS-426.
Figure 11E:
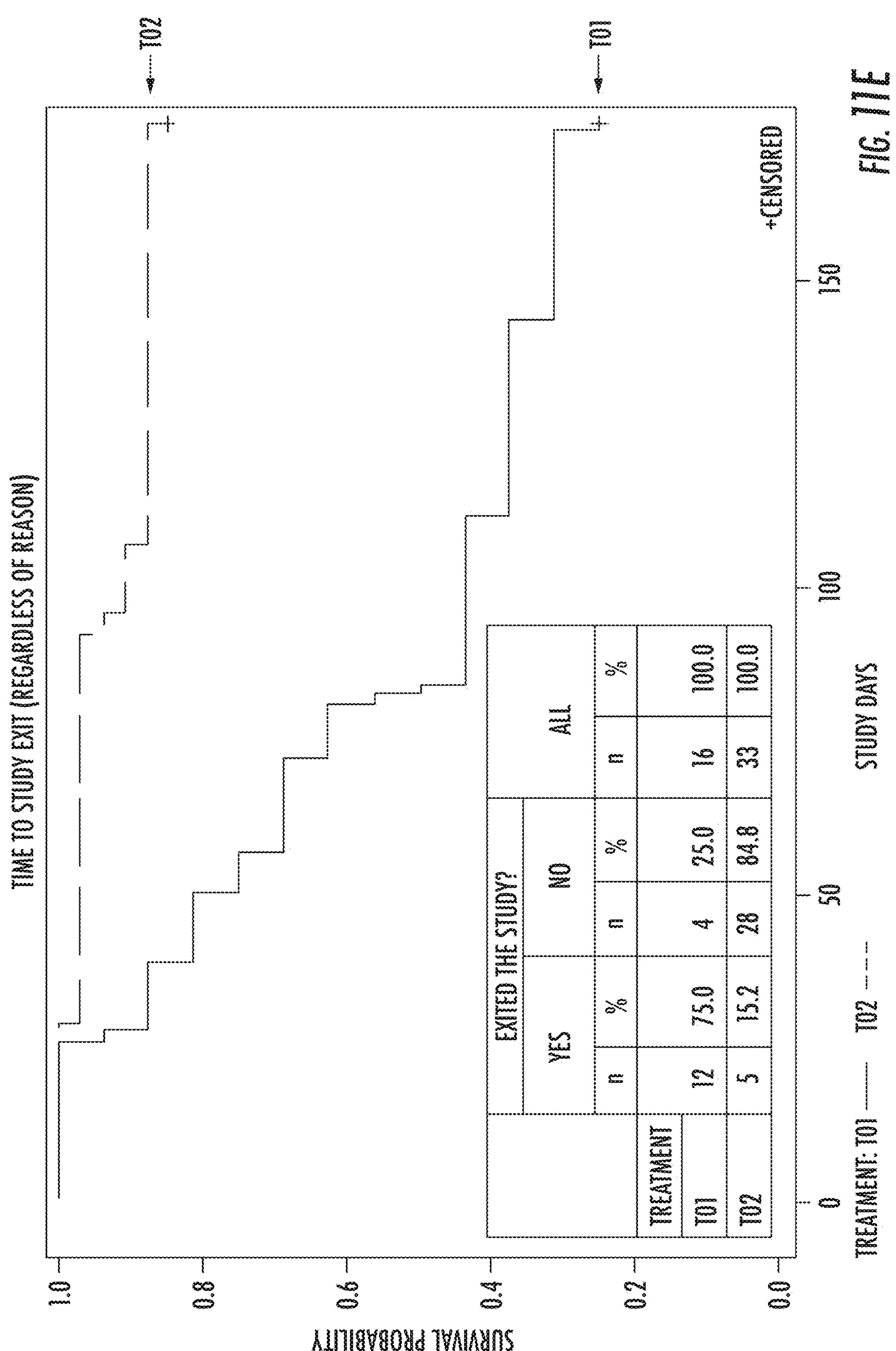
FIG. 11E is a graphical representation of the survival curves/time to study exit after treatment with ZTS-426.
Figure 11F:
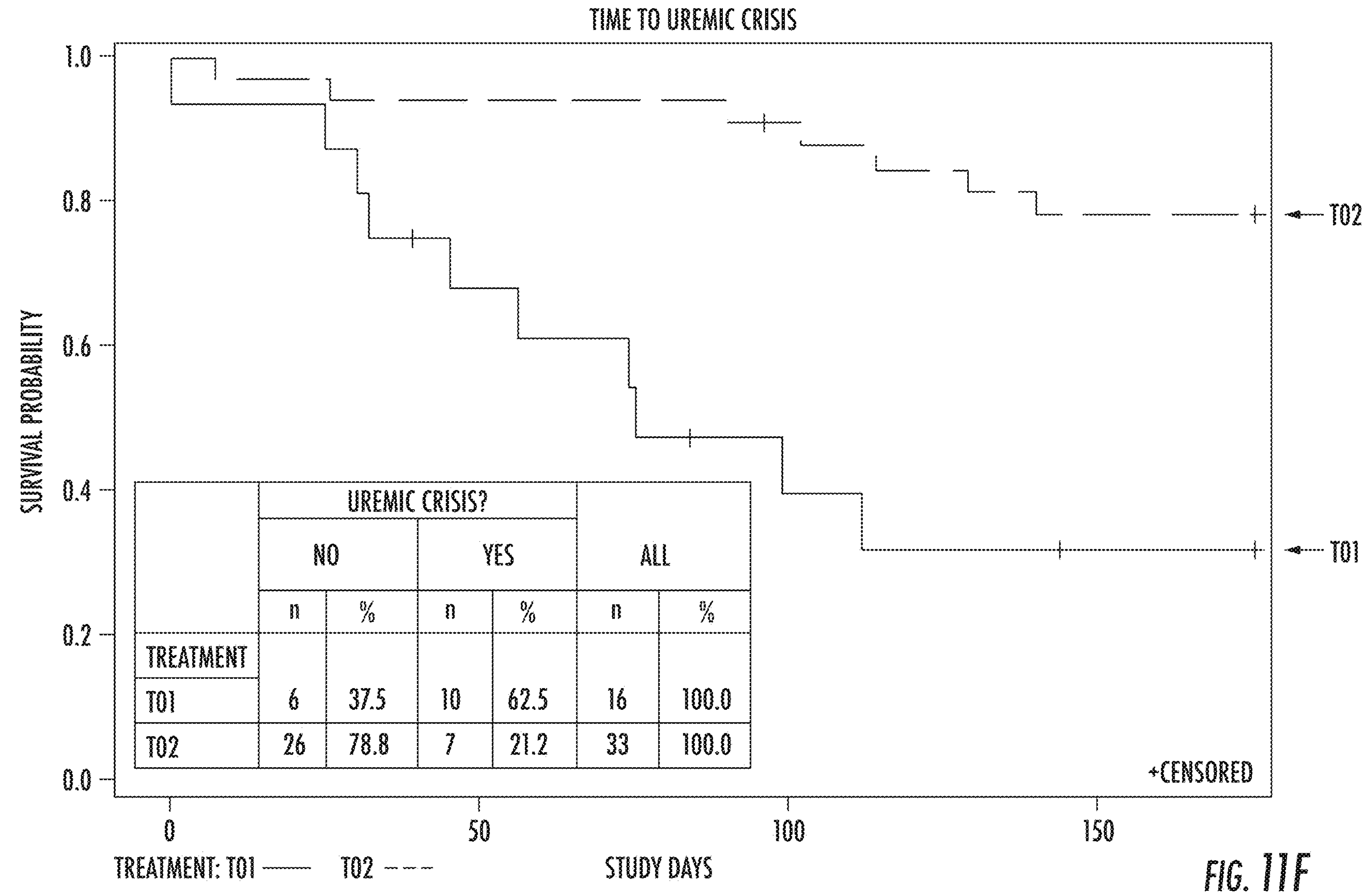
FIG. 11F is a graphical representation of the survival curves/time to uremic crisis after treatment with ZTS-426.

The study was designed to use a sample size re-assessment (SSR) adaptive design with two phases (Phase 1 and 2), and single interim analysis. The interim analysis was planned to be completed once 20 evaluable cases (IRIS stage 2 and 3: n=5 in T01 and n=15 in T02) had received three months of treatment in Phase 1. The results of the interim analysis were used to re-evaluate sample size and/or to adjust dose based on the treatment efficacy. Depending on the interim analysis results, four different scenarios were possible in Phase 2 based on the decision tree depicted in FIG. 10.

3-Month Interim Analysis

An interim analysis was completed at 3 months for the subset of dogs on the study that reached this timepoint. The number of dogs included in this analysis are listed below in Table 7.

TABLE 7

| Treatment Group | Stage 2 | Stage 3 | Total |
|---|---|---|---|
| T01 (CP) | 2 | 8 | 10 |
| T02 (IVP | 4 | 12 | 16 |
| Total | 6 | 20 | 26 |

The 3-month interim analysis evaluated the following parameters: Absolute and % change from pre-treatment in sCr, blood urea nitrogen (BUN), symmetric dimethylarginine (SDMA), parathyroid hormone (PTH), serum phosphorus (phos), UP/C, hematocrit (HCT), body weight (bwt), and owner-rated VAS results of QoL. Data showed a statistically significant (at $\alpha_1$=0.06201) results between TO1 and T02 were found on the following parameters: BUN, sCr, 1/sCr, % change from pre-treatment for 1/sCr, PTH, and SDMA in favor of the IVP-treated group. A trend (at $\alpha_1$=0.10) between T01 and T02 was observed for serum phos, % change from pre-treatment for sCr, phos, and SDMA in favor of the IVP-treated group.

6-Month Interim Analysis

An interim analysis was conducted, including study dogs which, at the time of the analysis, had at least 6 months of data (including dogs that were withdrawn before 6 months). This 6-month analysis included time to event (TTE) analyses (progression, survival curves) and in-life summaries. These were analyzed by IRIS stage and by treatment. The number of dogs included in this analysis are listed in Table 8.

TABLE 8

| Treatment Group | Stage 2 | Stage 3 | Total |
|---|---|---|---|
| T01 (CP) | 4 | 12 | 16 |
| T02 (IVP | 10 | 22 | 32 |
| Total | 14 | 34 | 48 |

In-life summaries included absolute and % change from pre-treatment in sCr, BUN, SDMA, PTH, serum phos, UPC, HCT, bwt, and owner-rated VAS results of QoL. The interim analysis evaluated the following variables and data is shown in Table 9.

Time to sCr doubling from baseline
Time to stage 4 (sCr>5.0, not attributed to uremic crisis)
Time to phos elevation (>4.5 mg/dL)
Time to death (including euthanasia)/withdrawal due to CKD
Time to study exit (regardless of reason for exit)
Time to uremic crisis (as determined by the Investigator)

TABLE 9

Results of the statistical analysis for contrast between T01 and T02 survival curves for TTE parameters at the 6 months interim analysis

| Variable | Stage 2 and 3 Combined | Stage 2 | Stage 3 |
|---|---|---|---|
| Time to sCr doubling | **p < 0.0001** | p = 0.3272 | **p < 0.0001** |
| Time to stage 4 (sCr >5.0) | **p = 0.0267** | p = 0.3272 | p = 0.0808 |
| Time to phos elevation (>4.5 mg/dL) | p = 0.2252 | **p = 0.0565** | p = 0.4868 |
| Time to death/withdrawal due to CKD | **p = 0.0004** | **p = 0.0044** | **p = 0.0147** |
| Time to exit (regardless of reason) | **p < 0.0001** | **p = 0.0009** | **p = 0.0007** |
| Time to uremic crisis | **p = 0.0003** | p = 0.1664 | **p = 0.0007** |

Significant results are shown in bold at $\alpha_1$ p < 0.06201

IRIS stages showed significant differences between the survival curves of T01 and T02 groups for time to sCr doubling, time to stage 4, time to death/withdrawal due to CKD, time to exit regardless of reason, and time to uremic crisis, in favor of the IVP-treated group. Survival curves for all IRIS stages at 6 months is depicted in FIG. 11 A-F. For IRIS stage 2, a significant difference was seen between the survival curves of T01 and T02 for time to phos elevation (>4.5 g/dL), time to death/withdrawal due to CKD, and time to exit regardless of reason, in favor of the IVP-treated group. For IRIS stage 3, a significant difference was seen between the survival curves of T01 and T02 for time to sCr doubling, time to death/withdrawal due to CKD, time to exit regardless of reason, and time to uremic crisis, in favor of the IVP-treated group. Treatment with ZTS-426 is demonstrated to delay the progression of CKD in dogs with naturally occurring disease via significant differences in TTE survival curves for variables that reflect the progression of CKD.

Felinization of Antibody 04H09

Using the same CDR grafting strategy described above for generating caninized antibodies using CDRs from antibody 04H09, felinized antibodies were also engineered to reduce risk of immunogenicity in cats. Feline framework sequences were identified from available feline IgG sequence databases.

Synthetic nucleotide constructs representing the felinized variable heavy and light chains for mAb 04H09 were made. Felinization efforts with mouse antibody 04H09 focused on three feline VH frameworks and three feline VL frameworks, as follows:

TABLE 10

| Alias | Heavy or light chain | SEQ ID NO | |
|---|---|---|---|
| | | Nucleic acid | Amino Acid |
| fel04H09-H636 | Heavy | 25 | 26 |
| fel04H09-H1-2 | Heavy | 27 | 28 |
| fel04H09-H618 | Heavy | 29 | 30 |
| fel04H09-K4-1 | Light | 31 | 32 |
| fel04H09-K36 | Light | 33 | 34 |
| fel04H09-K1-1 | Light | 35 | 36 |

Following subcloning of each variable chain into plasmids containing the respective feline heavy (SEQ ID NO: 131) or kappa constant (SEQ ID NO: 133) region, plasmids were co-transfected for antibody expression in HEK 293 cells. Making all possible combinations of these heavy and light chains resulted in nine combinations that were all capable of producing antibody from transient HEK expression: fel04H09 H636/K4-1 (SL501 fel04H09-17), fel04H09 H636/K36 (SL501 fel04H09-18), fel04H09 H636/K1-1 (SL501 fel04H09-19), fel04H09 H1-2/K4-1 (SL501 fel04H09-20), fel04H09 H1-2/K36 (SL501 fel04H09-21), fel04H09 H1-2/K1-1 (SL501 fel04H09-22), fel04H09 H618/K4-1 (SL501 fel04H09-23), fel04H09 H618/K36 (SL501 fel04H09-24), and fel04H09 H618/K1-1 (SL501 fel04H09-25) (see Table 11).

Felinized versions of mouse 04H09 mAb were expressed and characterized for their ability to bind feline TGFβ1, 2, and 3 via SPR (see Table 6). These results demonstrated that the felinized antibodies bound TGFβ1, 2, and 3 with high affinity. Two felinized 04H09 mAbs were tested for functional activity in CMVICs and in a feline kidney cell line and showed strong neutralization of TGFβ1 and no neutralization of TBFB2 to inhibit pSMAD signaling. Fel04H09-24 mAb showed weak neutralization of TGFβ3, while fel04H09-17 showed extremely weak neutralization of TGFβ3. No additional framework mutations were necessary.

TABLE 11

| Alias | HC | KC | KD [pM] TGFβ1 | TGFβ2 | TGFβ3 |
|---|---|---|---|---|---|
| fel04H09-17 | fel04H09 H636 | fel04H09 K4-1 | 0.99E−09 | 2.01E−08 | 4.50E−09 |
| fel04H09-18 | fel04H09 H636 | fel04H09 K36 | 4.17E−09 | 2.28E−08 | 1.58E−09 |
| fel04H09-19 | fel04H09 H636 | fel04H09 K1-1 | 3.96E−09 | 2.06E−08 | 1.59E−09 |
| fel04H09-20 | fel04H09 H1-2 | fel04H09 K4-1 | 5.87E−09 | 4.53E−08 | 3.04E−09 |
| fel04H09-21 | fel04H09 H1-2 | fel04H09 K36 | 5.63E−09 | 3.64E−08 | 2.08E−09 |
| fel04H09-22 | fel04H09 H1-2 | fel04H09 K1-1 | 6.78E−09 | 3.43E−08 | 3.48E−09 |
| fel04H09-23 | fel04H09 H618 | fel04H09 K4-1 | 4.22E−09 | 2.05E−08 | 2.38E−09 |
| fel04H09-24 | fel04H09 H618 | fel04H09 K36 | 3.12E−09 | 2.06E−08 | 1.21E−09 |
| fel04H09-25 | fel04H09 H618 | fel04H09 K1-1 | 4.18E−09 | 2.31E−08 | 1.45E−09 |

TABLE 12

| | | | CMVIC pSmad-3, IC50 [nM] | | | CRFK pSmad-3, IC50 [nM] | | |
|---|---|---|---|---|---|---|---|---|
| Alias | HC | KC | TGFβ1 | TGFβ2 | TGFβ3 | TGFβ1 | TGFβ2 | TGFβ3 |
| fel04H09-17 | fel04H09 H636 | fel04H09 K4-1 | 0.89 | none | 39.92 | 0.73 | none | 370.07 |
| fel04H09-18 | fel04H09 H636 | fel04H09 K36 | no test | no test | no test | no test | no test | no test |
| fel04H09-19 | fel04H09 H636 | fel04H09 K1-1 | no test | no test | no test | no test | no test | no test |
| fel04H09-20 | fel04H09 H1-2 | fel04H09 K4-1 | no test | no test | no test | no test | no test | no test |
| fel04H09-21 | fel04H09 H1-2 | fel04H09 K36 | no test | no test | no test | no test | no test | no test |
| fel04H09-22 | fel04H09 H1-2 | fel04H09 K1-1 | no test | no test | no test | no test | no test | no test |
| fel04H09-23 | fel04H09 H618 | fel04H09 K4-1 | no test | no test | no test | no test | no test | no test |
| fel04H09-24 | fel04H09 H618 | fel04H09 K36 | no test | no test | no test | 0.5 | none | 30.08 |
| fel04H09-25 | fel04H09 H618 | fel04H09 K1-1 | no test | no test | no test | no test | no test | no test |

Example 2

Anti-TGFβ1 Antibody

Construction of a Recombinant Human: Canine Chimeric Anti-TGFβ1 Antibody

An anti-TGFβ1 antibody was obtained by engineering a monoclonal antibody obtained via phage display of human TGFβ1 against the Cambridge Antibody Technology platform. This antibody is referred to herein as SL501. The sequences of the variable regions of the heavy and light chain of the engineered mouse anti-TGFβ1 antibody are as follows:

SEQ ID NO: 37: mouse SL501 VH nucleotide sequence;
SEQ ID NO: 38: mouse SL501 VH amino acid sequence;
SEQ ID NO: 39: mouse SL501VL nucleotide sequence;
SEQ ID NO: 40: mouse SL501VL amino acid sequence.

Further, the six CDRs for the SL501 antibody are listed in Table 13 below:

TABLE 13

| SEQ ID NO: | Description | Amino Acid Sequence |
|---|---|---|
| 41 | SL501 heavy chain CDR #1 (CDR-H1) | FSSYGMH |
| 42 | SL501 heavy chain CDR #2 (CDR-H2) | VISYDGSIKYY |
| 43 | SL501 heavy chain CDR #3 (CDR-H3) | TGEYSGYDTDPQYS |
| 44 | SL501 light chain CDR #1 (CDR-K1) | RASQGIGDDLG |
| 45 | SL501 light chain CDR #2 (CDR-K2) | GTSTLQS |
| 46 | SL501 light chain CDR #3 (CDR-K3) | LQDSNYPLT |

The same strategy described above for 04H09 chimeric antibodies was employed to generate chimeric human: canine antibodies that are highly specific towards active TGFβ1. The variable regions from the precursor human SL501 monoclonal antibody was used for this and combined with the constant region of canine heavy (SEQ ID NO:127) and light chains (SEQ ID NO:129) through subcloning into appropriate plasmids, as discussed above. The resulting chimeric antibodies (chi SL501) showed good expression in HEK293 transient expression systems and good binding affinity (see Table 14 below).

Caninization of Antibody SL501

As described above for the CDR grafting of 04H09, SL501 antibody was caninized by identifying the most appropriate canine germline sequences for both heavy and light chains. Sequences were selected for their homology to the precursor monoclonal antibody sequence and native canine CDRs were replaced with those of SL501 antibody. Two canine heavy chain variable frameworks (VH1 and VH2) and two canine kappa light chain variable frameworks (VL1 and VL2) were chosen for the initial caninization, resulting in the production of the following variable regions, please refer to Table 14:

TABLE 14

| Alias | Heavy or light chain | SEQ ID NO. Amino Acid |
|---|---|---|
| canSL501-VH1 | Heavy | 47 |
| canSL501-VH2 | Heavy | 48 |
| canSL501-VL1 | Light | 49 |
| canSL501-VL2 | Light | 51 |

Following subcloning of each variable chain into plasmids containing the respective canine heavy (SEQ ID NO. 127) or kappa constant (SEQ ID NO. 129) region, plasmids were co-transfected for antibody expression in HEK 293 cells in all possible combinations (VH1/VL1, VH1NL2, VH2NL1, and VH2NL2) to make four caninized antibody constructs. After expression, binding to TGFβ1 was assessed, as discussed above. Unfortunately, although all four of the caninized constructs expressed in transient HEK293 expression systems, none of these antibodies bound to TGFβ1 (see Table 15).

In an effort to isolate which chain was the cause of the loss of affinity of caninized SL501 antibody for TGFβ1, each caninized heavy and light chain was paired with the chimeric heavy and light chain to generate four distinct hetero-chimeric antibodies (canSL501-VH1 heavy chain (SEQ ID NO:47)+chiSL501-VL light chain (same as SEQ ID NO:40), canSL501-VH2 heavy chain (SEQ ID NO:48)+chiSL501-VL light chain (SEQ ID NO:40), chiSL501-VH heavy chain (same as SEQ ID NO:38)+canSL501-VL1 light chain (SEQ ID NO:49), and chiSL501-VH heavy chain+canSL501-VL2 light chain (SEQ ID NO: 51). After successful expression of these antibodies, affinity for TGFβ1 was again assessed (see Table 15).

The results of these binding studies demonstrated that when the chimeric heavy chain was paired with any of the caninized light chains, binding was restored. Concurrently, the heavy chain was reanalyzed and a third caninized variable heavy chain was produced, referred to herein as canSL501canSL501-VH3 (SEQ ID NOS: 54 [nucleotide] and 55 [amino acid]). An alignment of all three caninized heavy chains (canSL501-VH1, canSL501-VH2, and canSL501-VH3 supported evidence that the variable heavy chain framework 2 (FW2) required modification to maintain the TGFβ1 binding affinity of the chimeric antibody. Additional pairwise framework substitutions were performed to determine the extent of affinity modulation by this approach. One double mutant that contained amino acid substitutions at positions 44 and 46, within the framework 2 region, of can SL501-VH3 heavy chain was produced, which is referred to herein as can SL501-VH3-FW2 (SEQ ID NOS: 56 [nucleotide] and 57 [amino acid]). Co-expression of the can SL501-VH3-FW2 heavy chain with canSL501canSL501-VL1 light chain was found to not yield a functional antibody, but co-expression with canSL501canSL501-VL2 light chain was found to be successful. When the canSL501-VH3-FW2/can SL501-VL2 antibody was examined for TGFβ1 binding affinity, it was determined that this double mutant resulted in restored, and perhaps improved, TGFβ1 affinity when compared to the chimera (see Table 15).

TABLE 15

| | | SPR Full Concentration Titration KD [M] | | | CMVIC pSmad-3, IC50 [nM] | | |
|---|---|---|---|---|---|---|---|
| HC | KC | TGFβ1 | TGFβ2 | TGFβ3 | TGFβ1 | TGFβ2 | TGFβ3 |
| mouse-SL501-VH | mouse-SL501-VL | 7.05E−12 | no binding | no binding | no test | no test | no test |
| Chimera-SL501-VH (SEQ ID NO: 38) | Chimera-SL501-VL (SEQ ID NO: 40) | 4.72E−10 | no binding | no binding | no test | no test | no test |
| Can-SL501-VH1 (SEQ ID NO: 47) | Can-SL501-VL1 (SEQ ID NO: 49) | no binding | no test | no test | no test | no test | no test |
| Can-SL501_VH2 (SEQ ID NO: 48) | Can-SL501-VL1 (SEQ ID NO: 49) | no binding | no test | no test | no test | no test | no test |
| Can-SL501-VH1 (SEQ ID NO: 47) | Can-SL501-VL2 (SEQ ID NO: 51) | no binding | no test | no test | no test | no test | no test |
| Can-SL501_VH2 (SEQ ID NO: 48) | Can-SL501-VL2 (SEQ ID NO: 51) | no binding | no test | no test | no test | no test | no test |
| Can-SL501-VH1 (SEQ ID NO: 47) | Chimera-SL501-VL (SEQ ID NO: 40) | 1.10E−06 | no test | no test | no test | no test | no test |
| Can-SL501_VH2 (SEQ ID NO: 48) | Chimera-SL501-VL (SEQ ID NO: 40) | 1.09E−06 | no test | no test | no test | no test | no test |
| Chimera-SL501-VH (SEQ ID NO: 38) | Can-SL501-VL1 (SEQ ID NO: 49) | 6.08E−08 | no test | no test | no test | no test | no test |
| Chimera-SL501-VH (SEQ ID NO: 38) | Can-SL501-VL2 (SEQ ID NO: 51) | 1.92E−13 | no test | no test | no test | no test | no test |
| Chimera-SL501-VH (SEQ ID NO: 38) | CanSL501-VL-hybrid (SEQ ID NO: 53) | 4.28E−11 | no test | no test | no test | no test | no test |
| Can-SL501_VH1 (SEQ ID NO: 47) | CanSL501-VL-hybrid (SEQ ID NO: 53) | 4.01E−09 | no test | no test | no test | no test | no test |
| Can-SL501_VH3 (SEQ ID NO: 55) | Can-SL501-VL1 (SEQ ID NO: 49) | 2.18E−11 | no binding | no binding | 4.91 | none | none |
| Can-SL501_VH3_FW2 (SEQ ID NO: 57) | Can-SL501-VL1 (SEQ ID NO: 49) | DID NOT EXPRESS | | | | | |

Additionally, single amino acid substitutions were made at five distinct amino acid positions (D108, P109, Q110, Y111, and S112) in CDR-VH3 of the canSL501-VH3 (SEQ ID NO: 55) caninized variable heavy chain, as set forth below:

TABLE 16

| canSL501-VH3 amino acid: | Amino acids substituted at this position: |
|---|---|
| D108 | E, P, Q, N, S, T, K, R, H |
| P109 | S, H, Y, W, F, T, A, G |
| Q110 | S, N, D, E, K, R, H, T, V |
| Y111 | P, F, W, H, M, I, L, V, T, E |
| S112 | E, Q, N, T, A, G, P, D, L |

In total, 45 distinct variations of canSL501-VH3 heavy chain were made comprising the CDR3 sequences of canSL501-VH3 (SEQ ID NO: 55), each containing a single amino acid substitution (CDR sequences represented by SEQ ID NOs 135-179 and VH sequences comprising these substitutions represented by SEQ ID NO: 231-268). Each of these heavy chain peptides was then co-expressed with canSL501-VL2 light chain and TGFβ1 binding affinity was analyzed with single point KD as described above (see Table 10). Additionally, 15 selected variants had full titration binding by SPR (see Table 17) and potency against TGFβ1 SMAD phosphorylation (see Table 18).

TABLE 17

| Amino acid substitution in the Can-SL501-VH3 HC (SEQ ID NO: 55) | KC Can-SL501-VL2 (SEQ ID NO: 49) | Single Point SPR KD [M] TGFβ1 |
|---|---|---|
| D108E (SEQ ID NO. 225) | Can-SL501-VL2 | 3.41E−10 |
| D108P (SEQ ID NO. 226) | Can-SL501-VL2 | 3.51E−09 |
| D108Q (SEQ ID NO. 227) | Can-SL501-VL2 | 1.25E−09 |
| D108N (SEQ ID NO. 228) | Can-SL501-VL2 | 9.68E−09 |
| D108S (SEQ ID NO. 229) | Can-SL501-VL2 | 7.24E−10 |
| D108T (SEQ ID NO. 230) | Can-SL501-VL2 | 7.98E−10 |
| D108K (SEQ ID NO. 231) | Can-SL501-VL2 | 2.83E−10 |
| D108R (SEQ ID NO. 232) | Can-SL501-VL2 | 7.59E−10 |
| D108H (SEQ ID NO. 233) | Can-SL501-VL2 | 1.83E−09 |
| P109S (SEQ ID NO. 234) | Can-SL501-VL2 | 4.97E−09 |
| P109H (SEQ ID NO. 235) | Can-SL501-VL2 | 1.35E−09 |
| P109Y (SEQ ID NO. 236) | Can-SL501-VL2 | 8.40E−09 |
| P109W (SEQ ID NO. 237) | Can-SL501-VL2 | 6.90E−09 |
| P109F (SEQ ID NO. 238) | Can-SL501-VL2 | 5.34E−10 |
| P109T (SEQ ID NO. 239) | Can-SL501-VL2 | 7.52E−10 |
| P109A (SEQ ID NO. 240) | Can-SL501-VL2 | 1.10E−09 |
| P109G (SEQ ID NO. 241) | Can-SL501-VL2 | 1.59E−09 |
| Q110S (SEQ ID NO. 242) | Can-SL501-VL2 | 6.40E−09 |
| Q110N (SEQ ID NO. 243) | Can-SL501-VL2 | 5.64E−09 |
| Q110D (SEQ ID NO. 244) | Can-SL501-VL2 | 8.01E−09 |
| Q110E (SEQ ID NO. 245) | Can-SL501-VL2 | 1.35E−08 |
| Q110K (SEQ ID NO. 246) | Can-SL501-VL2 | 5.11E−09 |
| Q110R (SEQ ID NO. 247) | Can-SL501-VL2 | 8.38E−09 |
| Q110H (SEQ ID NO. 248) | Can-SL501-VL2 | 5.76E−09 |
| Q110T (SEQ ID NO. 249) | Can-SL501-VL2 | 5.61E−09 |
| Q110V (SEQ ID NO. 250) | Can-SL501-VL2 | 7.37E−09 |
| Y111P (SEQ ID NO. 251) | Can-SL501-VL2 | 7.46E−09 |
| Y111F (SEQ ID NO. 252) | Can-SL501-VL2 | 8.04E−09 |
| Y111W (SEQ ID NO. 253) | Can-SL501-VL2 | 1.39E−08 |
| Y111H (SEQ ID NO. 254) | Can-SL501-VL2 | 4.50E−09 |
| Y111M (SEQ ID NO. 255) | Can-SL501-VL2 | 1.17E−09 |
| Y111I (SEQ ID NO. 256) | Can-SL501-VL2 | 5.62E−10 |
| Y111L (SEQ ID NO. 257) | Can-SL501-VL2 | 1.11E−09 |
| Y111V (SEQ ID NO. 258) | Can-SL501-VL2 | 9.30E−10 |
| Y111T (SEQ ID NO. 259) | Can-SL501-VL2 | 4.57E−10 |
| Y111E (SEQ ID NO. 260) | Can-SL501-VL2 | 4.98E−09 |
| S112E (SEQ ID NO. 261) | Can-SL501-VL2 | 4.87E−10 |
| S112Q (SEQ ID NO. 262) | Can-SL501-VL2 | 4.80E−09 |
| S112N (SEQ ID NO. 263) | Can-SL501-VL2 | 3.40E−09 |
| S112T (SEQ ID NO. 264) | Can-SL501-VL2 | 3.51E−09 |
| S112A (SEQ ID NO. 265) | Can-SL501-VL2 | 8.77E−10 |
| S112G (SEQ ID NO. 266) | Can-SL501-VL2 | 7.62E−10 |
| S112P (SEQ ID NO. 267) | Can-SL501-VL2 | 2.80E−09 |
| S112D (SEQ ID NO. 268) | Can-SL501-VL2 | 7.00E−09 |
| S112L (SEQ ID NO. 269) | Can-SL501-VL2 | 6.97E−09 |

TABLE 18

| Amino acid substitution in the Can-SL501-VH3 HC | KC Can-SL501-VL2 (SEQ ID NO: 49) | KD [M] TGFβ1 | CMVIC pSmad-3, IC50 [nM] TGFβ1 |
|---|---|---|---|
| D108K (SEQ ID NO. 231) | Can-SL501-VL2 | 3.46E−11 | 10.88 |
| D108R (SEQ ID NO. 232) | Can-SL501-VL2 | 6.51E−11 | 25.23 |
| P109T (SEQ ID NO. 239) | Can-SL501-VL2 | 8.36E−11 | 30.02 |
| P109A (SEQ ID NO. 240) | Can-SL501-VL2 | 1.35E−10 | 20.77 |
| Q110N (SEQ ID NO. 243) | Can-SL501-VL2 | 8.09E−11 | 8.95 |
| Q110D (SEQ ID NO. 244) | Can-SL501-VL2 | 5.03E−11 | 4.83 |
| Q110E (SEQ ID NO. 245) | Can-SL501-VL2 | 6.57E−11 | 6.65 |
| Q110K (SEQ ID NO. 246) | Can-SL501-VL2 | 1.11E−10 | 30.5 |
| Y111F (SEQ ID NO. 252) | Can-SL501-VL2 | 6.50E−11 | 43.31 |
| Y111I (SEQ ID NO. 256) | Can-SL501-VL2 | 3.08E−11 | 50.23 |
| Y111L (SEQ ID NO. 257) | Can-SL501-VL2 | no test | 32.57 |

TABLE 18-continued

| Amino acid substitution in the Can-SL501-VH3 HC | KC Can-SL501-VL2 (SEQ ID NO: 49) | KD [M] TGFβ1 | CMVIC pSmad-3, IC50 [nM] TGFβ1 |
|---|---|---|---|
| Y111T (SEQ ID NO. 259) | Can-SL501-VL2 | 2.35E−11 | 19.59 |
| Y111E (SEQ ID NO. 260) | Can-SL501-VL2 | 2.38E−11 | 46.94 |
| S112E (SEQ ID NO. 261) | Can-SL501-VL2 | 1.53E−11 | 5.03 |
| S112Q (SEQ ID NO. 262) | Can-SL501-VL2 | 9.09E−12 | 5.02 |
| S112D (SEQ ID NO. 268) | Can-SL501-VL2 | 1.96E−11 | 8.78 |

In Vivo Efficacy of ZTS-501

Many rodent models of CKD are available and have been extensively used as pre-clinical models for the human disease, to investigate disease-specific mechanisms, molecular pathogenesis and to assess novel therapeutics. Examples include; 5/6 nephrectomy, unilateral ureteral obstruction, Thy-1 nephritis, Alport Syndrome, spontaneously hypertensive rat, and Munich Wistar Fromter rat. While these models have been proven to be useful, efficacy in these models, as with many other areas of therapeutic research, has not always translated into human clinical trial success. Therefore, while some rodent models may be appropriate to investigate relevant mechanisms the suitability of canine CKD models was evaluated.

As a model for canine CKD, the canine X-linked hereditary nephropathy (XLHN) model was employed. More than fifty years ago, veterinarians first recognized an inherited form of kidney disease in English Cocker Spaniels. Despite subsequent studies, the fundamental nature of the disorder remained in question until studies showed that the condition was an inherited disease of basement membrane (type IV) collagen, generally known as hereditary nephropathy (HN) and also called Alport syndrome in humans (Lees G E et al. Am J Vet Rs. 1999).

In the XLHN condition in dogs ("Alport dogs") molecular defects in the glomerular basement membrane (GBM) composition lead to a glomerular lesion that causes proteinuria and secondary chronic progressive tubulointerstitial injury that culminate in chronic renal failure. The clinical and histologic progression of the renal disease in these dogs is similar to that in dogs with other non-hereditary glomerular diseases (Table 19). Consequently, Alport dogs can be used to study canine renal disease as it involves the processes of progressive renal injury and scarring that is initiated by all causes of primary glomerular lesions.

TABLE 19

Comparison of clinical renal disease for justification of Alport model

| Canine Renal Disease (Glomerular) | Alport Dog Disease |
|---|---|
| Immune-mediated most common cause | Genetic disease (chromosome X-linked mutation) |
| Outcome: CKD | Outcome: CKD |
| Glomerular damage | Mainly glomerular pathology |
| Increased glomerular permeability | Pathogenesis driven by increased glomerular permeability (protein "leakage") |
| Variable levels of proteinuria | Severe proteinuria |
| Variable progression of glomerular damage | Severe glomerular damage |
| Variable progression towards tubular damage and interstitial fibrosis | Consequential severe tubular damage and interstitial fibrosis |
| Systemic consequences such as secondary hyperparathyroidism, and fibrous osteodystrophy | Classical progression to systemic disease, including secondary hyperparathyroidism and fibrous osteodystrophy |
| Progression from stage 1 to end-stage disease may take months to several years | Historically renal disease fully develops by ~28 weeks of age with average survival reported at 41 weeks |

The Alport Dog model is an aggressive disease model which compresses CKD pathogenesis from years to months. The entire course of the disease, including its earliest stages, can be studied prospectively with end stage renal disease (ESRD) occurring on average at 40-41 weeks of age for affected male dogs (Table 20) and at about 4-8 years for carrier female dogs.

TABLE 20

Timeline of disease progression in affected male Alport dogs

| Months of Age | Characteristic Pathology/Clinical Chemistry |
|---|---|
| 1 | Focal ultrastructural abnormalities of the GBM begin to develop. Characterized by a thickening and splitting of the GBM that gradually becomes more extensive (i.e., progressing from focal to global) and severe (i.e., progressing to greatly thickened) as the dog grows older |
| 2-4 | Structural changes in glomerular capillary wall lead to persistent proteinuria and starts the process to the injury of the entire kidney |
| 3-6 | Elevation of serum creatinine to IRIS stage 2 |
| 4-8 | Signs of azotemia are present IRIS stage 3-4 |
| 7-11 | IRIS stage 4-ESRD |

Using this model, several early urinary biomarkers for tubulointerstitial injury have been previously identified. Several of these biomarkers are well established in human tubulointerstitial damage and are under early evaluation in dogs with CKD. TGFβ expression has been shown to be upregulated in the kidneys of these dogs.

The Alport dog model was used to explore the safety and efficacy of ZTS-501 (VH: SEQ ID NO. 55, VL: SEQ ID NO.49) on the disease progression of CKD. Affected male Alport dogs, age matched non-affected litter mates, and beagles were used in these studies. These studies took place over a 2-year period with associated data collection. Across these 2 years, a total of ten dogs (n=8 affected male Alport dogs, n=1 non-affected Alport dog, and n=1 beagle) were dosed, SC, with ZTS-501, once or twice per week, at 5 mg/kg for up to 55 weeks. Efficacy in these studies was assessed via monitoring disease progression by evaluation of renal clinical pathology parameters (e.g. serum creatinine (sCr)) and biomarkers over time to a specific milestone, the number of days in each stage, and clinical observations (food intake/emesis/general health). All data was represented as a data parameter vs age in days, or as a time to a specific milestone One measure of disease progression in the Alport dog model is the time it takes to reach certain disease milestones, more specifically the amount of time (in days) that it takes an Alport dog to reach the next milestone. Initial studies were conducted prior to the establishment of IRIS staging and guidelines using instead a three-stage system based on serum creatinine (sCr) as follows:

Stage 1=sCr≥1.2 mg/dL

Stage 2=sCr≥2.4 mg/dL

Stage 3=sCr>5.0 mg/dL

It was hypothesized that increasing the time to each milestone had a significant effect of slowing progression of renal disease in these dogs.

Figure 8:
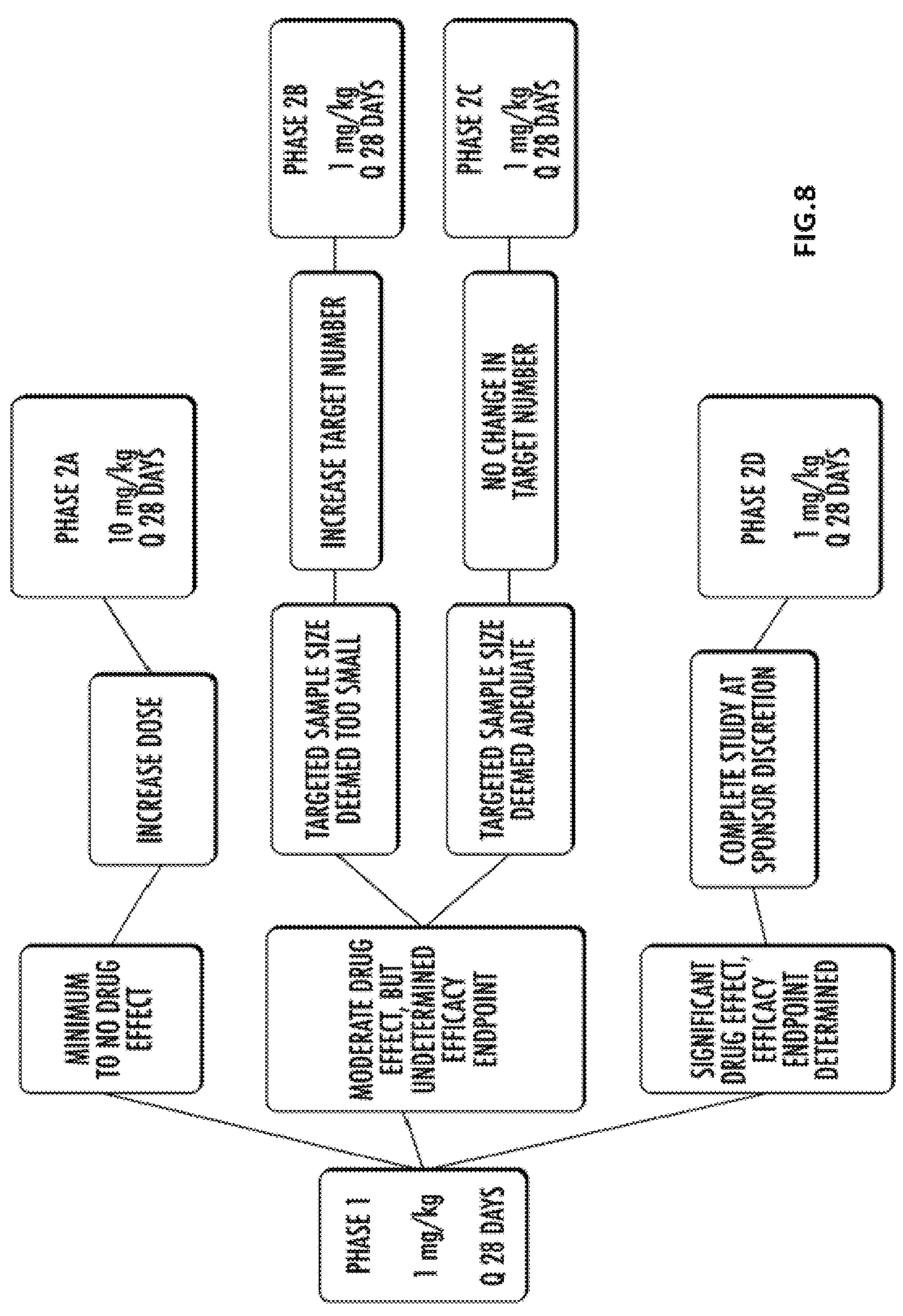
FIG. 8 represents a model of the superposition of the ZTS-426 Fab complex with the TGF01 bound TGFβRI/TGFβRII complexes.
Figure 9A:
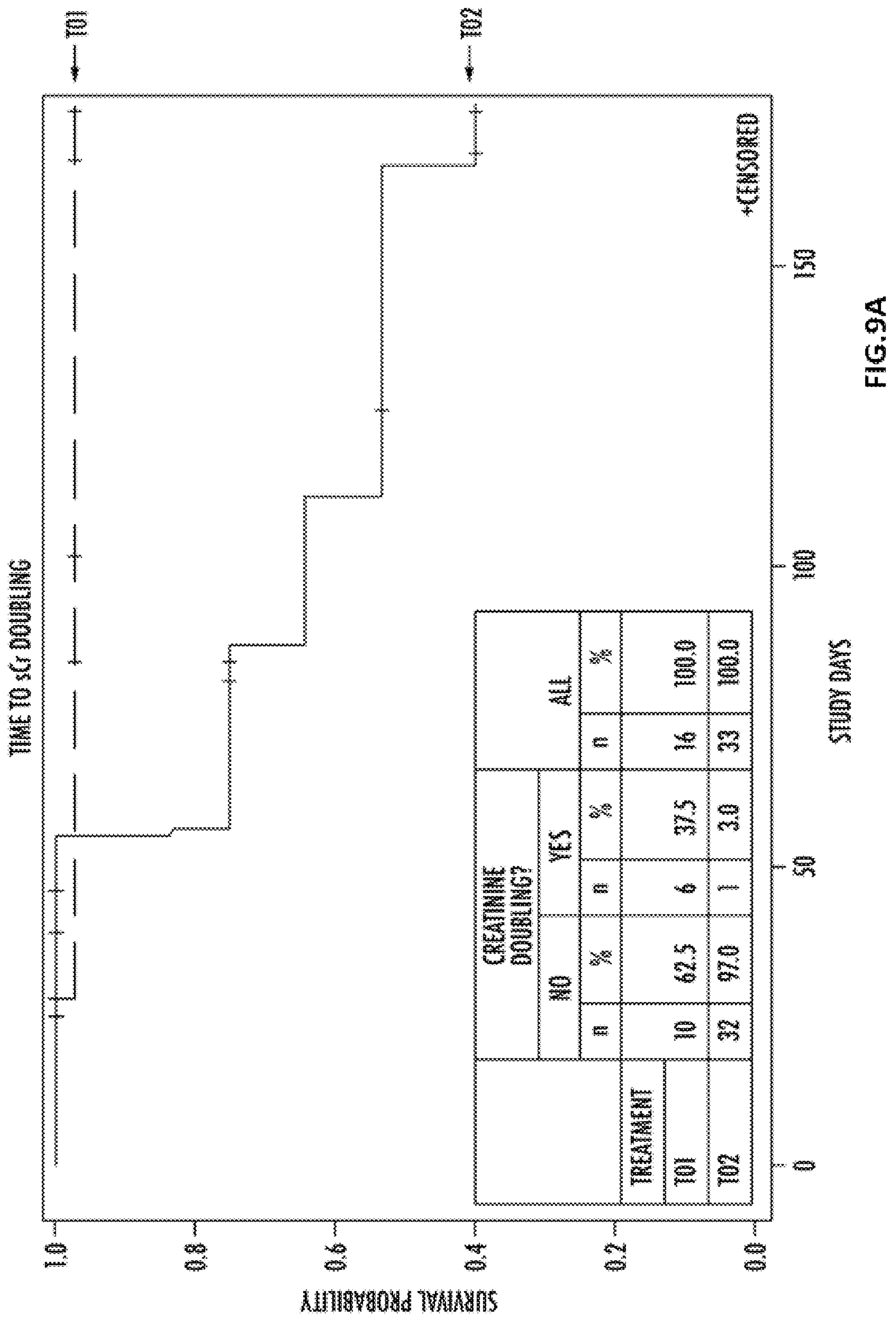
FIG. 9 is a graphical representation of the modulation of disease progression of Alport dogs treated with ZTS-426 at different doses.
Figure 9B:
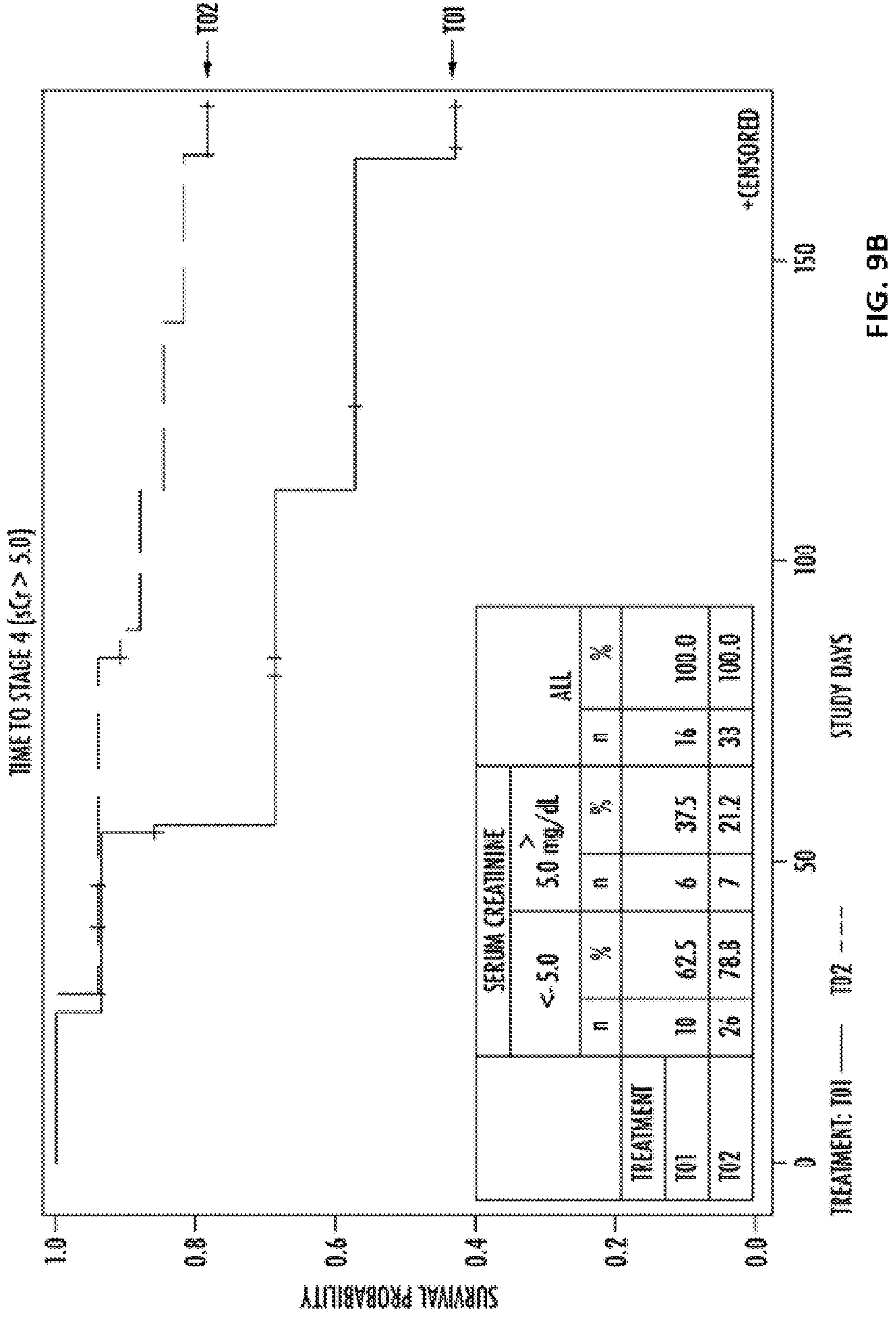
Figure 9C:
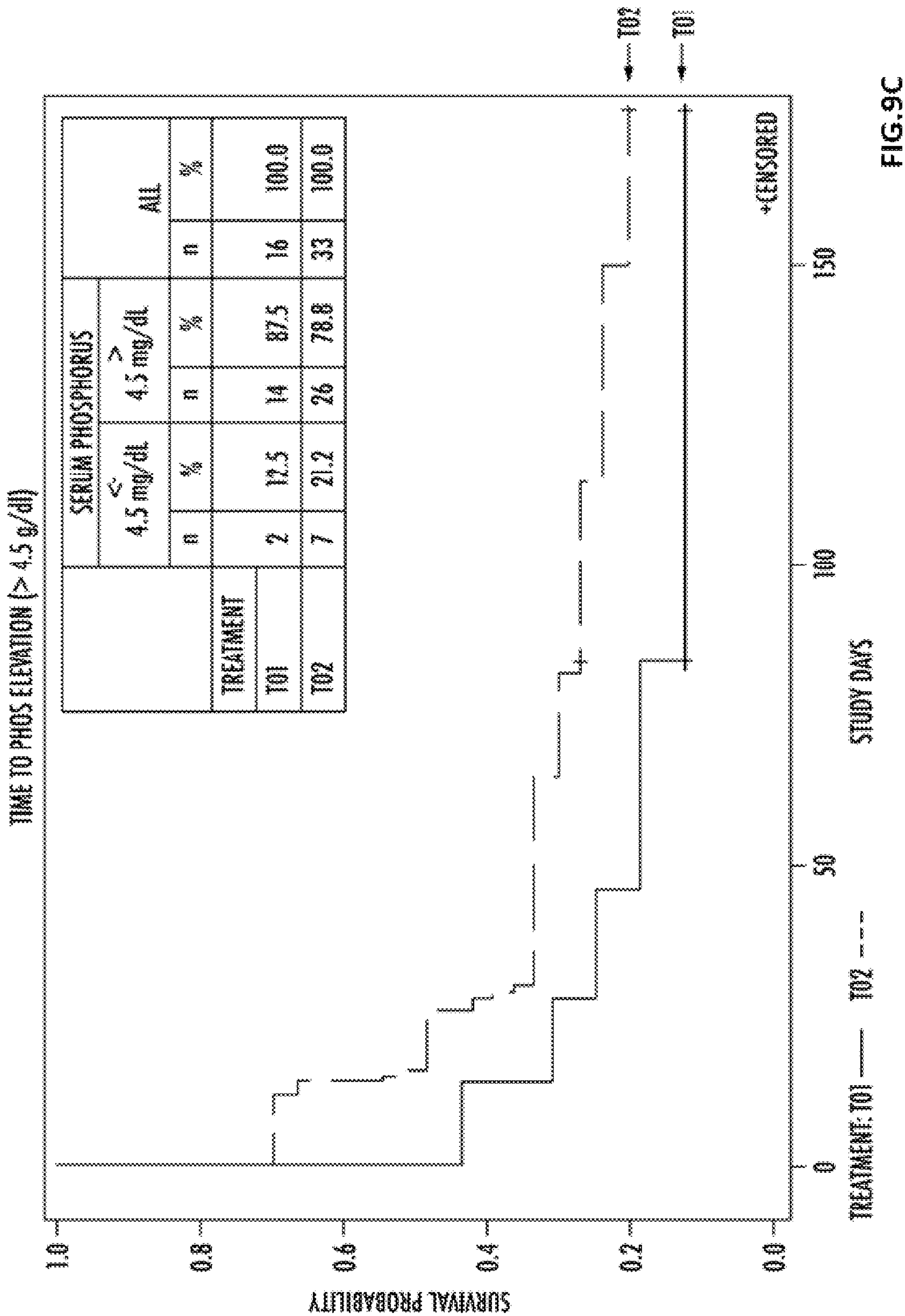
Figure 9D:
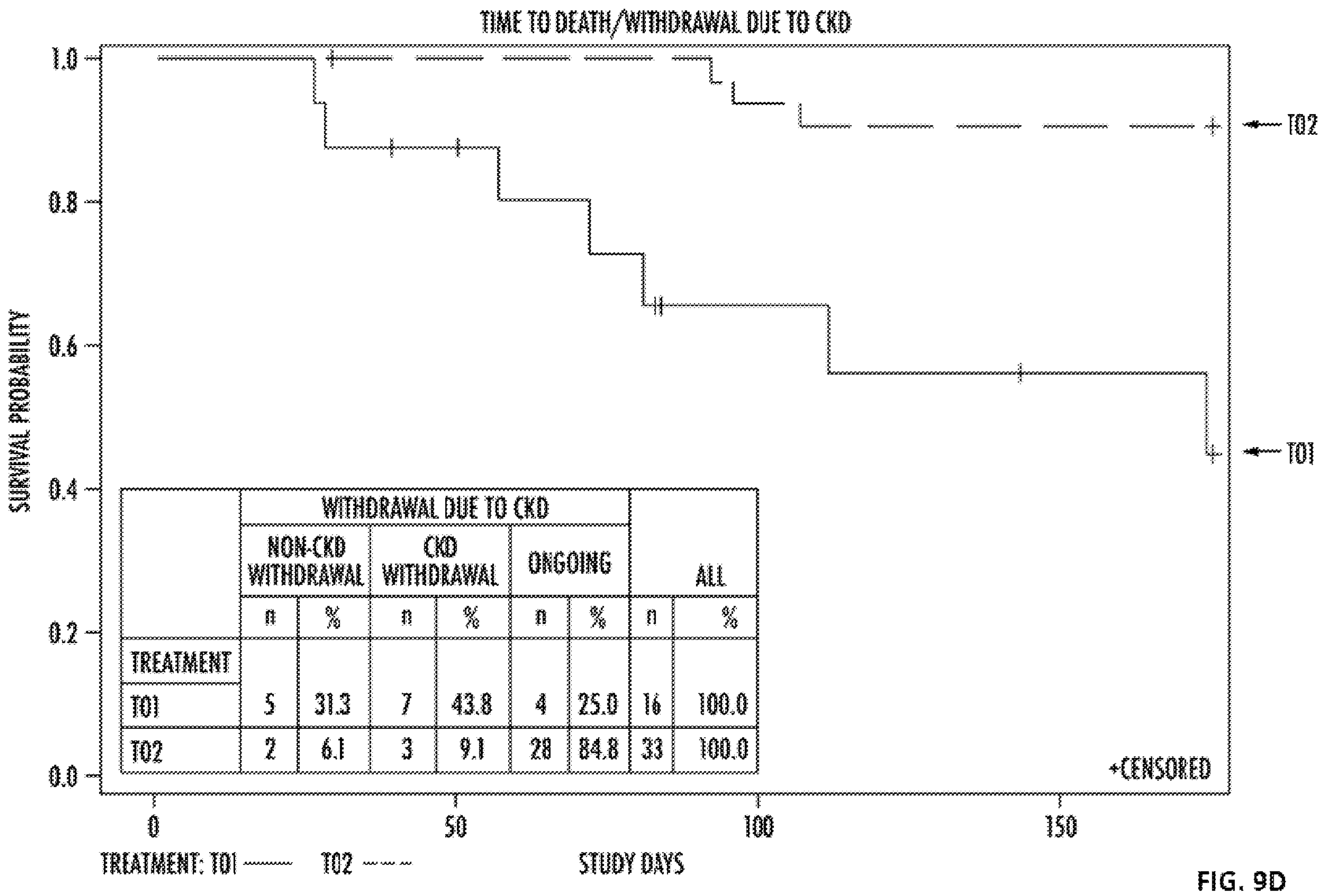
Figure 9E:
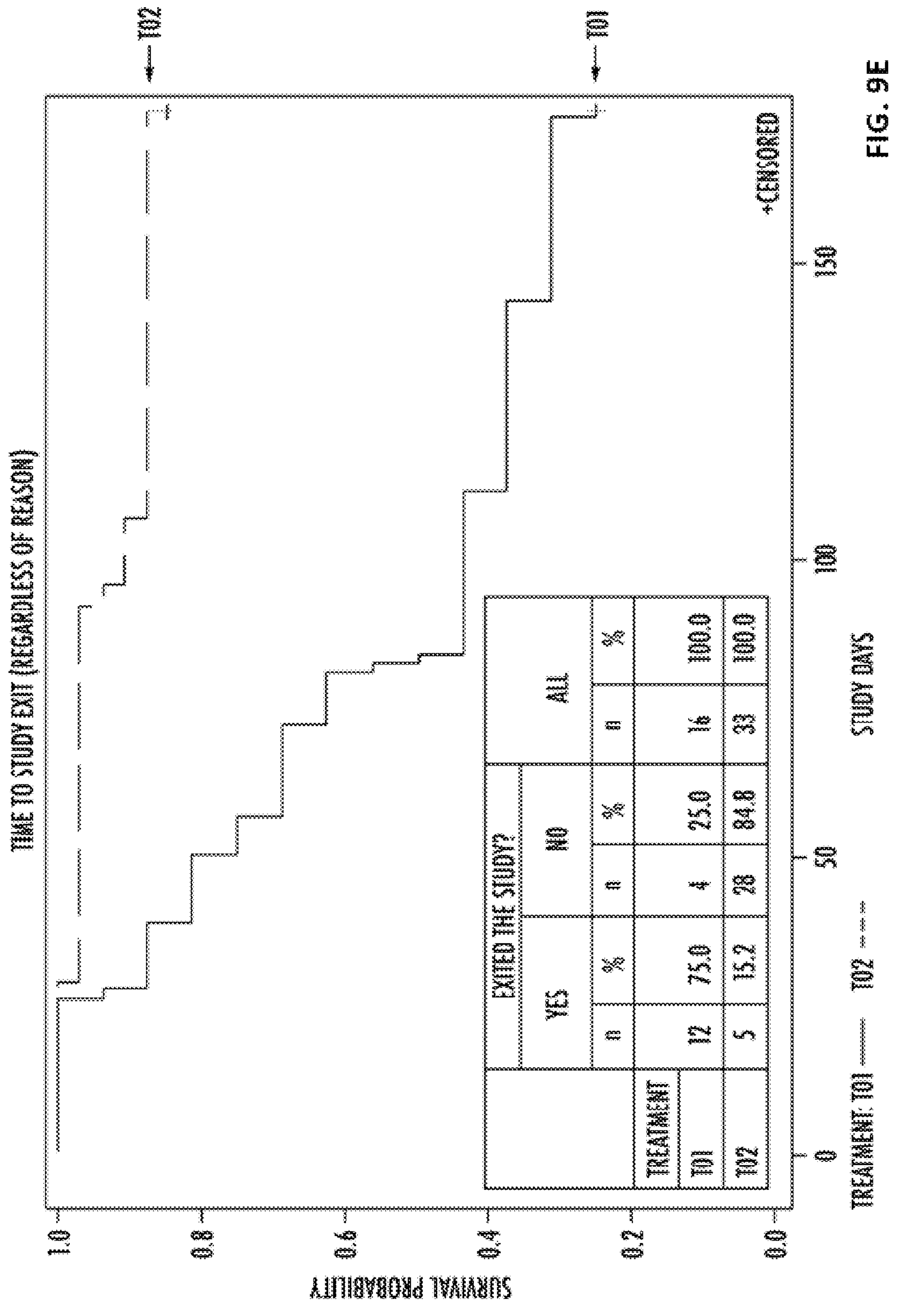
Figure 9F:
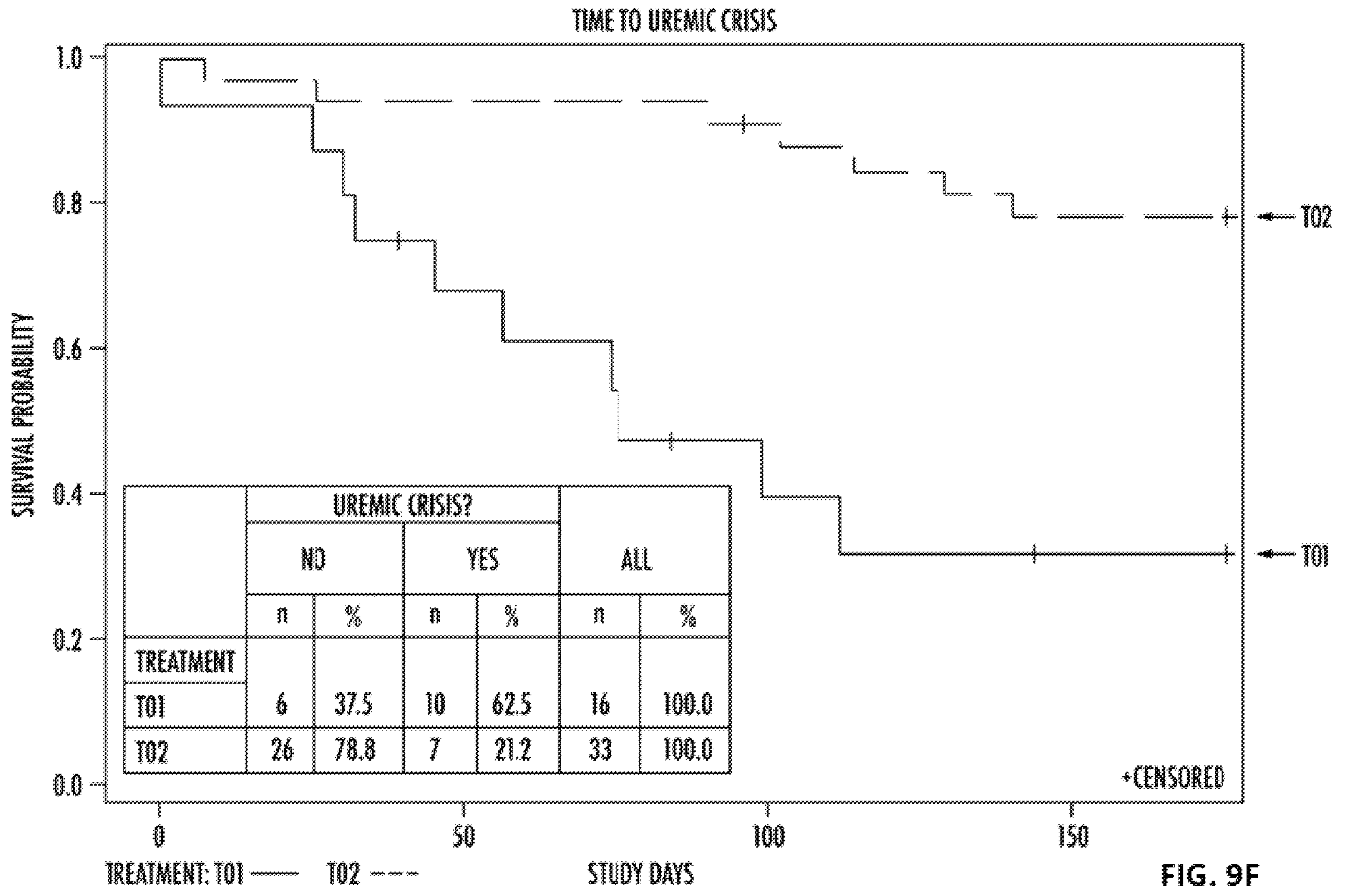

FIG. 8 shows the time to milestone of eight untreated affected male Alport dogs from a previous study that were used as historic controls, three untreated affected male Alport dogs (contemporaneous controls) and six Alport dogs treated with ZTS-501. Dogs treated with ZTS-501 were noted to have extended timelines to reach Stage 2 and 3. In clinical observations, a positive and marked impact was observed in clinical signs in dogs treated with ZTS-501. Untreated Alport dogs at ESRD demonstrated anorexia, emesis, lethargy, hunched posture, decreased activity level, and depression. In Alport dogs treated with ZTS-501, there were minimal clinical signs consistent with ESRD. It was observed that Alport dogs treated with ZTS-501 did not become anorexic at ESRD and had decreased number of emetic events as they approached ESRD. Treated Alport dogs averaged 5 emetic events, while the untreated Alport dogs averaged 24 emetic events during their lifespan. Overall, it was concluded that beneficial effects were noted within the ZTS-501 treated Alport dogs via extension of timeline to reach Stage 2 and 3 (described above) and clinical differences were observed between treated and untreated Alport dogs.

Felinization of the SL501 Antibody

As with the caninization of SL501 antibody, felinized antibodies were generated by taking the same CDR region sequences used for caninization and incorporating them with feline variable framework sequences. In addition to searching the feline databases for similar frameworks to the chimeric antibodies, the caninized antibody was used to search the database and provided additional feline germlines to investigate. Ultimately, a single variable heavy chain framework and a single variable light chain framework were selecting, resulting in the production of a single felinized variable heavy chain, referred to herein as felSL501-VH3-9 (SEQ ID NOS: 58 [nucleotide] and 59 [amino acid]), and a single felinized variable light chain, felSL501-VL1-1 (SEQ ID NOS: 60 [nucleotide] and 61 [amino acid]). Following subcloning of each variable chain into plasmids containing the respective feline heavy (SEQ ID NO: 131) or kappa (SEQ ID NO: 133) constant region plasmids were co-transfected for antibody expression in HEK 293 cells. Co-transfections were performed to give the following three combinations of heavy and light chains: 1) felSL501-VH3-9 heavy chain (SEQ ID NO: 59)+mouse light chain (SEQ ID NO: 40), 2) mouse heavy chain (SEQ ID NO: 38)+ felSL501-VL1-1 light chain (SEQ ID NO: 61), and 3) felSL501-VH3-9 heavy chain+felSL501-VL1-1 light chain. Following expression, TGFβ binding was investigated (see Table 21).

TABLE 21

| Alias | HC | LC | KD [pM] TGFβ1 | KD [pM] TGFβ2 | KD [pM] TGFβ3 | CMVIC pSmad-3, IC50 [nM] TGFβ1 | CMVIC pSmad-3, IC50 [nM] TGFβ2 | CMVIC pSmad-3, IC50 [nM] TGFβ3 |
|---|---|---|---|---|---|---|---|---|
| fel-TGFβ1-Spec | FelSL501-VH3-9 (SEQ ID NO: 59) | FelSL501-VL1-1 (SEQ ID NO: 61) | 3.75E−12 | none | none | 9.03 | none | none |
| fel-TGFβ 1_hetero-chimera-1 | FelSL501-VH3-9 (SEQ ID NO: 59) | mouse SL501 KC (SEQ ID NO: 40) | 2.62E−13 | none | none | 30.13 | none | none |
| fel-TGFβ1_hetero-chimera-2 | mouse SL501 HC (SEQ ID NO: 38) | FelSL501-VL1-1 (SEQ ID NO: 61) | 6.82E−11 | none | none | 11.87 | none | none |

TABLE 22-continued

| SEQ ID NO: | Description | Amino Acid Sequence |
|---|---|---|
| 70 | mHcLb light chain CDR #2 (CDR-K2) | LASNLES |
| 71 | mHcLb light chain CDR #3 (CDR-K3) | QQNNEDPLT |

Construction of Recombinant Mouse: Canine Chimeric Hclb

The same strategy described above for 04H09 chimeric antibodies was employed to generate chimeric antibodies that are highly specific towards active TGFβ 1, 2, and 3. The variable regions from the precursor mouse mHcLb monoclonal antibody (SEQ ID NOS: 62-65) were used for this and combined with the constant region of canine heavy (SEQ ID NO:127) and light chains (SEQ ID NO: 129) through subcloning into appropriate plasmids, as discussed above. The resulting chimeric antibodies (chiHcLb) showed good expression in HEK293 transient expression systems, good binding affinity, and excellent potency against TGFβ1 SMAD phosphorylation upon induction by all three TGFβ isoforms.

Example 3

Anti-TGFβ 1,2,3 Antibody

DNA Sequences Encoding Mouse Antibody Hclb

The murine anti-TGFβ1, 2, 3 "1D11" antibody (Dasch et al., J Immunol 1989 Mar. 1: 142(5): 1536-41) was identified and is referred to herein as mHcLb. The DNA encoding the variable heavy and variable light chains of this antibody was sequenced as described previously and the corresponding amino acid sequences of the variable regions of the heavy and light chains were deduced from that DNA sequence. The sequences determined for the mHcLb antibody are as follows:

SEQ ID NO: 62: mHcLb VH nucleotide sequence;
SEQ ID NO: 63: mHcLb VH amino acid sequence;
SEQ ID NO: 64: mHcLb VL nucleotide sequence;
SEQ ID NO: 65: mHcLb VL amino acid sequence.

Further, the six CDRs for the mHcLb monoclonal antibody are as follows:

TABLE 22

| SEQ ID NO: | Description | Amino Acid Sequence |
|---|---|---|
| 66 | mHcLb heavy chain CDR #1 (CDR-H1) | GYIFITY |
| 67 | mHcLb heavy chain CDR #2 (CDR-H2) | FPASGS |
| 68 | mHcLb heavy chain CDR #3 (CDR-H3) | GDGNYALDAMDY |
| 69 | mHcLb light chain CDR #1 (CDR-K1) | RASESVDSYGNSFMH |

Caninization of Antibody HcLb

As described above for the CDR grafting of 04H09, mHcLb antibody was caninized by identifying the most appropriate canine germline sequences for both heavy and light chains. Sequences were selected for their homology to the precursor monoclonal antibody sequence and native canine CDRs were replaced with those of mHcLb antibody. Three canine heavy chain variable frameworks (VH1, VH2, and VH3) and five canine kappa light chain variable frameworks (VL1, VL2, VL3, VL4, and VL5) were chosen for the initial caninization, resulting in the production of the following variable regions:

TABLE 23

| Alias | Heavy or light chain | SEQ ID NO for Nucleic acid | SEQ ID NO for Amino Acid |
|---|---|---|---|
| canHcLb-VH1 | Heavy | 72 | 73 |
| canHcLb-VH2 | Heavy | 74 | 75 |
| canHcLb-VH3 | Heavy | 76 | 77 |
| canHcLb-VL1 | Light | 78 | 79 |
| canHcLb-VL2 | Light | 80 | 81 |
| canHcLb-VL3 | Light | 82 | 83 |
| canHcLb-VL4 | Light | 84 | 85 |
| canHcLb-VL5 | Light | 86 | 87 |

Following subcloning of each variable chain into plasmids containing the respective canine heavy (SEQ ID NO: 127) or kappa (SEQ ID NO: 129) constant region plasmids were co-transfected for antibody expression in HEK 293 cells in all possible combinations (chiHcLb-VH/chiHcLb-VL, chiHcLb-VH/VL1, chiHcLb-VH/VL2, chiHcLb-VH/VL3, chiHcLb-VH/VL4, chiHcLb-VH/VL5, VH1/chiHcLb-VL, VH1NL1, VH1NL2, VH1NL3, VH1NL4, VH1NL5, VH2/chiHcLb-VL, VH2NL1, VH2NL2, VH2NL3, VH2NL4, VH2NL5, VH3/chiHcLb-VL, VH3NL1, VH3VL2, VH3NL3, VH3NL4, and VH3NL5) to make numerous caninized antibody constructs. All but two of the caninized constructs expressed in transient HEK293 expression systems. After expression, binding to all three TGFβ isoforms was assessed, as discussed above.

As the data shows, some affinity was lost upon caninization. Potency measurements for a subset of analyzed antibodies containing the kappa chain from chiHcLb-VL or canHclb-VL3 are shown in the table. All caninized antibodies tested lost some affinity from speciation and therefore affinity maturation was undertaken to attempt to regain the potency observed for the mouse antibody.

Affinity Maturation of Antibody Hclb

In an attempt initial to increase binding affinity, two point mutations (S79P and Q73K) were engineered into the Framework 2 region of the canHcLb-VL4 variable light chain, both individually and in combination, thereby producing three new variable light regions referred to as follows:

TABLE 24

| Alias | Amino Acid Substitution(s) | SEQ ID NO for Nucleic acid | SEQ ID NO for Amino Acid |
|---|---|---|---|
| canHcLb-VL4-S71P | S71P | 88 | 89 |
| canHvLb-VL4-Q73K | Q73K | 90 | 91 |
| canHcLb-VL4-S71P-Q73K | S71P and Q73K | 92 | 93 |

Each of these light chain peptides was combined with the canine constant light region (SEQ ID NO: 129), and then these light chains were co-expressed with the canHcLb-VH1 (SEQ ID NO. 73) heavy chain. Following expression, TGFβ1,2 and 3 binding affinity was analyzed as described above (for data see Table 25). All three constructs expressed active protein; however, no affinity to TGFβ1, 2, or 3 was gained by these mutations. Further maturation was thus undertaken in an attempt to increase binding affinity.

TABLE 25

| | | | SPR Full Concentration Titration KD [M] | | | pSmad-3 IC50 [nM] | | |
|---|---|---|---|---|---|---|---|---|
| Alias | HC | KC | TGFβ 1 | TGFβ 2 | TGFβ 3 | TGFβ 1 | TGFβ 2 | TGFβ 3 |
| mHcLb | mHcLb-VH | mHcLb_VL | 5.05E−09 | 5.86E−10 | 2.23E−10 | 1.52 | 10.96 | 1.11 |
| canchimHcLb | chiHcLb-VH | chiHcLb-VL | 4.33E−09 | 3.70E−10 | 6.79E−12 | | | |
| chimHK1 | chiHcLb-VH | canHcLb-VL1 | 1.82E−08 | 5.57E−09 | 6.72E−09 | | | |
| chimHK2 | chiHcLb-VH | canHcLb-VL2 | 2.12E−08 | 1.91E−08 | 1.14E−08 | | | |
| chimHK3 | chiHcLb-VH | canHcLb-VL3 | 1.29E−08 | 6.50E−09 | 3.45E−09 | | | |
| chimHK4 | chiHcLb-VH | canHcLb-VL4 | 4.26E−09 | 1.63E−09 | 1.95E−09 | 22.89 | 12.99 | 2.47 |
| chimHK5 | chiHcLb-VH | canHcLb-VL5 | 1.40E−08 | 1.20E−08 | 5.28E−09 | | | |
| H1chimK | canHcLb-VH1 | chiHcLb-VL | 6.52E−09 | 6.83E−10 | 1.03E−09 | | | |
| H1K1 | canHcLb-VH1 | canHcLb-VL1 | 5.47E−09 | 1.27E−08 | 1.34E−08 | | | |
| H1K2 | canHcLb-VH1 | canHcLb-VL2 | 9.96E−09 | 6.24E−09 | 6.77E−09 | | | |
| H1K3 | canHcLb-VH1 | canHcLb-VL3 | 2.76E−08 | 1.03E−08 | 8.69E−09 | | | |
| H1K4 | canHcLb-VH1 | canHcLb-VL4 | 7.65E−09 | 2.88E−09 | 3.33E−09 | 5.34 | 9.46 | 2.16 |
| H1K5 | canHcLb-VH1 | canHcLb-VL5 | 9.68E−09 | 2.14E−08 | 1.32E−08 | | | |
| H2chimK | canHcLb-VH2 | chiHcLb-VL | 1.63E−08 | 6.62E−09 | 2.26E−09 | | | |
| H2K1 | canHcLb-VH2 | canHcLb-VL1 | 2.84E−09 | 4.01E−08 | 2.28E−08 | | | |
| H2K2 | canHcLb-VH2 | canHcLb-VL2 | 1.86E−08 | 9.14E−09 | 9.99E−09 | | | |
| H2K3 | canHcLb-VH2 | canHcLb-VL3 | 1.01E−06 | 3.87E−09 | 2.47E−09 | | | |
| H2K4 | canHcLb-VH2 | canHcLb-VL4 | 1.22E−08 | 6.51E−09 | 3.20E−09 | | | |
| H2K5 | canHcLb-VH2 | canHcLb-VL5 | 2.86E−08 | 2.66E−08 | 3.37E−08 | | | |
| H3chimK | canHcLb-VH3 | chiHcLb-VL | 6.55E−09 | 7.90E−10 | 1.21E−09 | 10.15 | 9.79 | 1.96 |
| H3K1 | canHcLb-VH3 | canHcLb-VL1 | 3.28E−09 | 7.63E−09 | 4.10E−09 | | | |
| H3K2 | canHcLb-VH3 | canHcLb-VL2 | | | | | | |
| H3K3 | canHcLb-VH3 | canHcLb-VL3 | 2.09E−08 | 8.28E−09 | 3.90E−09 | | | |
| H3K4 | canHcLb-VH3 | canHcLb-VL4 | | | | | | |
| H3K5 | canHcLb-VH3 | canHcLb-VL5 | 8.52E−09 | 5.47E−09 | 5.67E−09 | | | |
| H1K4_S71P | canHcLb-VH1 | HcLb_VL4_S71P | 1.81E−08 | 1.2E−08 | 5.08E−09 | | | |
| H1K4_Q73K | canHcLb-VH1 | HcLb_VL4_073K | 1.84E−08 | 1.3E−08 | 4.74E−09 | | | |
| H1K4_S71P_Q73K | canHcLb-VH1 | HcLb_VL4_S71P_Q73K | 1.64E−08 | 1.1E−08 | 4.02E−09 | | | |

Affinity maturation of caninized Hclb "H1K4" (canHcLb-VH1: SEQ ID NO: 73 and canHcLb-VL4: SEQ ID NO:85) antibody was necessary to return the affinity of the caninized mAb to that of the progenitor mouse antibody. An antibody library was designed to contain individual point mutations within the antibody sequence in the CDR regions only. Site-saturation mutagenesis (SSM) was used to sample each natural amino acid (Cysteine was excluded) within the regions selected for maturation. This SSM library was constructed to identify beneficial mutations in CDRH1, CDRH2, CDRH3, and CDRL3. This library was constructed as a single-chain antibody (scFv) library via gene synthesis (GenScript, NJ) and was subcloned into a phagemid vector used for phage display panning and selections. The size of this mutagenesis library was approximately 1E9 and was amplified in TG1 *E. coli* cells.

The SSM Hclb library was used for biopanning via phage display against TGFβ1, TGFβ2, and TGFβ3 in order to identify mutations to enhance antibody affinity. Five rounds of panning were performed to screen a diverse scFv phage library. Antigen TGFβ1, B2 and B3 were coated to magnetic beads at a range of 10 ug to 0.25 ug, decreasing antigen amounts coated with each subsequent bio-panning round. The coated beads were then blocked with a customized blocking agent. Excess of $10^{11}$-$10^{12}$ scFV phage input was used for each bio-panning round during the binding step. A customized washing agent with increased number and length of washes was used for each successive round. Post-washing bound scFV phages were eluted using excess concentrations of a target related monoclonal antibody. Each bio-panning round output was collected and DNA was isolated. Next generation sequencing was used to analyze enrichment of sequences over each subsequent round. Raw sequencing reads were analyzed for 3 prime trimming and to remove sequence adapters to discard low quality sequences. Antibody sequence used as database and quality trimmed raw reads were blasted and used as queries. E-values of 0.001 chosen as threshold which roughly translated to at least a match of 14 amino acids over alignment length. Best alignment was chosen for each read. A customize internal script was written to convert the alignments to a data matrix where abundance of each amino acid at each position is calculated. Differential selection to calculate selection at each position for all samples as compared to the initial library. This produced log 2 ratios for each amino acid at each site. The output was used to calculate slopes and p-values. Negative slopes indicated a depletion of a particular amino acid at a specific location while positive slopes indicate abundance. Amino acids with positive slopes at specific locations were compiled for further testing and confirmation. Hundreds of theoretically enriched sequences were converted into full IgGs and expressed in transient cells. Results of expression for individual and combined mutations are provided. Single dilution SPR analysis on the full IgGs was performed for initial screening. Full titration SPR analysis was performed on good binders for KD confirmations and subsequent pSmad inhibition assays were performed to obtain IC50 values. Over 300 antibodies were evaluated as described herein. Binding results and functional potencies for mAbs that exhibited improved binding and/or functional properties associated with at least one or more of the TGFβ1, B2 or B3 proteins are included in Table 26 below with amino acid substitutions included in Table 27 below. As stated, over 300 antibodies were screened and 28 antibodies demonstrated improved binding and functional properties and are exemplified herein.

TABLE 26

| | | | SPR Full Concentration Titration KD [nM] | | | pSmad-3, IC50 [nM] | | |
|---|---|---|---|---|---|---|---|---|
| Alias | HC | KC | TGFβ1 | TGFβ2 | TGFβ3 | TGFβ1 | TGFβ2 | TGFβ3 |
| HcLb_H1K4 | HcLb-VH1 (SEQ ID NO: 73) | canHcLb-VL4 (SEQ ID NO: 85) | 7.7 | 2.88 | 3.33 | 5.34 | 6.28 | 2.16 |
| 27 | HcLb/mat/P/H3/100/DY (SEQ ID NO: 181) | canHcLb_VL4 (SEQ ID NO: 85) | | | | 1.43 | 8.24 | 1.70 |
| 73 | HcLb/mat/P/H3/D100/Y (SEQ ID NO: 181) | HcLb/mat/K3/237/ND (SEQ ID NO: 216) | | | | 1.17 | 8.42 | 1.24 |
| 91 | HcLb/mat/P/H2/S55W (SEQ ID NO: 183) | canHcLb_VL4 (SEQ ID NO: 85) | | | | 2.16 | 4.43 | 2.31 |
| 187 | canHcLb/A54G/D100Y (SEQ ID NO: 185) | canHcLb_VL4 (SEQ ID NO: 85) | | | | 0.82 | 2.08 | 8.61 |
| 188 | canHcLb/S55W/D100Y (SEQ ID NO: 187) | canHcLb_VL4 (SEQ ID NO: 85) | 3.96 | 0.937 | 0.417 | 2.73 | 2.29 | 1.46 |
| 189 | canHcLb/S55W/D100Y (SEQ ID NO: 187) | canHcLb/237ND/ 242TS (SEQ ID NO: 218) | 2.65 | 0.922 | 0.226 | 2.21 | 3.29 | 2.13 |
| 190 | canHcLb/A54G/D100Y (SEQ ID NO: 185) | canHcLb/237ND/ 242TS (SEQ ID NO: 218) | | | | 3.26 | 2.77 | 7.79 |
| 205 | canHcLb/S55W/D100Y/ T28/I (SEQ ID NO: 189) | canHcLb/237ND/ 242TS (SEQ ID NO: 218) | 1.78 | 2.09 | 0.005 | | | |
| 217 | canHcLb/S55W/D100Y/ I30/M (SEQ ID NO: 191) | canHcLb/237ND/ 242TS (SEQ ID NO: 218) | 2.58 | 3.91 | 0.676 | 0.78 | 1.71 | 1.44 |
| 233 | canHcLb/55SW/100DY/ 57/SM (SEQ ID NO: 193) | canHcLb/237ND/ 242TS (SEQ ID NO: 218) | 2.03 | 3.98 | 0.457 | 0.71 | 1.68 | 1.33 |
| 237 | canHcLb/55SW/100DY/ 57/SV (SEQ ID NO: 195) | canHcLb/237ND/ 242TS (SEQ ID NO: 218) | 2.27 | 4.07 | 0.476 | 0.76 | 1.60 | 1.05 |
| 239 | canHcLb/55SW/100DY/ 31/TK (SEQ ID NO: 197) | canHcLb/237ND/ 242TS (SEQ ID NO: 218) | 3.53 | 6.44 | 0.431 | 1.43 | 5.42 | 1.54 |
| 257 | canHcLb/55SW/100DY/ 30IM/31TK (SEQ ID NO: 199) | canHcLb/237ND/ 242TS (SEQ ID NO: 218) | 2.03 | 4.72 | 0.649 | 0.70 | 2.02 | 1.60 |
| 258 | canHcLb/55SW/100DY/ 30IM/31TK (SEQ ID NO: 199) | canHcLb_VL4 (SEQ ID NO: 85) | 3.81 | 4.4 | 8.6 | 0.61 | 0.79 | 1.09 |
| 259 | canHcLb/55SW/100DY/ 57/SM (SEQ ID NO: 193) | canHcLb_VL4 (SEQ ID NO: 85) | 3.05 | 3.75 | 0.78 | 0.99 | 1.37 | 1.48 |

TABLE 26-continued

| Alias | HC | KC | SPR Full Concentration Titration KD [nM] TGFβ1 | TGFβ2 | TGFβ3 | pSmad-3, IC50 [nM] TGFβ1 | TGFβ2 | TGFβ3 |
|---|---|---|---|---|---|---|---|---|
| 260 | canHcLb/55SW/100DY/57/SV (SEQ ID NO: 195) | canHcLb_VL4 (SEQ ID NO: 85) | 3.79 | 4.36 | 0.79 | 1.33 | 1.64 | 1.24 |
| 261 | canHcLb/55SW/100DY/30/IM (SEQ ID NO: 191) | canHcLb_VL4 (SEQ ID NO: 85) | 6.18 | 3.92 | 0.87 | 0.69 | 1.15 | 1.20 |
| 262 | canHcLb/55SW/100DY/31/TK (SEQ ID NO: 197) | canHcLb_VL4 (SEQ ID NO: 85) | 6.18 | 6.73 | 0.856 | 3.16 | 1.85 | 1.37 |
| 263 | canHcLb/55SW/100DY/28/TI (SEQ ID NO: 189) | canHcLb_VL4 (SEQ ID NO: 85) | 3.76 | 2.91 | 0.37 | 1.41 | 2.10 | 1.03 |
| 264 | canHcLb/55SW/100DY/30IM/31TK/28TI (SEQ ID NO: 201) | canHcLb/237ND/242TS (SEQ ID NO: 218) | 2.69 | 3.89 | 3.75 | | | |
| 265 | canHcLb/55SW/100DY/30IM/31TK/57SM (SEQ ID NO: 203) | canHcLb/237ND/242TS (SEQ ID NO: 218) | 3.24 | 2.82 | 0.7 | | | |
| 266 | canHcLb/55SW/100DY/30IM/31TK/28TI/57SM (SEQ ID NO: 205) | canHcLb/237ND/242TS (SEQ ID NO: 218) | 2.4 | 2.9 | 0.453 | | | |
| 267 | canHcLb/55SW/100DY/30IM/31TK/28TI (SEQ ID NO: 201) | canHcLb_VL4 (SEQ ID NO: 85) | 5.1 | 3.77 | 1.01 | | | |
| 268 | canHcLb/55SW/100DY/30IM/31TK/28TI/57SM (SEQ ID NO: 205) | canHcLb_VL4 (SEQ ID NO: 85) | 5.34 | 3.96 | 1.03 | | | |
| 269 | canHcLb/55SW/100DY/57SM/30IM (SEQ ID NO: 207) | canHcLb/237ND/242TS (SEQ ID NO: 218) | 4.4 | 3.05 | 0.99 | | | |
| 270 | canHcLb/55SW/100DY/57SV/30IM (SEQ ID NO: 209) | canHcLb/237ND/242TS (SEQ ID NO: 218) | 5.35 | 3.5 | 1.19 | | | |
| 271 | canHcLb/55SW/100DY/57SM/30IM/31TF (SEQ ID NO: 211) | canHcLb/237ND/242TS (SEQ ID NO: 218) | 2.3 | 1.28 | 0.957 | | | |
| 272 | canHcLb/55SW/100DY/57SM/30IM/31TF/28TK (SEQ ID NO: 213) | canHcLb/237ND/242TS (SEQ ID NO: 218) | 2.39 | 2.02 | 0.895 | | | |
| 275 | canHcLb/55SW/100DY/57SM/30IW/31TF/28TK (SEQ ID NO: 215 | canHcLb/237ND/242TS (SEQ ID NO: 218) | 2.39 | 2.91 | 0.824 | | | |

TABLE 27

| Alias | HC | KC | Amino Acid Substitutions HC CDR1 SEQ ID NO) | HC CDR2 SEQ ID NO) | HC CDR3 SEQ ID NO) | LC CDR3 SEQ ID NO) |
|---|---|---|---|---|---|---|
| 27 | HcLb/mat/P/H3/100/DY (SEQ ID NO: 181) | canHcLb_VL4 (SEQ ID NO: 85) | | | D100Y (283) | |
| 73 | HcLb/mat/P/H3/100/DY (SEQ ID NO: 181) | HcLb/mat/K3/237/ND (SEQ ID NO: 216) | | | D100Y (283) | N237D (284) |
| 91 | HcLb/mat/P/H2/55/SW (SEQ ID NO: 183) | canHcLb_VL4_WT (SEQ ID NO: 85) | | S55W (280) | | |
| 187 | canHcLb/54AG/100DY (SEQ ID NO: 185) | canHcLb_VL4_WT (SEQ ID NO: 85) | | A54G (279) | D100Y (283) | |
| 188 | canHcLb/55SW/100DY (SEQ ID NO: 187) | canHcLb_VL4_WT (SEQ ID NO: 85) | | S55W (280) | D100Y (283) | |
| 189 | canHcLb/55SW/100DY (SEQ ID NO: 187) | canHcLb/237ND/242TS (SEQ ID NO: 218) | | S55W (280) | D100Y (283) | N237D, T242S (286) |
| 190 | canHcLb/54AG/100DY (SEQ ID NO: 185) | canHcLb/237ND/242TS (SEQ ID NO: 218) | | | D100Y (283) | N237D, T242S (286) |
| 205 | canHcLb/55SW/100DY/28/TI (SEQ ID NO: 189) | canHcLb/237ND/242TS (SEQ ID NO: 218) | T28I (274) | S55W (280) | D100Y (283) | N237D, T242S (286) |

TABLE 27-continued

| Alias | HC | KC | Amino Acid Substitutions HC CDR1 SEQ ID NO) | HC CDR2 SEQ ID NO) | HC CDR3 SEQ ID NO) | LC CDR3 SEQ ID NO) |
|---|---|---|---|---|---|---|
| 217 | canHcLb/55SW/100DY/30/IM (SEQ ID NO: 191) | canHcLb/237ND/242TS (SEQ ID NO: 218) | I30M (275) | S55W (280) | D100Y (283) | N237D, T242S (286) |
| 233 | canHcLb/55SW/100DY/57/SM (SEQ ID NO: 193) | canHcLb/237ND/242TS (SEQ ID NO: 218) | | S57M (281) | D100Y (283) | N237D, T242S (286) |
| 237 | canHcLb/55SW/100DY/57/SV (SEQ ID NO: 195) | canHcLb/237ND/242TS (SEQ ID NO: 218) | | S55W, S57M (282) | D100Y (283) | |
| 239 | canHcLb/55SW/100DY/31/TK (SEQ ID NO: 197) | canHcLb/237ND/242TS (SEQ ID NO: 218) | | S55W (280) | D100Y (283) | |
| 257 | canHcLb/55SW/100DY/ 30IM/31TK (SEQ ID NO: 199) | canHcLb/237ND/242TS (SEQ ID NO: 218) | I30M (275) | S55W (280) | D100Y (283) | |
| 258 | canHcLb/55SW/100DY/ 30IM/31TK (SEQ ID NO: 199) | canHcLb_VL4 (SEQ ID NO: 85) | I30M (275) | S55W (280) | D100Y (283) | |
| 259 | canHcLb/55SW/100DY/57/SM (SEQ ID NO: 193) | canHcLb_VL4 (SEQ ID NO: 85) | | S55W, S57M (282) | D100Y (283) | |
| 260 | canHcLb/55SW/100DY/57/SV (SEQ ID NO: 195) | canHcLb_VL4 (SEQ ID NO: 85) | | S55W, S57M (282) | D100Y (283) | |
| 261 | canHcLb/55SW/100DY/30/IM (SEQ ID NO: 191) | canHcLb_VL4 (SEQ ID NO: 85) | I30M (275) | S55W (280) | D100Y (283) | |
| 262 | canHcLb/55SW/100DY/31/TK (SEQ ID NO: 197) | canHcLb_VL4 (SEQ ID NO: 85) | T31K (276) | S55W (280) | D100Y (283) | |
| 263 | canHcLb/55SW/100DY/28/TI (SEQ ID NO: 189) | canHcLb_VL4 (SEQ ID NO: 85) | T28I (274) | S55W (280) | D100Y (283) | |
| 264 | canHcLb/55SW/100DY/ 30IM/31TK/28TI (SEQ ID NO: 201) | canHcLb/237ND/242TS (SEQ ID NO: 218) | T28I, I30M, T31K (278) | S55W (280) | D100Y (283) | N237D, T242S (286) |
| 265 | canHcLb/55SW/100DY/ 30IM/31TK/57SM (SEQ ID NO: 203) | canHcLb/237ND/242TS (SEQ ID NO: 218) | I30M, T31K (277) | S55W, S57M (282) | D100Y (283) | N237D, T242S (286) |
| 266 | canHcLb/55SW/100DY/ 30IM/31TK/28TI/57SM (SEQ ID NO: 205) | canHcLb/237ND/242TS (SEQ ID NO: 218) | T28I, I30M, T31K (278) | S55W, S57M (282) | D100Y (283) | N237D, T242S (286) |
| 267 | canHcLb/55SW/100DY/ 30IM/31TK/28T1 (SEQ ID NO: 201) | canHcLb_VL4 (SEQ ID NO: 85) | T28I, I30M, T31K (278) | S55W (280) | D100Y (283) | |
| 268 | canHcLb/S55W/D100Y/I30M/ T31K/T28I/S57M (SEQ ID NO: 205) | canHcLb_VL4 (SEQ ID NO: 85) | T28I, I30M, T31K (278) | S55W, S57M (282) | D100Y (283) | |
| 275 | canHcLb/S55W/D100Y/S57M/ I30M/T31F/T28I (SEQ ID NO: 215) | canHcLb/237ND/242TS (SEQ ID NO: 218) | T28I, I30M, T31F (278) | S55W, S57M (282) | D100Y (283) | N237D, T242S (286) |

Felinization of Antibody HcLb

As with the caninization of mHcLb antibody, felinized antibodies were generated by taking the same CDR region sequences used for caninization and incorporating them with feline variable framework sequences. Feline databases were searched for similar frameworks to the chimeric and/or caninized antibodies to identify feline germlines to investigate. Initially, two heavy chain frameworks and four light chain frameworks were selecting, resulting in the production of the following felinized variable regions:

TABLE 28

| Alias | Heavy or light chain | SEQ ID NO for Nucleic acid | Amino Acid |
|---|---|---|---|
| felHcLb-H636 | Heavy | 94 | 95 |
| felHcLb-H1-1 | Heavy | 96 | 97 |
| felHcLb-K1-1 | Light | 98 | 99 |
| felHcLb-K36 | Light | 100 | 101 |
| felHcLb-K4-1 | Light | 102 | 103 |
| felHcLb-K2D-2 | Light | 104 | 105 |

Following subcloning of each variable chain into plasmids containing the respective feline heavy (SEQ ID NO: 132) or kappa (SEQ ID NO: 134) constant region plasmids were co-transfected for antibody expression in HEK 293 cells. Co-transfections were performed to give the following five combinations of heavy and light chains: 1) felHcLb-H636 heavy chain+felHcLb-K1-1 light chain, 2) felHcLb-H1-1 heavy chain+felHcLb-K36 light chain, 3) felHcLb-H1-1 heavy chain+felHcLb-K1-1 light chain, 4) felHcLb-H1-1 heavy chain+felHcLb-K4-1 light chain, and 5) felHcLb-H1-1 heavy chain+felHcLb-K2D-2 light chain. Following expression, TGFβ binding was investigated via SPR (see Table 29). The results demonstrated that the felinized antibodies bound TGFβ1, 2, and 3 very weakly.

TABLE 29

| | | | KD [pM] | | |
|---|---|---|---|---|---|
| Alias | HC | KC | TGFβ1 | TGFβ2 | TGFβ3 |
| felHclb-2 | felHclbH636 | felHclbK1-1 | 3.19E−06 | 2.34E−06 | 3.12E−06 |
| felHclb-13 | felHclbH1-1 | felHclbK36 | 2.55E−06 | 4.15E−06 | 1.62E−06 |
| felHclb-14 | felHclbH1-1 | felHclbK1-1 | 9.47E−08 | 2.84E−06 | 3.56E−06 |
| felHclb-15 | felHclbH1-1 | felHclbK4-1 | 2.21E−08 | 3.75E−07 | 2.66E−06 |
| felHclb-16 | felHclbH1-1 | felHclbK2D2 | 1.5E−07 | 5.93E−06 | 3.00E−06 |

In an attempt to obtain felinized antibodies with increased affinity, additional felinized HcLb heavy chains were developed through the identification of additional heavy chain frameworks (referred to as H618 and H634) and through the construction of HcLb CDRH2 variants. These CDRH2 variants were made based on differences between software designation of CDR regions; e.g., Kabat vs Chothia. Initially CDR regions were designated by using the Kabat method, however different analysis suggested CDRs that were suggested as having longer sequences. For HcLb, this dissimilarity is particularly pronounced for CDRH2, and to a smaller degree for CDRH1. Thus, the original felinization of HcLb was based on the shorter CDR output from Kabat, however these mAbs lost affinity to TGFβ. Thus, a panel of extended CDRH2 variants was generated based on the having longer sequences. These variants have an "x" at the end of their name and are indicated in the following table.

TABLE 30

| | Original | SEQ ID NO for | |
|---|---|---|---|
| Alias | (HcLb CDRH2) or modified (HcLb CDRH2x) CDR region? | Nucleic acid | Amino Acid |
| felHcLb-H618s | Original HcLb CDRH2 | 106 | 107 |
| felHcLb-H636x | Extended CDRH2 | 108 | 109 |
| felHcLb-H1-1x | Extended CDRH2 | 110 | 111 |
| felHcLb-H618x | Extended CDRH2 | 112 | 113 |
| felHcLb-H634x | Extended CDRH2 | 114 | 115 |

The modified CDR region employed for all of these is referred to as CDRH2x, which possesses the following amino acid sequence: QIFPASGSTNYNEMFEG (SEQ ID NO:116). Following subcloning of each of these additional variable heavy chains into plasmids listed in Table 31 containing the respective feline heavy constant region (nucleotide sequence for feline heavy chain constant region SEQ ID NO:131 and the nucleotide sequence for feline light chain constant region SEQ ID NO: 133) plasmids were co-transfected for antibody expression in HEK 293 cells. Co-transfections were performed to give 19 distinct combinations of heavy and light chains which were then investigated for TGFβ binding via SPR. Results demonstrated that these felinized antibodies had negligible TGFβ binding against all three isotypes. Table 32 shows the heavy and light chain pairing that showed little, if any binding.

TABLE 31

| Alias | HC | KC |
|---|---|---|
| felHclbH636x-K36 | felHclbH636x (SEQ ID NO: 109) | felHclbK36 (SEQ ID NO: 101) |
| felHclbH1-1x-K36 | felHclbH1-1x (SEQ ID NO: 111) | felHclbK36 (SEQ ID NO: 101) |
| felHclbH618s-K36 | felHclbH618s (SEQ ID NO: 113) | felHclbK36 (SEQ ID NO: 101) |
| felHclbH618x-K36 | felHclbH618x (SEQ ID NO: 113) | felHclbK36 (SEQ ID NO: 101) |
| felHclbH636x-K1-1 | felHclbH636x (SEQ ID NO: 109) | felHclbK1-1 (SEQ ID NO: 105) |
| felHclbH1-1x-K1-1 | felHclbH1-1x (SEQ ID NO: 111) | felHclbK1-1 (SEQ ID NO: 105) |
| felHclbH634x-K1-1 | felHclbH634x (SEQ ID NO: 115) | felHclbK1-1 (SEQ ID NO: 105) |
| felHclbH618s-K1-1 | felHclbH618s (SEQ ID NO: 113) | felHclbK1-1 (SEQ ID NO: 105) |
| felHclbH618x-K1-1 | felHclbH618x (SEQ ID NO: 113) | felHclbK1-1 (SEQ ID NO: 105) |
| felHclbH636x-K4-1 | felHclbH636x (SEQ ID NO: 109) | felHclbK4-1 (nt SEQ ID NO: 102 |
| felHclbH1-1x-K4-1 | felHclbH1-1x (SEQ ID NO: 111) | felHclbK4-1 (nt SEQ ID NO: 102 |
| felHclbH634x-K4-1 | felHclbH634x (SEQ ID NO: 115) | felHclbK4-1 (nt SEQ ID NO: 102 |
| felHclbH618s-K4-1 | felHclbH618s (SEQ ID NO: 113) | felHclbK4-1 (nt SEQ ID NO: 102 |
| felHclbH618x-K4-1 | felHclbH618x (SEQ ID NO: 113) | felHclbK4-1 (nt SEQ ID NO: 102 |
| felHclbH636x-KD2-2 | felHclbH636x (SEQ ID NO: 109) | felHclbK2D-2 (SEQ ID NO: 103) |
| felHclbH1-1x-KD2-2 | felHclbH1-1x (SEQ ID NO: 111) | felHclbK2D-2 (SEQ ID NO: 103) |
| felHclbH634x-KD2-2 | felHclbH634x (SEQ ID NO: 115) | felHclbK2D-2 (SEQ ID NO: 103) |
| felHclbH618s-KD2-2 | felHclbH618s (SEQ ID NO: 113) | felHclbK2D-2 (SEQ ID NO: 103) |
| felHclbH618x-KD2-2 | felHclbH618x (SEQ ID NO: 113) | felHclbK2D-2 (SEQ ID NO: 103) |

Following this result, and in an attempt to regain affinity in the felinized mAbs, six of the above-described felinized HcLb heavy chains with the best TGFβ3 binding were paired with the original mouse light chain (mHcLb-VL) or one of the caninized versions of the light chain (canHcLb-VL4). Similarly, four of the above-discussed felinized HcLb light chains were paired with the original mouse heavy chain (mHcLb-VH) or one of the caninized versions of the heavy chain (canHcLb-VH1). These mAbs are defined herein as "hetero-pairings" as the felinized chains are paired with chains of other species. All hetero-pairings expressed except the four with mouse heavy chain. However, only the caninized heavy chain (canHcLb-VH 1) paired with the felinized kappa chains restored high affinity binding of the felinized antibodies to TGFβ1, 2, and 3 (see Table 32).

TABLE 32

| Alias | HC | KC | KD [pM] TGFβ 1 | TGFβ 2 | TGFβ 3 |
|---|---|---|---|---|---|
| felHclb_heterochimera-1 | felHclbH636 | canHclb_VL4 | no binding | no binding | no binding |
| felHclb_heterochimera-2 | felHclbH1-1 | canHclb_VL4 | no binding | no binding | no binding |
| felHclb_heterochimera-3 | felHclbH636x | canHclb_VL4 | no binding | no binding | no binding |
| felHclb_heterochimera-4 | felHclbH1-1x | canHclb_VL4 | no binding | no binding | no binding |
| felHclb_heterochimera-5 | felHclbH618s | canHclb_VL4 | no binding | no binding | no binding |
| felHclb_heterochimera-6 | felHclbH618x | canHclb_VL4 | 1.02E−05 | 9.91E−06 | 1.32E−06 |
| felHclb_heterochimera-7 | canHclb_VH1 | felHclbK36 | 2.22E−08 | 7.76E−09 | 4.42E−09 |
| felHclb_heterochimera-8 | canHclb_VH1 | felHclbK1-1 | 2.41E−08 | 7.57E−09 | 3.96E−09 |
| felHclb_heterochimera-9 | canHclb_VH1 | felHclbK4-1 | 2.66E−08 | 1.04E−08 | 5.62E−09 |
| felHclb_heterochimera-10 | canHclb_VH1 | felHclbK2D-2 | 6.73E−08 | 3.24E−08 | 1.69E−08 |
| felHclb_heterochimera-11 | felHclbH636 | mHclbVL | no binding | no binding | no binding |
| felHclb_heterochimera-12 | felHclbH1-1 | mHclbVL | no binding | no binding | no binding |
| felHclb_heterochimera-13 | felHclbH636x | mHclbVL | no binding | no binding | no binding |
| felHclb_heterochimera-14 | felHclbH1-1x | mHclbVL | no binding | no binding | no binding |
| felHclb_heterochimera-15 | felHclbH618s | mHclbVL | no binding | no binding | no binding |
| felHclb_heterochimera-16 | felHclbH618x | mHclbVL | no binding | no binding | no binding |

Based on the results obtained from the hetero-pairings, it was deduced that the felinized heavy chain was responsible for the loss of TGFβ binding affinity. In a further effort to restore affinity to the felinized versions of HcLb, heavy chain CDR1 variants were generated using the same method described above for CDRH2 variant generation. More specifically, two different variant downstream extended versions of the heavy chain CDR1 region were generated, either WMN or YMN:

TABLE 33

| | | |
|---|---|---|
| Original mHcLb CDRH1 | GYIFITY | SEQ ID NO: 66 |
| WMN variant CDRH1 (CDRH1-WMN) | GYIFITYWMN | SEQ ID NO: 117 |
| MN variant CDRH1 (CDRH1-MN) | GYIFITYYMN | SEQ ID NO: 118 |

These CDRH1 variants were incorporated into the felHcLb-H1-1 variable heavy region, both with and without the CDRH2 variant region discussed above, thereby creating four additional felinized variable heavy regions:

TABLE 34

| Alias | HcLb CDRH1 and H2 | SEQ ID NO for Nucleic acid | Amino Acid |
|---|---|---|---|
| felHcLb-H1-1WMN | Variant CDRH1-WMN Mouse CDRH2 | 119 | 120 |
| felHcLb-H1-1xWMN | Variant CDRH1-WMN Variant CDRH2x | 121 | 122 |
| felHcLb-H1-1MN | Variant CDRH1-MN Mouse CDRH2 | 123 | 124 |
| felHcLb-H1-1xMN | Variant CDRH1-MN Variant CDRH2x | 125 | 126 |

Following subcloning of each of these additional variable heavy regions into plasmids containing the respective feline heavy constant region (nucleotide sequence for feline heavy chain constant region SEQ ID NO:131 and the nucleotide sequence for feline light chain constant region SEQ ID NO: 133), plasmids were co-transfected with felHcLb-K1-1 light chain, described above, for antibody expression in HEK 293 cells. Following expression, TGFβ binding was investigated via SPR. The felHcLb-H1-1×WMN antibody, which included variants in both CDRH1 and CDRH2 regions, restored high affinity binding to TGFβ1, 2, and 3 and resulted in strong neutralization of TGFβ1, 2, and 3 pSMAD functional activity in primary canine valve interstitial cells (see Table 35).

TABLE 35

| Alias | HC | KC | KD [pM] TGFβ 1 | TGFβ 2 | TGFβ 3 | CMVIC pSmad-3, IC50 [nM] TGFβ 1 | TGFβ 2 | TGFβ 3 |
|---|---|---|---|---|---|---|---|---|
| felHclb 1-1WMN | felHclbH1-1WMN | felHclbK1-1 | 3.13E−07 | 1.44E−08 | 5.60E−09 | 69.67 | 121.13 | 10.05 |
| felHclb 1-1xWMN | felHclbH1-1xWMN | felHclbK1-1 | 2.00E−08 | 6.99E−09 | 3.12E−11 | 0.35 | 1.99 | 0.53 |
| felHclb 1-1YMN | felHclbH1-1YMN | felHclbK1-1 | 2.63E−04 | 1.70E−07 | 4.76E−06 | no test | no test | no test |
| felHclb 1-1YMN | felHclbH1-1xYMN | felHclbK1-1 | 1.54E−05 | 7.65E−08 | 1.73E−08 | no test | no test | no test |

Pharmacokinetics of ZTS-4155

A study to determine the subcutaneous and intravenous pharmacokinetics of caninized anti-TGFβ1,2,3 monoclonal antibody, ZTS-4155 (VH: SEQ ID NO.73, VL: SEQ ID NO.85), in dogs. Study design is represented in Table 36.

TABLE 36

| Study Period | Dose (mg/kg) | Dose Vol. (mL/kg) | Animal No. | Treatment Route |
|---|---|---|---|---|
| 1 | 2.0 | 0.20 | 1-4 | SC |
| 2 | 2.0 | 0.20 | 1-4 | SC |
| 3 | 2.0 | 0.20 | 1-4 | IV |

Pharmacokinetic calculations were performed using the noncompartmental approach (linear trapezoidal rule for AUC calculation) with the aid of Watson (v7.4.1, Thermo Electron Corp., Philadelphia, PA). PK parameters were calculated for Periods 1, 2, and 3 using data from Study Days 0-28, Study Days 28-56, and Study Days 56-84, respectively. Bioavailability was calculated using Microsoft Excel to correct for carryover of period one into period two, and period two into period three. Bioavailability was based on estimated $AUC_{0-\infty}$ of the subcutaneous doses relative to the intravenous dose.

TABLE 37

Serum ZTS-4155 concentrations (μg/mL) in the dog

| Period | Time (Days) | Dog 1 | Dog 2 | Dog 3 | Dog 4 | Mean | SD | % CV |
|---|---|---|---|---|---|---|---|---|
| Period 1 | 0 | BLQ | BLQ | BLQ | BLQ | BLQ | NC | NC |
| (SC | 1 | 5.28 | 28.4 | 23.5 | 17.7 | 18.7 | 9.97 | 53.3 |
| Dose) | 3 | 14.1 | 28.1 | 25.9 | 18.6 | 21.7 | 6.48 | 29.9 |
| | 7 | 13.4 | 24.3 | 18.8 | 15.6 | 18 | 4.73 | 26.3 |
| | 14 | 2.6 | 7.5 | 4.46 | 7.32 | 5.47 | 2.37 | 43.3 |
| | 21 | 0.0934 | 1.96 | 1 | 2.44 | 1.37 | 1.04 | 75.9 |
| | 28 | 0.01 | 0.682 | 0.288 | 0.724 | 0.426 | 0.34 | 79.8 |
| Period 2 | 29 | 13.4 | 32.1 | 21.2 | 18.1 | 21.2 | 7.94 | 37.5 |
| (SC | 31 | 13.4 | 31.5 | 25.6 | 17.2 | 21.9 | 8.17 | 37.3 |
| Dose) | 35 | 5.67 | 22.8 | 18.8 | 13.4 | 15.2 | 7.41 | 48.8 |
| | 42 | 0.37 | 7.97 | 4.55 | 8.18 | 5.27 | 3.66 | 69.4 |
| | 49 | 0.0945 | 2.08 | 0.986 | 2.6 | 1.44 | 1.12 | 77.8 |
| | 56 | 0.0172 | 0.778 | 0.28 | 0.844 | 0.48 | 0.398 | 82.9 |
| Period 3 | 56.01 | 38.6 | 18.7 | 28.8 | 25.4 | 27.9 | 8.29 | 29.7 |
| (IV | 57 | 20.4 | 16.9 | 17.8 | 23.3 | 19.6 | 2.88 | 14.7 |
| Dose) | 58 | 14.5 | 12.7 | 9.59 | 14.2 | 12.7 | 2.25 | 17.7 |
| | 63 | 3.79 | 5.18 | 5.37 | 5.18 | 4.88 | 0.732 | 15 |
| | 70 | 1.17 | 1.39 | 1.72 | 1.55 | 1.46 | 0.234 | 16 |
| | 77 | 0.819 | 0.339 | 0.823 | 0.494 | 0.619 | 0.242 | 39.1 |
| | 84 | 0.368 | 0.0935 | 0.274 | 0.105 | 0.21 | 0.134 | 63.8 |

Doses administered on Day 0, Day 28 and Day 56. Samples on dose days were collected prior to dosing.

TABLE 38

Serum ZTS-4155 pharmacokinetics in the dog for Period 1 (2.0 mg/kg subcutaneous dose on Day 0)

| Parameter | Units | Dog 1 | Dog 2 | Dog 3 | Dog 4 | Mean | S.D. | % CV |
|---|---|---|---|---|---|---|---|---|
| Cmax | μg/mL | 14.1 | 28.4 | 25.9 | 18.6 | 21.8 | 6.58 | 30.3 |
| Tmax | Days | 3.0 | 1.0 | 3.0 | 3.0 | 2.5 | 1.0 | 40.0 |
| T½ | Days | 1.74 | 4.05 | 3.54 | 4.19 | 3.38 | 1.13 | 33.4 |
| AUC0-28 d | μg*Days/mL | 143 | 329 | 256 | 239 | 242 | 76.5 | 31.7 |
| AUC0-inf | μg*Days/mL | 143 | 333 | 257 | 243 | 244 | 78.1 | 32.0 |
| Bioavailability | | 114 | 323 | 227 | 203 | 217 | 86 | 39.6 |

TABLE 19

Serum ZTS-4155 pharmacokinetics in the dog for Period 2 (2.0 mg/kg subcutaneous dose on Day 28)

| Parameter | Units | Dog 1 | Dog 2 | Dog 3 | Dog 4 | Mean | S.D. | % CV |
|---|---|---|---|---|---|---|---|---|
| Cmax | μg/mL | 13.4 | 32.1 | 25.6 | 18.1 | 22.3 | 8.24 | 37.0 |
| Tmax | Days | 1.0 | 1.0 | 3.0 | 1.0 | 1.5 | 1.0 | 66.7 |
| T½ | Days | 3.16 | 4.17 | 3.48 | 4.27 | 3.77 | 0.537 | 14.3 |

TABLE 19-continued

| Serum ZTS-4155 pharmacokinetics in the dog for Period 2 (2.0 mg/kg subcutaneous dose on Day 28) | | | | | | | | |
|---|---|---|---|---|---|---|---|---|
| Parameter | Units | Dog 1 | Dog 2 | Dog 3 | Dog 4 | Mean | S.D. | % CV |
| AUC28-56 d | μg*Day5/mL | 94.8 | 341 | 252 | 231 | 230 | 102 | 44.3 |
| AUC28-inf | μg*Days/mL | 94.9 | 346 | 253 | 236 | 232 | 104 | 44.6 |
| Bioavailability | | 76 | 332 | 223 | 193 | 206 | 105 | 51.1 |

TABLE 40

| Serum ZTS-4155 pharmacokinetics in the dog for Period 3 (2.0 mg/kg intravenous dose on Day 56) | | | | | | | | |
|---|---|---|---|---|---|---|---|---|
| Parameter | Units | Dog 1 | Dog 2 | Dog 3 | Dog 4 | Mean | S.D. | % CV |
| CL | mL/min/kg | 0.0111 | 0.0129 | 0.0122 | 0.0111 | 0.0118 | 0.000885 | 7.5 |
| Vdss | mL/kg | 91.6 | 89.5 | 106 | 74.1 | 90.3 | 13.1 | 14.5 |
| T½ | Days | 8.39 | 3.59 | 5.28 | 3.60 | 5.22 | 2.26 | 43.4 |
| AUC56-84 d | μg*Days/mL | 121 | 108 | 112 | 124 | 116 | 7.50 | 6.5 |
| AUC56-inf | μg*Days/mL | 125 | 108 | 114 | 125 | 118 | 8.45 | 7.2 |

Figure 12:
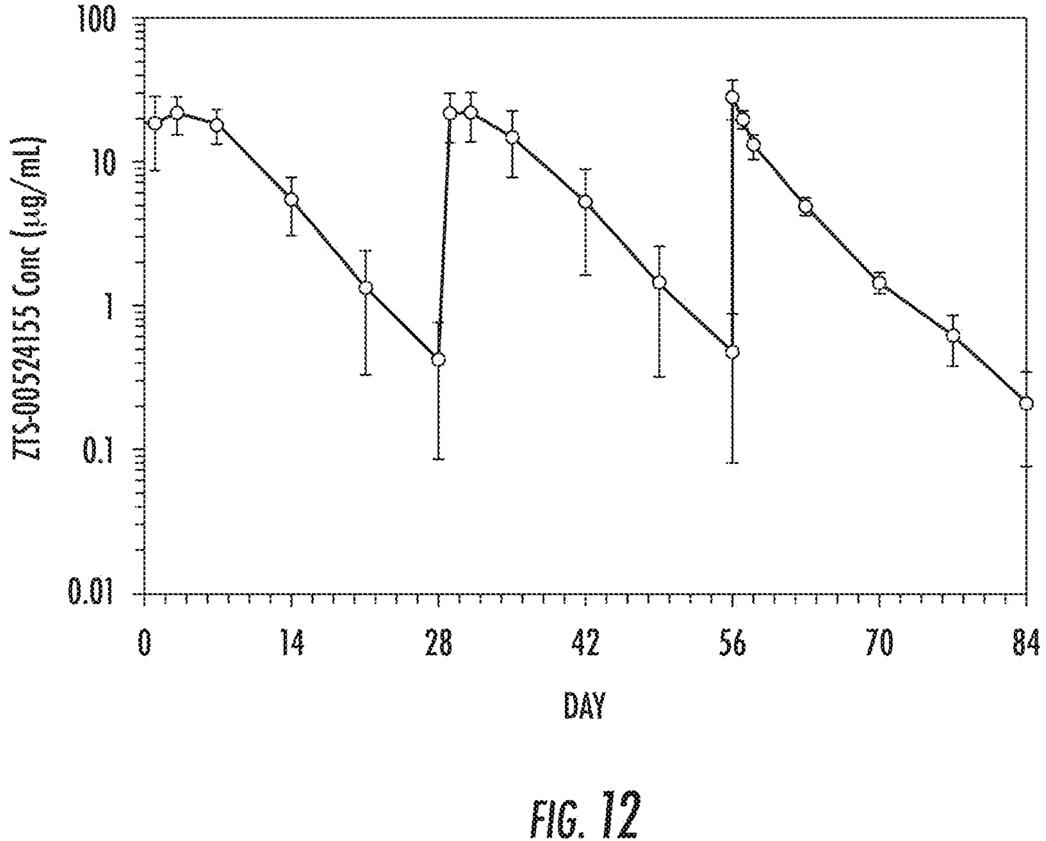
FIG. 12 is a graphical representation of the mean dog serum of ZTS-4155 concentration-time graph.

FIG. 12 represents the mean dog serum ZTS-4155 concentration time graph. Error bars indicate one standard deviation. The half-life for ZTS-4155 was determined to be approximately 4.1 days.

Example 4

Epitope Mapping Via Hydrogen Deuterium Exchange

Hydrogen Deuterium Exchange (HDX) experiments were used to determine the epitopes on TGFβ1 to which each antibody series binds. This method establishes the peptide level epitope on TGFβ1 targeted by each mAb by HDX mass spectrometry. For each mAb analysis, TGFβ1 is incubated in deuterium oxide in the presence and absence of mAb, is digested, and fragments are then analyzed and compared for hydrogen/deuterium exchange via mass spectrometry.

More specifically, the method was carried out as follows: One milligram of TGFβ1 was reconstituted in 500 μL control buffer (50 mM phosphate, 100 mM sodium chloride at pH 7.4). 10 μL human TGFβ1 (10 μg) (PeproTech) or 10 μL human TGF01 & mAb mixture (10 μg:70 μg) was incubated with 70 μL deuterium oxide labeling buffer (50 mM sodium phosphate, 100 mM sodium chloride at pD 7.4) for 1 min, 10 min and 1 hr. Hydrogen/deuterium exchange was quenched by adding 160 μL of 8 M urea, 0.85 M TCEP buffer (final pH is 4.0). Subsequently, the quenched samples were subjected to on column pepsin digestion and LC-MS analysis. The mass spectra were recorded in MS only mode.

For pepsin digestion, 10 μg of human TGFβ1 in 80 μL control buffer (50 mM phosphate, 100 mM sodium chloride at pH 7.4) was denatured by adding 160 μL of 8 M urea, 0.85 M TCEP buffer (final pH is 4.0) and incubating the mixture for 3 min at 6° C. Then, the mixture was subjected to pepsin digestion using an-house packed pepsin column (2.1×30 mm) at 11° C. and the resultant peptides was analyzed using a UPLC-MS system comprised of a Waters Acquity UPLC coupled to a Q Exactive™ Hybrid Quadrupole-Orbitrap Mass Spectrometer (Thermo). The peptides were trapped and then separated on a 50 mm×1 mm C8 column with a 20.5 min gradient from 2-32% solvent B (0.2% formic acid in acetonitrile). Solvent A is 0.2% formic acid in water. The injection valve and pepsin column and their related connecting tubings are inside a cooling box maintained at 11° C. And the second switching valve, trap column, C8 column and their related connecting stainless steel tubings are inside a chilled circulating box maintained at 0° C. Peptide identification is done through searching MS/MS data against the mouse TGFβ1 sequence with Mascot. The mass tolerance for the precursor and product ions is 10 ppm and 0.02 Da, respectively.

Raw MS data was processed using HDX WorkBench, software for the analysis of H/D exchange MS data (*J. Am. Soc. Mass Spectrom.* 2012, 23 (9), 1512-1521). The deuterium levels were calculated using the average mass difference between the deuteriated peptide and its native form (to).

The following antibodies were characterized via this method: 04H09 (murine), can04H09 (VH1NL4), SL501 (murine), canSL501 (caninized VH3/FW2/Q110D+VL2), mHcLb (murine), and canHcLb (caninized). The resulting epitope regions are shown in FIG. 1 and are represented as peptide stretches. As reference, the sequence of human TGFβ1 (100% identical to canine and feline) is shown above the table. Strong deuterium exchange responses are represented thus indicating that this is a clear epitope for that antibody. Secondary epitopes also represented showed modest reduction in deuterium uptake upon mAb binding and are likely peripheral regions of the epitope.

We claim:

1. A caninized antigen binding protein that specifically binds Transforming Growth Factor Beta-1 (TGFβ1) and wherein said antigen binding protein further specifically binds to canine Transforming Growth Factor Beta-3 (TGFβ3), wherein said protein comprises:

a. a heavy chain variable region (VH) comprising:

i. a Complimentary Determining Region 1 (CDR1) comprising an amino acid sequence comprising SEQ ID NO. 5;

ii. a Complimentary Determining Region 2 (CDR2) comprising an amino acid sequence comprising SEQ ID NO. 6;

iii. a Complimentary Determining Region 3 (CDR3) comprising an amino acid sequence comprising SEQ ID NO: 7; and b. a light chain variable region (VL) comprising:

i. a Complimentary Determining Region 1 (CDR1) comprising an amino acid sequence comprising SEQ ID NO. 8;

ii. a Complimentary Determining Region 2 (CDR2) comprising an amino acid sequence comprising SEQ ID NO. 9; and iii. a Complimentary Determining Region 3 (CDR3) comprising an amino acid sequence comprising SEQ ID NO: 10.

2. The antigen binding protein of claim 1, wherein the antigen binding protein comprises:

a. a heavy chain variable region (VH) comprising amino acid sequences selected from the group consisting of: SEQ ID NO:12; SEQ ID NO:14; SEQ ID NO:16; and b. a light chain variable region (VL) comprising amino acid sequence SEQ ID NO:24.

3. The antigen binding protein of claim 2, wherein said antigen binding protein comprises a heavy chain variable region (VH) comprising amino acid sequence SEQ ID NO. 12; and a light chain variable region (VL) SEQ ID NO. 24.

4. The antigen binding protein of claim 3, wherein said antigen binding protein further comprises a constant region of the heavy chain comprising SEQ ID NO.127 and the constant region of the light chain comprising SEQ ID NO. 129.

5. The antigen binding protein of claim 1, wherein said protein is selected from the group consisting of: a monoclonal antigen binding protein; a tetrameric antigen binding protein, a tetravalent antigen binding protein, a multispecific antigen binding protein, and a fusion protein.

6. The antigen binding protein of claim 5, wherein said antigen binding protein is a monoclonal antigen binding protein.

7. A pharmaceutical composition comprising the antigen binding protein of claim 1 and a pharmaceutically acceptable carrier.

8. A method of inhibiting TGFβ in a subject in need thereof by administering to said subject the pharmaceutical composition of claim 7.

* * * * *

SEQUENCE LISTING

```
<160> NUMBER OF SEQ ID NOS: 293

<210> SEQ ID NO 1
<211> LENGTH: 351
<212> TYPE: DNA
```

<213> ORGANISM: Mus musculus

<400> SEQUENCE: 1
caggtccagc tacagcagtc tggggctgag ctggtgaagc ctggggcctc agtgaagatt 60
tcctgcaaag cttctggcta cgcattcagt agctcctgga tgaactgggt gaagcagagg 120
cctggaaagg gtcttgagtg gattggacag atttatcctg gagatggtga tactaactac 180
aatggaaagt tcaagggtaa agccacactg actgcagaca aatcctccag cacagcctac 240
atgcaactca gcagcctgac atctgaggac tctgcggtct atttctgtgc aagacactat 300
gatggttcca ctgactactg gggccaaggc accactctca cagtctcctc a 351

<210> SEQ ID NO 2
<211> LENGTH: 117
<212> TYPE: PRT
<213> ORGANISM: Mus musculus

<400> SEQUENCE: 2

Gln Val Gln Leu Gln Gln Ser Gly Ala Glu Leu Val Lys Pro Gly Ala
1 5 10 15

Ser Val Lys Ile Ser Cys Lys Ala Ser Gly Tyr Ala Phe Ser Ser Ser
20 25 30

Trp Met Asn Trp Val Lys Gln Arg Pro Gly Lys Gly Leu Glu Trp Ile
35 40 45

Gly Gln Ile Tyr Pro Gly Asp Gly Asp Thr Asn Tyr Asn Gly Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg His Tyr Asp Gly Ser Thr Asp Tyr Trp Gly Gln Gly Thr Thr
100 105 110

Leu Thr Val Ser Ser
115

<210> SEQ ID NO 3
<211> LENGTH: 321
<212> TYPE: DNA
<213> ORGANISM: Mus musculus

<400> SEQUENCE: 3
gacatccaga tgactcagtc tccagcctcc ctatctgtat ctgtgggaga aactgtcacc 60
atcacatgtc gagcaagtga aaatatttac agtaatttag catggtatca gcagaaacag 120
ggaaaatctc ctcagctcct ggtctatgct gcaacaaact tagcagatgg tgtgccatca 180
aggttcagtg gcagtggatc aggcacacag tattccctca agatcaatag tctgcagtct 240
gaagattttg ggagttatta ctgtcaacat ttttggggta ctccgtacac gttcggaggg 300
gggaccaagc tggaaataaa a 321

<210> SEQ ID NO 4
<211> LENGTH: 107
<212> TYPE: PRT
<213> ORGANISM: Mus musculus

<400> SEQUENCE: 4

Asp Ile Gln Met Thr Gln Ser Pro Ala Ser Leu Ser Val Ser Val Gly
1 5 10 15

```
Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys
            100                 105


<210> SEQ ID NO 5
<211> LENGTH: 5
<212> TYPE: PRT
<213> ORGANISM: Mus musculus

<400> SEQUENCE: 5

Ser Ser Trp Met Asn
1               5


<210> SEQ ID NO 6
<211> LENGTH: 17
<212> TYPE: PRT
<213> ORGANISM: Mus musculus

<400> SEQUENCE: 6

Gln Ile Tyr Pro Gly Asp Gly Asp Thr Asn Tyr Asn Gly Lys Phe Lys
1               5                   10                  15

Gly


<210> SEQ ID NO 7
<211> LENGTH: 10
<212> TYPE: PRT
<213> ORGANISM: Mus musculus

<400> SEQUENCE: 7

Ala Arg His Tyr Asp Gly Ser Thr Asp Tyr
1               5                   10


<210> SEQ ID NO 8
<211> LENGTH: 11
<212> TYPE: PRT
<213> ORGANISM: Mus musculus

<400> SEQUENCE: 8

Arg Ala Ser Glu Asn Ile Tyr Ser Asn Leu Ala
1               5                   10


<210> SEQ ID NO 9
<211> LENGTH: 7
<212> TYPE: PRT
<213> ORGANISM: Mus musculus

<400> SEQUENCE: 9

Ala Ala Thr Asn Leu Ala Asp
1               5


<210> SEQ ID NO 10
<211> LENGTH: 9
<212> TYPE: PRT
```

<213> ORGANISM: Mus musculus

<400> SEQUENCE: 10

Gln His Phe Trp Gly Thr Pro Tyr Thr
1 5

<210> SEQ ID NO 11
<211> LENGTH: 351
<212> TYPE: DNA
<213> ORGANISM: Artificial Sequence
<220> FEATURE:
<223> OTHER INFORMATION: Can04H09-VH1

<400> SEQUENCE: 11
gaggtgcagc tggtgcagtc cggagctgag gtgaagaagc caggagcttc cgtgaaggtg 60
agctgcaaga catctggcta caccttcatc tccagctgga tgaactgggt gagacaggct 120
ccaggagctg gcctggactg gatgggccag atctaccctg gcgacggcga tacaaactat 180
aatggcaagt ttaagggaag ggtgaccctg acagctgaca ccagcacatc taccgcttac 240
atggagctgt cttccctgag ggccggcgat atcgccgtgt actattgtgc ccggcactat 300
gacggctcca ccgattactg ggccagggc acactggtga ccgtctcgag c 351

<210> SEQ ID NO 12
<211> LENGTH: 117
<212> TYPE: PRT
<213> ORGANISM: Artificial Sequence
<220> FEATURE:
<223> OTHER INFORMATION: Can04H09-VH1

<400> SEQUENCE: 12

Glu Val Gln Leu Val Gln Ser Gly Ala Glu Val Lys Lys Pro Gly Ala
1 5 10 15

Ser Val Lys Val Ser Cys Lys Thr Ser Gly Tyr Thr Phe Ile Ser Ser
20 25 30

Trp Met Asn Trp Val Arg Gln Ala Pro Gly Ala Gly Leu Asp Trp Met
35 40 45

Gly Gln Ile Tyr Pro Gly Asp Gly Asp Thr Asn Tyr Asn Gly Lys Phe
50 55 60

Lys Gly Arg Val Thr Leu Thr Ala Asp Thr Ser Thr Ser Thr Ala Tyr
65 70 75 80

Met Glu Leu Ser Ser Leu Arg Ala Gly Asp Ile Ala Val Tyr Tyr Cys
85 90 95

Ala Arg His Tyr Asp Gly Ser Thr Asp Tyr Trp Gly Gln Gly Thr Leu
100 105 110

Val Thr Val Ser Ser
115

<210> SEQ ID NO 13
<211> LENGTH: 351
<212> TYPE: DNA
<213> ORGANISM: Artificial Sequence
<220> FEATURE:
<223> OTHER INFORMATION: Can04H09-VH2

<400> SEQUENCE: 13
gaggtgcagc tggtgcagtc cgccgctgag gtgaagaagc caggcgcctc tgtgaaggtg 60
tcctgcaaga cctccggcta cagcttcaca tccagctgga tgaactgggt gcagcaggct 120
ccaggcaagg gcctggactg gatgggacag atctaccctg gcgacggcga taccaactat 180

```
aatggcaagt ttaagggcag ggtgaccctg acagccgaca agagcacctc tacagcttac    240

atggagctgt cttccctgag gagcgaggat gccgccgtgt actattgtgc ccggcactat    300

gacggctcta cagattactg ggccagggc accctggtga cagtctcgag c              351


<210> SEQ ID NO 14
<211> LENGTH: 117
<212> TYPE: PRT
<213> ORGANISM: Artificial Sequence
<220> FEATURE:
<223> OTHER INFORMATION: Can04H09-VH2

<400> SEQUENCE: 14

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Ser Ser
            20                  25                  30

Trp Met Asn Trp Val Gln Gln Ala Pro Gly Lys Gly Leu Asp Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Ala Ala Val Tyr Tyr Cys
                85                  90                  95

Ala Arg His Tyr Asp Gly Ser Thr Asp Tyr Trp Gly Gln Gly Thr Leu
            100                 105                 110

Val Thr Val Ser Ser
        115


<210> SEQ ID NO 15
<211> LENGTH: 351
<212> TYPE: DNA
<213> ORGANISM: Artificial Sequence
<220> FEATURE:
<223> OTHER INFORMATION: Can04H09-VH3

<400> SEQUENCE: 15

gaggtgcagc tggtgcagtc cgccgctgag gtgaagaagc caggcgcctc cgtgaaggtg     60

agctgcaaga catctggcta caccttcaca tccagctgga tgaactgggt gcagcaggct    120

ccaggagctg gcctggactg gatgggccag atctaccctg gcgacggcga taccaactat    180

aatggcaagt ttaagggcag ggtgaccctg acagccgaca ccagcacatc taccgcttac    240

atggagctgt cttccctgag ggccgaggat acagccgtgt actattgtgc tcggcactat    300

gacggctcca ccgattactg ggccagggc acactggtga ccgtctcgag c              351


<210> SEQ ID NO 16
<211> LENGTH: 117
<212> TYPE: PRT
<213> ORGANISM: Artificial Sequence
<220> FEATURE:
<223> OTHER INFORMATION: Can04H09-VH3

<400> SEQUENCE: 16

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Thr Phe Thr Ser Ser
            20                  25                  30

Trp Met Asn Trp Val Gln Gln Ala Pro Gly Ala Gly Leu Asp Trp Met
```

```
        35                  40                  45

Gly Gln Ile Tyr Pro Gly Asp Gly Asp Thr Asn Tyr Asn Gly Lys Phe
    50                  55                  60

Lys Gly Arg Val Thr Leu Thr Ala Asp Thr Ser Thr Ser Thr Ala Tyr
65                  70                  75                  80

Met Glu Leu Ser Ser Leu Arg Ala Glu Asp Thr Ala Val Tyr Tyr Cys
                85                  90                  95

Ala Arg His Tyr Asp Gly Ser Thr Asp Tyr Trp Gly Gln Gly Thr Leu
            100                 105                 110

Val Thr Val Ser Ser
        115


<210> SEQ ID NO 17
<211> LENGTH: 306
<212> TYPE: DNA
<213> ORGANISM: Artificial Sequence
<220> FEATURE:
<223> OTHER INFORMATION: Can04H09-VK1

<400> SEQUENCE: 17

gacatcgtga tgacccagaa cccactgtcc ctgagcgtgt ctcccggcga gacagcctcc     60

atcagctgca gggcttctga gaacatctac tccaatctgg cctggttcag acagaagcca    120

ggacagagcc ctcagcgcct gatctatgcc gctaccaatc tggctgacgg cgtgcctgat    180

agattctctg gatccggaag cggcaccgac ttcaccctga ggatctctcg ggtggaggcc    240

gacgatacag gcgtgtacta ttgtcagcac ttctggggca ccccatacac atttggccag    300

ggtacc                                                               306


<210> SEQ ID NO 18
<211> LENGTH: 103
<212> TYPE: PRT
<213> ORGANISM: Artificial Sequence
<220> FEATURE:
<223> OTHER INFORMATION: Can04H09-VK1

<400> SEQUENCE: 18

Asp Ile Val Met Thr Gln Asn Pro Leu Ser Leu Ser Val Ser Pro Gly
1               5                   10                  15

Glu Thr Ala Ser Ile Ser Cys Arg Ala Ser Glu Asn Ile Tyr Ser Asn
            20                  25                  30

Leu Ala Trp Phe Arg Gln Lys Pro Gly Gln Ser Pro Gln Arg Leu Ile
        35                  40                  45

Tyr Ala Ala Thr Asn Leu Ala Asp Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Thr Gly Val Tyr Tyr Cys Gln His Phe Trp Gly Thr Pro Tyr
                85                  90                  95

Thr Phe Gly Gln Gly Thr Lys
            100


<210> SEQ ID NO 19
<211> LENGTH: 306
<212> TYPE: DNA
<213> ORGANISM: Artificial Sequence
<220> FEATURE:
<223> OTHER INFORMATION: Can04H09-VK2

<400> SEQUENCE: 19
```

```
gacaccgtgc tgacccagac accccccttcc ctgagcctgt ctccaggaga gccagcttcc     60

atcagctgca gagcttctga gaacatctac tccaatctgg cctggttcag gcagaagcct    120

ggacagtccc cacagcggct gatcaacgcc gctaccaatc tggctgacgg cgtgcccgac    180

aggttctccg gatccggaag cggcacagac ttctccctga agatcaactc tgtggccgct    240

gacgatgccg gcatctacta ttgtcagcac ttctggggca cccccttatac cttctcccag    300

ggtacc                                                               306


<210> SEQ ID NO 20
<211> LENGTH: 103
<212> TYPE: PRT
<213> ORGANISM: Artificial Sequence
<220> FEATURE:
<223> OTHER INFORMATION: Can04H09-VK2

<400> SEQUENCE: 20

Asp Thr Val Leu Thr Gln Thr Pro Pro Ser Leu Ser Leu Ser Pro Gly
1               5                   10                  15

Glu Pro Ala Ser Ile Ser Cys Arg Ala Ser Glu Asn Ile Tyr Ser Asn
            20                  25                  30

Leu Ala Trp Phe Arg Gln Lys Pro Gly Gln Ser Pro Gln Arg Leu Ile
        35                  40                  45

Asn Ala Ala Thr Asn Leu Ala Asp Gly Val Pro Asp Arg Phe Ser Gly
    50                  55                  60

Ser Gly Ser Gly Thr Asp Phe Ser Leu Lys Ile Asn Ser Val Ala Ala
65                  70                  75                  80

Asp Asp Ala Gly Ile Tyr Tyr Cys Gln His Phe Trp Gly Thr Pro Tyr
                85                  90                  95

Thr Phe Ser Gln Gly Thr Lys
            100


<210> SEQ ID NO 21
<211> LENGTH: 306
<212> TYPE: DNA
<213> ORGANISM: Artificial Sequence
<220> FEATURE:
<223> OTHER INFORMATION: Can04H09-VK3

<400> SEQUENCE: 21

gagatcgtga tgacccagtc ccctgcttct ctgtccctga gccaggagga gaaggtgacc     60

atcacatgca gggcctctga gaacatctac tccaatctgg cttggtatca gcagaagccc    120

ggccaggccc ctaagctgct gatctacgcc gctacaaacc tggctgacgg cgtgccaagc    180

cggttctctg gatccggaag cggcaccgac ttctctttta caatctccag cctggagcca    240

gaggatgtgg ccgtgtacta ttgtcagcac ttctggggca ccccctatac atttggccag    300

ggtacc                                                               306


<210> SEQ ID NO 22
<211> LENGTH: 103
<212> TYPE: PRT
<213> ORGANISM: Artificial Sequence
<220> FEATURE:
<223> OTHER INFORMATION: Can04H09-VK3

<400> SEQUENCE: 22

Glu Ile Val Met Thr Gln Ser Pro Ala Ser Leu Ser Leu Ser Gln Glu
1               5                   10                  15
```

```
Glu Lys Val Thr Ile Thr Cys Arg Ala Ser Glu Asn Ile Tyr Ser Asn
            20                  25                  30

Leu Ala Trp Tyr Gln Gln Lys Pro Gly Gln Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Gln His Phe Trp Gly Thr Pro Tyr
                85                  90                  95

Thr Phe Gly Gln Gly Thr Lys
            100


<210> SEQ ID NO 23
<211> LENGTH: 306
<212> TYPE: DNA
<213> ORGANISM: Artificial Sequence
<220> FEATURE:
<223> OTHER INFORMATION: Can04H09-VK4

<400> SEQUENCE: 23

gagatcgtga tgacccagtc ccctgcttct ctgtccctga gccagggcga gaaggtgacc      60

atcacatgca gggcctctga gaacatctac tccaatctgg cttggtatca gcagcggccc     120

ggacaggctc ctaagctgct gatctacgcc gctacaaacc tggctgacgg cgtgccaagc     180

aggttctctg gatccggaag cggcaccgac ttttctctga caatctccag cctggagcca     240

gaggatgtgg ccgtgtacta ttgtcagcac ttctggggca ccccctatac atttggccag     300

ggtacc                                                                306


<210> SEQ ID NO 24
<211> LENGTH: 103
<212> TYPE: PRT
<213> ORGANISM: Artificial Sequence
<220> FEATURE:
<223> OTHER INFORMATION: Can04H09-VK4

<400> SEQUENCE: 24

Glu Ile Val Met Thr Gln Ser Pro Ala Ser Leu Ser Leu Ser Gln Gly
1               5                   10                  15

Glu Lys Val Thr Ile Thr Cys Arg Ala Ser Glu Asn Ile Tyr Ser Asn
            20                  25                  30

Leu Ala Trp Tyr Gln Gln Arg Pro Gly Gln Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Ser Leu Thr Ile Ser Ser Leu Glu Pro
65                  70                  75                  80

Glu Asp Val Ala Val Tyr Tyr Cys Gln His Phe Trp Gly Thr Pro Tyr
                85                  90                  95

Thr Phe Gly Gln Gly Thr Lys
            100


<210> SEQ ID NO 25
<211> LENGTH: 420
<212> TYPE: DNA
<213> ORGANISM: Artificial Sequence
<220> FEATURE:
<223> OTHER INFORMATION: Fel04H09-H636
```

<400> SEQUENCE: 25

```
aagcttgcca ccatggagtg gtcttgggtc tttctgttct ttctgagtgt taccaccggc     60
gtgcactcac aggtgctgct tgttcagtct ggtgctgaag ttcgcagacc aggcgccagc    120
gtgaagattt tctgtaaagc cagcggctac agcttcacca gcagctggat gaactggctg    180
agacaggccc ctgctcaggg ctttgagtgg atgggacaaa tctaccctgg cgacggcgac    240
accaactaca acggcaagtt taagggcaga ctgaccctga ccgccgacac cagcacagat    300
acagcctaca tggaactgag cagcctgaga agcgccgata ccgccgtgta ctactgcgcc    360
agacactacg atggcagcac cgattattgg ggccacggca ccattgtgac agtctcgagc    420
```

<210> SEQ ID NO 26
<211> LENGTH: 117
<212> TYPE: PRT
<213> ORGANISM: Artificial Sequence
<220> FEATURE:
<223> OTHER INFORMATION: Fel04H09-H636

<400> SEQUENCE: 26

```
Gln Val Leu Leu Val Gln Ser Gly Ala Glu Val Arg Arg Pro Gly Ala
1               5                   10                  15

Ser Val Lys Ile Phe Cys Lys Ala Ser Gly Tyr Ser Phe Thr Ser Ser
            20                  25                  30

Trp Met Asn Trp Leu Arg Gln Ala Pro Ala Gln Gly Phe Glu Trp Met
        35                  40                  45

Gly Gln Ile Tyr Pro Gly Asp Gly Asp Thr Asn Tyr Asn Gly Lys Phe
    50                  55                  60

Lys Gly Arg Leu Thr Leu Thr Ala Asp Thr Ser Thr Asp Thr Ala Tyr
65                  70                  75                  80

Met Glu Leu Ser Ser Leu Arg Ser Ala Asp Thr Ala Val Tyr Tyr Cys
                85                  90                  95

Ala Arg His Tyr Asp Gly Ser Thr Asp Tyr Trp Gly His Gly Thr Ile
            100                 105                 110

Val Thr Val Ser Ser
        115
```

<210> SEQ ID NO 27
<211> LENGTH: 420
<212> TYPE: DNA
<213> ORGANISM: Artificial Sequence
<220> FEATURE:
<223> OTHER INFORMATION: Fel04H09-H1-2

<400> SEQUENCE: 27

```
aagcttgcca ccatggagtg gtcttgggtc tttctgttct ttctgagtgt taccaccggc     60
gtgcactcac aggtgctgct tgttcagtct ggcgccgaag tgcggaaacc tgaggccagc    120
gtgaagattt tctgcaaggc cagcggctac agcttcacca gcagctggat gaactgggtc    180
cgacaggctc ctgctcaggg ctttgagtgg atgggccaaa tctatcctgg cgacggcgac    240
accaactaca acggcaagtt taagggcaga ctgaccctga ccgccgacac cagcacaaac    300
acagcctaca tggaactgag cagcctgaga agcaccgaca tggccgtgta ctactgcgcc    360
agacactacg acggcagcac agattattgg ggccagggcg ctctggtcac agtctcgagc    420
```

<210> SEQ ID NO 28
<211> LENGTH: 117
<212> TYPE: PRT
<213> ORGANISM: Artificial Sequence
<220> FEATURE:
<223> OTHER INFORMATION: Fel04H09-H1-2

<400> SEQUENCE: 28

```
Gln Val Leu Leu Val Gln Ser Gly Ala Glu Val Arg Lys Pro Glu Ala
1               5                   10                  15

Ser Val Lys Ile Phe Cys Lys Ala Ser Gly Tyr Ser Phe Thr Ser Ser
            20                  25                  30

Trp Met Asn Trp Val Arg Gln Ala Pro Ala Gln Gly Phe Glu Trp Met
        35                  40                  45

Gly Gln Ile Tyr Pro Gly Asp Gly Asp Thr Asn Tyr Asn Gly Lys Phe
    50                  55                  60

Lys Gly Arg Leu Thr Leu Thr Ala Asp Thr Ser Thr Asn Thr Ala Tyr
65                  70                  75                  80

Met Glu Leu Ser Ser Leu Arg Ser Thr Asp Met Ala Val Tyr Tyr Cys
                85                  90                  95

Ala Arg His Tyr Asp Gly Ser Thr Asp Tyr Trp Gly Gln Gly Ala Leu
            100                 105                 110

Val Thr Val Ser Ser
        115
```

<210> SEQ ID NO 29
<211> LENGTH: 420
<212> TYPE: DNA
<213> ORGANISM: Artificial Sequence
<220> FEATURE:
<223> OTHER INFORMATION: Fel04H09-H618

<400> SEQUENCE: 29

```
aagcttgcca ccatggagtg gtcttgggtc tttctgttct ttctgagtgt taccaccggc      60

gtgcactcac aggtgctgct tgttcagtct ggcgccgaag ttcggaaacc aggcgccagc     120

gtgaagattt tctgcaaggc cagcggctac agcttcacca gcagctggat gaactggctg     180

agacaggccc ctgaacaggg cctcgaatgg atgggacaaa tctaccctgg cgacggcgac     240

accaactaca acggcaagtt taagggcaga ctgaccctga ccgccgacac cagcacaaac     300

acagcctaca tggaactgag cagcctgaga agcgccgata ccgccatgta ctactgcgcc     360

agacactacg acggcagcac agattattgg ggccagggcg ctctggtcac agtctcgagc     420
```

<210> SEQ ID NO 30
<211> LENGTH: 117
<212> TYPE: PRT
<213> ORGANISM: Artificial Sequence
<220> FEATURE:
<223> OTHER INFORMATION: Fel04H09-H618

<400> SEQUENCE: 30

```
Gln Val Leu Leu Val Gln Ser Gly Ala Glu Val Arg Lys Pro Gly Ala
1               5                   10                  15

Ser Val Lys Ile Phe Cys Lys Ala Ser Gly Tyr Ser Phe Thr Ser Ser
            20                  25                  30

Trp Met Asn Trp Leu Arg Gln Ala Pro Glu Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
```

```
                85                  90                  95

Ala Arg His Tyr Asp Gly Ser Thr Asp Tyr Trp Gly Gln Gly Ala Leu
            100                 105                 110

Val Thr Val Ser Ser
        115


<210> SEQ ID NO 31
<211> LENGTH: 379
<212> TYPE: DNA
<213> ORGANISM: Artificial Sequence
<220> FEATURE:
<223> OTHER INFORMATION: Fel04H09-K4-1

<400> SEQUENCE: 31

aagcttggcc accatgagtg ttcctaccca agtgctggga ctgctgctgc tgtggctgac     60

agatgctcgg tgcgccatca caatgacaca gagccctgga tctctggccg gctctcctgg    120

acagcaagtg accatgaatt gccgggccag cgagaacatc tacagcaacc tggcctggta    180

tcagcagaag cccggacagc accctaagct gctgatctac gccgccacaa atctggccga    240

tggcgtgcca gatagatttt ctggcagcgg ctctggcacc gacttcaccc tgacaattag    300

caacctgcag gccgaggacg tggccagcta ctactgtcag cacttttggg gcacccctta    360

cacctttggc ggaggtacc                                                 379


<210> SEQ ID NO 32
<211> LENGTH: 102
<212> TYPE: PRT
<213> ORGANISM: Artificial Sequence
<220> FEATURE:
<223> OTHER INFORMATION: Fel04H09-K4-1

<400> SEQUENCE: 32

Ala Ile Thr Met Thr Gln Ser Pro Gly Ser Leu Ala Gly Ser Pro Gly
1               5                   10                  15

Gln Gln Val Thr Met Asn Cys Arg Ala Ser Glu Asn Ile Tyr Ser Asn
            20                  25                  30

Leu Ala Trp Tyr Gln Gln Lys Pro Gly Gln His Pro Lys Leu Leu Ile
        35                  40                  45

Tyr Ala Ala Thr Asn Leu Ala Asp Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Gln His Phe Trp Gly Thr Pro Tyr
                85                  90                  95

Thr Phe Gly Gly Gly Thr
            100


<210> SEQ ID NO 33
<211> LENGTH: 379
<212> TYPE: DNA
<213> ORGANISM: Artificial Sequence
<220> FEATURE:
<223> OTHER INFORMATION: Fel04H09-K36

<400> SEQUENCE: 33

aagcttggcc accatgagtg ttcctaccca agtgctggga ctgctgctgc tgtggctgac     60

agatgctcgg tgcgacatcg tgatgaccca gacacctctg agcctgcctg ttacacctgg    120

cgagcctgcc agcatctctt gcagagccag cgagaacatc tacagcaacc tggcctggta    180
```

```
tctgcagaag cccggacagt ctcccagact gctgatctac gccgccacaa atctggccga    240

tggcgtgcca agcagatttt ctggcagcgg ctctggcacc gacttcaccc tgagaattag    300

cagcgtggaa gccgacgacg tgggcgtgta ctactgtcag cacttttggg gcacccctta    360

caccttcgga cagggtacc                                                 379
```

<210> SEQ ID NO 34
<211> LENGTH: 102
<212> TYPE: PRT
<213> ORGANISM: Artificial Sequence
<220> FEATURE:
<223> OTHER INFORMATION: Fel04H09-K36

<400> SEQUENCE: 34

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Glu Asn Ile Tyr Ser Asn
            20                  25                  30

Leu Ala Trp Tyr Leu Gln Lys Pro Gly Gln Ser Pro Arg Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Arg Ile Ser Ser Val Glu Ala
65                  70                  75                  80

Asp Asp Val Gly Val Tyr Tyr Cys Gln His Phe Trp Gly Thr Pro Tyr
                85                  90                  95

Thr Phe Gly Gln Gly Thr
            100
```

<210> SEQ ID NO 35
<211> LENGTH: 379
<212> TYPE: DNA
<213> ORGANISM: Artificial Sequence
<220> FEATURE:
<223> OTHER INFORMATION: Fel04H09-K1-1

<400> SEQUENCE: 35

```
aagcttggcc accatgagtg ttcctaccca agtgctggga ctgctgctgc tgtggctgac     60

agatgctcgg tgcgagatcc agatgacaca gagccctagc agcctgtctg cctctcctgg    120

cgatagagtg accatcacct gtcgggccag cgagaacatc tacagcaacc tggcctggta    180

tcagcagaaa cccggcaagg tgcccaagct gctgatctac gctgccacaa atctggccga    240

tggcgtgcca agcagatttt ctggaagcgg cagcggcacc gacttcaccc tgaccatatc    300

tagcctggaa cctgaggacg ccgccaccta ctactgtcag cacttttggg gcacccctta    360

cacctttggc ggcggtacc                                                 379
```

<210> SEQ ID NO 36
<211> LENGTH: 102
<212> TYPE: PRT
<213> ORGANISM: Artificial Sequence
<220> FEATURE:
<223> OTHER INFORMATION: Fel04H09-K1-1

<400> SEQUENCE: 36

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Asn Ile Tyr Ser Asn
            20                  25                  30
```

```
Leu Ala Trp Tyr Gln Gln Lys Pro Gly Lys Val Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Gln His Phe Trp Gly Thr Pro Tyr
                85                  90                  95

Thr Phe Gly Gly Gly Thr
            100


<210> SEQ ID NO 37
<211> LENGTH: 369
<212> TYPE: DNA
<213> ORGANISM: Mus musculus

<400> SEQUENCE: 37

gaggtccagc tggtggagtc tgggggaggc gtggtccagc ctgggaggtc cctgagactc      60

tcctgtgcag cctctggatt caccttcagt agctatggca tgcactgggt ccgccaggct     120

ccaggcaagg agctggagtg ggtggcagtt atatcatatg atggaagtat taaatactat     180

gcagactccg tgaagggccg attcaccatc tccagagaca attccaagaa cacgctgtat     240

ctgcaaatga acagcctgag agctgaggac acggctgtgt attactgtgc gcgaactggt     300

gaatatagtg gctacgatac ggacccccag tactcctggg ggcaagggac cacggtcacc     360

gtctcctca                                                             369


<210> SEQ ID NO 38
<211> LENGTH: 123
<212> TYPE: PRT
<213> ORGANISM: Mus musculus

<400> SEQUENCE: 38

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120


<210> SEQ ID NO 39
<211> LENGTH: 321
<212> TYPE: DNA
<213> ORGANISM: Mus musculus

<400> SEQUENCE: 39

gaaattgtgc tgactcagtc tccatcctcc ctgtctgcat ctgtaggaga cagagtcacc      60
```

```
atcacttgcc gggcaagtca gggcattgga gatgatttgg gctggtatca gcagaagcca    120

gggaaagccc ctatcctcct gatctatggt acatccactt tacaaagtgg ggtcccgtca    180

aggttcagcg gcagtggatc tggcacagat ttcactctca ccatcaacag cctgcagcct    240

gaagattttg caacttatta ctgtctacaa gattccaatt acccgctcac tttcggcgga    300

ggtaccaagc tcgagatcaa a                                              321
```

<210> SEQ ID NO 40
<211> LENGTH: 103
<212> TYPE: PRT
<213> ORGANISM: Mus musculus

<400> SEQUENCE: 40

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Lys
            100
```

<210> SEQ ID NO 41
<211> LENGTH: 7
<212> TYPE: PRT
<213> ORGANISM: Mus musculus

<400> SEQUENCE: 41

```
Phe Ser Ser Tyr Gly Met His
1               5
```

<210> SEQ ID NO 42
<211> LENGTH: 11
<212> TYPE: PRT
<213> ORGANISM: Mus musculus

<400> SEQUENCE: 42

```
Val Ile Ser Tyr Asp Gly Ser Ile Lys Tyr Tyr
1               5                   10
```

<210> SEQ ID NO 43
<211> LENGTH: 14
<212> TYPE: PRT
<213> ORGANISM: Mus musculus

<400> SEQUENCE: 43

```
Thr Gly Glu Tyr Ser Gly Tyr Asp Thr Asp Pro Gln Tyr Ser
1               5                   10
```

<210> SEQ ID NO 44
<211> LENGTH: 11
<212> TYPE: PRT
<213> ORGANISM: Mus musculus

<400> SEQUENCE: 44

```
Arg Ala Ser Gln Gly Ile Gly Asp Asp Leu Gly
1               5                   10


<210> SEQ ID NO 45
<211> LENGTH: 7
<212> TYPE: PRT
<213> ORGANISM: Mus musculus

<400> SEQUENCE: 45

Gly Thr Ser Thr Leu Gln Ser
1               5


<210> SEQ ID NO 46
<211> LENGTH: 9
<212> TYPE: PRT
<213> ORGANISM: Mus musculus

<400> SEQUENCE: 46

Leu Gln Asp Ser Asn Tyr Pro Leu Thr
1               5


<210> SEQ ID NO 47
<211> LENGTH: 123
<212> TYPE: PRT
<213> ORGANISM: Artificial Sequence
<220> FEATURE:
<223> OTHER INFORMATION: Can SL501-VH1

<400> SEQUENCE: 47

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Gln Trp Val
        35                  40                  45

Ala Val Ile Ser Tyr Asp Gly Ser Ile Lys Tyr Tyr Thr Asp Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Ala Glu Asp Thr Ala Val Tyr Tyr Cys
                85                  90                  95

Ala Lys Thr Gly Glu Tyr Ser Gly Tyr Asp Thr Asp Pro Gln Tyr Ser
            100                 105                 110

Trp Gly Gln Gly Thr Leu Val Thr Val Ser Ser
        115                 120


<210> SEQ ID NO 48
<211> LENGTH: 123
<212> TYPE: PRT
<213> ORGANISM: Artificial Sequence
<220> FEATURE:
<223> OTHER INFORMATION: Can SL501-VH2

<400> SEQUENCE: 48

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Gln Trp Val
        35                  40                  45
```

```
Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Thr Gly Glu Tyr Ser Gly Tyr Asp Thr Asp Pro Gln Tyr Ser
            100                 105                 110

Trp Gly Gln Gly Thr Leu Val Thr Val Ser Ser
        115                 120


<210> SEQ ID NO 49
<211> LENGTH: 103
<212> TYPE: PRT
<213> ORGANISM: Artificial Sequence
<220> FEATURE:
<223> OTHER INFORMATION: Can SL501-VK1

<400> SEQUENCE: 49

Glu Ile Val Met Thr Gln Ser Pro Ala Ser Leu Ser Leu Ser Gln Glu
1               5                   10                  15

Glu Lys Val Thr Ile Thr Cys Arg Ala Ser Gln Gly Ile Gly Asp Asp
            20                  25                  30

Leu Gly Trp Tyr Gln Gln Lys Pro Gly Gln Ala Pro Lys Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Leu Gln Asp Ser Asn Tyr Pro Leu
                85                  90                  95

Thr Phe Gly Ala Gly Thr Lys
            100


<210> SEQ ID NO 50
<211> LENGTH: 309
<212> TYPE: DNA
<213> ORGANISM: Artificial Sequence
<220> FEATURE:
<223> OTHER INFORMATION: Can SL501-VK2

<400> SEQUENCE: 50

gagatcgtga tgacccagag ccctggctct ctggccggat ctgctggcga gagcgtgtcc      60

atcaactgca gagcctctca gggcatcggc gacgacctgg gctggtatca gcagaagccc     120

ggcgagaggc ccaagctgct gatctacggc accagcaccc tgcagagcgg agtgcctgcc     180

agattttcca gcagcggcag cggcaccgac ttcaccctga ccatcaacaa cctgcaggcc     240

gaggacgtgg gcgactacta ctgtctgcaa gacagcaact accccctgac ctttggcgcc     300

ggtaccaag                                                             309


<210> SEQ ID NO 51
<211> LENGTH: 103
<212> TYPE: PRT
<213> ORGANISM: Artificial Sequence
<220> FEATURE:
<223> OTHER INFORMATION: Can SL501-VK2

<400> SEQUENCE: 51

Glu Ile Val Met Thr Gln Ser Pro Gly Ser Leu Ala Gly Ser Ala Gly
```

```
1               5                   10                  15

Glu Ser Val Ser Ile Asn Cys Arg Ala Ser Gln Gly Ile Gly Asp Asp
            20                  25                  30

Leu Gly Trp Tyr Gln Gln Lys Pro Gly Glu Arg Pro Lys Leu Leu Ile
        35                  40                  45

Tyr Gly Thr Ser Thr Leu Gln Ser Gly Val Pro Ala Arg Phe Ser Ser
    50                  55                  60

Ser Gly Ser Gly Thr Asp Phe Thr Leu Thr Ile Asn Asn Leu Gln Ala
65                  70                  75                  80

Glu Asp Val Gly Asp Tyr Tyr Cys Leu Gln Asp Ser Asn Tyr Pro Leu
                85                  90                  95

Thr Phe Gly Ala Gly Thr Lys
            100


<210> SEQ ID NO 52
<211> LENGTH: 309
<212> TYPE: DNA
<213> ORGANISM: Artificial Sequence
<220> FEATURE:
<223> OTHER INFORMATION: Can SL501-VK-Hybrid

<400> SEQUENCE: 52

gagatcgtgc tgacccagtc cccttccagc ctgtctgcct ctgtgggcga cagagtgacc      60

atcacctgtc gggcctctca gggcatcggc gacgatctgg gatggtatca gcagaagcca     120

ggccaggccc ccaagctgct gatctacggc acctccacac tgcagtccgg cgtgccctct     180

agattctccg gctctggctc cggcaccgac ttcagcttca ccatctccag cctggaaccc     240

gaggacgtgg ccgtgtacta ctgtctgcaa gactccaact accccctgac cttcggcgga     300

ggtaccaag                                                             309


<210> SEQ ID NO 53
<211> LENGTH: 103
<212> TYPE: PRT
<213> ORGANISM: Artificial Sequence
<220> FEATURE:
<223> OTHER INFORMATION: Can SL501-VK-Hybrid

<400> SEQUENCE: 53

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Gln Ala Pro Lys Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Leu Gln Asp Ser Asn Tyr Pro Leu
                85                  90                  95

Thr Phe Gly Gly Gly Thr Lys
            100


<210> SEQ ID NO 54
<211> LENGTH: 369
<212> TYPE: DNA
<213> ORGANISM: Artificial Sequence
<220> FEATURE:
```

<223> OTHER INFORMATION: Can SL501-VH3

<400> SEQUENCE: 54

```
gaagtgcagc tggtggaatc tggcggcgac ctcgtgaagc ctggcggctc tctgagactg     60

tcctgtgtgg cctccggctt caccttctcc agctacggca tgcactgggt gcgacaggcc    120

cctggaaaag gcctgcagtg ggtggccgtg atctcctacg acggctccat caagtactac    180

gccgacgccg tgaagggccg gttcaccatc agcagagaca acgccaagaa caccctgtac    240

ctgcagatga actccctgcg ggccgaggac accgccgtgt actactgtgc tagaaccggc    300

gagtactccg gctacgatac cgacccccag tactcttggg gccagggcac cacagtgacc    360

gtctcgagc                                                             369
```

<210> SEQ ID NO 55
<211> LENGTH: 123
<212> TYPE: PRT
<213> ORGANISM: Artificial Sequence
<220> FEATURE:
<223> OTHER INFORMATION: Can SL501-VH3

<400> SEQUENCE: 55

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Gln Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120
```

<210> SEQ ID NO 56
<211> LENGTH: 369
<212> TYPE: DNA
<213> ORGANISM: Artificial Sequence
<220> FEATURE:
<223> OTHER INFORMATION: SL501-VH3-FW2

<400> SEQUENCE: 56

```
gaagtgcagc tggtggaatc tggcggcgac ctcgtgaagc ctggcggctc tctgagactg     60

tcctgtgtgg cctccggctt caccttctcc agctacggca tgcactgggt gcgacaggcc    120

cctggaaaag agctggagtg ggtggccgtg atctcctacg acggctccat caagtactac    180

gccgacgccg tgaagggccg gttcaccatc agcagagaca acgccaagaa caccctgtac    240

ctgcagatga actccctgcg ggccgaggac accgccgtgt actactgtgc tagaaccggc    300

gagtactccg gctacgatac cgacccccag tactcttggg gccagggcac cacagtgacc    360

gtctcgagc                                                             369
```

<210> SEQ ID NO 57
<211> LENGTH: 123

```
<212> TYPE: PRT
<213> ORGANISM: Artificial Sequence
<220> FEATURE:
<223> OTHER INFORMATION: SL501-VH3-FW2

<400> SEQUENCE: 57

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120


<210> SEQ ID NO 58
<211> LENGTH: 369
<212> TYPE: DNA
<213> ORGANISM: Artificial Sequence
<220> FEATURE:
<223> OTHER INFORMATION: Fel SL501-VH3-9

<400> SEQUENCE: 58

gacgtacaac tcgtggaaag cggtggggat ctcgtcaaac caggggggttc cctccgtctc     60

acttgcgtag catcaggttt cactttctcc agttacggaa tgcattgggt gaggcaggcc    120

cccggcaagg aattggaatg ggtagcagta atatcctacg atgggtccat caagtactac    180

gcagatgcag tcaagggacg gttcactatc agtcgtgaca atgccaaaaa caccctgtac    240

ttgcagatga acagcctcaa gactgaggat accgcaactt attattgcgc tcgtacagga    300

gaatacagtg ggtacgatac tgaccctcaa tactcatggg gacaaggcac aacagtaaca    360

gtctcgagc                                                            369


<210> SEQ ID NO 59
<211> LENGTH: 123
<212> TYPE: PRT
<213> ORGANISM: Artificial Sequence
<220> FEATURE:
<223> OTHER INFORMATION: Fel SL501-VH3-9

<400> SEQUENCE: 59

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Lys Thr Glu Asp Thr Ala Thr Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120


<210> SEQ ID NO 60
<211> LENGTH: 309
<212> TYPE: DNA
<213> ORGANISM: Artificial Sequence
<220> FEATURE:
<223> OTHER INFORMATION: Fel SL501-VK1-1

<400> SEQUENCE: 60

gaaattcaga tgacccagag tccttccagt cttagtgcct cacccggaga tagggtcacc      60

attacttgta gggcaagcca ggggatcgga gacgatcttg ggtggtatca gcaaaaacca     120

ggtaaggttc caaaactttt gatctatggt actagcaccc tccaatctgg ggtgccaagt     180

cggttctccg gtagcggctc agggactgac ttcactttga caatttcaag tctggaacca     240

gaagacgcag ctacatatta ttgccttcag gattccaatt acccacttac cttcggaggg     300

ggtaccaaa                                                             309


<210> SEQ ID NO 61
<211> LENGTH: 103
<212> TYPE: PRT
<213> ORGANISM: Artificial Sequence
<220> FEATURE:
<223> OTHER INFORMATION: Fel SL501-VK1-1

<400> SEQUENCE: 61

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Val Pro Lys Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Asp Ser Asn Tyr Pro Leu
                85                  90                  95

Thr Phe Gly Gly Gly Thr Lys
            100


<210> SEQ ID NO 62
<211> LENGTH: 345
<212> TYPE: DNA
<213> ORGANISM: Mus musculus

<400> SEQUENCE: 62

caggtgcagc tggaggagtc aggacctgag ctggtgaggc ctggggcttc agtgaagctg      60

tcctgcaagg cttctggcta tatcttcatc acctactgga tgaactgggt gaagcagagg     120

cctggacagg gccttgagtg gattggacag atttttcctg caagtggtag tactaactac     180

aatgagatgt tcgagggcaa ggccacattg actgtagaca catcctccag cacagcctac     240
```

```
atgcagctca gcagcctgac atctgaggac tctgcggtct attactgtgc aagaggagat    300

ggtaactacg ccctggatgc tatggactac tggggtcaag gaacc                    345
```

<210> SEQ ID NO 63
<211> LENGTH: 117
<212> TYPE: PRT
<213> ORGANISM: Mus musculus

<400> SEQUENCE: 63

```
Leu Pro Gln Val Gln Leu Glu Glu Ser Gly Pro Glu Leu Val Arg Pro
1               5                   10                  15

Gly Ala Ser Val Lys Leu Ser Cys Lys Ala Ser Gly Tyr Ile Phe Ile
            20                  25                  30

Thr Tyr Trp Met Asn Trp Val Lys Gln Arg Pro Gly Gln Gly Leu Glu
        35                  40                  45

Trp Ile Gly Gln Ile Phe Pro Ala Ser Gly Ser Thr Asn Tyr Asn Glu
    50                  55                  60

Met Phe Glu Gly Lys Ala Thr Leu Thr Val Asp Thr Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Gly Asp Gly Asn Tyr Ala Leu Asp Ala Met Asp Tyr
            100                 105                 110

Trp Gly Gln Gly Thr
        115
```

<210> SEQ ID NO 64
<211> LENGTH: 321
<212> TYPE: DNA
<213> ORGANISM: Mus musculus

<400> SEQUENCE: 64

```
gacattgtgc tgacacagac tccagcttct ttggctgtgt ctctagggca gagggccacc     60

atatcctgca gagccagtga aagtgttgat agttatggca atagttttat gcactggtac    120

cagcagaaat caggacagcc acccaaactc ctcatctatc ttgcatccaa cctagaatct    180

ggggtccctg ccaggttcag tggcagtggg tctaggacag acttcaccct caccattgat    240

cctgtggagg ctgatgatgc tgcaacctat tactgtcagc aaaataatga ggatccgctc    300

acgttcggtg ctgggaccaa g                                              321
```

<210> SEQ ID NO 65
<211> LENGTH: 107
<212> TYPE: PRT
<213> ORGANISM: Mus musculus

<400> SEQUENCE: 65

```
Asp Ile Val Leu Thr Gln Thr Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80
```

Pro Val Glu Ala Asp Asp Ala Ala Thr Tyr Tyr Cys Gln Gln Asn Asn
85 90 95

Glu Asp Pro Leu Thr Phe Gly Ala Gly Thr Lys
100 105

<210> SEQ ID NO 66
<211> LENGTH: 7
<212> TYPE: PRT
<213> ORGANISM: Mus musculus

<400> SEQUENCE: 66

Gly Tyr Ile Phe Ile Thr Tyr
1 5

<210> SEQ ID NO 67
<211> LENGTH: 6
<212> TYPE: PRT
<213> ORGANISM: Mus musculus

<400> SEQUENCE: 67

Phe Pro Ala Ser Gly Ser
1 5

<210> SEQ ID NO 68
<211> LENGTH: 12
<212> TYPE: PRT
<213> ORGANISM: Mus musculus

<400> SEQUENCE: 68

Gly Asp Gly Asn Tyr Ala Leu Asp Ala Met Asp Tyr
1 5 10

<210> SEQ ID NO 69
<211> LENGTH: 15
<212> TYPE: PRT
<213> ORGANISM: Mus musculus

<400> SEQUENCE: 69

Arg Ala Ser Glu Ser Val Asp Ser Tyr Gly Asn Ser Phe Met His
1 5 10 15

<210> SEQ ID NO 70
<211> LENGTH: 7
<212> TYPE: PRT
<213> ORGANISM: Mus musculus

<400> SEQUENCE: 70

Leu Ala Ser Asn Leu Glu Ser
1 5

<210> SEQ ID NO 71
<211> LENGTH: 9
<212> TYPE: PRT
<213> ORGANISM: Mus musculus

<400> SEQUENCE: 71

Gln Gln Asn Asn Glu Asp Pro Leu Thr
1 5

<210> SEQ ID NO 72
<211> LENGTH: 354
<212> TYPE: DNA
<213> ORGANISM: Artificial Sequence
<220> FEATURE:
<223> OTHER INFORMATION: CanHcLb-VH1

<400> SEQUENCE: 72
gaggtgcagt tggttcagtc cggcgccgag gtgaagaagc ccggggcctc tgtaaaggtc 60
agctgcaaga ctagcggata tacatttatc acatactgga tgaactgggt ccgacaagcc 120
cctggtgccg gcctggattg gatgggccag atcttcccag caagcggatc taccaattac 180
aatgagatgt tcgagggtag ggtgaccctc acagctgata ccagtacttc aactgcatac 240
atggaactga gttccctgag agcaggcgac atcgcagttt actattgtgc ccgaggcgac 300
ggcaattatg cactggatgc tatggactac tggggtcagg gaaccctggt gaca 354

<210> SEQ ID NO 73
<211> LENGTH: 118
<212> TYPE: PRT
<213> ORGANISM: Artificial Sequence
<220> FEATURE:
<223> OTHER INFORMATION: CanHcLb-VH1

<400> SEQUENCE: 73

Glu Val Gln Leu Val Gln Ser Gly Ala Glu Val Lys Lys Pro Gly Ala
1 5 10 15

Ser Val Lys Val Ser Cys Lys Thr Ser Gly Tyr Thr Phe Ile Thr Tyr
20 25 30

Trp Met Asn Trp Val Arg Gln Ala Pro Gly Ala Gly Leu Asp Trp Met
35 40 45

Gly Gln Ile Phe Pro Ala Ser Gly Ser Thr Asn Tyr Asn Glu Met Phe
50 55 60

Glu Gly Arg Val Thr Leu Thr Ala Asp Thr Ser Thr Ser Thr Ala Tyr
65 70 75 80

Met Glu Leu Ser Ser Leu Arg Ala Gly Asp Ile Ala Val Tyr Tyr Cys
85 90 95

Ala Arg Gly Asp Gly Asn Tyr Ala Leu Asp Ala Met Asp Tyr Trp Gly
100 105 110

Gln Gly Thr Leu Val Thr
115

<210> SEQ ID NO 74
<211> LENGTH: 354
<212> TYPE: DNA
<213> ORGANISM: Artificial Sequence
<220> FEATURE:
<223> OTHER INFORMATION: CanHcLb-VH2

<400> SEQUENCE: 74
gaagtgcagc tggtgcagtc tgccgcagaa gttaagaagc ccggtgccag cgtgaaagtc 60
agctgcaaga catctggcta ttcattcacc acctactgga tgaactgggt gcaacaggct 120
cccggaaaag gcctcgattg gatgggtcag atctttcccg cttctggctc cacaaattat 180
aatgaaatgt tcgaagggag agtgaccctg accgttgaca ctagtactag taccgcctac 240
atggagctca gcagcctgcg cgccgaggac gctgccgtgt actattgcgc tcgcggtgat 300
ggtaactacg ctcttgatgc aatggattat tggggtcagg gaaccttggt cacc 354

<210> SEQ ID NO 75
<211> LENGTH: 118
<212> TYPE: PRT
<213> ORGANISM: Artificial Sequence
<220> FEATURE:
<223> OTHER INFORMATION: CanHcLb-VH2

```
<400> SEQUENCE: 75

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Thr Tyr
            20                  25                  30

Trp Met Asn Trp Val Gln Gln Ala Pro Gly Lys Gly Leu Asp Trp Met
        35                  40                  45

Gly Gln Ile Phe Pro Ala Ser Gly Ser Thr Asn Tyr Asn Glu Met Phe
    50                  55                  60

Glu Gly Arg Val Thr Leu Thr Val Asp Thr Ser Thr Ser Thr Ala Tyr
65                  70                  75                  80

Met Glu Leu Ser Ser Leu Arg Ala Glu Asp Ala Ala Val Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Leu Val Thr
        115


<210> SEQ ID NO 76
<211> LENGTH: 354
<212> TYPE: DNA
<213> ORGANISM: Artificial Sequence
<220> FEATURE:
<223> OTHER INFORMATION: CanHcLb-VH3

<400> SEQUENCE: 76

gaggtccagc tcgtccagtc tggtgcagaa gtcaaaaagc ctggtgcctc cgtgaaggtt     60

tcttgtaaga cttctggcta cacatttatc acctactgga tgaattgggt gagacaggcc    120

cccggggccg gccttgactg gatgggccaa atctttcctg cctccgggag tacaaactac    180

aacgaaatgt ttgaaggtag agtgacactg accgcagata cctccacatc caccgcatac    240

atggagctta gctctcttag ggcaggggat attgccgttt actactgtgc tcgcggtgat    300

gggaactacg cactggacgc catggactac tgggggcagg gaaccttggt caca          354


<210> SEQ ID NO 77
<211> LENGTH: 118
<212> TYPE: PRT
<213> ORGANISM: Artificial Sequence
<220> FEATURE:
<223> OTHER INFORMATION: CanHcLb-VH3

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Ser Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Asp Gly Asn Tyr Ala Leu Asp Ala Met Asp Tyr Trp Gly
            100                 105                 110
```

Gln Gly Thr Leu Val Thr
115

<210> SEQ ID NO 78
<211> LENGTH: 312
<212> TYPE: DNA
<213> ORGANISM: Artificial Sequence
<220> FEATURE:
<223> OTHER INFORMATION: CanHcLb-VK1

<400> SEQUENCE: 78
gacatcgtaa tgactcaaac ccccctgagt ctttctgtct cccctggcga gccagcatct 60
atttcttgcc gcgcatccga gtcagtggat tcttatggaa atagtttcat gcattggttc 120
caacagaagc ccgggcagtc cccccaacgc ctcatatacc tggcttcaaa tcttgagtcc 180
ggggttcccg acaggtttag cgggtccggg tcagggacag acttcaccct caggatttca 240
cgagtcgaag cagatgatgc cggtgtgtat tattgtcaac agaataacga ggaccctctg 300
acttttggcc ag 312

<210> SEQ ID NO 79
<211> LENGTH: 104
<212> TYPE: PRT
<213> ORGANISM: Artificial Sequence
<220> FEATURE:
<223> OTHER INFORMATION: CanHcLb-VK1

<400> SEQUENCE: 79

Asp Ile Val Met Thr Gln Thr Pro Leu Ser Leu Ser Val Ser Pro Gly
1 5 10 15

Glu Pro Ala Ser Ile Ser Cys Arg Ala Ser Glu Ser Val Asp Ser Tyr
20 25 30

Gly Asn Ser Phe Met His Trp Phe Gln Gln Lys Pro Gly Gln Ser Pro
35 40 45

Gln Arg Leu Ile Tyr Leu Ala Ser Asn Leu Glu Ser Gly Val Pro Asp
50 55 60

Arg Phe Ser Gly Ser Gly Ser Gly Thr Asp Phe Thr Leu Arg Ile Ser
65 70 75 80

Arg Val Glu Ala Asp Asp Ala Gly Val Tyr Tyr Cys Gln Gln Asn Asn
85 90 95

Glu Asp Pro Leu Thr Phe Gly Gln
100

<210> SEQ ID NO 80
<211> LENGTH: 312
<212> TYPE: DNA
<213> ORGANISM: Artificial Sequence
<220> FEATURE:
<223> OTHER INFORMATION: CanHcLb-VK2

<400> SEQUENCE: 80
gacatcgtga tgacccaaac tccattgtcc ctgtccgtgt cccccggaga gactgctagc 60
atatcctgtc gcgccagtga gtctgtggac tcatacggca acagcttcat gcattggttt 120
cggcaaaagc ctggccagtc ccctcagggg ctgatttatc ttgcttccaa ccttgaatct 180
ggcgtccctg atagattctc tggaagcggg tccggtactg actttacact caggatctca 240
cgggtggaag ctgatgacgc aggggtttac tattgccagc agaacaacga ggaccctctg 300
acatttggac aa 312

<210> SEQ ID NO 81
<211> LENGTH: 104
<212> TYPE: PRT
<213> ORGANISM: Artificial Sequence
<220> FEATURE:
<223> OTHER INFORMATION: CanHcLb-VK2

<400> SEQUENCE: 81

```
Asp Ile Val Met Thr Gln Thr Pro Leu Ser Leu Ser Val Ser Pro Gly
1               5                   10                  15

Glu Thr Ala Ser Ile Ser Cys Arg Ala Ser Glu Ser Val Asp Ser Tyr
            20                  25                  30

Gly Asn Ser Phe Met His Trp Phe Arg Gln Lys Pro Gly Gln Ser Pro
        35                  40                  45

Gln Gly Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Asn Asn
                85                  90                  95

Glu Asp Pro Leu Thr Phe Gly Gln
            100
```

<210> SEQ ID NO 82
<211> LENGTH: 312
<212> TYPE: DNA
<213> ORGANISM: Artificial Sequence
<220> FEATURE:
<223> OTHER INFORMATION: CanHcLb-VK3

<400> SEQUENCE: 82

```
gatatcgtga tgacacaaac tccactctca ttgagcgtaa gccccggaga gacagccagc     60

atatcatgcc gggctagtga aagcgtggat tcttatggga actcatttat gcactggttc    120

cggcagaagc caggacagag tccccagaga ctcatctacc tggcaagtaa cctcgaatct    180

ggtgtgccag accgttttag tggtagcggt agcgggaccg acttcacact gagaatcagc    240

cgtgtggaag ctgacgatac tggggtttat tactgtcagc agaacaacga ggaccctctg    300

accttcggcc aa                                                         312
```

<210> SEQ ID NO 83
<211> LENGTH: 104
<212> TYPE: PRT
<213> ORGANISM: Artificial Sequence
<220> FEATURE:
<223> OTHER INFORMATION: CanHcLb-VK3

<400> SEQUENCE: 83

```
Asp Ile Val Met Thr Gln Thr Pro Leu Ser Leu Ser Val Ser Pro Gly
1               5                   10                  15

Glu Thr Ala Ser Ile Ser Cys Arg Ala Ser Glu Ser Val Asp Ser Tyr
            20                  25                  30

Gly Asn Ser Phe Met His Trp Phe Arg Gln Lys Pro Gly Gln Ser Pro
        35                  40                  45

Gln Arg Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Thr Gly Val Tyr Tyr Cys Gln Gln Asn Asn
                85                  90                  95
```

```
Glu Asp Pro Leu Thr Phe Gly Gln
            100


<210> SEQ ID NO 84
<211> LENGTH: 312
<212> TYPE: DNA
<213> ORGANISM: Artificial Sequence
<220> FEATURE:
<223> OTHER INFORMATION: CanHcLb-VK4

<400> SEQUENCE: 84

gatattgtga tgacacagac tccaccctcc ctttctgtca gccctcggga gaccgcctcc     60

attagctgtc gcgccagtga gtccgtcgat tcctacggaa atagcttcat gcactggtat    120

ctgcagaaac caggtcagtc tcctcaattg ctgatctacc tggcttctaa cctggaaagc    180

ggtgtgtcag ataggttttc cggaagtggt agcggaactg actttaccct gcgtatttcc    240

cgagtggaag ccaatgacac tggtgtttac tactgtcagc agaataacga agaccccctg    300

acctttggcc ag                                                        312


<210> SEQ ID NO 85
<211> LENGTH: 104
<212> TYPE: PRT
<213> ORGANISM: Artificial Sequence
<220> FEATURE:
<223> OTHER INFORMATION: CanHcLb-VK4

<400> SEQUENCE: 85

Asp Ile Val Met Thr Gln Thr Pro Pro Ser Leu Ser Val Ser Pro Arg
1               5                   10                  15

Glu Thr Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Ser Pro
        35                  40                  45

Gln Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asn
                85                  90                  95

Glu Asp Pro Leu Thr Phe Gly Gln
            100


<210> SEQ ID NO 86
<211> LENGTH: 312
<212> TYPE: DNA
<213> ORGANISM: Artificial Sequence
<220> FEATURE:
<223> OTHER INFORMATION: CanHcLb-VK5

<400> SEQUENCE: 86

gatattgtca tgactcagac cccactgagt ttgagtgtca gtcctggaga gcctgccagc     60

ataagttgcc gcgcatcaga gagtgtggat tcttacggca attctttcat gcattggttc    120

cagcagaagc ccggccagag cccacagagg ctgatttact tggcttcaaa cttggaaagt    180

ggagttcctg accggtttag cggctctggg tccggcaccg actttacact ccgtatcagt    240

cgcgtggaag ccgatgacgc tggggtctat tactgtcagc agaacaatga ggacccactg    300

acctttggtc ag                                                        312
```

<210> SEQ ID NO 87
<211> LENGTH: 104
<212> TYPE: PRT
<213> ORGANISM: Artificial Sequence
<220> FEATURE:
<223> OTHER INFORMATION: CanHcLb-VK5

<400> SEQUENCE: 87

```
Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Ser Tyr
            20                  25                  30

Gly Asn Ser Phe Met His Trp Phe Gln Gln Lys Pro Gly Gln Ser Pro
        35                  40                  45

Gln Arg Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Asn Asn
                85                  90                  95

Glu Asp Pro Leu Thr Phe Gly Gln
            100
```

<210> SEQ ID NO 88
<211> LENGTH: 312
<212> TYPE: DNA
<213> ORGANISM: Artificial Sequence
<220> FEATURE:
<223> OTHER INFORMATION: canHcLb-VK4-S71P

<400> SEQUENCE: 88

```
gatattgtga tgacacagac tccaccctcc ctttctgtca gccctcggga gaccgcctcc     60

attagctgtc gcgccagtga gtccgtcgat tcctacggaa atagcttcat gcactggtat    120

ctgcagaaac caggtcagcc tcctcaattg ctgatctacc tggcttctaa cctggaaagc    180

ggtgtgtcag ataggttttc cggaagtggt agcggaactg actttaccct gcgtatttcc    240

cgagtggaag ccaatgacac tggtgtttac tactgtcagc agaataacga agaccccctg    300

acctttggcc ag                                                        312
```

<210> SEQ ID NO 89
<211> LENGTH: 102
<212> TYPE: PRT
<213> ORGANISM: Artificial Sequence
<220> FEATURE:
<223> OTHER INFORMATION: canHcLb-VK4-S71P

<400> SEQUENCE: 89

```
Asp Ile Val Met Thr Gln Thr Pro Pro Ser Leu Ser Val Ser Pro Arg
1               5                   10                  15

Glu Thr Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asn
```

```
                85                  90                  95

Glu Asp Pro Leu Thr Phe
            100


<210> SEQ ID NO 90
<211> LENGTH: 312
<212> TYPE: DNA
<213> ORGANISM: Artificial Sequence
<220> FEATURE:
<223> OTHER INFORMATION: canHcLb-VK4-Q73K

<400> SEQUENCE: 90

gatattgtga tgacacagac tccaccctcc ctttctgtca gccctcggga gaccgcctcc     60

attagctgtc gcgccagtga gtccgtcgat tcctacggaa atagcttcat gcactggtat    120

ctgcagaaac caggtcagtc tcctaaattg ctgatctacc tggcttctaa cctggaaagc    180

ggtgtgtcag ataggttttc cggaagtggt agcggaactg actttaccct gcgtatttcc    240

cgagtggaag ccaatgacac tggtgtttac tactgtcagc agaataacga agaccccctg    300

acctttggcc ag                                                        312


<210> SEQ ID NO 91
<211> LENGTH: 104
<212> TYPE: PRT
<213> ORGANISM: Artificial Sequence
<220> FEATURE:
<223> OTHER INFORMATION: canHcLb-VK4-Q73K

<400> SEQUENCE: 91

Asp Ile Val Met Thr Gln Thr Pro Pro Ser Leu Ser Val Ser Pro Arg
1               5                   10                  15

Glu Thr Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Ser Pro
        35                  40                  45

Lys Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asn
                85                  90                  95

Glu Asp Pro Leu Thr Phe Gly Gln
            100


<210> SEQ ID NO 92
<211> LENGTH: 312
<212> TYPE: DNA
<213> ORGANISM: Artificial Sequence
<220> FEATURE:
<223> OTHER INFORMATION: canHcLb-VK4-S71P-Q73K

<400> SEQUENCE: 92

gatattgtga tgacacagac tccaccctcc ctttctgtca gccctcggga gaccgcctcc     60

attagctgtc gcgccagtga gtccgtcgat tcctacggaa atagcttcat gcactggtat    120

ctgcagaaac caggtcagcc tcctaaattg ctgatctacc tggcttctaa cctggaaagc    180

ggtgtgtcag ataggttttc cggaagtggt agcggaactg actttaccct gcgtatttcc    240

cgagtggaag ccaatgacac tggtgtttac tactgtcagc agaataacga agaccccctg    300

acctttggcc ag                                                        312
```

<210> SEQ ID NO 93
<211> LENGTH: 104
<212> TYPE: PRT
<213> ORGANISM: Artificial Sequence
<220> FEATURE:
<223> OTHER INFORMATION: canHcLb-VK4-S71P-Q73K

<400> SEQUENCE: 93

```
Asp Ile Val Met Thr Gln Thr Pro Pro Ser Leu Ser Val Ser Pro Arg
1               5                   10                  15

Glu Thr Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Pro Pro
        35                  40                  45

Lys Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asn
                85                  90                  95

Glu Asp Pro Leu Thr Phe Gly Gln
            100
```

<210> SEQ ID NO 94
<211> LENGTH: 432
<212> TYPE: DNA
<213> ORGANISM: Artificial Sequence
<220> FEATURE:
<223> OTHER INFORMATION: FelHcLb-H636

<400> SEQUENCE: 94

```
aagcttgcca ccatggagtg gtcttgggtc tttctgttct ttctgagtgt taccaccggc      60

gtgcactcac aggtgctgct tgttcagtct ggtgctgaag ttcgcagacc aggcgccagc     120

gtgaagattt tctgtaaagc cagcggctac atcttcatca cctactacat gcactggctg     180

cggcaggccc ctgctcaggg atttgagtgg atgggcagca tctttcctgc cagcggcagc     240

acaagctacg cccagaaatt tcaggggaga ctgaccctga ccgccgacac aagcacagac     300

acagcctaca tggaactgag cagcctgaga agcgccgaca ccgccgtgta ttattgtgcc     360

agaggcgacg gcaactacgc cctggatgct atggattatt ggggccacgg caccatcgtg     420

acagtctcga gc                                                         432
```

<210> SEQ ID NO 95
<211> LENGTH: 121
<212> TYPE: PRT
<213> ORGANISM: Artificial Sequence
<220> FEATURE:
<223> OTHER INFORMATION: FelHcLb-H636

<400> SEQUENCE: 95

```
Gln Val Leu Leu Val Gln Ser Gly Ala Glu Val Arg Arg Pro Gly Ala
1               5                   10                  15

Ser Val Lys Ile Phe Cys Lys Ala Ser Gly Tyr Ile Phe Ile Thr Tyr
            20                  25                  30

Tyr Met His Trp Leu Arg Gln Ala Pro Ala Gln Gly Phe Glu Trp Met
        35                  40                  45

Gly Ser Ile Phe Pro Ala Ser Gly Ser Thr Ser Tyr Ala Gln Lys Phe
    50                  55                  60
```

```
Gln Gly Arg Leu Thr Leu Thr Ala Asp Thr Ser Thr Asp Thr Ala Tyr
65                  70                  75                  80

Met Glu Leu Ser Ser Leu Arg Ser Ala Asp Thr Ala Val Tyr Tyr Cys
                85                  90                  95

Ala Arg Gly Asp Gly Asn Tyr Ala Leu Asp Ala Met Asp Tyr Trp Gly
            100                 105                 110

His Gly Thr Ile Val Thr Val Ser Ser
        115                 120
```

<210> SEQ ID NO 96
<211> LENGTH: 432
<212> TYPE: DNA
<213> ORGANISM: Artificial Sequence
<220> FEATURE:
<223> OTHER INFORMATION: FelHcLb-H1-1

<400> SEQUENCE: 96

```
aagcttgcca ccatggagtg gtcttgggtc tttctgttct ttctgagtgt taccaccggc      60

gtgcactcac aggtgctgct tgttcagtct ggcgctgaag ttcggactcc tggcgcctcc     120

gtgaagattt tctgtaaagc cagcggctac atcttcatca cctactacat gcactgggtc     180

cgacagagcc ctgctcaggg acttgagtgg atgggcagca tctttcctgc cagcggcagc     240

acaagctacg cccagaaatt tcaggggaga ctgaccctga ccgccgacac aagcacaaac     300

accgcctaca tggaactgag cagcctgaga agcgccgaca ccgccatgta ttattgtgcc     360

agaggcgacg gcaactacgc cctggatgct atggattatt ggggccaggg caccagcgtg     420

acagtctcga gc                                                         432
```

<210> SEQ ID NO 97
<211> LENGTH: 121
<212> TYPE: PRT
<213> ORGANISM: Artificial Sequence
<220> FEATURE:
<223> OTHER INFORMATION: FelHcLb-H1-1

<400> SEQUENCE: 97

```
Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ile Phe Ile Thr Tyr
            20                  25                  30

Tyr Met His Trp Val Arg Gln Ser Pro Ala Gln Gly Leu Glu Trp Met
        35                  40                  45

Gly Ser Ile Phe Pro Ala Ser Gly Ser Thr Ser Tyr Ala Gln Lys Phe
    50                  55                  60

Gln Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Ser Val Thr Val Ser Ser
        115                 120
```

<210> SEQ ID NO 98
<211> LENGTH: 391
<212> TYPE: DNA
<213> ORGANISM: Artificial Sequence
<220> FEATURE:

<223> OTHER INFORMATION: FelHcLb-K1-1

<400> SEQUENCE: 98

```
aagcttggcc accatgagtg ttcctaccca agtgctggga ctgctgctgc tgtggctgac     60
agatgctcgg tgcgagatcc agatgacaca gagccctagc agcctgtctg cctctcctgg    120
cgatagagtg accatcacct gtagagccag cgagtccgtg gacagctacg gcaatagctt    180
catgcactgg tatcagcaga aacccggcaa ggtgcccaag ctgctgatct acctggccag    240
caatctggaa agcggcgtgc caagcagatt ttctggcagc ggctctggca ccgacttcac    300
cctgaccatt tctagcctgg aacctgagga cgccgccacc tactactgcc agcagaacaa    360
tgaggaccct ctgacctttg gcgccggtac c                                 391
```

<210> SEQ ID NO 99
<211> LENGTH: 106
<212> TYPE: PRT
<213> ORGANISM: Artificial Sequence
<220> FEATURE:
<223> OTHER INFORMATION: FelHcLb-K1-1

<400> SEQUENCE: 99

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Val Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Asn Asn
                85                  90                  95

Glu Asp Pro Leu Thr Phe Gly Ala Gly Thr
            100                 105
```

<210> SEQ ID NO 100
<211> LENGTH: 391
<212> TYPE: DNA
<213> ORGANISM: Artificial Sequence
<220> FEATURE:
<223> OTHER INFORMATION: FelHcLb-K36

<400> SEQUENCE: 100

```
aagcttggcc accatgagtg ttcctaccca agtgctggga ctgctgctgc tgtggctgac     60
agatgctcgg tgcgacatcg tgatgaccca gacacctctg agcctgcctg ttacacctgg    120
cgagcctgcc agcatctctt gtagagccag cgagtctgtg gacagctacg gcaacagctt    180
catgcactgg tatctgcaga agcccggaca gagccccaga ctgctgatct acctggccag    240
caatctggaa agcggcgtgc caagcagatt ttctggcagc ggctctggca ccgacttcac    300
cctgagaatt agcagcgtgg aagccgacga cgtgggcgtg tactactgcc agcagaacaa    360
tgaggaccct ctgacctttg gcgccggtac c                                 391
```

<210> SEQ ID NO 101
<211> LENGTH: 106
<212> TYPE: PRT
<213> ORGANISM: Artificial Sequence
<220> FEATURE:

<223> OTHER INFORMATION: FelHcLb-K36

<400> SEQUENCE: 101

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Ser Pro
        35                  40                  45

Arg Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Arg Ile Ser
65                  70                  75                  80

Ser Val Glu Ala Asp Asp Val Gly Val Tyr Tyr Cys Gln Gln Asn Asn
                85                  90                  95

Glu Asp Pro Leu Thr Phe Gly Ala Gly Thr
            100                 105
```

<210> SEQ ID NO 102
<211> LENGTH: 391
<212> TYPE: DNA
<213> ORGANISM: Artificial Sequence
<220> FEATURE:
<223> OTHER INFORMATION: FelHcLb-K4-1

<400> SEQUENCE: 102

```
aagcttggcc accatgagtg ttcctaccca agtgctggga ctgctgctgc tgtggctgac     60

agatgctcgg tgcgccatca caatgacaca gagccctgga tctctggccg gctctcctgg    120

acagcaagtg accatgaatt gcagagccag cgagagcgtg gacagctacg gcaatagctt    180

catgcactgg tatcagcaga agcccggaca gcaccccaag ctgctgatct acctggccag    240

caatctggaa agcggcgtgc cagatagatt ttctggcagc ggctctggca ccgacttcac    300

cctgacaatt agcaacctgc aggccgagga cgtggccagc tactactgtc agcagaacaa    360

cgaggaccct ctgacctttg gagccggtac c                                    391
```

<210> SEQ ID NO 103
<211> LENGTH: 106
<212> TYPE: PRT
<213> ORGANISM: Artificial Sequence
<220> FEATURE:
<223> OTHER INFORMATION: FelHcLb- K4-1

<400> SEQUENCE: 103

```
Ala Ile Thr Met Thr Gln Ser Pro Gly Ser Leu Ala Gly Ser Pro Gly
1               5                   10                  15

Gln Gln Val Thr Met Asn Cys Arg Ala Ser Glu Ser Val Asp Ser Tyr
            20                  25                  30

Gly Asn Ser Phe Met His Trp Tyr Gln Gln Lys Pro Gly Gln His Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Asn Leu Gln Ala Glu Asp Val Ala Ser Tyr Tyr Cys Gln Gln Asn Asn
                85                  90                  95

Glu Asp Pro Leu Thr Phe Gly Ala Gly Thr
            100                 105
```

<210> SEQ ID NO 104
<211> LENGTH: 391
<212> TYPE: DNA
<213> ORGANISM: Artificial Sequence
<220> FEATURE:
<223> OTHER INFORMATION: FelHcLb- K2D-2

<400> SEQUENCE: 104

```
aagcttggcc accatgagtg ttcctaccca agtgctggga ctgctgctgc tgtggctgac     60

agatgctcgg tgcgacgtgg tcatgacaca gacacctctg agcctgcctg tgacacctgg    120

cgaacctgcc tctatctctt gtagagccag cgagtccgtg gacagctacg gcaatagctt    180

catgcactgg tatctgcaga agcccggaca gagccccaga aggctgatct acctggccag    240

caatctggaa agcggcgtgc cagatagatt ttctggcagc ggctctggca ccgacttcac    300

cctgagaatc agcagagtgg aagccgacga cgtgggcgtg tactactgcc agcagaacaa    360

tgaggaccct ctgacctttg gcgccggtac c                                   391
```

<210> SEQ ID NO 105
<211> LENGTH: 106
<212> TYPE: PRT
<213> ORGANISM: Artificial Sequence
<220> FEATURE:
<223> OTHER INFORMATION: FelHcLb- K2D-2

<400> SEQUENCE: 105

```
Asp Val Val Met Thr Gln Thr Pro Leu Ser Leu Pro Val Thr Pro Gly
1               5                   10                  15

Glu Pro Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Ser Pro
        35                  40                  45

Arg Arg Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Val Gly Val Tyr Tyr Cys Gln Gln Asn Asn
                85                  90                  95

Glu Asp Pro Leu Thr Phe Gly Ala Gly Thr
            100                 105
```

<210> SEQ ID NO 106
<211> LENGTH: 432
<212> TYPE: DNA
<213> ORGANISM: Artificial Sequence
<220> FEATURE:
<223> OTHER INFORMATION: FelHcLb-H618s

<400> SEQUENCE: 106

```
aagcttgcca ccatggagtg gtcttgggtc tttctgttct ttctgagtgt taccaccggc     60

gtgcactcac aggtgctgct tgttcagtct ggcgccgaag ttcggaaacc aggcgccagc    120

gtgaagattt tctgcaaggc cagcggctac accttcatca cctactacat gcactggctg    180

cggcaggccc ctgaacaagg acttgagtgg atgggcagaa tcttccctgc cagcggcagc    240

acaagctacg cccagaaatt tcaggggaga ctgaccctga ccgccgacac aagcacaaac    300

accgcctaca tggaactgag cagcctgaga agcgccgaca ccgccatgta ttattgtgcc    360

agaggcgacg gcaactacgc cctggatgct atggattatt ggggccaggg cgctctggtc    420
```

```
acagtctcga gc                                                          432


<210> SEQ ID NO 107
<211> LENGTH: 121
<212> TYPE: PRT
<213> ORGANISM: Artificial Sequence
<220> FEATURE:
<223> OTHER INFORMATION: FelHcLb-H618s

<400> SEQUENCE: 107

Gln Val Leu Leu Val Gln Ser Gly Ala Glu Val Arg Lys Pro Gly Ala
1               5                   10                  15

Ser Val Lys Ile Phe Cys Lys Ala Ser Gly Tyr Thr Phe Ile Thr Tyr
            20                  25                  30

Tyr Met His Trp Leu Arg Gln Ala Pro Glu Gln Gly Leu Glu Trp Met
        35                  40                  45

Gly Arg Ile Phe Pro Ala Ser Gly Ser Thr Ser Tyr Ala Gln Lys Phe
    50                  55                  60

Gln Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
            100                 105                 110

Gln Gly Ala Leu Val Thr Val Ser Ser
        115                 120


<210> SEQ ID NO 108
<211> LENGTH: 432
<212> TYPE: DNA
<213> ORGANISM: Artificial Sequence
<220> FEATURE:
<223> OTHER INFORMATION: FelHcLb-H636x

<400> SEQUENCE: 108

aagcttgcca ccatggagtg gtcttgggtc tttctgttct ttctgagtgt taccaccggc     60

gtgcactcac aggtgctgct tgttcagtct ggtgctgaag ttcgcagacc aggcgccagc    120

gtgaagattt tctgtaaagc cagcggctac atcttcatca cctactacat gcactggctg    180

cggcaggccc ctgctcaggg atttgaatgg atgggccaga ttttccctgc cagcggcagc    240

accaactaca acgagatgtt tgagggcaga ctgaccctga ccgccgatac cagcacagac    300

acagcctaca tggaactgag cagcctgaga agcgccgaca ccgccgtgta ttattgtgcc    360

agaggcgacg gcaactacgc cctggatgct atggattatt ggggccacgg caccatcgtg    420

acagtctcga gc                                                        432


<210> SEQ ID NO 109
<211> LENGTH: 121
<212> TYPE: PRT
<213> ORGANISM: Artificial Sequence
<220> FEATURE:
<223> OTHER INFORMATION: FelHcLb-H636x

<400> SEQUENCE: 109

Gln Val Leu Leu Val Gln Ser Gly Ala Glu Val Arg Arg Pro Gly Ala
1               5                   10                  15

Ser Val Lys Ile Phe Cys Lys Ala Ser Gly Tyr Ile Phe Ile Thr Tyr
            20                  25                  30
```

```
Tyr Met His Trp Leu Arg Gln Ala Pro Ala Gln Gly Phe Glu Trp Met
        35                  40                  45

Gly Gln Ile Phe Pro Ala Ser Gly Ser Thr Asn Tyr Asn Glu Met Phe
    50                  55                  60

Glu Gly Arg Leu Thr Leu Thr Ala Asp Thr Ser Thr Asp Thr Ala Tyr
65                  70                  75                  80

Met Glu Leu Ser Ser Leu Arg Ser Ala Asp Thr Ala Val Tyr Tyr Cys
                85                  90                  95

Ala Arg Gly Asp Gly Asn Tyr Ala Leu Asp Ala Met Asp Tyr Trp Gly
            100                 105                 110

His Gly Thr Ile Val Thr Val Ser Ser
        115                 120


<210> SEQ ID NO 110
<211> LENGTH: 432
<212> TYPE: DNA
<213> ORGANISM: Artificial Sequence
<220> FEATURE:
<223> OTHER INFORMATION: FelHcLb-H1-1x

<400> SEQUENCE: 110

aagcttgcca ccatggagtg gtcttgggtc tttctgttct ttctgagtgt taccaccggc     60

gtgcactcac aggtgctgct tgttcagtct ggcgctgaag ttcggactcc tggcgcctcc    120

gtgaagattt tctgtaaagc cagcggctac atcttcatca cctactacat gcactgggtc    180

cgacagagcc ctgctcaggg acttgagtgg atgggccaga tttttcctgc cagcggcagc    240

accaactaca acgagatgtt tgagggcaga ctgaccctga ccgccgacac aagcacaaac    300

accgcctaca tggaactgag cagcctgaga agcgccgaca ccgccatgta ttattgtgcc    360

agaggcgacg gcaactacgc cctggatgct atggattatt ggggccaggg caccagcgtg    420

acagtctcga gc                                                        432


<210> SEQ ID NO 111
<211> LENGTH: 121
<212> TYPE: PRT
<213> ORGANISM: Artificial Sequence
<220> FEATURE:
<223> OTHER INFORMATION: FelHcLb-H1-1x

<400> SEQUENCE: 111

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ile Phe Ile Thr Tyr
            20                  25                  30

Tyr Met His Trp Val Arg Gln Ser Pro Ala Gln Gly Leu Glu Trp Met
        35                  40                  45

Gly Gln Ile Phe Pro Ala Ser Gly Ser Thr Asn Tyr Asn Glu Met Phe
    50                  55                  60

Glu Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Ser Val Thr Val Ser Ser
        115                 120
```

<210> SEQ ID NO 112
<211> LENGTH: 432
<212> TYPE: DNA
<213> ORGANISM: Artificial Sequence
<220> FEATURE:
<223> OTHER INFORMATION: FelHcLb-H618x

<400> SEQUENCE: 112
aagcttgcca ccatggagtg gtcttgggtc tttctgttct ttctgagtgt taccaccggc 60
gtgcactcac aggtgctgct tgttcagtct ggcgccgaag ttcggaaacc aggcgccagc 120
gtgaagattt tctgcaaggc cagcggctac accttcatca cctactacat gcactggctg 180
cggcaggccc ctgaacaagg acttgagtgg atgggccaga ttttccctgc cagcggcagc 240
accaactaca acgagatgtt tgagggcaga ctgaccctga ccgccgacac aagcacaaac 300
accgcctaca tggaactgag cagcctgaga agcgccgaca ccgccatgta ttattgtgcc 360
agaggcgacg gcaactacgc cctggatgct atggattatt ggggccaggg cgctctggtc 420
acagtctcga gc 432

<210> SEQ ID NO 113
<211> LENGTH: 121
<212> TYPE: PRT
<213> ORGANISM: Artificial Sequence
<220> FEATURE:
<223> OTHER INFORMATION: FelHcLb-H618x

<400> SEQUENCE: 113

Gln Val Leu Leu Val Gln Ser Gly Ala Glu Val Arg Lys Pro Gly Ala
1 5 10 15

Ser Val Lys Ile Phe Cys Lys Ala Ser Gly Tyr Thr Phe Ile Thr Tyr
20 25 30

Tyr Met His Trp Leu Arg Gln Ala Pro Glu Gln Gly Leu Glu Trp Met
35 40 45

Gly Gln Ile Phe Pro Ala Ser Gly Ser Thr Asn Tyr Asn Glu Met Phe
50 55 60

Glu Gly Arg Leu Thr Leu Thr Ala Asp Thr Ser Thr Asn Thr Ala Tyr
65 70 75 80

Met Glu Leu Ser Ser Leu Arg Ser Ala Asp Thr Ala Met Tyr Tyr Cys
85 90 95

Ala Arg Gly Asp Gly Asn Tyr Ala Leu Asp Ala Met Asp Tyr Trp Gly
100 105 110

Gln Gly Ala Leu Val Thr Val Ser Ser
115 120

<210> SEQ ID NO 114
<211> LENGTH: 432
<212> TYPE: DNA
<213> ORGANISM: Artificial Sequence
<220> FEATURE:
<223> OTHER INFORMATION: FelHcLb-H634x

<400> SEQUENCE: 114
aagcttgcca ccatggagtg gtcttgggtc tttctgttct ttctgagtgt taccaccggc 60
gtgcactcac aggtgctgct tgttcagtct ggcgccgaag ttcggaaacc aggcgccagc 120
gtgaagattt tctgcaagac cagcggctac accttcatca cctactacgt gcactggctg 180
agacaggccc ctgctcaggg atttgagtgg atgggccaga tttttcctgc cagcggcagc 240
accaactaca acgagatgtt tgagggcaga ctgaccctga ccgccgacac aagcacaaac 300

```
accgcctaca tggaactgag cagcctgaga agcgccgaca ccgccgtgta ttattgtgcc    360

agaggcgacg gcaactacgc cctggatgct atggattatt ggggccaggg cgctctggtc    420

acagtctcga gc                                                        432
```

```
<210> SEQ ID NO 115
<211> LENGTH: 121
<212> TYPE: PRT
<213> ORGANISM: Artificial Sequence
<220> FEATURE:
<223> OTHER INFORMATION: FelHcLb-H634x

<400> SEQUENCE: 115

Gln Val Leu Leu Val Gln Ser Gly Ala Glu Val Arg Lys Pro Gly Ala
1               5                   10                  15

Ser Val Lys Ile Phe Cys Lys Thr Ser Gly Tyr Thr Phe Ile Thr Tyr
            20                  25                  30

Tyr Val His Trp Leu Arg Gln Ala Pro Ala Gln Gly Phe Glu Trp Met
        35                  40                  45

Gly Gln Ile Phe Pro Ala Ser Gly Ser Thr Asn Tyr Asn Glu Met Phe
    50                  55                  60

Glu Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Val Tyr Tyr Cys
                85                  90                  95

Ala Arg Gly Asp Gly Asn Tyr Ala Leu Asp Ala Met Asp Tyr Trp Gly
            100                 105                 110

Gln Gly Ala Leu Val Thr Val Ser Ser
        115                 120


<210> SEQ ID NO 116
<211> LENGTH: 17
<212> TYPE: PRT
<213> ORGANISM: Artificial Sequence
<220> FEATURE:
<223> OTHER INFORMATION: mHcLb CDR-H2x

<400> SEQUENCE: 116

Gln Ile Phe Pro Ala Ser Gly Ser Thr Asn Tyr Asn Glu Met Phe Glu
1               5                   10                  15

Gly


<210> SEQ ID NO 117
<211> LENGTH: 10
<212> TYPE: PRT
<213> ORGANISM: Artificial Sequence
<220> FEATURE:
<223> OTHER INFORMATION: as mHcLb CDR-H1-WMN

<400> SEQUENCE: 117

Gly Tyr Ile Phe Ile Thr Tyr Trp Met Asn
1               5                   10


<210> SEQ ID NO 118
<211> LENGTH: 10
<212> TYPE: PRT
<213> ORGANISM: Artificial Sequence
<220> FEATURE:
<223> OTHER INFORMATION: mHcLb CDR-H1-MN

<400> SEQUENCE: 118

Gly Tyr Ile Phe Ile Thr Tyr Tyr Met Asn
```

1 5 10

<210> SEQ ID NO 119
<211> LENGTH: 432
<212> TYPE: DNA
<213> ORGANISM: Artificial Sequence
<220> FEATURE:
<223> OTHER INFORMATION: FelHcLb-H1-1WMN

<400> SEQUENCE: 119
aagcttgcca ccatggagtg gtcttgggtc tttctgttct ttctgagtgt taccaccggc 60
gtgcactcac aggtgctgct tgttcagtct ggcgctgaag ttcggactcc tggcgcctcc 120
gtgaagattt tctgtaaagc cagcggctac atcttcatca cctactggat gaactgggtc 180
cgacagagcc ctgctcaggg acttgagtgg atgggcagca tctttcctgc cagcggcagc 240
acaagctacg cccagaaatt tcaggggaga ctgaccctga ccgccgacac aagcacaaac 300
accgcctaca tggaactgag cagcctgaga agcgccgaca ccgccatgta ttattgtgcc 360
agaggcgacg gcaactacgc cctggatgct atggattatt ggggccaggg caccagcgtg 420
acagtctcga gc 432

<210> SEQ ID NO 120
<211> LENGTH: 121
<212> TYPE: PRT
<213> ORGANISM: Artificial Sequence
<220> FEATURE:
<223> OTHER INFORMATION: FelHcLb-H1-1WMN

<400> SEQUENCE: 120

Gln Val Leu Leu Val Gln Ser Gly Ala Glu Val Arg Thr Pro Gly Ala
1 5 10 15

Ser Val Lys Ile Phe Cys Lys Ala Ser Gly Tyr Ile Phe Ile Thr Tyr
20 25 30

Trp Met Asn Trp Val Arg Gln Ser Pro Ala Gln Gly Leu Glu Trp Met
35 40 45

Gly Ser Ile Phe Pro Ala Ser Gly Ser Thr Ser Tyr Ala Gln Lys Phe
50 55 60

Gln Gly Arg Leu Thr Leu Thr Ala Asp Thr Ser Thr Asn Thr Ala Tyr
65 70 75 80

Met Glu Leu Ser Ser Leu Arg Ser Ala Asp Thr Ala Met Tyr Tyr Cys
85 90 95

Ala Arg Gly Asp Gly Asn Tyr Ala Leu Asp Ala Met Asp Tyr Trp Gly
100 105 110

Gln Gly Thr Ser Val Thr Val Ser Ser
115 120

<210> SEQ ID NO 121
<211> LENGTH: 432
<212> TYPE: DNA
<213> ORGANISM: Artificial Sequence
<220> FEATURE:
<223> OTHER INFORMATION: FelHcLb-H1-1xWMN

<400> SEQUENCE: 121
aagcttgcca ccatggagtg gtcttgggtc tttctgttct ttctgagtgt taccaccggc 60
gtgcactcac aggtgctgct tgttcagtct ggcgctgaag ttcggactcc tggcgcctcc 120
gtgaagattt tctgtaaagc cagcggctac atcttcatca cctactggat gaactgggtc 180
cgacagagcc ctgctcaggg acttgagtgg atgggccaga tttttcctgc cagcggcagc 240

```
accaactaca acgagatgtt tgagggcaga ctgaccctga ccgccgacac aagcacaaac    300

accgcctaca tggaactgag cagcctgaga agcgccgaca ccgccatgta ttattgtgcc    360

agaggcgacg gcaactacgc cctggatgct atggattatt ggggccaggg caccagcgtg    420

acagtctcga gc                                                         432
```

```
<210> SEQ ID NO 122
<211> LENGTH: 121
<212> TYPE: PRT
<213> ORGANISM: Artificial Sequence
<220> FEATURE:
<223> OTHER INFORMATION: FelHcLb-H1-1xWMN

<400> SEQUENCE: 122

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ile Phe Ile Thr Tyr
            20                  25                  30

Trp Met Asn Trp Val Arg Gln Ser Pro Ala Gln Gly Leu Glu Trp Met
        35                  40                  45

Gly Gln Ile Phe Pro Ala Ser Gly Ser Thr Asn Tyr Asn Glu Met Phe
    50                  55                  60

Glu Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Ser Val Thr Val Ser Ser
        115                 120
```

```
<210> SEQ ID NO 123
<211> LENGTH: 432
<212> TYPE: DNA
<213> ORGANISM: Artificial Sequence
<220> FEATURE:
<223> OTHER INFORMATION: FelHcLb-H1-1MN

<400> SEQUENCE: 123

aagcttgcca ccatggagtg gtcttgggtc tttctgttct ttctgagtgt taccaccggc     60

gtgcactcac aggtgctgct tgttcagtct ggcgctgaag ttcggactcc tggcgcctcc    120

gtgaagattt tctgtaaagc cagcggctac atcttcatca cctactacat gaactgggtc    180

cgacagagcc ctgctcaggg acttgagtgg atgggcagca tctttcctgc cagcggcagc    240

acaagctacg cccagaaatt tcaggggaga ctgaccctga ccgccgacac aagcacaaac    300

accgcctaca tggaactgag cagcctgaga agcgccgaca ccgccatgta ttattgtgcc    360

agaggcgacg gcaactacgc cctggatgct atggattatt ggggccaggg caccagcgtg    420

acagtctcga gc                                                         432
```

```
<210> SEQ ID NO 124
<211> LENGTH: 121
<212> TYPE: PRT
<213> ORGANISM: Artificial Sequence
<220> FEATURE:
<223> OTHER INFORMATION: FelHcLb-H1-1MN

<400> SEQUENCE: 124
```

```
Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ile Phe Ile Thr Tyr
            20                  25                  30

Tyr Met Asn Trp Val Arg Gln Ser Pro Ala Gln Gly Leu Glu Trp Met
        35                  40                  45

Gly Ser Ile Phe Pro Ala Ser Gly Ser Thr Ser Tyr Ala Gln Lys Phe
    50                  55                  60

Gln Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Ser Val Thr Val Ser Ser
        115                 120


<210> SEQ ID NO 125
<211> LENGTH: 432
<212> TYPE: DNA
<213> ORGANISM: Artificial Sequence
<220> FEATURE:
<223> OTHER INFORMATION: FelHcLb-H1-1xMN

<400> SEQUENCE: 125

aagcttgcca ccatggagtg gtcttgggtc tttctgttct ttctgagtgt taccaccggc      60

gtgcactcac aggtgctgct tgttcagtct ggcgctgaag ttcggactcc tggcgcctcc     120

gtgaagattt tctgtaaagc cagcggctac atcttcatca cctactacat gaactgggtc     180

cgacagagcc ctgctcaggg acttgagtgg atgggccaga tttttcctgc cagcggcagc     240

accaactaca acgagatgtt tgagggcaga ctgaccctga ccgccgacac aagcacaaac     300

accgcctaca tggaactgag cagcctgaga agcgccgaca ccgccatgta ttattgtgcc     360

agaggcgacg gcaactacgc cctggatgct atggattatt ggggccaggg caccagcgtg     420

acagtctcga gc                                                         432


<210> SEQ ID NO 126
<211> LENGTH: 121
<212> TYPE: PRT
<213> ORGANISM: Artificial Sequence
<220> FEATURE:
<223> OTHER INFORMATION: FelHcLb-H1-1xMN

<400> SEQUENCE: 126

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ile Phe Ile Thr Tyr
            20                  25                  30

Tyr Met Asn Trp Val Arg Gln Ser Pro Ala Gln Gly Leu Glu Trp Met
        35                  40                  45

Gly Gln Ile Phe Pro Ala Ser Gly Ser Thr Asn Tyr Asn Glu Met Phe
    50                  55                  60

Glu Gly Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Gly Asp Gly Asn Tyr Ala Leu Asp Ala Met Asp Tyr Trp Gly
```

```
            100                 105                 110

Gln Gly Thr Ser Val Thr Val Ser Ser
        115                 120


<210> SEQ ID NO 127
<211> LENGTH: 335
<212> TYPE: PRT
<213> ORGANISM: Canis familiaris

<400> SEQUENCE: 127

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Ala Ala Gly Ala Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335


<210> SEQ ID NO 128
<211> LENGTH: 1011
```

<212> TYPE: DNA
<213> ORGANISM: Canis familiaris

<400> SEQUENCE: 128

```
gcctcaacaa ctgctcctag cgtgtttccc ctggccccta gctgcggaag tacctcaggc      60

agcacagtgg ccctggcttg tctggtgtct ggatatttcc ctgagccagt gaccgtgagt     120

tggaacagcg gctctctgac ctccggggtg cacacatttc catctgtgct gcagtctagt     180

ggcctgtact ccctgtcaag catggtgact gtgccttcct ctaggtggcc atcagaaact     240

ttcacctgca acgtggccca tcccgccagc aagaccaaag tggacaagcc cgtgcctaaa     300

agggagaatg gaagggtgcc aagaccacct gattgcccta agtgtccagc tccagaagcg     360

gcgggagcac caagcgtgtt catctttcca cccaagccca aagacacact gctgattgct     420

agaactcccg aggtgacctg cgtggtggtg gacctggatc cagaggaccc cgaagtgcag     480

atctcctggt tcgtggatgg gaagcagatg cagacagcca aaactcagcc tcgggaggaa     540

cagtttaacg gaacctatag agtggtgtct gtgctgccaa ttggacacca ggactggctg     600

aagggcaaac agtttacatg caaggtgaac aacaaggccc tgcctagtcc aatcgagagg     660

actatttcaa aagctagggg acaggctcat cagccttccg tgtatgtgct gcctccatcc     720

cgggaggaac tgtctaagaa cacagtgagt ctgacttgtc tgatcaaaga tttctttccc     780

cctgacattg atgtggagtg gcagagcaat gggcagcagg agccagaatc caagtacaga     840

accacaccac cccagctgga cgaagatggc tcctatttcc tgtacagtaa gctgtcagtg     900

gacaaatcta ggtggcagcg cggggatacc tttatctgcg ccgtgatgca cgaggctctg     960

cacaatcatt acacacaaga aagtctgtca catagccccg gcaagtagta g            1011
```

<210> SEQ ID NO 129
<211> LENGTH: 106
<212> TYPE: PRT
<213> ORGANISM: Canis familiaris

<400> SEQUENCE: 129

```
Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105
```

<210> SEQ ID NO 130
<211> LENGTH: 324
<212> TYPE: DNA
<213> ORGANISM: Canis familiaris

<400> SEQUENCE: 130

```
cggaacgacg cccagcccgc cgtgtacctg ttccagccca gccccgatca gctgcacacc      60

ggcagcgctt cagtcgtctg cctgctgaac agcttctacc ccaaggacat caacgtgaag     120
```

```
tggaaggtgg acggcgtgat ccaggacacc ggcatccagg aaagcgtcac cgagcaggac    180

aaggacagca cctacagcct gagcagcacc ctgaccatgt ccagcaccga gtacctgagc    240

cacgagctgt atagctgcga gatcacccac aagagcctgc ctagcaccct gatcaagagc    300

ttccagcgga gcgagtgcta gtag                                           324


<210> SEQ ID NO 131
<211> LENGTH: 335
<212> TYPE: PRT
<213> ORGANISM: Felis catus

<400> SEQUENCE: 131

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Ala Ala Gly Ala Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 132
<211> LENGTH: 1011
<212> TYPE: DNA
<213> ORGANISM: Felis catus

<400> SEQUENCE: 132
gcctccacca cggccccatc ggtgttccca ctggccccca gctgcgggac cacatctggc 60
gccaccgtgg ccctggcctg cctggtgtta ggctacttcc ctgagccggt gaccgtgtcc 120
tggaactccg gcgccctgac cagcggtgtg cacaccttcc cggccgtcct gcaggcctcg 180
gggctgtact ctctcagcag catggtgaca gtgccctcca gcaggtggct cagtgacacc 240
ttcacctgca acgtggccca cccgcccagc aacaccaagg tggacaagac cgtgcgcaaa 300
acagaccacc caccgggacc caaaccctgc gactgtccca aatgcccacc ccctgagatg 360
cttggaggac cgtccatctt catcttcccc ccaaaaccca aggacaccct ctcgatttcc 420
cggacgcccg aggtcacatg cttggtggtg gacttgggcc cagatgactc cgatgtccag 480
atcacatggt ttgtggataa cacccaggtg tacacagcca agacgagtcc gcgtgaggag 540
cagttcaaca gcacctaccg tgtggtcagt gtcctcccca tcctacacca ggactggctc 600
aaggggaagg agttcaagtg caaggtcaac agcaaatccc tcccctcccc catcgagagg 660
accatctcca aggccaaagg acagccccac gagccccagg tgtacgtcct gcctccagcc 720
caggaggagc tcagcaggaa caaagtcagt gtgacctgcc tgatcaaatc cttccacccg 780
cctgacattg ccgtcgagtg ggagatcacc ggacagccgg agccagagaa caactaccgg 840
acgaccccgc cccagctgga cagcgacggg acctacttcg tgtacagcaa gctctcggtg 900
gacaggtccc actggcagag gggaaacacc tacacctgct cggtgtcaca cgaagctctg 960
cacagccacc acacacagaa atccctcacc cagtctccgg gtaaatagta g 1011

<210> SEQ ID NO 133
<211> LENGTH: 110
<212> TYPE: PRT
<213> ORGANISM: Felis catus

<400> SEQUENCE: 133

Arg Ser Asp Ala Gln Pro Ser Val Phe Leu Phe Gln Pro Ser Leu Asp
1 5 10 15

Glu Leu His Thr Gly Ser Ala Ser Ile Val Cys Ile Leu Asn Asp Phe
20 25 30

Tyr Pro Lys Glu Val Asn Val Lys Trp Lys Val Asp Gly Val Val Gln
35 40 45

Asn Lys Gly Ile Gln Glu Ser Thr Thr Glu Gln Asn Ser Lys Asp Ser
50 55 60

Thr Tyr Ser Leu Ser Ser Thr Leu Thr Met Ser Ser Thr Glu Tyr Gln
65 70 75 80

Ser His Glu Lys Phe Ser Cys Glu Val Thr His Lys Ser Leu Ala Ser
85 90 95

Thr Leu Val Lys Ser Phe Gln Arg Ser Glu Cys Gln Arg Glu
100 105 110

<210> SEQ ID NO 134
<211> LENGTH: 336
<212> TYPE: DNA
<213> ORGANISM: Felis catus

<400> SEQUENCE: 134
cggagtgatg ctcagccatc tgtctttctc ttccaaccat ctctggacga gttacataca 60
ggaagtgcct ctatcgtgtg catattgaat gacttctacc ccaaagaggt caatgtcaag 120
tggaaagtgg atggcgtagt ccaaaacaaa ggcatccagg agagcaccac agagcagaac 180
agcaaggaca gcacctacag cctcagcagc accctgacga tgtccagtac ggagtaccaa 240
agtcatgaaa agttctcctg cgaggtcact cacaagagcc tggcctccac cctcgtcaag 300
agcttccaga ggagcgagtg tcagagagag tgatga 336

<210> SEQ ID NO 135
<211> LENGTH: 13
<212> TYPE: PRT
<213> ORGANISM: Artificial Sequence
<220> FEATURE:
<223> OTHER INFORMATION: D108E amino acid sequence in CDR H3 in the heavy chain variable region (VH) of Can SL501-VH3

<400> SEQUENCE: 135

Gly Glu Tyr Ser Gly Tyr Asp Thr Glu Pro Gln Tyr Ser
1 5 10

<210> SEQ ID NO 136
<211> LENGTH: 13
<212> TYPE: PRT
<213> ORGANISM: Artificial Sequence
<220> FEATURE:
<223> OTHER INFORMATION: D108P amino acid sequence in CDR H3 in the heavy chain variable region (VH) of Can SL501-VH3

<400> SEQUENCE: 136

Gly Glu Tyr Ser Gly Tyr Asp Thr Pro Pro Gln Tyr Ser
1 5 10

<210> SEQ ID NO 137
<211> LENGTH: 13
<212> TYPE: PRT
<213> ORGANISM: Artificial Sequence
<220> FEATURE:
<223> OTHER INFORMATION: D108Q amino acid sequence in CDR H3 in the heavy chain variable region (VH) of Can SL501-VH3

<400> SEQUENCE: 137

Gly Glu Tyr Ser Gly Tyr Asp Thr Gln Pro Gln Tyr Ser
1 5 10

<210> SEQ ID NO 138
<211> LENGTH: 13
<212> TYPE: PRT
<213> ORGANISM: Artificial Sequence
<220> FEATURE:
<223> OTHER INFORMATION: D108N amino acid sequence in CDR H3 in the heavy chain variable region (VH) of Can SL501-VH3

<400> SEQUENCE: 138

Gly Glu Tyr Ser Gly Tyr Asp Thr Asn Pro Gln Tyr Ser
1 5 10

<210> SEQ ID NO 139
<211> LENGTH: 13
<212> TYPE: PRT
<213> ORGANISM: Artificial Sequence
<220> FEATURE:
<223> OTHER INFORMATION: D108S amino acid sequence in CDR H3 in the heavy chain variable region (VH) of Can SL501-VH3

<400> SEQUENCE: 139

Gly Glu Tyr Ser Gly Tyr Asp Thr Ser Pro Gln Tyr Ser
1 5 10

<210> SEQ ID NO 140
<211> LENGTH: 13
<212> TYPE: PRT
<213> ORGANISM: Artificial Sequence
<220> FEATURE:
<223> OTHER INFORMATION: D108T amino acid sequence in CDR H3 in the heavy chain variable region (VH) of Can SL501-VH3

<400> SEQUENCE: 140

Gly Glu Tyr Ser Gly Tyr Asp Thr Thr Pro Gln Tyr Ser
1 5 10

<210> SEQ ID NO 141
<211> LENGTH: 13
<212> TYPE: PRT
<213> ORGANISM: Artificial Sequence
<220> FEATURE:
<223> OTHER INFORMATION: D108K amino acid sequence in CDR H3 in the heavy chain variable region (VH) of Can SL501-VH3

<400> SEQUENCE: 141

Gly Glu Tyr Ser Gly Tyr Asp Thr Lys Pro Gln Tyr Ser
1 5 10

<210> SEQ ID NO 142
<211> LENGTH: 13
<212> TYPE: PRT
<213> ORGANISM: Artificial Sequence
<220> FEATURE:
<223> OTHER INFORMATION: D108R amino acid sequence in CDR H3 in the heavy chain variable region (VH) of Can SL501-VH3

<400> SEQUENCE: 142

Gly Glu Tyr Ser Gly Tyr Asp Thr Arg Pro Gln Tyr Ser
1 5 10

<210> SEQ ID NO 143
<211> LENGTH: 13
<212> TYPE: PRT
<213> ORGANISM: Artificial Sequence
<220> FEATURE:
<223> OTHER INFORMATION: D108H amino acid sequence in CDR H3 in the heavy chain variable region (VH) of Can SL501-VH3

<400> SEQUENCE: 143

Gly Glu Tyr Ser Gly Tyr Asp Thr His Pro Gln Tyr Ser
1 5 10

<210> SEQ ID NO 144
<211> LENGTH: 13
<212> TYPE: PRT
<213> ORGANISM: Artificial Sequence
<220> FEATURE:
<223> OTHER INFORMATION: P109S amino acid sequence in CDR H3 in the heavy chain variable region (VH) of Can SL501-VH3

<400> SEQUENCE: 144

Gly Glu Tyr Ser Gly Tyr Asp Thr Asp Ser Gln Tyr Ser
1 5 10

<210> SEQ ID NO 145
<211> LENGTH: 13
<212> TYPE: PRT
<213> ORGANISM: Artificial Sequence
<220> FEATURE:
<223> OTHER INFORMATION: P109H amino acid sequence in CDR H3 in the heavy chain variable region (VH) of Can SL501-VH3

<400> SEQUENCE: 145

Gly Glu Tyr Ser Gly Tyr Asp Thr Asp His Gln Tyr Ser
1 5 10

<210> SEQ ID NO 146
<211> LENGTH: 13
<212> TYPE: PRT
<213> ORGANISM: Artificial Sequence
<220> FEATURE:
<223> OTHER INFORMATION: P109Y amino acid sequence in CDR H3 in the heavy chain variable region (VH) of Can SL501-VH3

<400> SEQUENCE: 146

Gly Glu Tyr Ser Gly Tyr Asp Thr Asp Tyr Gln Tyr Ser
1 5 10

<210> SEQ ID NO 147
<211> LENGTH: 13
<212> TYPE: PRT
<213> ORGANISM: Artificial Sequence
<220> FEATURE:
<223> OTHER INFORMATION: P109W amino acid sequence in CDR H3 in the heavy chain variable region (VH) of Can SL501-VH3

<400> SEQUENCE: 147

Gly Glu Tyr Ser Gly Tyr Asp Thr Asp Trp Gln Tyr Ser
1 5 10

<210> SEQ ID NO 148
<211> LENGTH: 13
<212> TYPE: PRT
<213> ORGANISM: Artificial Sequence
<220> FEATURE:
<223> OTHER INFORMATION: P109F amino acid sequence in CDR H3 in the heavy chain variable region (VH) of Can SL501-VH3

<400> SEQUENCE: 148

Gly Glu Tyr Ser Gly Tyr Asp Thr Asp Phe Gln Tyr Ser
1 5 10

<210> SEQ ID NO 149
<211> LENGTH: 13
<212> TYPE: PRT
<213> ORGANISM: Artificial Sequence
<220> FEATURE:
<223> OTHER INFORMATION: P109T amino acid sequence in CDR H3 in the heavy chain variable region (VH) of Can SL501-VH3

<400> SEQUENCE: 149

Gly Glu Tyr Ser Gly Tyr Asp Thr Asp Thr Gln Tyr Ser
1 5 10

<210> SEQ ID NO 150
<211> LENGTH: 13
<212> TYPE: PRT
<213> ORGANISM: Artificial Sequence
<220> FEATURE:
<223> OTHER INFORMATION: P109A amino acid sequence in CDR H3 in the heavy chain variable region (VH) of Can SL501-VH3

<400> SEQUENCE: 150

Gly Glu Tyr Ser Gly Tyr Asp Thr Asp Ala Gln Tyr Ser
1 5 10

<210> SEQ ID NO 151
<211> LENGTH: 13
<212> TYPE: PRT
<213> ORGANISM: Artificial Sequence
<220> FEATURE:
<223> OTHER INFORMATION: P109G amino acid sequence in CDR H3 in the heavy chain variable region (VH) of Can SL501-VH3

<400> SEQUENCE: 151

```
Gly Glu Tyr Ser Gly Tyr Asp Thr Asp Gly Gln Tyr Ser
1               5                   10
```

<210> SEQ ID NO 152
<211> LENGTH: 13
<212> TYPE: PRT
<213> ORGANISM: Artificial Sequence
<220> FEATURE:
<223> OTHER INFORMATION: Q110S amino acid sequence in CDR H3 in the heavy chain variable region (VH) of Can SL501-VH3

<400> SEQUENCE: 152

```
Gly Glu Tyr Ser Gly Tyr Asp Thr Asp Pro Ser Tyr Ser
1               5                   10
```

<210> SEQ ID NO 153
<211> LENGTH: 13
<212> TYPE: PRT
<213> ORGANISM: Artificial Sequence
<220> FEATURE:
<223> OTHER INFORMATION: Q110N amino acid sequence in CDR H3 in the heavy chain variable region (VH) of Can SL501-VH3

<400> SEQUENCE: 153

```
Gly Glu Tyr Ser Gly Tyr Asp Thr Asp Pro Asn Tyr Ser
1               5                   10
```

<210> SEQ ID NO 154
<211> LENGTH: 13
<212> TYPE: PRT
<213> ORGANISM: Artificial Sequence
<220> FEATURE:
<223> OTHER INFORMATION: Q110D amino acid sequence in CDR H3 in the heavy chain variable region (VH) of Can SL501-VH3

<400> SEQUENCE: 154

```
Gly Glu Tyr Ser Gly Tyr Asp Thr Asp Pro Asp Tyr Ser
1               5                   10
```

<210> SEQ ID NO 155
<211> LENGTH: 13
<212> TYPE: PRT
<213> ORGANISM: Artificial Sequence
<220> FEATURE:
<223> OTHER INFORMATION: Q110E amino acid sequence in CDR H3 in the heavy chain variable region (VH) of Can SL501-VH3

<400> SEQUENCE: 155

```
Gly Glu Tyr Ser Gly Tyr Asp Thr Asp Pro Glu Tyr Ser
1               5                   10
```

<210> SEQ ID NO 156
<211> LENGTH: 13
<212> TYPE: PRT
<213> ORGANISM: Artificial Sequence
<220> FEATURE:
<223> OTHER INFORMATION: Q110K amino acid sequence in CDR H3 in the heavy chain variable region (VH) of Can SL501-VH3

<400> SEQUENCE: 156

Gly Glu Tyr Ser Gly Tyr Asp Thr Asp Pro Lys Tyr Ser
1 5 10

<210> SEQ ID NO 157
<211> LENGTH: 13
<212> TYPE: PRT
<213> ORGANISM: Artificial Sequence
<220> FEATURE:
<223> OTHER INFORMATION: Q110R amino acid sequence in CDR H3 in the heavy chain variable region (VH) of Can SL501-VH3

<400> SEQUENCE: 157

Gly Glu Tyr Ser Gly Tyr Asp Thr Asp Pro Arg Tyr Ser
1 5 10

<210> SEQ ID NO 158
<211> LENGTH: 13
<212> TYPE: PRT
<213> ORGANISM: Artificial Sequence
<220> FEATURE:
<223> OTHER INFORMATION: Q110H amino acid sequence in CDR H3 in the heavy chain variable region (VH) of Can SL501-VH3

<400> SEQUENCE: 158

Gly Glu Tyr Ser Gly Tyr Asp Thr Asp Pro His Tyr Ser
1 5 10

<210> SEQ ID NO 159
<211> LENGTH: 13
<212> TYPE: PRT
<213> ORGANISM: Artificial Sequence
<220> FEATURE:
<223> OTHER INFORMATION: Q110T amino acid sequence in CDR H3 in the heavy chain variable region (VH) of Can SL501-VH3

<400> SEQUENCE: 159

Gly Glu Tyr Ser Gly Tyr Asp Thr Asp Pro Thr Tyr Ser
1 5 10

<210> SEQ ID NO 160
<211> LENGTH: 13
<212> TYPE: PRT
<213> ORGANISM: Artificial Sequence
<220> FEATURE:
<223> OTHER INFORMATION: Q110V amino acid sequence in CDR H3 in the heavy chain variable region (VH) of Can SL501-VH3

<400> SEQUENCE: 160

Gly Glu Tyr Ser Gly Tyr Asp Thr Asp Pro Val Tyr Ser
1 5 10

<210> SEQ ID NO 161
<211> LENGTH: 13
<212> TYPE: PRT
<213> ORGANISM: Artificial Sequence
<220> FEATURE:
<223> OTHER INFORMATION: Y111P amino acid sequence in CDR H3 in the heavy chain variable region (VH) of Can SL501-VH3

<400> SEQUENCE: 161

Gly Glu Tyr Ser Gly Tyr Asp Thr Asp Pro Gln Pro Ser
1 5 10

<210> SEQ ID NO 162
<211> LENGTH: 13
<212> TYPE: PRT

<213> ORGANISM: Artificial Sequence
<220> FEATURE:
<223> OTHER INFORMATION: Y111F amino acid sequence in CDR H3 in the heavy chain variable region (VH) of Can SL501-VH3

<400> SEQUENCE: 162

```
Gly Glu Tyr Ser Gly Tyr Asp Thr Asp Pro Gln Phe Ser
1               5                   10
```

<210> SEQ ID NO 163
<211> LENGTH: 13
<212> TYPE: PRT
<213> ORGANISM: Artificial Sequence
<220> FEATURE:
<223> OTHER INFORMATION: Y111W amino acid sequence in CDR H3 in the heavy chain variable region (VH) of Can SL501-VH3

<400> SEQUENCE: 163

```
Gly Glu Tyr Ser Gly Tyr Asp Thr Asp Pro Gln Trp Ser
1               5                   10
```

<210> SEQ ID NO 164
<211> LENGTH: 13
<212> TYPE: PRT
<213> ORGANISM: Artificial Sequence
<220> FEATURE:
<223> OTHER INFORMATION: Y111H amino acid sequence in CDR H3 in the heavy chain variable region (VH) of Can SL501-VH3

<400> SEQUENCE: 164

```
Gly Glu Tyr Ser Gly Tyr Asp Thr Asp Pro Gln His Ser
1               5                   10
```

<210> SEQ ID NO 165
<211> LENGTH: 13
<212> TYPE: PRT
<213> ORGANISM: Artificial Sequence
<220> FEATURE:
<223> OTHER INFORMATION: Y111M amino acid sequence in CDR H3 in the heavy chain variable region (VH) of Can SL501-VH3

<400> SEQUENCE: 165

```
Gly Glu Tyr Ser Gly Tyr Asp Thr Asp Pro Gln Met Ser
1               5                   10
```

<210> SEQ ID NO 166
<211> LENGTH: 13
<212> TYPE: PRT
<213> ORGANISM: Artificial Sequence
<220> FEATURE:
<223> OTHER INFORMATION: Y111I amino acid sequence in CDR H3 in the heavy chain variable region (VH) of Can SL501-VH3

<400> SEQUENCE: 166

```
Gly Glu Tyr Ser Gly Tyr Asp Thr Asp Pro Gln Ile Ser
1               5                   10
```

<210> SEQ ID NO 167
<211> LENGTH: 13
<212> TYPE: PRT
<213> ORGANISM: Artificial Sequence
<220> FEATURE:
<223> OTHER INFORMATION: Y111L amino acid sequence in CDR H3 in the heavy chain variable region (VH) of Can SL501-VH3

<400> SEQUENCE: 167

```
Gly Glu Tyr Ser Gly Tyr Asp Thr Asp Pro Gln Leu Ser
1               5                   10
```

<210> SEQ ID NO 168
<211> LENGTH: 13
<212> TYPE: PRT
<213> ORGANISM: Artificial Sequence
<220> FEATURE:
<223> OTHER INFORMATION: Y111V amino acid sequence in CDR H3 in the heavy chain variable region (VH) of Can SL501-VH3

<400> SEQUENCE: 168

Gly Glu Tyr Ser Gly Tyr Asp Thr Asp Pro Gln Val Ser
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Y111T amino acid sequence in CDR H3 in the heavy chain variable region (VH) of Can SL501-VH3

<400> SEQUENCE: 169

Gly Glu Tyr Ser Gly Tyr Asp Thr Asp Pro Gln Thr Ser
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Y111E amino acid sequence in CDR H3 in the heavy chain variable region (VH) of Can SL501-VH3

<400> SEQUENCE: 170

Gly Glu Tyr Ser Gly Tyr Asp Thr Asp Pro Gln Glu Ser
1               5                   10

<210> SEQ ID NO 171
<211> LENGTH: 13
<212> TYPE: PRT
<213> ORGANISM: Artificial Sequence
<220> FEATURE:
<223> OTHER INFORMATION: S112E) amino acid sequence in CDR H3 in the heavy chain variable region (VH) of Can SL501-VH3

<400> SEQUENCE: 171

Gly Glu Tyr Ser Gly Tyr Asp Thr Asp Pro Gln Tyr Glu
1               5                   10

<210> SEQ ID NO 172
<211> LENGTH: 13
<212> TYPE: PRT
<213> ORGANISM: Artificial Sequence
<220> FEATURE:
<223> OTHER INFORMATION: S112Q amino acid sequence in CDR H3 in the heavy chain variable region (VH) of Can SL501-VH3

<400> SEQUENCE: 172

Gly Glu Tyr Ser Gly Tyr Asp Thr Asp Pro Gln Tyr Gln
1               5                   10

<210> SEQ ID NO 173
<211> LENGTH: 13
<212> TYPE: PRT
<213> ORGANISM: Artificial Sequence
<220> FEATURE:
<223> OTHER INFORMATION: S112N amino acid sequence in CDR H3 in the heavy chain variable region (VH) of Can SL501-VH3

<400> SEQUENCE: 173

Gly Glu Tyr Ser Gly Tyr Asp Thr Asp Pro Gln Tyr Asn
1 5 10

<210> SEQ ID NO 174
<211> LENGTH: 13
<212> TYPE: PRT
<213> ORGANISM: Artificial Sequence
<220> FEATURE:
<223> OTHER INFORMATION: S112T amino acid sequence in CDR H3 in the heavy chain variable region (VH) of Can SL501-VH3

<400> SEQUENCE: 174

Gly Glu Tyr Ser Gly Tyr Asp Thr Asp Pro Gln Tyr Thr
1 5 10

<210> SEQ ID NO 175
<211> LENGTH: 13
<212> TYPE: PRT
<213> ORGANISM: Artificial Sequence
<220> FEATURE:
<223> OTHER INFORMATION: S112A amino acid sequence in CDR H3 in the heavy chain variable region (VH) of Can SL501-VH3

<400> SEQUENCE: 175

Gly Glu Tyr Ser Gly Tyr Asp Thr Asp Pro Gln Tyr Ala
1 5 10

<210> SEQ ID NO 176
<211> LENGTH: 13
<212> TYPE: PRT
<213> ORGANISM: Artificial Sequence
<220> FEATURE:
<223> OTHER INFORMATION: S112G amino acid sequence in CDR H3 in the heavy chain variable region (VH) of Can SL501-VH3

<400> SEQUENCE: 176

Gly Glu Tyr Ser Gly Tyr Asp Thr Asp Pro Gln Tyr Gly
1 5 10

<210> SEQ ID NO 177
<211> LENGTH: 13
<212> TYPE: PRT
<213> ORGANISM: Artificial Sequence
<220> FEATURE:
<223> OTHER INFORMATION: S112P amino acid sequence in CDR H3 in the heavy chain variable region (VH) of Can SL501-VH3

<400> SEQUENCE: 177

Gly Glu Tyr Ser Gly Tyr Asp Thr Asp Pro Gln Tyr Pro
1 5 10

<210> SEQ ID NO 178
<211> LENGTH: 13
<212> TYPE: PRT
<213> ORGANISM: Artificial Sequence
<220> FEATURE:
<223> OTHER INFORMATION: S112D amino acid sequence in CDR H3 in the heavy chain variable region (VH) of Can SL501-VH3

<400> SEQUENCE: 178

Gly Glu Tyr Ser Gly Tyr Asp Thr Asp Pro Gln Tyr Asp
1 5 10

<210> SEQ ID NO 179
<211> LENGTH: 13

<212> TYPE: PRT
<213> ORGANISM: Artificial Sequence
<220> FEATURE:
<223> OTHER INFORMATION: S112L amino acid sequence in CDR H3 in the heavy chain variable region (VH) of Can SL501-VH3

<400> SEQUENCE: 179

```
Gly Glu Tyr Ser Gly Tyr Asp Thr Asp Pro Gln Tyr Leu
1               5                   10
```

<210> SEQ ID NO 180
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody HcLb/mat/P/H3/100/DY

<400> SEQUENCE: 180

```
gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag caagcggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 181
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody HcLb/mat/P/H3/100/DY

<400> SEQUENCE: 181

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Ser Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 182
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody HcLb/mat/P/H2/55/SW

<400> SEQUENCE: 182

```
gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggcgac    300

ggcaattatg cactggatgc tatggactac tggggtcagg gaaccctggt gacagtctcg    360

agc                                                                   363
```

<210> SEQ ID NO 183
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody HcLb/mat/P/H2/55/SW

<400> SEQUENCE: 183

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 184
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/54AG/100DY

<400> SEQUENCE: 184

```
gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag gaagcggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                   363
```

<210> SEQ ID NO 185

<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody canHcLb/54AG/100DY

<400> SEQUENCE: 185

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Gly Ser Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 186
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY

<400> SEQUENCE: 186

```
gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 187
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody canHcLb/55SW/100DY

<400> SEQUENCE: 187

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
```

```
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 188
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/28/TI

<400> SEQUENCE: 188

gaggtgcagt tggttcagtc cggcgccgag gtgaagaagc ccggggcctc tgtaaaggtc     60

agctgcaaga ctagcggata tatatttatc acatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363


<210> SEQ ID NO 189
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/28/TI

<400> SEQUENCE: 189

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Ile Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 190
<211> LENGTH: 363
<212> TYPE: DNA
<213> ORGANISM: Artificial Sequence
```

```
<220> FEATURE:
<223> OTHER INFORMATION: (VH) of affinity matured caninized Hclb H1K4
      antibody canHcLb/55SW/100DY/30/IM

<400> SEQUENCE: 190

gaggtgcagt tggttcagtc cggcgccgag gtgaagaagc ccggggcctc tgtaaaggtc     60

agctgcaaga ctagcggata tacatttatg acatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363


<210> SEQ ID NO 191
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/30/IM

<400> SEQUENCE: 191

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Met Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 192
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody CanHcLb/55SW/100DY/57/SM

<400> SEQUENCE: 192

gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 193
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody CanHcLb/55SW/100DY/57/SM

<400> SEQUENCE: 193

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 194
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/57/SV

<400> SEQUENCE: 194

```
gaggtgcagt tggttcagtc cggcgccgag gtgaagaagc ccggggcctc tgtaaaggtc     60

agctgcaaga ctagcggata tacatttatc acatactgga tgaactgggt ccgacaagcc    120

cctggtgccg gcctggattg gatgggccag atcttcccag catggggagt taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 195
<211> LENGTH: 122
<212> TYPE: PRT
<213> ORGANISM: Artificial Sequence
<220> FEATURE:
<223> OTHER INFORMATION: (VH) of affinity matured caninized Hclb H1K4 antibody referred to herein as canHcLb/55SW/100DY/57/SV

<400> SEQUENCE: 195

```
Ser Glu Val Gln Leu Val Gln Ser Gly Ala Glu Val Lys Lys Pro Gly
1               5                   10                  15

Ala Ser Val Lys Val Ser Cys Lys Thr Ser Gly Tyr Thr Phe Ile Thr
            20                  25                  30

Tyr Trp Met Asn Trp Val Arg Gln Ala Pro Gly Ala Gly Leu Asp Trp
```

```
        35                  40                  45

Met Gly Gln Ile Phe Pro Ala Trp Gly Val Thr Asn Tyr Asn Glu Met
    50                  55                  60

Phe Glu Gly Arg Val Thr Leu Thr Ala Asp Thr Ser Thr Ser Thr Ala
65                  70                  75                  80

Tyr Met Glu Leu Ser Ser Leu Arg Ala Gly Asp Ile Ala Val Tyr Tyr
                85                  90                  95

Cys Ala Arg Gly Tyr Gly Asn Tyr Ala Leu Asp Ala Met Asp Tyr Trp
            100                 105                 110

Gly Gln Gly Thr Leu Val Thr Val Ser Ser
        115                 120


<210> SEQ ID NO 196
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/31/TK

<400> SEQUENCE: 196

gaggtgcagt tggttcagtc cggcgccgag gtgaagaagc ccggggcctc tgtaaaggtc      60

agctgcaaga ctagcggata tacatttatc aaatactgga tgaactgggt ccgacaagcc     120

cctggtgccg gcctggattg gatgggccag atcttcccag catggggatc taccaattac     180

aatgagatgt tcgagggtag ggtgaccctc acagctgata ccagtacttc aactgcatac     240

atggaactga gttccctgag agcaggcgac atcgcagttt actattgtgc ccgaggctat     300

ggcaattatg cactggatgc tatggactac tggggtcagg gaaccctggt gacagtctcg     360

agc                                                                   363


<210> SEQ ID NO 197
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/31/TK

<400> SEQUENCE: 197

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Lys Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 198
```

<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/30IM/31TK

<400> SEQUENCE: 198

```
gaggtgcagt tggttcagtc cggcgccgag gtgaagaagc ccggggcctc tgtaaaggtc     60

agctgcaaga ctagcggata tacatttatg aaatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 199
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody canHcLb/55SW/100DY/30IM/31TK

<400> SEQUENCE: 199

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Met Lys Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 200
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/30IM/31TK/28TI

<400> SEQUENCE: 200

```
gaggtgcagt tggttcagtc cggcgccgag gtgaagaagc ccggggcctc tgtaaaggtc     60

agctgcaaga ctagcggata tatatttatg aaatactgga tgaactgggt ccgacaagcc    120

cctggtgccg gcctggattg gatgggccag atcttcccag catggggatc taccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300
```

```
ggcaattatg cactggatgc tatggactac tggggtcagg gaaccctggt gacagtctcg    360

agc                                                                   363


<210> SEQ ID NO 201
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/30IM/31TK/28TI

<400> SEQUENCE: 201

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Ile Phe Met Lys Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 202
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/30IM/31TK/57SM

<400> SEQUENCE: 202

gaggtgcagt tggttcagtc cggcgccgag gtgaagaagc ccggggcctc tgtaaaggtc     60

agctgcaaga ctagcggata tacatttatg aaatactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                   363


<210> SEQ ID NO 203
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/30IM/31TK/57SM

<400> SEQUENCE: 203

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Met Lys Tyr
```

```
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 204
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/30IM/31TK/28TI/57SM

<400> SEQUENCE: 204

gaggtgcagt tggttcagtc cggcgccgag gtgaagaagc ccggggcctc tgtaaaggtc     60

agctgcaaga ctagcggata tatatttatg aaatactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363


<210> SEQ ID NO 205
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/30IM/31TK/28TI/57SM

<400> SEQUENCE: 205

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Ile Phe Met Lys Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 206
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/57SM/30IM

<400> SEQUENCE: 206

```
gaggtgcagt tggttcagtc cggcgccgag gtgaagaagc ccggggcctc tgtaaaggtc     60

agctgcaaga ctagcggata tacatttatg acatactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 207
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody canHcLb/55SW/100DY/57SM/30IM

<400> SEQUENCE: 207

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Met Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 208
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/57SV/30IM

<400> SEQUENCE: 208

```
gaggtgcagt tggttcagtc cggcgccgag gtgaagaagc ccggggcctc tgtaaaggtc     60

agctgcaaga ctagcggata tacatttatg acatactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240
```

```
atggaactga gttccctgag agcaggcgac atcgcagttt actattgtgc ccgaggctat    300

ggcaattatg cactggatgc tatggactac tggggtcagg gaaccctggt gacagtctcg    360

agc                                                                   363


<210> SEQ ID NO 209
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/57SV/30IM

<400> SEQUENCE: 209

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Met Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 210
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/57SM/30IM/31TF

<400> SEQUENCE: 210

gaggtgcagt tggttcagtc cggcgccgag gtgaagaagc ccggggcctc tgtaaaggtc     60

agctgcaaga ctagcggata tacatttatg ttctactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                   363


<210> SEQ ID NO 211
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/57SM/30IM/31TF

<400> SEQUENCE: 211

Glu Val Gln Leu Val Gln Ser Gly Ala Glu Val Lys Lys Pro Gly Ala
```

```
1               5                   10                  15

Ser Val Lys Val Ser Cys Lys Thr Ser Gly Tyr Thr Phe Met Phe Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120
```

<210> SEQ ID NO 212
<211> LENGTH: 363
<212> TYPE: DNA
<213> ORGANISM: Artificial Sequence
<220> FEATURE:
<223> OTHER INFORMATION: (VH) of affinity matured caninized Hclb H1K4 antibody canHcLb/55SW/100DY/57SM/30IM/31TF/28TK

<400> SEQUENCE: 212

```
gaggtgcagt tggttcagtc cggcgccgag gtgaagaagc ccggggcctc tgtaaaggtc     60

agctgcaaga ctagcggata taaatttatg ttctactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363
```

<210> SEQ ID NO 213
<211> LENGTH: 121
<212> TYPE: PRT
<213> ORGANISM: Artificial Sequence
<220> FEATURE:
<223> OTHER INFORMATION: (VH) of affinity matured caninized Hclb H1K4 antibody canHcLb/55SW/100DY/57SM/30IM/31TF/28TK

<400> SEQUENCE: 213

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Lys Phe Met Phe Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110
```

```
Gln Gly Thr Leu Val Thr Val Ser Ser
        115                 120


<210> SEQ ID NO 214
<211> LENGTH: 363
<212> TYPE: DNA
<213> ORGANISM: Artificial Sequence
<220> FEATURE:
<223> OTHER INFORMATION: (VH) of affinity matured caninized Hclb H1K4
      antibody canHcLb/55SW/100DY/57SM/30IW/31TF/28TK

<400> SEQUENCE: 214

gaggtgcagt tggttcagtc cggcgccgag gtgaagaagc ccggggcctc tgtaaaggtc     60

agctgcaaga ctagcggata taaattttgg ttctactgga tgaactgggt ccgacaagcc    120

cctggtgccg gcctggattg gatgggccag atcttcccag catggggaat gaccaattac    180

aatgagatgt tcgagggtag ggtgaccctc acagctgata ccagtacttc aactgcatac    240

atggaactga gttccctgag agcaggcgac atcgcagttt actattgtgc ccgaggctat    300

ggcaattatg cactggatgc tatggactac tggggtcagg gaaccctggt gacagtctcg    360

agc                                                                  363


<210> SEQ ID NO 215
<211> LENGTH: 121
<212> TYPE: PRT
<213> ORGANISM: Artificial Sequence
<220> FEATURE:
<223> OTHER INFORMATION: (VH) of affinity matured caninized Hclb H1K4
      antibody canHcLb/55SW/100DY/57SM/30IW/31TF/28TK

<400> SEQUENCE: 215

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Lys Phe Trp Phe Tyr
            20                  25                  30

Trp Met Asn Trp Val Arg Gln Ala Pro Gly Ala Gly Leu Asp Trp Met
        35                  40                  45

Gly Gln Ile Phe Pro Ala Trp Gly Met Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120


<210> SEQ ID NO 216
<211> LENGTH: 321
<212> TYPE: DNA
<213> ORGANISM: Artificial Sequence
<220> FEATURE:
<223> OTHER INFORMATION: (VL) of affinity matured caninized Hclb H1K4
      antibody HcLb/mat/K3/237/ND

<400> SEQUENCE: 216

gatattgtga tgacacagac tccaccctcc ctttctgtca gccctcggga gaccgcctcc     60

attagctgtc gcgccagtga gtccgtcgat tcctacggaa atagcttcat gcactggtat    120
```

ctgcagaaac caggtcagtc tcctcaattg ctgatctacc tggcttctaa cctggaaagc 180
ggtgtgtcag ataggttttc cggaagtggt agcggaactg actttaccct gcgtatttcc 240
cgagtggaag ccaatgacac tggtgtttac tactgtcagc agaatgacga agaccccctg 300
acctttggcc agggtaccaa g 321

<210> SEQ ID NO 217
<211> LENGTH: 107
<212> TYPE: PRT
<213> ORGANISM: Artificial Sequence
<220> FEATURE:
<223> OTHER INFORMATION: (VL) of affinity matured caninized Hclb H1K4 antibody HcLb/mat/K3/237/ND

<400> SEQUENCE: 217

Asp Ile Val Met Thr Gln Thr Pro Pro Ser Leu Ser Val Ser Pro Arg
1 5 10 15

Glu Thr Ala Ser Ile Ser Cys Arg Ala Ser Glu Ser Val Asp Ser Tyr
20 25 30

Gly Asn Ser Phe Met His Trp Tyr Leu Gln Lys Pro Gly Gln Ser Pro
35 40 45

Gln Leu Leu Ile Tyr Leu Ala Ser Asn Leu Glu Ser Gly Val Ser Asp
50 55 60

Arg Phe Ser Gly Ser Gly Ser Gly Thr Asp Phe Thr Leu Arg Ile Ser
65 70 75 80

Arg Val Glu Ala Asn Asp Thr Gly Val Tyr Tyr Cys Gln Gln Asn Asp
85 90 95

Glu Asp Pro Leu Thr Phe Gly Gln Gly Thr Lys
100 105

<210> SEQ ID NO 218
<211> LENGTH: 321
<212> TYPE: DNA
<213> ORGANISM: Artificial Sequence
<220> FEATURE:
<223> OTHER INFORMATION: (VL) of affinity matured caninized Hclb H1K4 antibody canHcLb/237ND/242TS

<400> SEQUENCE: 218
gatattgtga tgacacagac tccaccctcc ctttctgtca gccctcggga gaccgcctcc 60
attagctgtc gcgccagtga gtccgtcgat tcctacggaa atagcttcat gcactggtat 120
ctgcagaaac caggtcagtc tcctcaattg ctgatctacc tggcttctaa cctggaaagc 180
ggtgtgtcag ataggttttc cggaagtggt agcggaactg actttaccct gcgtatttcc 240
cgagtggaag ccaatgacac tggtgtttac tactgtcagc agaatgacga agaccccctg 300
agctttggcc agggtaccaa g 321

<210> SEQ ID NO 219
<211> LENGTH: 107
<212> TYPE: PRT
<213> ORGANISM: Artificial Sequence
<220> FEATURE:
<223> OTHER INFORMATION: (VL) of affinity matured caninized Hclb H1K4 antibody canHcLb/237ND/242TS

<400> SEQUENCE: 219

Asp Ile Val Met Thr Gln Thr Pro Pro Ser Leu Ser Val Ser Pro Arg
1 5 10 15

Glu Thr Ala Ser Ile Ser Cys Arg Ala Ser Glu Ser Val Asp Ser Tyr
20 25 30

```
Gly Asn Ser Phe Met His Trp Tyr Leu Gln Lys Pro Gly Gln Ser Pro
        35                  40                  45

Gln Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asp
                85                  90                  95

Glu Asp Pro Leu Ser Phe Gly Gln Gly Thr Lys
            100                 105


<210> SEQ ID NO 220
<211> LENGTH: 390
<212> TYPE: PRT
<213> ORGANISM: Canis familiaris

<400> SEQUENCE: 220

Met Pro Pro Ser Gly Leu Arg Leu Leu Pro Leu Leu Leu Pro Leu Leu
1               5                   10                  15

Arg Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ser Ser Pro Pro Ser
    50                  55                  60

Gln Gly Glu Val Pro Pro Val Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Asn Thr Asn Lys Ile Tyr Glu Lys Val Lys Lys Ser Pro
        115                 120                 125

His Ser Ile Tyr Met Leu Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Ala Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Thr
            180                 185                 190

Pro Glu Trp Leu Ser Phe Asp Val Thr Gly Val Val Arg Gln Trp Leu
        195                 200                 205

Ser His Gly Gly Glu Val Glu Gly Phe Arg Leu Ser Ala His Cys Ser
    210                 215                 220

Cys Asp Ser Lys Asp Asn Thr Leu Gln Val Asp Ile Asn Gly Phe Ser
225                 230                 235                 240

Ser Ser Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
            260                 265                 270

Ser Ser Arg Gln Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
```

```
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 221
<211> LENGTH: 390
<212> TYPE: PRT
<213> ORGANISM: Homo sapiens

<400> SEQUENCE: 221

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270
```

```
Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 222
<211> LENGTH: 390
<212> TYPE: PRT
<213> ORGANISM: Felis catus

<400> SEQUENCE: 222

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Asn Thr Asn Lys Ile Tyr Glu Lys Val Gln Arg Thr Pro
        115                 120                 125

His Ser Ile Tyr Met Leu Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Ala Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Thr
            180                 185                 190

Pro Glu Trp Leu Ser Phe Asp Val Thr Gly Val Val Arg Gln Trp Leu
        195                 200                 205

Ser His Gly Gly Glu Val Glu Gly Phe Arg Leu Ser Ala His Cys Ser
    210                 215                 220

Cys Asp Ser Lys Asp Asn Thr Leu Gln Val Asp Ile Asn Gly Phe Ser
225                 230                 235                 240

Ser Ser Arg Arg Gly Asp Leu Ala Thr Ile His Gly Met Asn Arg Pro
                245                 250                 255
```

```
Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 223
<211> LENGTH: 112
<212> TYPE: PRT
<213> ORGANISM: Artificial Sequence
<220> FEATURE:
<223> OTHER INFORMATION: TGFB1 FRAGMENT CONTAINING EPITOPE AS IN FIGURE 1

<400> SEQUENCE: 223

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 224
<211> LENGTH: 13
<212> TYPE: PRT
<213> ORGANISM: Artificial Sequence
<220> FEATURE:
<223> OTHER INFORMATION: VH CDR3 of the SL501 antibody: “TGEYSGYDT(X1)(X2)(X3)( X4)” wherein (X1) can be (K or R), wherein (X2) can be (T or A), wherein (X3) can be (Q, N, D, E or K) and wherein X4 can be (S, E, Q or D)
<220> FEATURE:
<221> NAME/KEY: VARIANT
<222> LOCATION: (10)..(10)
<223> OTHER INFORMATION: REPLACE=“R”
<220> FEATURE:
<221> NAME/KEY: VARIANT
<222> LOCATION: (11)..(11)
<223> OTHER INFORMATION: REPLACE=“A”
<220> FEATURE:

```
<221> NAME/KEY: VARIANT
<222> LOCATION: (12)..(12)
<223> OTHER INFORMATION: REPLACE="N" or "D" or "E" or "K"
<220> FEATURE:
<221> NAME/KEY: VARIANT
<222> LOCATION: (13)..(13)
<223> OTHER INFORMATION: REPLACE="E" or "Q" or "D"

<400> SEQUENCE: 224

Thr Gly Glu Tyr Ser Gly Tyr Asp Thr Lys Thr Gln Ser
1               5                   10


<210> SEQ ID NO 225
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108E point mutation

<400> SEQUENCE: 225

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Glu Pro Gln Tyr Ser
            100                 105                 110

Trp Gly Gln Gly Thr Thr Val Thr Val Ser Ser
        115                 120


<210> SEQ ID NO 226
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108P point mutation

<400> SEQUENCE: 226

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Pro Pro Gln Tyr Ser
            100                 105                 110
```

```
Trp Gly Gln Gly Thr Thr Val Thr Val Ser Ser
        115                 120


<210> SEQ ID NO 227
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108Q point mutation

<400> SEQUENCE: 227

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Gln Pro Gln Tyr Ser
            100                 105                 110

Trp Gly Gln Gly Thr Thr Val Thr Val Ser Ser
        115                 120


<210> SEQ ID NO 228
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108N point mutation

<400> SEQUENCE: 228

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asn Pro Gln Tyr Ser
            100                 105                 110

Trp Gly Gln Gly Thr Thr Val Thr Val Ser Ser
        115                 120


<210> SEQ ID NO 229
<211> LENGTH: 123
<212> TYPE: PRT
<213> ORGANISM: Artificial Sequence
```

<220> FEATURE:
<223> OTHER INFORMATION: (VH) of caninized SL501 antibody comprising the D108S point mutation

<400> SEQUENCE: 229

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Ser Pro Gln Tyr Ser
            100                 105                 110

Trp Gly Gln Gly Thr Thr Val Thr Val Ser Ser
        115                 120
```

<210> SEQ ID NO 230
<211> LENGTH: 123
<212> TYPE: PRT
<213> ORGANISM: Artificial Sequence
<220> FEATURE:
<223> OTHER INFORMATION: (VH) of caninized SL501 antibody comprising the D108T point mutation

<400> SEQUENCE: 230

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Thr Pro Gln Tyr Ser
            100                 105                 110

Trp Gly Gln Gly Thr Thr Val Thr Val Ser Ser
        115                 120
```

<210> SEQ ID NO 231
<211> LENGTH: 123
<212> TYPE: PRT
<213> ORGANISM: Artificial Sequence
<220> FEATURE:
<223> OTHER INFORMATION: (VH) of caninized SL501 antibody comprising the D108K point mutation

<400> SEQUENCE: 231

```
Glu Val Gln Leu Val Glu Ser Gly Gly Asp Leu Val Lys Pro Gly Gly
1               5                   10                  15
```

```
Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Lys Pro Gln Tyr Ser
            100                 105                 110

Trp Gly Gln Gly Thr Thr Val Thr Val Ser Ser
        115                 120


<210> SEQ ID NO 232
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108R point mutation

<400> SEQUENCE: 232

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Arg Pro Gln Tyr Ser
            100                 105                 110

Trp Gly Gln Gly Thr Thr Val Thr Val Ser Ser
        115                 120


<210> SEQ ID NO 233
<211> LENGTH: 123
<212> TYPE: PRT
<213> ORGANISM: Artificial Sequence
<220> FEATURE:
<223> OTHER INFORMATION: (VH) of caninized SL501 antibody comprising the
      D108H point mutation

<400> SEQUENCE: 233

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60
```

```
Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr His Pro Gln Tyr Ser
            100                 105                 110

Trp Gly Gln Gly Thr Thr Val Thr Val Ser Ser
        115                 120


<210> SEQ ID NO 234
<211> LENGTH: 123
<212> TYPE: PRT
<213> ORGANISM: Artificial Sequence
<220> FEATURE:
<223> OTHER INFORMATION: (VH) of caninized SL501 antibody comprising the
      P109S point mutation

<400> SEQUENCE: 234

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Ser Gln Tyr Ser
            100                 105                 110

Trp Gly Gln Gly Thr Thr Val Thr Val Ser Ser
        115                 120


<210> SEQ ID NO 235
<211> LENGTH: 123
<212> TYPE: PRT
<213> ORGANISM: Artificial Sequence
<220> FEATURE:
<223> OTHER INFORMATION: (VH) of caninized SL501 antibody comprising the
      P109H point mutation

<400> SEQUENCE: 235

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp His Gln Tyr Ser
            100                 105                 110
```

```
Trp Gly Gln Gly Thr Thr Val Thr Val Ser Ser
        115                 120


<210> SEQ ID NO 236
<211> LENGTH: 123
<212> TYPE: PRT
<213> ORGANISM: Artificial Sequence
<220> FEATURE:
<223> OTHER INFORMATION: (VH) of caninized SL501 antibody comprising the
      P109Y point mutation

<400> SEQUENCE: 236

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Tyr Gln Tyr Ser
            100                 105                 110

Trp Gly Gln Gly Thr Thr Val Thr Val Ser Ser
        115                 120


<210> SEQ ID NO 237
<211> LENGTH: 123
<212> TYPE: PRT
<213> ORGANISM: Artificial Sequence
<220> FEATURE:
<223> OTHER INFORMATION: (VH) of caninized SL501 antibody comprising the
      P109W point mutation

<400> SEQUENCE: 237

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Trp Gln Tyr Ser
            100                 105                 110

Trp Gly Gln Gly Thr Thr Val Thr Val Ser Ser
        115                 120


<210> SEQ ID NO 238
<211> LENGTH: 123
<212> TYPE: PRT
<213> ORGANISM: Artificial Sequence
<220> FEATURE:
```

<223> OTHER INFORMATION: (VH) of caninized SL501 antibody comprising the P109F point mutation

<400> SEQUENCE: 238

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Phe Gln Tyr Ser
            100                 105                 110

Trp Gly Gln Gly Thr Thr Val Thr Val Ser Ser
        115                 120
```

<210> SEQ ID NO 239
<211> LENGTH: 123
<212> TYPE: PRT
<213> ORGANISM: Artificial Sequence
<220> FEATURE:
<223> OTHER INFORMATION: (VH) of caninized SL501 antibody comprising the P109T point mutation

<400> SEQUENCE: 239

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Thr Gln Tyr Ser
            100                 105                 110

Trp Gly Gln Gly Thr Thr Val Thr Val Ser Ser
        115                 120
```

<210> SEQ ID NO 240
<211> LENGTH: 123
<212> TYPE: PRT
<213> ORGANISM: Artificial Sequence
<220> FEATURE:
<223> OTHER INFORMATION: (VH) of caninized SL501 antibody comprising the P109A point mutation

<400> SEQUENCE: 240

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
```

```
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Ala Gln Tyr Ser
            100                 105                 110

Trp Gly Gln Gly Thr Thr Val Thr Val Ser Ser
        115                 120


<210> SEQ ID NO 241
<211> LENGTH: 123
<212> TYPE: PRT
<213> ORGANISM: Artificial Sequence
<220> FEATURE:
<223> OTHER INFORMATION: (VH) of caninized SL501 antibody comprising the
      P109G point mutation

<400> SEQUENCE: 241

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Gly Gln Tyr Ser
            100                 105                 110

Trp Gly Gln Gly Thr Thr Val Thr Val Ser Ser
        115                 120


<210> SEQ ID NO 242
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Q110S point mutation

<400> SEQUENCE: 242

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Ser Tyr Ser
            100                 105                 110

Trp Gly Gln Gly Thr Thr Val Thr Val Ser Ser
        115                 120


<210> SEQ ID NO 243
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Q110N point mutation

<400> SEQUENCE: 243

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Asn Tyr Ser
            100                 105                 110

Trp Gly Gln Gly Thr Thr Val Thr Val Ser Ser
        115                 120


<210> SEQ ID NO 244
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Q110D point mutation

<400> SEQUENCE: 244

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Asp Tyr Ser
            100                 105                 110

Trp Gly Gln Gly Thr Thr Val Thr Val Ser Ser
```

```
        115                 120


<210> SEQ ID NO 245
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Q110E point mutation

<400> SEQUENCE: 245

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Glu Tyr Ser
            100                 105                 110

Trp Gly Gln Gly Thr Thr Val Thr Val Ser Ser
        115                 120


<210> SEQ ID NO 246
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Q110K point mutation

<400> SEQUENCE: 246

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Lys Tyr Ser
            100                 105                 110

Trp Gly Gln Gly Thr Thr Val Thr Val Ser Ser
        115                 120


<210> SEQ ID NO 247
<211> LENGTH: 123
<212> TYPE: PRT
<213> ORGANISM: Artificial Sequence
<220> FEATURE:
<223> OTHER INFORMATION: (VH) of caninized SL501 antibody comprising the
```

Q110R point mutation

<400> SEQUENCE: 247

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Arg Tyr Ser
            100                 105                 110

Trp Gly Gln Gly Thr Thr Val Thr Val Ser Ser
        115                 120
```

<210> SEQ ID NO 248
<211> LENGTH: 123
<212> TYPE: PRT
<213> ORGANISM: Artificial Sequence
<220> FEATURE:
<223> OTHER INFORMATION: (VH) of caninized SL501 antibody comprising the Q110H point mutation

<400> SEQUENCE: 248

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro His Tyr Ser
            100                 105                 110

Trp Gly Gln Gly Thr Thr Val Thr Val Ser Ser
        115                 120
```

<210> SEQ ID NO 249
<211> LENGTH: 123
<212> TYPE: PRT
<213> ORGANISM: Artificial Sequence
<220> FEATURE:
<223> OTHER INFORMATION: (VH) of caninized SL501 antibody comprising the Q110T point mutation

<400> SEQUENCE: 249

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30
```

```
Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Thr Tyr Ser
            100                 105                 110

Trp Gly Gln Gly Thr Thr Val Thr Val Ser Ser
        115                 120
```

<210> SEQ ID NO 250
<211> LENGTH: 123
<212> TYPE: PRT
<213> ORGANISM: Artificial Sequence
<220> FEATURE:
<223> OTHER INFORMATION: (VH) of caninized SL501 antibody comprising the Q110V point mutation

<400> SEQUENCE: 250

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Val Tyr Ser
            100                 105                 110

Trp Gly Gln Gly Thr Thr Val Thr Val Ser Ser
        115                 120
```

<210> SEQ ID NO 251
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111P point mutation

<400> SEQUENCE: 251

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Pro Ser
            100                 105                 110

Trp Gly Gln Gly Thr Thr Val Thr Val Ser Ser
        115                 120


<210> SEQ ID NO 252
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Y111F point mutation

<400> SEQUENCE: 252

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Phe Ser
            100                 105                 110

Trp Gly Gln Gly Thr Thr Val Thr Val Ser Ser
        115                 120


<210> SEQ ID NO 253
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Y111W point mutation

<400> SEQUENCE: 253

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Trp Ser
            100                 105                 110

Trp Gly Gln Gly Thr Thr Val Thr Val Ser Ser
        115                 120
```

<210> SEQ ID NO 254
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111H point mutation

<400> SEQUENCE: 254

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln His Ser
            100                 105                 110

Trp Gly Gln Gly Thr Thr Val Thr Val Ser Ser
        115                 120
```

<210> SEQ ID NO 255
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111M point mutation

<400> SEQUENCE: 255

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Met Ser
            100                 105                 110

Trp Gly Gln Gly Thr Thr Val Thr Val Ser Ser
        115                 120
```

<210> SEQ ID NO 256
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111I point mutation

<400> SEQUENCE: 256

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Ile Ser
            100                 105                 110

Trp Gly Gln Gly Thr Thr Val Thr Val Ser Ser
        115                 120
```

<210> SEQ ID NO 257
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111L point mutation

<400> SEQUENCE: 257

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Leu Ser
            100                 105                 110

Trp Gly Gln Gly Thr Thr Val Thr Val Ser Ser
        115                 120
```

<210> SEQ ID NO 258
<211> LENGTH: 123
<212> TYPE: PRT
<213> ORGANISM: Artificial Sequence
<220> FEATURE:
<223> OTHER INFORMATION: (VH) of caninized SL501 antibody comprising the Y111V point mutation

<400> SEQUENCE: 258

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30
```

```
Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Val Ser
            100                 105                 110

Trp Gly Gln Gly Thr Thr Val Thr Val Ser Ser
        115                 120


<210> SEQ ID NO 259
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Y111T point mutation

<400> SEQUENCE: 259

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Thr Ser
            100                 105                 110

Trp Gly Gln Gly Thr Thr Val Thr Val Ser Ser
        115                 120


<210> SEQ ID NO 260
<211> LENGTH: 123
<212> TYPE: PRT
<213> ORGANISM: Artificial Sequence
<220> FEATURE:
<223> OTHER INFORMATION: (VH) of caninized SL501 antibody comprising the
      Y111E point mutation

<400> SEQUENCE: 260

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Glu Ser
            100                 105                 110

Trp Gly Gln Gly Thr Thr Val Thr Val Ser Ser
        115                 120
```

<210> SEQ ID NO 261
<211> LENGTH: 123
<212> TYPE: PRT
<213> ORGANISM: Artificial Sequence
<220> FEATURE:
<223> OTHER INFORMATION: (VH) of caninized SL501 antibody comprising the S112E point mutation

<400> SEQUENCE: 261

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Glu
            100                 105                 110

Trp Gly Gln Gly Thr Thr Val Thr Val Ser Ser
        115                 120
```

<210> SEQ ID NO 262
<211> LENGTH: 123
<212> TYPE: PRT
<213> ORGANISM: Artificial Sequence
<220> FEATURE:
<223> OTHER INFORMATION: (VH) of caninized SL501 antibody comprising the S112Q point mutation

<400> SEQUENCE: 262

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Gln
            100                 105                 110

Trp Gly Gln Gly Thr Thr Val Thr Val Ser Ser
        115                 120
```

<210> SEQ ID NO 263
<211> LENGTH: 123
<212> TYPE: PRT
<213> ORGANISM: Artificial Sequence
<220> FEATURE:
<223> OTHER INFORMATION: (VH) of caninized SL501 antibody comprising the S112N point mutation

<400> SEQUENCE: 263

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Asn
            100                 105                 110

Trp Gly Gln Gly Thr Thr Val Thr Val Ser Ser
        115                 120
```

<210> SEQ ID NO 264
<211> LENGTH: 123
<212> TYPE: PRT
<213> ORGANISM: Artificial Sequence
<220> FEATURE:
<223> OTHER INFORMATION: (VH) of caninized SL501 antibody comprising the S112T point mutation

<400> SEQUENCE: 264

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Thr
            100                 105                 110

Trp Gly Gln Gly Thr Thr Val Thr Val Ser Ser
        115                 120
```

<210> SEQ ID NO 265
<211> LENGTH: 123
<212> TYPE: PRT
<213> ORGANISM: Artificial Sequence
<220> FEATURE:
<223> OTHER INFORMATION: (VH) of caninized SL501 antibody comprising the S112A point mutation

<400> SEQUENCE: 265

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Ser Tyr
20 25 30

Gly Met His Trp Val Arg Gln Ala Pro Gly Lys Glu Leu Glu Trp Val
35 40 45

Ala Val Ile Ser Tyr Asp Gly Ser Ile Lys Tyr Tyr Ala Asp Ala Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Gly Glu Tyr Ser Gly Tyr Asp Thr Asp Pro Gln Tyr Ala
100 105 110

Trp Gly Gln Gly Thr Thr Val Thr Val Ser Ser
115 120

<210> SEQ ID NO 266
<211> LENGTH: 123
<212> TYPE: PRT
<213> ORGANISM: Artificial Sequence
<220> FEATURE:
<223> OTHER INFORMATION: (VH) of caninized SL501 antibody comprising the S112G point mutation

<400> SEQUENCE: 266

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Ser Tyr
20 25 30

Gly Met His Trp Val Arg Gln Ala Pro Gly Lys Glu Leu Glu Trp Val
35 40 45

Ala Val Ile Ser Tyr Asp Gly Ser Ile Lys Tyr Tyr Ala Asp Ala Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Gly Glu Tyr Ser Gly Tyr Asp Thr Asp Pro Gln Tyr Gly
100 105 110

Trp Gly Gln Gly Thr Thr Val Thr Val Ser Ser
115 120

<210> SEQ ID NO 267
<211> LENGTH: 123
<212> TYPE: PRT
<213> ORGANISM: Artificial Sequence
<220> FEATURE:
<223> OTHER INFORMATION: (VH) of caninized SL501 antibody comprising the S112P point mutation

<400> SEQUENCE: 267

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Ser Tyr
20 25 30

Gly Met His Trp Val Arg Gln Ala Pro Gly Lys Glu Leu Glu Trp Val

```
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Pro
            100                 105                 110

Trp Gly Gln Gly Thr Thr Val Thr Val Ser Ser
        115                 120


<210> SEQ ID NO 268
<211> LENGTH: 123
<212> TYPE: PRT
<213> ORGANISM: Artificial Sequence
<220> FEATURE:
<223> OTHER INFORMATION: (VH) of caninized SL501 antibody comprising the
      S112D point mutation

<400> SEQUENCE: 268

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Asp
            100                 105                 110

Trp Gly Gln Gly Thr Thr Val Thr Val Ser Ser
        115                 120


<210> SEQ ID NO 269
<211> LENGTH: 123
<212> TYPE: PRT
<213> ORGANISM: Artificial Sequence
<220> FEATURE:
<223> OTHER INFORMATION: (VH) of caninized SL501 antibody comprising the
      S112L point mutation

<400> SEQUENCE: 269

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Thr Gly Glu Tyr Ser Gly Tyr Asp Thr Asp Pro Gln Tyr Leu
            100                 105                 110

Trp Gly Gln Gly Thr Thr Val Thr Val Ser Ser
        115                 120


<210> SEQ ID NO 270
<211> LENGTH: 7
<212> TYPE: PRT
<213> ORGANISM: Artificial Sequence
<220> FEATURE:
<223> OTHER INFORMATION: (VH) CDR1 of the HcLB mAb comprising the amino
      acid sequence of: G-Y-(X1)-F-(X2)-(X3)-Y wherein (X1) comprises T
      or I, (X2) comprises I or M and (X3) comprises T or K.
<220> FEATURE:
<221> NAME/KEY: VARIANT
<222> LOCATION: (3)..(3)
<223> OTHER INFORMATION: REPLACE= I
<220> FEATURE:
<221> NAME/KEY: VARIANT
<222> LOCATION: (5)..(5)
<223> OTHER INFORMATION: REPLACE= M
<220> FEATURE:
<221> NAME/KEY: VARIANT
<222> LOCATION: (6)..(6)
<223> OTHER INFORMATION: REPLACE= K

<400> SEQUENCE: 270

Gly Tyr Thr Phe Ile Thr Tyr
1               5


<210> SEQ ID NO 271
<211> LENGTH: 6
<212> TYPE: PRT
<213> ORGANISM: Artificial Sequence
<220> FEATURE:
<223> OTHER INFORMATION: (VH) CDR2 of the HcLB mAb comprising the amino
      acid sequence of: F-P-(X4)-(X5)-G-(X6) wherein (X4) comprises A or
      G, (X5) comprises S or W and (X6) comprises S, M or V
<220> FEATURE:
<221> NAME/KEY: VARIANT
<222> LOCATION: (3)..(3)
<223> OTHER INFORMATION: REPLACE= G
<220> FEATURE:
<221> NAME/KEY: VARIANT
<222> LOCATION: (4)..(4)
<223> OTHER INFORMATION: REPLACE= W
<220> FEATURE:
<221> NAME/KEY: VARIANT
<222> LOCATION: (6)..(6)
<223> OTHER INFORMATION: REPLACE= M or V

<400> SEQUENCE: 271

Phe Pro Ala Ser Gly Ser
1               5


<210> SEQ ID NO 272
<211> LENGTH: 8
<212> TYPE: PRT
<213> ORGANISM: Artificial Sequence
<220> FEATURE:
<223> OTHER INFORMATION: (VH) CDR3 of the HcLB  mAb comprising the amino
      acid sequence of: G-(X7)-G-N-Y-A-L-D-A-M-D-Y wherein (X7)
      comprises D or Y.
<220> FEATURE:
<221> NAME/KEY: VARIANT
<222> LOCATION: (2)..(2)
<223> OTHER INFORMATION: REPLACE= Y

<400> SEQUENCE: 272

Gly Asp Gly Asn Tyr Ala Leu Asp
```

```
1               5


<210> SEQ ID NO 273
<211> LENGTH: 9
<212> TYPE: PRT
<213> ORGANISM: Artificial Sequence
<220> FEATURE:
<223> OTHER INFORMATION: (VL) CDR3 of the HcLB mAb comprising the amino
      acid sequence of: Q-Q-N-(X8)-E-D-P-L-(X9) wherein (X8) comprises N
      or D and (X9) comprises T or S
<220> FEATURE:
<221> NAME/KEY: VARIANT
<222> LOCATION: (4)..(4)
<223> OTHER INFORMATION: REPLACE= D
<220> FEATURE:
<221> NAME/KEY: VARIANT
<222> LOCATION: (9)..(9)
<223> OTHER INFORMATION: REPLACE= D

<400> SEQUENCE: 273

Gln Gln Asn Asn Glu Asp Pro Leu Thr
1               5


<210> SEQ ID NO 274
<211> LENGTH: 7
<212> TYPE: PRT
<213> ORGANISM: Artificial Sequence
<220> FEATURE:
<223> OTHER INFORMATION: CDR1 of the variable region of the heavy chain
      (VH) the HcLB antibody comprising the T28I point mutation

<400> SEQUENCE: 274

Gly Tyr Ile Phe Ile Thr Tyr
1               5


<210> SEQ ID NO 275
<211> LENGTH: 7
<212> TYPE: PRT
<213> ORGANISM: Artificial Sequence
<220> FEATURE:
<223> OTHER INFORMATION: CDR1 of the variable region of the heavy chain
      (VH) of the HcLB antibody comprising the I30M point mutation

<400> SEQUENCE: 275

Gly Tyr Ile Phe Met Thr Tyr
1               5


<210> SEQ ID NO 276
<211> LENGTH: 7
<212> TYPE: PRT
<213> ORGANISM: Artificial Sequence
<220> FEATURE:
<223> OTHER INFORMATION: CDR1of the variable region of the heavy chain
      (VH) of the HcLB antibody comprising the T31K point mutation

<400> SEQUENCE: 276

Gly Tyr Thr Phe Ile Lys Tyr
1               5


<210> SEQ ID NO 277
<211> LENGTH: 7
<212> TYPE: PRT
<213> ORGANISM: Artificial Sequence
<220> FEATURE:
<223> OTHER INFORMATION: CDR1of the variable region of the heavy chain
      (VH) of the HcLB antibody comprising the I30M and T31K point
      mutation

<400> SEQUENCE: 277
```

```
Gly Tyr Ile Phe Met Lys Tyr
1               5


<210> SEQ ID NO 278
<211> LENGTH: 7
<212> TYPE: PRT
<213> ORGANISM: Artificial Sequence
<220> FEATURE:
<223> OTHER INFORMATION: CDR1of the variable region of the heavy chain
      (VH) of the HcLB antibody comprising the T28I, I30M and T31K point
      mutations

<400> SEQUENCE: 278

Gly Tyr Ile Phe Met Lys Tyr
1               5


<210> SEQ ID NO 279
<211> LENGTH: 6
<212> TYPE: PRT
<213> ORGANISM: Artificial Sequence
<220> FEATURE:
<223> OTHER INFORMATION: CDR2of the variable region of the heavy chain
      (VH) of the HcLB antibody comprising the A54G point mutation

<400> SEQUENCE: 279

Phe Pro Gly Ser Gly Ser
1               5


<210> SEQ ID NO 280
<211> LENGTH: 6
<212> TYPE: PRT
<213> ORGANISM: Artificial Sequence
<220> FEATURE:
<223> OTHER INFORMATION: CDR2 of the variable region of the heavy chain
      (VH) of the HcLB antibody comprising the S55W point mutation

<400> SEQUENCE: 280

Phe Pro Ala Trp Gly Ser
1               5


<210> SEQ ID NO 281
<211> LENGTH: 6
<212> TYPE: PRT
<213> ORGANISM: Artificial Sequence
<220> FEATURE:
<223> OTHER INFORMATION: CDR2 of the variable region of the heavy chain
      (VH) of the HcLB antibody comprising the S57M point mutation

<400> SEQUENCE: 281

Phe Pro Ala Ser Gly Met
1               5


<210> SEQ ID NO 282
<211> LENGTH: 6
<212> TYPE: PRT
<213> ORGANISM: Artificial Sequence
<220> FEATURE:
<223> OTHER INFORMATION: CDR2 of the variable region of the heavy chain
      (VH) of the HcLB antibody comprising the S55W and S57M point
      mutations

<400> SEQUENCE: 282

Phe Pro Ala Trp Gly Met
1               5


<210> SEQ ID NO 283
<211> LENGTH: 12
<212> TYPE: PRT
```

<213> ORGANISM: Artificial Sequence
<220> FEATURE:
<223> OTHER INFORMATION: CDR3 of the variable region of the heavy chain (VH) of the HcLB antibody comprising the D100Y point mutation

<400> SEQUENCE: 283

Gly Tyr Gly Asn Tyr Ala Leu Asp Ala Met Asp Tyr
1               5                   10

<210> SEQ ID NO 284
<211> LENGTH: 9
<212> TYPE: PRT
<213> ORGANISM: Artificial Sequence
<220> FEATURE:
<223> OTHER INFORMATION: CDR3 of the variable region of the light chain (VL) of the HcLB antibody comprising the N237D point mutation

<400> SEQUENCE: 284

Gln Gln Asn Asp Glu Asp Pro Leu Thr
1               5

<210> SEQ ID NO 285
<211> LENGTH: 9
<212> TYPE: PRT
<213> ORGANISM: Artificial Sequence
<220> FEATURE:
<223> OTHER INFORMATION: CDR3 of the variable region of the light chain (VH) of the HcLB antibody comprising the T242S point mutation

<400> SEQUENCE: 285

Gln Gln Asn Asn Glu Asp Pro Leu Ser
1               5

<210> SEQ ID NO 286
<211> LENGTH: 9
<212> TYPE: PRT
<213> ORGANISM: Artificial Sequence
<220> FEATURE:
<223> OTHER INFORMATION: CDR3 of the variable region of the light chain (VL) of the HcLB antibody comprising the N237D and T242S point mutations

<400> SEQUENCE: 286

Gln Gln Asn Asp Glu Asp Pro Leu Ser
1               5

<210> SEQ ID NO 287
<211> LENGTH: 1005
<212> TYPE: DNA
<213> ORGANISM: Canis familiaris

<400> SEQUENCE: 287
gcctcaacaa ctgctcctag cgtgtttccc ctggccccta gctgcggaag tacctcaggc     60
agcacagtgg ccctggcttg tctggtgtct ggatatttcc ctgagccagt gaccgtgagt    120
tggaacagcg gctctctgac ctccggggtg cacacatttc catctgtgct gcagtctagt    180
ggcctgtact ccctgtcaag catggtgact gtgccttcct ctaggtggcc atcagaaact    240
ttcacctgca acgtggccca tcccgccagc aagaccaaag tggacaagcc cgtgcctaaa    300
agggagaatg gaagggtgcc aagaccacct gattgcccta agtgtccagc tccagaagcg    360
gcgggagcac caagcgtgtt catctttcca cccaagccca aagacacact gctgattgct    420
agaactcccg aggtgacctg cgtggtggtg gacctggatc cagaggaccc cgaagtgcag    480
atctcctggt tcgtggatgg gaagcagatg cagacagcca aaactcagcc tcgggaggaa    540

```
cagtttaacg gaacctatag agtggtgtct gtgctgccaa ttggacacca ggactggctg    600

aagggcaaac agtttacatg caaggtgaac aacaaggccc tgcctagtcc aatcgagagg    660

actatttcaa aagctagggg acaggctcat cagccttccg tgtatgtgct gcctccatcc    720

cgggaggaac tgtctaagaa cacagtgagt ctgacttgtc tgatcaaaga tttctttccc    780

cctgacattg atgtggagtg gcagagcaat gggcagcagg agccagaatc caagtacaga    840

accacaccac cccagctgga cgaagatggc tcctatttcc tgtacagtaa gctgtcagtg    900

gacaaatcta ggtggcagcg cggggatacc tttatctgcg ccgtgatgca cgaggctctg    960

cacaatcatt acacacaaga aagtctgtca catagccccg gcaag                   1005
```

```
<210> SEQ ID NO 288
<211> LENGTH: 335
<212> TYPE: PRT
<213> ORGANISM: Canis familiaris

<400> SEQUENCE: 288

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Ala Ala Gly Ala Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
```

```
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335


<210> SEQ ID NO 289
<211> LENGTH: 1005
<212> TYPE: DNA
<213> ORGANISM: Felis catus

<400> SEQUENCE: 289

gcctccacca cggccccatc ggtgttccca ctggccccca gctgcgggac cacatctggc     60

gccaccgtgg ccctggcctg cctggtgtta ggctacttcc ctgagccggt gaccgtgtcc    120

tggaactccg gcgccctgac cagcggtgtg cacaccttcc cggccgtcct gcaggcctcg    180

gggctgtact ctctcagcag catggtgaca gtgccctcca gcaggtggct cagtgacacc    240

ttcacctgca acgtggccca cccgcccagc aacaccaagg tggacaagac cgtgcgcaaa    300

acagaccacc caccgggacc caaaccctgc gactgtccca aatgcccacc ccctgagatg    360

cttggaggac cgtccatctt catcttcccc ccaaaaccca aggacaccct ctcgatttcc    420

cggacgcccg aggtcacatg cttggtggtg gacttgggcc cagatgactc cgatgtccag    480

atcacatggt ttgtggataa cacccaggtg tacacagcca agacgagtcc gcgtgaggag    540

cagttcaaca gcacctaccg tgtggtcagt gtcctcccca tcctacacca ggactggctc    600

aaggggaagg agttcaagtg caaggtcaac agcaaatccc tcccctcccc catcgagagg    660

accatctcca aggccaaagg acagccccac gagccccagg tgtacgtcct gcctccagcc    720

caggaggagc tcagcaggaa caaagtcagt gtgacctgcc tgatcaaatc cttccacccg    780

cctgacattg ccgtcgagtg ggagatcacc ggacagccgg agccagagaa caactaccgg    840

acgaccccgc cccagctgga cagcgacggg acctacttcg tgtacagcaa gctctcggtg    900

gacaggtccc actggcagag ggggaaacacc tacacctgct cggtgtcaca cgaagctctg    960

cacagccacc acacacagaa atccctcacc cagtctccgg gtaaa                   1005


<210> SEQ ID NO 290
<211> LENGTH: 335
<212> TYPE: PRT
<213> ORGANISM: Felis catus

<400> SEQUENCE: 290

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110
```

```
Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 291
<211> LENGTH: 1008
<212> TYPE: DNA
<213> ORGANISM: Canis familiaris

<400> SEQUENCE: 291

```
gcctcaacaa ctgctcctag cgtgtttccc ctggccccta gctgcggaag tacctcaggc     60

agcacagtgg ccctggcttg tctggtgtct ggatatttcc ctgagccagt gaccgtgagt    120

tggaacagcg gctctctgac ctccggggtg cacacatttc catctgtgct gcagtctagt    180

ggcctgtact ccctgtcaag catggtgact gtgccttcct ctaggtggcc atcagaaact    240

ttcacctgca acgtggccca tcccgccagc aagaccaaag tggacaagcc cgtgcctaaa    300

agggagaatg gaagggtgcc aagaccacct gattgcccta agtgtccagc tccagaaatg    360

ctgggaggac caagcgtgtt catctttcca cccaagccca aagacacact gctgattgct    420

agaactcccg aggtgacctg cgtggtggtg gacctggatc cagaggaccc cgaagtgcag    480

atctcctggt tcgtggatgg gaagcagatg cagacagcca aaactcagcc tcgggaggaa    540

cagtttaacg gaacctatag agtggtgtct gtgctgccaa ttggacacca ggactggctg    600

aagggcaaac agtttacatg caaggtgaac aacaaggccc tgcctagtcc aatcgagagg    660

actatttcaa aagctagggg acaggctcat cagccttccg tgtatgtgct gcctccatcc    720

cgggaggaac tgtctaagaa cacagtgagt ctgacttgtc tgatcaaaga tttctttccc    780

cctgacattg atgtggagtg gcagagcaat gggcagcagg agccagaatc caagtacaga    840

accacaccac cccagctgga cgaagatggc tcctatttcc tgtacagtaa gctgtcagtg    900
```

```
gacaaatcta ggtggcagcg cggggatacc tttatctgcg ccgtgatgca cgaggctctg    960

cacaatcatt acacacaaga aagtctgtca catagccccg gcaagtag               1008


<210> SEQ ID NO 292
<211> LENGTH: 335
<212> TYPE: PRT
<213> ORGANISM: Canis familiaris

<400> SEQUENCE: 292

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335


<210> SEQ ID NO 293
<211> LENGTH: 309
```

-continued

```
<212> TYPE: DNA
<213> ORGANISM: artificial sequence
<220> FEATURE:
<223> OTHER INFORMATION: Can SL501-VK1

<400> SEQUENCE: 293

gaaattgtga tgacccagag cccggcgagc ctgagcctga gccaggaaga aaaagtgacc      60

attacctgcc gcgcgagcca gggcattggc gatgatctgg gctggtatca gcagaaaccg     120

ggccaggcgc cgaaactgct gatttatggc accagcaccc tgcagagcgg cgtgccgagc     180

cgctttagcg gcagcggcag cggcaccgat tttagcttta ccattagcag cctggaaccg     240

gaagatgtgg cggtgtatta ttgcctgcag gatagcaact atccgctgac ctttggcgcg     300

ggcaccaaa                                                             309
```